(12) United States Patent
Straus

(10) Patent No.: US 12,287,332 B2
(45) Date of Patent: Apr. 29, 2025

(54) TEST CARTRIDGES

(71) Applicant: First Light Diagnostics, Inc., Chelmsford, MA (US)

(72) Inventor: Don Straus, Cambridge, MA (US)

(73) Assignee: First Light Diagnostics, Inc., Chelmsford, MA (US)

( * ) Notice: Subject to any disclaimer, the term of this patent is extended or adjusted under 35 U.S.C. 154(b) by 581 days.

(21) Appl. No.: 17/282,623

(22) PCT Filed: Oct. 4, 2019

(86) PCT No.: PCT/US2019/054887
§ 371 (c)(1),
(2) Date: Apr. 2, 2021

(87) PCT Pub. No.: WO2020/073018
PCT Pub. Date: Apr. 9, 2020

(65) Prior Publication Data
US 2023/0241603 A1 Aug. 3, 2023

Related U.S. Application Data

(60) Provisional application No. 62/741,253, filed on Oct. 4, 2018.

(51) Int. Cl.
*G01N 33/543* (2006.01)
*B01L 3/00* (2006.01)
(Continued)

(52) U.S. Cl.
CPC .. *G01N 33/54333* (2013.01); *B01L 3/502715* (2013.01); *B01L 3/502738* (2013.01);
(Continued)

(58) Field of Classification Search
CPC ......... G01N 33/54333; G01N 21/6428; G01N 35/025; G01N 2021/6439;
(Continued)

(56) References Cited

U.S. PATENT DOCUMENTS 2,672,431 A 3/1954 Goetz
2,761,813 A 9/1956 Goetz
(Continued)

FOREIGN PATENT DOCUMENTS

AU 760425 B2 5/2003
CN 2486557 Y 4/2002
(Continued)

OTHER PUBLICATIONS

Al-Hakiem, 1982, Development of Fluoroimmunoassays for the Determination of Individual or Combined Levels of Procainamide and N-Acetylprocainamide in Serum, J Immunoassay 3(1):91-110.
(Continued)

*Primary Examiner* — Jill A Warden
*Assistant Examiner* — John McGuirk
(74) *Attorney, Agent, or Firm* — Ballard Spahr LLP

(57) ABSTRACT

The disclosure provides cartridges that are pre-loaded with reagents for performing antimicrobial susceptibility testing (AST) and FISH testing. Cartridges of the disclosure include various incubation wells loaded with different antimicrobial agents for differential growth analysis. Imaging wells with species-specific microbial probes, fluorescent tags, magnetic particles and dye-cushion layers allow for tagging and imaging of target microbes for differential growth analysis.

18 Claims, 60 Drawing Sheets

(51) Int. Cl.
*C12Q 1/18* (2006.01)
*C12Q 1/20* (2006.01)
*C12Q 1/6841* (2018.01)
*C12Q 1/689* (2018.01)
*G01N 21/64* (2006.01)
*G01N 35/02* (2006.01)

(52) U.S. Cl.
CPC .......... B01L 3/502761 (2013.01); *C12Q 1/18* (2013.01); *C12Q 1/20* (2013.01); *C12Q 1/6841* (2013.01); *C12Q 1/689* (2013.01); *G01N 35/025* (2013.01); *B01L 2200/021* (2013.01); *B01L 2200/0647* (2013.01); *B01L 2200/16* (2013.01); *B01L 2300/0627* (2013.01); *B01L 2300/0864* (2013.01); *B01L 2300/18* (2013.01); *B01L 2400/043* (2013.01); *B01L 2400/065* (2013.01); *G01N 21/6428* (2013.01); *G01N 2021/6439* (2013.01)

(58) Field of Classification Search
CPC . G01N 2035/00346; G01N 2035/0436; G01N 35/0099; G01N 2035/00356; G01N 2035/0446; G01N 35/0098; B01L 3/502715; B01L 3/502738; B01L 3/502761; B01L 2200/021; B01L 2200/0647; B01L 2200/16; B01L 2300/0627; B01L 2300/0864; B01L 2300/18; B01L 2400/043; B01L 2400/065; B01L 2200/04; B01L 2300/042; B01L 2300/043; B01L 2300/0867; B01L 2300/087; B01L 2300/0636; B01L 9/00; C12Q 1/18; C12Q 1/20; C12Q 1/6841; C12Q 1/689
See application file for complete search history.

(56) References Cited

U.S. PATENT DOCUMENTS

| | | |
|---|---|---|
| 3,694,317 A | 9/1972 | Scher |
| 3,981,776 A | 9/1976 | Saxholm |
| 4,097,586 A | 6/1978 | Gross |
| 4,098,876 A | 7/1978 | Piasio et al. |
| 4,115,535 A | 9/1978 | Giaever |
| 4,125,375 A | 11/1978 | Hunter |
| 4,129,419 A | 12/1978 | Hermann, Jr. |
| 4,141,687 A | 2/1979 | Forrest et al. |
| 4,157,323 A | 6/1979 | Yen et al. |
| 4,177,253 A | 12/1979 | Davies et al. |
| 4,222,744 A | 9/1980 | McConnell |
| 4,436,826 A | 3/1984 | Wang |
| 4,438,068 A | 3/1984 | Forrest |
| 4,454,233 A | 6/1984 | Wang |
| 4,455,370 A | 6/1984 | Bartelsman et al. |
| 4,477,578 A | 10/1984 | Miles et al. |
| 4,537,861 A | 8/1985 | Elings et al. |
| 4,562,157 A | 12/1985 | Lowe et al. |
| 4,565,783 A | 1/1986 | Hansen et al. |
| 4,582,810 A | 4/1986 | Rosenstein |
| 4,587,213 A | 5/1986 | Malecki |
| 4,614,585 A | 9/1986 | Mehra et al. |
| 4,693,972 A | 9/1987 | Mansour et al. |
| 4,731,337 A | 3/1988 | Luotola et al. |
| 4,745,077 A | 5/1988 | Holian et al. |
| 4,750,820 A | 6/1988 | Pareigat |
| 4,777,137 A | 10/1988 | Lemonnier |
| 4,777,145 A | 10/1988 | Luotola et al. |
| 4,912,037 A | 3/1990 | Lemonnier |
| 4,922,092 A | 5/1990 | Rushbrooke et al. |
| 4,959,301 A | 9/1990 | Weaver et al. |
| 4,981,783 A | 1/1991 | Augenlicht |
| 4,988,302 A | 1/1991 | Smith et al. |
| 4,988,618 A | 1/1991 | Li et al. |
| 5,073,497 A | 12/1991 | Schwartz |
| 5,089,413 A | 2/1992 | Nelson et al. |
| 5,130,733 A | 7/1992 | Taniguchi et al. |
| 5,137,812 A | 8/1992 | Matner |
| 5,190,666 A | 3/1993 | Bisconte |
| 5,232,838 A | 8/1993 | Nelson et al. |
| 5,238,810 A | 8/1993 | Fujiwara et al. |
| 5,258,284 A | 11/1993 | Morris, Jr. et al. |
| 5,262,526 A | 11/1993 | Sasamoto et al. |
| 5,292,644 A | 3/1994 | Berg |
| 5,306,420 A | 4/1994 | Bisconte |
| 5,321,545 A | 6/1994 | Bisconte |
| 5,348,885 A | 9/1994 | Labarthe |
| 5,355,215 A | 10/1994 | Schroeder et al. |
| 5,366,867 A | 11/1994 | Kawakami et al. |
| 5,464,749 A | 11/1995 | Schwarzberg et al. |
| 5,474,910 A | 12/1995 | Alfano |
| 5,510,246 A | 4/1996 | Morgan |
| 5,538,857 A | 7/1996 | Rosenthal et al. |
| 5,541,069 A | 7/1996 | Mortensen et al. |
| 5,552,272 A | 9/1996 | Bogart |
| 5,558,839 A | 9/1996 | Matte et al. |
| 5,582,982 A | 12/1996 | Cubbage et al. |
| 5,585,241 A | 12/1996 | Lindmo |
| 5,604,351 A | 2/1997 | Bisconte |
| 5,606,413 A | 2/1997 | Bellus et al. |
| 5,624,850 A | 4/1997 | Kumar et al. |
| 5,648,274 A | 7/1997 | Chandler |
| 5,652,939 A | 7/1997 | Verlinden et al. |
| 5,653,939 A | 8/1997 | Hollis et al. |
| 5,663,057 A | 9/1997 | Drocourt et al. |
| 5,672,880 A | 9/1997 | Kain |
| 5,681,530 A | 10/1997 | Kuster et al. |
| 5,681,712 A | 10/1997 | Nelson |
| 5,694,478 A | 12/1997 | Braier et al. |
| 5,705,402 A | 1/1998 | Leland et al. |
| 5,736,405 A | 4/1998 | Alfano et al. |
| 5,744,322 A | 4/1998 | Krejcarek et al. |
| 5,766,868 A | 6/1998 | Seto |
| 5,792,617 A | 8/1998 | Rotman |
| 5,814,454 A | 9/1998 | Ju |
| 5,821,066 A | 10/1998 | Pyle et al. |
| 5,828,716 A | 10/1998 | Bisconte de Saint Julien |
| 5,852,498 A | 12/1998 | Youvan et al. |
| 5,861,251 A | 1/1999 | Park et al. |
| 5,861,270 A | 1/1999 | Nelis |
| 5,861,306 A | 1/1999 | Pugh et al. |
| 5,891,394 A | 4/1999 | Drocourt et al. |
| 5,914,245 A | 6/1999 | Bylina et al. |
| 5,958,790 A | 9/1999 | Cerny |
| 5,968,766 A | 10/1999 | Powers |
| 5,976,892 A | 11/1999 | Bisconte |
| 5,981,180 A | 11/1999 | Chandler et al. |
| 5,985,675 A | 11/1999 | Charm et al. |
| 5,989,835 A | 11/1999 | Dunlay et al. |
| 5,993,740 A | 11/1999 | Niiyama et al. |
| 6,048,723 A | 4/2000 | Banes |
| 6,051,393 A | 4/2000 | Jones et al. |
| 6,051,395 A | 4/2000 | Rocco |
| 6,121,055 A | 9/2000 | Hargreaves |
| 6,122,396 A | 9/2000 | King et al. |
| 6,130,931 A | 10/2000 | Laurila et al. |
| 6,140,653 A | 10/2000 | Che |
| 6,165,742 A | 12/2000 | Øfjord et al. |
| 6,171,780 B1 | 1/2001 | Pham et al. |
| 6,200,762 B1 | 3/2001 | Zlokarnik et al. |
| 6,214,560 B1 | 4/2001 | Yguerabide et al. |
| 6,258,326 B1 | 7/2001 | Modlin |
| 6,259,807 B1 | 7/2001 | Ravkin |
| 6,268,222 B1 | 7/2001 | Chandler et al. |
| 6,274,384 B1 | 8/2001 | Starzl et al. |
| 6,287,849 B1 | 9/2001 | McNerney et al. |
| 6,306,589 B1 | 10/2001 | Muller et al. |
| 6,309,822 B1 | 10/2001 | Fodor et al. |
| 6,345,115 B1 | 2/2002 | Ramm et al. |
| 6,358,730 B1 | 3/2002 | Kane |
| 6,472,166 B1 | 10/2002 | Wardlaw et al. |
| 6,582,912 B1 | 6/2003 | Rousseau et al. |
| 6,602,704 B1 | 8/2003 | Maxwell et al. |

(56) References Cited

U.S. PATENT DOCUMENTS

| | | |
|---|---|---|
| 6,623,983 B1 | 9/2003 | Terstappen et al. |
| 6,649,418 B1 | 11/2003 | Geisberg |
| 6,664,528 B1 | 12/2003 | Cartlidge et al. |
| 6,710,879 B1 | 3/2004 | Hansen et al. |
| 6,727,071 B1 | 4/2004 | Dunlay et al. |
| 6,764,648 B1 | 7/2004 | Roach et al. |
| 6,790,655 B2 | 9/2004 | Lyman et al. |
| 6,792,132 B1 | 9/2004 | Hara et al. |
| 6,852,527 B2 | 2/2005 | Chan et al. |
| 6,919,960 B2 | 7/2005 | Hansen et al. |
| 6,969,607 B2 | 11/2005 | Minton |
| 7,068,365 B2 | 6/2006 | Hansen et al. |
| 7,110,585 B2 | 9/2006 | Cork et al. |
| 7,160,687 B1 | 1/2007 | Kapur et al. |
| 7,582,415 B2 | 9/2009 | Straus |
| 7,763,405 B2 | 7/2010 | Wu et al. |
| 7,763,455 B2 | 7/2010 | Cima et al. |
| 7,820,430 B2 | 10/2010 | Weng et al. |
| 8,021,848 B2 | 9/2011 | Straus |
| 9,090,462 B2 | 7/2015 | Straus |
| 9,290,382 B2 | 3/2016 | Straus |
| 9,632,085 B2 | 4/2017 | Super et al. |
| 9,643,180 B2 | 5/2017 | Abrams et al. |
| 2001/0039032 A1 | 11/2001 | Matsumura et al. |
| 2001/0039060 A1 | 11/2001 | Siiman et al. |
| 2002/0028471 A1 | 3/2002 | Oberhardt |
| 2002/0055092 A1 | 5/2002 | Hochman |
| 2002/0137106 A1 | 9/2002 | Leung et al. |
| 2003/0036058 A1 | 2/2003 | Becker et al. |
| 2003/0068638 A1 | 4/2003 | Cork et al. |
| 2003/0082516 A1 | 5/2003 | Straus |
| 2003/0143580 A1 | 7/2003 | Straus |
| 2003/0170613 A1 | 9/2003 | Straus |
| 2004/0048395 A1 | 3/2004 | Lee et al. |
| 2004/0171121 A1 | 9/2004 | Leppla et al. |
| 2004/0172000 A1 | 9/2004 | Roe et al. |
| 2004/0246483 A1 | 12/2004 | Hansen et al. |
| 2005/0013737 A1 | 1/2005 | Chow et al. |
| 2005/0053942 A1 | 3/2005 | Kauppinen et al. |
| 2005/0148085 A1 | 7/2005 | Larsen |
| 2005/0152955 A1 | 7/2005 | Akhave et al. |
| 2005/0153430 A1 | 7/2005 | Ohtaka |
| 2005/0191687 A1 | 9/2005 | Wang et al. |
| 2005/0220670 A1 | 10/2005 | Palmieri et al. |
| 2005/0221403 A1 | 10/2005 | Gazenko |
| 2005/0225766 A1 | 10/2005 | Hansen et al. |
| 2005/0226779 A1 | 10/2005 | Oldham et al. |
| 2006/0006067 A1 | 1/2006 | Unger |
| 2006/0046246 A1 | 3/2006 | Zeng et al. |
| 2006/0051816 A1 | 3/2006 | Hsieh et al. |
| 2006/0121055 A1 | 6/2006 | Campbell et al. |
| 2006/0129327 A1 | 6/2006 | Kim et al. |
| 2006/0188967 A1 | 8/2006 | Nalin et al. |
| 2006/0210435 A1 | 9/2006 | Alavie et al. |
| 2006/0216696 A1 | 9/2006 | Goguen |
| 2006/0256340 A1 | 11/2006 | Hansen et al. |
| 2006/0292552 A1 | 12/2006 | Haquette et al. |
| 2007/0014695 A1 | 1/2007 | Yue et al. |
| 2007/0172899 A1 | 7/2007 | Graham et al. |
| 2007/0184546 A1 | 8/2007 | Farrelly et al. |
| 2007/0202681 A1 | 8/2007 | Wang |
| 2007/0212681 A1 | 9/2007 | Shapiro et al. |
| 2007/0212747 A1 | 9/2007 | Browne et al. |
| 2008/0003571 A1 | 1/2008 | McKernan et al. |
| 2008/0014576 A1 | 1/2008 | Jovanovich et al. |
| 2008/0032328 A1 | 2/2008 | Cline et al. |
| 2008/0038738 A1 | 2/2008 | Weigum et al. |
| 2008/0200343 A1 | 8/2008 | Clemens et al. |
| 2008/0206099 A1 | 8/2008 | Aruga et al. |
| 2009/0075274 A1 | 3/2009 | Slepnev et al. |
| 2009/0137029 A1 | 5/2009 | Breidenthal et al. |
| 2009/0315987 A1 | 12/2009 | Straus |
| 2010/0028986 A1 | 2/2010 | Hanafusa |
| 2010/0248281 A1 | 9/2010 | Straus |
| 2011/0028563 A1 | 2/2011 | Found |
| 2012/0045826 A1 | 2/2012 | Yantz et al. |
| 2012/0046203 A1 | 2/2012 | Walsh et al. |
| 2012/0149007 A1 | 6/2012 | Abrams et al. |
| 2013/0011566 A1 | 1/2013 | Colin et al. |
| 2013/0216454 A1 | 8/2013 | Blecka et al. |
| 2015/0152467 A1 | 6/2015 | Ingber et al. |
| 2016/0152694 A1 | 6/2016 | Ambrosino et al. |
| 2016/0289729 A1 | 10/2016 | Richards et al. |
| 2017/0029864 A1 | 2/2017 | Straus |
| 2017/0144155 A1* | 5/2017 | Bohm ................ B01L 7/52 |
| 2018/0015454 A1* | 1/2018 | Wright ............. B01L 3/502 |
| 2018/0088141 A1 | 3/2018 | Vacic et al. |
| 2018/0243741 A1 | 8/2018 | Unger et al. |
| 2019/0324034 A1 | 10/2019 | Bowers et al. |
| 2019/0366338 A1 | 12/2019 | Yantz et al. |

FOREIGN PATENT DOCUMENTS

| | | |
|---|---|---|
| CN | 101254482 A | 9/2008 |
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 0753732 A2 | 1/1997 |
| EP | 1207394 A2 | 5/2002 |
| EP | 1508374 A2 | 2/2005 |
| JP | S62-501647 A | 7/1987 |
| JP | H02-502405 A | 8/1990 |
| JP | H02-278155 A | 11/1990 |
| JP | H3-83598 | 4/1991 |
| JP | H08-201391 A | 8/1996 |
| JP | 10295362 | 11/1998 |
| JP | H11-148901 A | 6/1999 |
| JP | H11-346795 A | 12/1999 |
| JP | 2000-508778 A | 7/2000 |
| JP | 2000-509827 A | 8/2000 |
| JP | 2000-275258 A | 10/2000 |
| JP | 3102240 B2 | 10/2000 |
| JP | 2001-224355 A | 8/2001 |
| JP | 2001-512875 A | 8/2001 |
| JP | 2002-125656 A | 5/2002 |
| JP | 2003-294596 A | 10/2003 |
| JP | 2004-070039 A | 3/2004 |
| JP | 2004-125799 A | 4/2004 |
| JP | 2005-502354 A | 1/2005 |
| JP | 2006-087336 A | 4/2006 |
| JP | 2006-162466 A | 6/2006 |
| JP | 2007-526807 A | 9/2007 |
| JP | 2008-96223 A | 4/2008 |
| JP | 2008-513022 A | 5/2008 |
| JP | 2009-513111 A | 4/2009 |
| WO | 83/01581 A1 | 5/1983 |
| WO | 86/04684 A1 | 8/1986 |
| WO | 89/05456 A1 | 6/1989 |
| WO | 92/05448 A2 | 4/1992 |
| WO | 97/40181 A1 | 10/1997 |
| WO | 9744664 A1 | 11/1997 |
| WO | 98/38490 A1 | 9/1998 |
| WO | 98/50577 A1 | 11/1998 |
| WO | 99/08233 A1 | 2/1999 |
| WO | 9920789 A1 | 4/1999 |
| WO | 99/35483 A1 | 7/1999 |
| WO | 99/36577 A1 | 7/1999 |
| WO | 99/40176 A1 | 8/1999 |
| WO | 9958948 A2 | 11/1999 |
| WO | 0004382 A1 | 1/2000 |
| WO | 0047766 A1 | 8/2000 |
| WO | 01/57522 A2 | 8/2001 |
| WO | 01/61348 A1 | 8/2001 |
| WO | 03/022999 A2 | 3/2003 |
| WO | 03/036290 A1 | 5/2003 |
| WO | 03/073817 A2 | 9/2003 |
| WO | 2005/082254 A2 | 9/2005 |
| WO | 2006/032044 A2 | 3/2006 |
| WO | 2006/106962 A1 | 10/2006 |
| WO | 2007/038478 A2 | 4/2007 |
| WO | 2007/145091 A1 | 12/2007 |
| WO | 2008/005998 A2 | 1/2008 |

(56) References Cited

FOREIGN PATENT DOCUMENTS

| WO | 2008108027 A1 | 9/2008 |
|---|---|---|
| WO | 2010/036808 A1 | 4/2010 |
| WO | 2010/036827 A1 | 4/2010 |
| WO | 2010/036829 A1 | 4/2010 |
| WO | 2011/117545 A1 | 9/2011 |
| WO | 2012/035302 A1 | 3/2012 |
| WO | 2013/070730 A2 | 5/2013 |
| WO | 2013/158666 A1 | 10/2013 |
| WO | 2015/083165 A1 | 6/2015 |
| WO | 2018/111630 A2 | 6/2018 |
| WO | 2020/073015 A1 | 4/2020 |
| WO | 2020/073018 A2 | 4/2020 |

OTHER PUBLICATIONS

Allman, 1981, Fluoroimmunoassay of Progesterone in Human Serum of Plasma, Clin Chem 27:1176-1176.

Batchelor, 2012, Light and Optics, Machine Vision Handbook, Springer-Verlag, 157-258.

Catalogue of Becton, 2003, Dickinson and Company, p. 28, 29, 32-35, 150 and 151, Japan.

CCD detectors (http://www.astrosurf.com/re/chip.html) published online Feb. 22, 2001, from web archive http://web.archive.org/web/20010222014106/http://astrosurf.com/re/chip.html, retrieved Apr. 12, 2012, 5 pages.

Clean Technology, 1995, 5(8):60-61 (no english translation provided).

Colony Counter (http://www.topac.com/acolyte.html), retrieved Apr. 12, 2005, 3 pages.

Colony Counter Models and Specifications (http://biologics-inc.com/cc-models.htm), retreived Apr. 15, 2005, 3 pages.

Corkidi, 1998, COVASIAM: An Image Analysis Method That Allows Detection of Confluent Microbial Colonies and Colonies of Various Sizes for Automated Counting, Appl Environ Microbiol 64(4):1400-1404.

Crowther, 2000, Methods in Molecular Biology, The ELISA Guidebook, Humana Press, 425 pages.

Definition and Procedure for the Determination of the Method Detection Limit, Appendix B to 40 C.F.R. § 136, available at http://access.gpo.gov, retreived Nov. 20, 2007, pp. 343-346.

Digital Multi-Purpose High Resolution Colony and Plaque Counter, http://www.loats.com/mla.html, retreived Apr. 12, 2005, 3 pages.

Esteban, 1992, Improved Direct Epifluorescent Filter Technique for Rapid Bioburden Control in Intravenous Solutions, J. Parenter. Sci. Technol. 46146-149.

Findlay, 1993, Automated closed-vessel sstem for in vitro diagnostics based on polymerase chain reation, Clin Chem, 39(9):1927-1933.

Freydiere, 1991, Detection of *Salmonellae* by using Rambach agar and by a C8 esterase spot test, J. Clin Microbiol. 29(10):2357-2360.

Frost, 1921, Improved Technic for the Micro or Little Plate Method of Counting Bacteria in Milk, J. Infect. Dis. 28(2):176-187.

Gite, 2018, A Rapid, Accurate, Single Molecule Counting Method Detects Clostridium difficile Toxin B in Stool Samples, Scientific Reports, 8:1-8.

Gray, 2011, Identification of micro-organisms after milliflex rapid detection—a possibility to Identify nonsterile findings in the milliflex rapid sterility test, PDA J Pharm Sci Technol. 65(1):42-54.

Graziani-Bowering, 1997, A quick, easy and inexpensive method for the isolation of human peripheral blood monocytes, J of Immunol Methods, 207(2):157-168.

Innovative Plate Holder for ProtoCOL, http://www.synbiosis.com retrieved Oct. 16, 2002, 2 pages.

Int Search Report and Written Op mailed Feb. 19, 2020, for Int Application No. PCT/US2019/054885, filed Oct. 4, 2019 (12 pages).

Int Search Report and Written Op mailed Jan. 13, 2010, for Int Application No. PCT/US2009/58237, filed Sep. 24, 2009, (10 pages).

Int Search Report and Written Op mailed Jan. 16, 2020, for Int Application No. PCT/US2019/054884, filed Oct. 4, 2019 (7 pages).

Int Search Report and Written Op mailed Jan. 17, 2020, for Int Application No. PCT/US2019/054887, filed Oct. 4, 2019 (12 pages).

Int Search Report and Written Op mailed Jan. 17, 2020, for Int Application No. PCT/US2019/054888, filed Oct. 4, 2019 (12 pages).

Int Search Report and Written Op mailed Jul. 10, 2019, for Int Application No. PCT/US2019/028397, filed Apr. 19, 2019 (11 pages).

Int Search Report and Written Op mailed Nov. 20, 2009, for Int Application No. PCT/US2009/058274, filed Sep. 24, 2009 (10 pages).

Kamentsky, 2001, Laser Scanning Cytometry, Methods Cell Biol. 63:51-87.

Kepner, 1994, Use of fluorochromes fo direct enumeration of total bacteria in environmental samples: past and present, Microbiol Rev. 58(4):603-615.

Kroll, 1989, A Laser-Light Pulse Counting Method for Automatic and Sensitive Counting of Bacteria Stained with Acridine Orange, J. Appl. Bacteriol. 66:161-167.

Lamture, 1994, Direct Detection of Nucleic Acid Hybridization on the Surface of a Charge Coupled Device, Nucleic Acids Res. 22(11):2121-2125.

Loates Associates Inc., 1999, System Specifications http://www.loats.com/order_info.html, retrieved Apr. 12, 2005, 7 pages.

Loats, 1990, LAI High-Resolution Automated Colony Counting System—Mouse Lymphoma Assay: Performance Analysis, http://loats.com/docs/HRCCval/HRCCval.htm, pp. 1-11.

Logtenberg, 1985, Enumeration of (Auto) Antibody Producing Cells in Human Using the "Spot-ELISA," Immunol. Lett. 9:343-347.

London, 2010, An Automated System for Rapid Non-Destructive Enumeration of Growing Microbes, PLoS One 5(1): e8609, 16 pages.

Masuko, 1991, A Novel Method for Detection and Counting of Single Bacteria in a Wide Field Using an Ultra-High-Sensitivity TV Camera Without a Microscope, FEMS Microbiol. Lett. 81:287-290.

Masuko, 1991, Rapid Detection and Counting of Single Bacteria in a Wide Field Using a Photon-Counting TV Camera, FEMS Microbiol. Lett. 83:231-238.

Mignon-Godefroy, 1997, Solid Phase Cytometry for Detection of Rare Events, Cytometry 27, pp. 336-344.

Miraglia, 1999, Homogeneous Cell-and Bead-Based Assays for High Throughput Screening Using Fluorometric Microvolume Assay Technology, J. Biomol. Screen. 4:193-204.

Moore, 1998, Lymphocyte fractionation using immunomagnetic colloid and a dipole magnet flow sorter, J Biochem Biophys Methods, 37:11-33.

Nargessi, 1980, Magnetizable Sold-Phase Fluoroimmunoassay of Thyroxines by a Sequential Addition Technique. Clin Chem 26(12):1701-1703.

Nargessi, 1984, Immunoassays for Serum C-Reactive Protein Employing Fluorophore-Labelled Reactants, J. Immunol. Methods 71:17-24.

Nealson, 1978, Isolation, identification, and manipulation of luminous bacteria, Methods Enzymol. 57:153-166.

Nebe-von-Caron, 2000, Analysis of bacterial function by multicolour fluorescence flow cytometry and single cell sorting, J. Microbiol Methods, 42(1):97-114.

Nelis, 2000, Enzymatic Detection of Coliforms and *Escherichia coli* Within 4 Hours, Water Air and Soil Pollut. 123:43-52.

Patterson, 1966, A wide angle camera for photographic search of the ocean bottom, SPIE, C-XII-1-8.

PerkinElmer, Inc., 2007, GeneScreenTM Hybridization Transfer Membranes: transfer and detection protocols, Application Notes, available at http://las.perkinelmer.com, retrieved Feb. 27, 2007.

Porter, 1980, The use of DAPI for identifying and counting aqquatic microflora, Limnol Oceanogr. 25(5):943-948.

Rousseau, 1999, New Miniaturized Highly Sensitive Immunassay Device for Quantitative Measurement of Soluble or Particular Antigen or Antibodies in a Liquid Sample, Clin. Chem. 45(9):1685-1687.

(56) References Cited

OTHER PUBLICATIONS

Schultz, 2000, Single Target Molecule Detection with Nonbleaching Multicolor Optical Immunolabels, Proc. Natl. Acad. Sci. USA 97(3):996-1001.

Sorcerer Automated Colony Counting, 2002, Perceptive Instruments, 2 pages.

Supplementary European Search Report and Written Opinion for European Application No. EP 09816857, date of mailing: Mar. 20, 2012, 8 pages.

Susa, 1998, *Legionella pneumophila* infection in intratracheally inoculated T cell-depleted or -nondepleted A/J mice, J Immunol, 160: 316-321.

Technical Specification http://www.perceptive.co.uk/products/_scc/techspec.html, retrieved Apr. 12, 2005, 2 pages.

Texas Instruments TC211 192×165 Pixel CCD Image Sensor description dated Jan. 1990, 13 pages.

Thomas, 2000, Making gold nanoparticles glow: enhanced emission from a surface-bound fluoroprobe, J Am Chem Soc, 122:2655-2656.

Tibbe, 1999, Optical Tracking and Detection of Immunomagnetically Selected and Aligned Cells, Nature Biotechnol. 17:1210-1213.

Van Pouche, 2000, A 210-min Solid Phase Cytometry Test for the Enumeration of *Escherichia coli* in Drinking Water, J. Appl. Microbiol. 89:390-396.

Van Poucke, 1999, Solid Phase Cytometry-Based Enzymatic Detection of Coliforms in Drinking Water Within 4 h, Water Supply 17:67-72.

Van Poucke, 2000, Rapid Detection of Fluorescent and Chemiluminescent Total Coliforms and *Escherichia coli* on Membrane Filters J. Microbiol. Methods 42:233-214.

Vidon, 2001, A Simple Chemiluminescence-Based Method for Rapid Enumeration of *Listeria* spp. Microcolonies, J. Appl. Microbiol. 90:988-993.

Viinikka, 1981, A Two-Site Immunofluorometric Assay for Human Placental Lactogen, Clin. Chim. Acta. 114:1-9.

Waggoner, 1990, Fluorescent Probes for Cytometry, Flow Cytometry and Sorting, Wiley-Liss, 209-225.

Wellman, 2006, Magenetically-Assisted Transport Evanescent Field Fluoroimmunoassay, Anal, Chem. 78:4450-4456.

Wilson, 1995, Use of the IUL Countermat Automatic Colony Counter for Spiral Plated Total Viable Counts, Appl. Environ. Microbiol. 61:3158-3160.

Wolniak, 2004, BSCI 427 Principles of Microscopy Fall 2004 Syllabus, http://www.life.umd.edu/cbmg/faculty/wolniak/wolniakmicro.html, retrieved Nov. 8, 2007, 8 pages.

Yasui, 1997, Imaging of *Lactobacillus brevis* Single Cells and Microcolonies Without a Microscope by an Ultrasensitive Chemiluminescent Enzyme Immunoassay with a Photon-counting Television Camera, Appl. Environ. Microbiol. 63:4528-4533.

Zhao, 2004, Competitive Immunoassay for Microliter Protein Samples with Magnetic Beads and Near-infared Fluorescence Detection, Anal Chem. 76:1871-1876.

\* cited by examiner

| Bacterial Target | FISH Probes | Labeled | Final Concentration | Sequence | Comments | |
|---|---|---|---|---|---|---|
| E. coli | Eco469 | Alexa647N | 0.3 μM | /5Alex647N/GTCAATGAGCAAAGG | Eco649 H1 | (SEQ ID NO: 1) |
| | Eco469 H1 | No label | 3 μM | ACTCCCTTCCTCCCCGCTG | Went with Eco649 | (SEQ ID NO: 2) |
| | Eco469 H2 | No label | 3 μM | GGTGTGTTCTTCTGCGGGTAA | | (SEQ ID NO: 3) |
| | Eco649 | Alexa647 | 0.3 μM | /5Alex647N/TACGAGACTCAAGCT | Eco649 H1 | (SEQ ID NO: 4) |
| | Eco649 H1 | No label | 3 μM | AGTATAGATGLAGTTCCAG | Went with Eco649 | (SEQ ID NO: 5) |
| | Eco649 H2 | No label | 3 μM | TCCGCACCTGAGLGTCAGTC | | (SEQ ID NO: 6) |
| P. aeruginosa | Pae002 | Alexa647N | 0.2 μM | /5Alex647N/CTTCAAAGATCCTTT/3Alex647N/ | All probes were used in same mixture | (SEQ ID NO: 7) |
| | Pae002 H1 | No label | 1.5 μM | CGGTACGGGGCTATCACCCA | | (SEQ ID NO: 8) |
| | Pae002 H2 | No label | 1.5 μM | GCTCCGGTCCTACTGATTCA | | (SEQ ID NO: 9) |
| | Pae004 H1 | No label | 1.5 μM | GGGCTAATCCCGGTTGCTCG | | (SEQ ID NO: 10) |
| | Pae004 H2 | No label | 5 μM | ACTTCCAGAGGGTTCCGCTA | | (SEQ ID NO: 11) |
| | Pae005 H2 | No label | 1.5 μM | CCAGTGAGATCTCATCTTGAG | | (SEQ ID NO: 12) |
| | Pae005 H3 | No label | 5 μM | CGTCGTAGGTCTTGACGGCCC | | (SEQ ID NO: 13) |
| K. pneumoniae | Kpn001 | Alexa647N | 0.6 μM | /5Alex647N/CACGTACACACAGCG/3Alex647N/ | All probes were used in same mixture | (SEQ ID NO: 14) |
| | Kpn003_2 | Alexa647 | 0.2 μM | /5Alex647N/CTTCGACTGGTCAGC/3Alex647N/ | | (SEQ ID NO: 15) |
| | Kleb001 H1 | No label | 6 μM | TGCCTTCTCCGAAGTACGG | | (SEQ ID NO: 16) |
| | Kleb235 H3 | No label | 1.5 μM | GCCAGTCGGTATCTTCGACTG | | (SEQ ID NO: 17) |
| | Kpn003 H3 | No label | 6 μM | ACAGTTGCAGCCAGCTGGTAT | | (SEQ ID NO: 18) |
| E. faecalis | UT1 338 A | Alexa647N | 0.6 μM | /5Alex647N/ACTGCTGCCT | | (SEQ ID NO: 19) |
| | UT1 338 B | Alexa647N | 0.6 μM | CCGTAGGAGT/3Alex647N/ | All probes were used in same mixture | (SEQ ID NO: 20) |
| | Eco338 H1 | No label | 3 μM | CTGGACGGTGTCAGTTC | | (SEQ ID NO: 21) |
| | Eco338 H2 | No label | 3 μM | CCCATTGTGCAATATTCCCT | | (SEQ ID NO: 22) |
| | Entero338 H1 | No label | 3 μM | TGGCCCGTGTCTCAGTCC | | (SEQ ID NO: 23) |
| | Entero338 H2 | No label | 3 μM | TCCATTGCCGAAGATTCCCT | | (SEQ ID NO: 24) |

FIG. 17

| Bacterial Target | FISH Probes | Labeled | Final Concentration | Sequence | |
|---|---|---|---|---|---|
| E. coli | Eco469 | Alexa647N | 0.6 µM | /5Alex647N/GTCAATGAGCAAAGG | (SEQ ID NO: 26) |
| | Eco469 H1 | No label | 3 µM | ACTCCCTTCCTCTCCCGCTG | (SEQ ID NO: 27) |
| | Eco469 H2 | No label | 3 µM | GGTGCTTCTTCTGCGGGTAA | (SEQ ID NO: 28) |
| P. aeruginosa | Pae002 | Alexa647N | 0.4 µM | /5Alex647N/CTTCAAAGATCCTTT/3Alex647N/ | (SEQ ID NO: 29) |
| | Pae002 H1 | No label | 1.5 µM | CGCGTACGGGGCTATCACCCA | (SEQ ID NO: 30) |
| | Pae002 H2 | No label | 1.5 µM | GCTCCGTCCTACTCGATTCA | (SEQ ID NO: 31) |
| | Pae024 H1 | No label | 1.5 µM | GGGCTAATCCCCGTTGCTG | (SEQ ID NO: 32) |
| | Pae024 H2 | No label | 5 µM | ACTTCCAGAGATCTCATCTTGAG | (SEQ ID NO: 33) |
| | Pae005 H2 | No label | 1.5 µM | CCAGTGAGATCTTCGACGGCC | (SEQ ID NO: 34) |
| | Pae005 H3 | No label | 5 µM | CGTCGTAGTCTTCGACGGCCC | (SEQ ID NO: 35) |
| K. pneumoniae | Kpn003_2 | Alexa647N | 0.4 µM | /5Alex647N/CTTCGACTGGTCTCAGC/3Alex647N/ | (SEQ ID NO: 36) |
| | Kleb001 H1 | No label | 6 µM | TGCCTTCTCCCGAAGTTACGG | (SEQ ID NO: 37) |
| | Kleb235 H3 | No label | 1.5 µM | GCCAGCTGGTATCTTCGACTG | (SEQ ID NO: 38) |
| | Kpn003 H3 | No label | 6 µM | ACAGTTGCAGCCAGCTGGTAT | (SEQ ID NO: 39) |
| E. faecalis | L1_Ent003 (LNA) | Alexa647N | 0.3 µM | /5Alex647N/CAAA+AAC+A+ACK+GG | (SEQ ID NO: 40) |
| | L2_Ent004 (LNA) | Alexa647N | 0.3 µM | /5Alex647N/TGC+ATT+CCTTA | (SEQ ID NO: 41) |
| | Ent003 H1 | No label | 5.6 µM | AGGAATATCAACCTGTRTCC | (SEQ ID NO: 42) |
| | Ent003 H2_1 | No label | 5.6 µM | CTMCTGCGTCCCTCCATTGCTCA | (SEQ ID NO: 43) |
| | Ent003 H3 | No label | 5.6 µM | GTTTRCGGTACGGGCMGYTGT | (SEQ ID NO: 44) |
| | Ent003 H4 | No label | 5.6 µM | TTTCTCACTAGAAGCTTTTCT | (SEQ ID NO: 45) |
| | Ent004 H4_2 | No label | 5.6 µM | CAGGAACTTCGSTACTATTAT | (SEQ ID NO: 46) |
| | Ent004 H2 Efls | No label | 5.6 µM | GGACATGCACTTCCAATGGCA | (SEQ ID NO: 47) |
| P. mirabilis | Prot631 (LNA) | Alexa647N | 0.6 µM | /5Alex647N/C+TGACTTAATT+GACC | (SEQ ID NO: 48) |
| | Prot631 H1 | No label | 3 µM | CCTGGTGCGCTTTAGGCC | (SEQ ID NO: 49) |
| | Prot631 H2 | No label | 3 µM | TTAAGCTCGGGGCTTTCACA | (SEQ ID NO: 50) |

FIG. 20

| Bacteria Tested For Cross-reactivity | Reason for inclusion |
|---|---|
| K. oxytoca | UTI pathogen |
| K. pneumoniae | UTI pathogen, close relative |
| P. aeruginosa | UTI pathogen |
| P. mirabilis | UTI pathogen |
| E. faecium | UTI pathogen |
| E. faecalis | UTI pathogen |
| S. aureus | UTI pathogen, rare skin commensal |
| S. saprophyticus | UTI pathogen |
| S. agalactiae | UTI pathogen |
| S. epidermidis | Skin commensal |
| A. baumanii | UTI pathogen |
| M. luteus | Skin commensal |
| S. enterica | Close relative |
| K. aerogenes | Close relative, UTI pathogen |
| C. fruendii | Close relative, UTI pathogen |
| S. marcescens | UTI pathogen |

FIG. 21

| Bacterial Target | FISH Probes | Labeled | Final Concentration | Sequence | Comments | |
|---|---|---|---|---|---|---|
| E. coli | Eco0649 | Alexa647N | 0.6 µM | /5Alex647N/GTCAATGAGCAAAGG | | (SEQ ID NO: 51) |
| | Eco649 H1 | No label | 3 µM | ACTCCTCCTCCCCGCTG | Eco0649 H1 Went with Eco0649 | (SEQ ID NO: 52) |
| | Eco649 H2 | No label | 3 µM | GGTGCTTCTTCCGGGTAA | | (SEQ ID NO: 53) |
| | Eco0649 | Alexa647N | 0.6 µM | /5Alex647N/TACGAGACTCAAGCT | | (SEQ ID NO: 54) |
| | Eco649 H1 | No label | 3 µM | AGTATCAGATGCAGTTCCAG | Eco0649 H1 Went with Eco0649 | (SEQ ID NO: 55) |
| | Eco649 H2 | No label | 3 µM | TTCGCACTGAGCGTCAGTC | | (SEQ ID NO: 56) |
| P. aeruginosa | Pae002 | Alexa647N | 0.4 µM | /5Alex647N/CTTCAAAGATCTTT/3Alex647N/ | | (SEQ ID NO: 57) |
| | Pae003 H1 | No label | 1.5 µM | CCGTACGCGGCTATCACCCA | | (SEQ ID NO: 58) |
| | Pae002 H2 | No label | 1.5 µM | GGTCCGTCCTACTGGATTCA | All probes were used in same mixture | (SEQ ID NO: 59) |
| | Pae004 H1 | No label | 1.5 µM | GGGCTAATCCCCGTTCGTCG | | (SEQ ID NO: 60) |
| | Pae004 H2 | No label | 5 µM | ACTTCACAGAAGGTTCCGCTA | | (SEQ ID NO: 61) |
| | Pae005 H2 | No label | 1.5 µM | CCAGTGAGATCTCATCTTGAG | | (SEQ ID NO: 62) |
| | Pae005 H3 | No label | 5 µM | CGTGTAGTCTTGACGGCCC | | (SEQ ID NO: 63) |
| K. pneumoniae | Kpn001 | Alexa647N | 0.6 µM | /5Alex647N/CACCTACACCAGCG/3Alex647N/ | | (SEQ ID NO: 64) |
| | Kpn003_2 | Alexa647N | 0.2 µM | /5Alex647N/CTTCGACTGGTCAGC/3Alex647N/ | | (SEQ ID NO: 65) |
| | Kleb001 H1 | No label | 6 µM | TGCCTCTCCCGAAGTTACGG | | (SEQ ID NO: 66) |
| | Kleb23S H3 | No label | 1.5 µM | CCCAGCTGGTATCTTCGACTG | All probes were used in same mixture | (SEQ ID NO: 67) |
| | Kpn003 H3 | No label | 6 µM | ACAGTTGCAGCCAGCTGGTAT | | (SEQ ID NO: 68) |
| E. faecalis | L1_Ent003 (LNA) | Alexa647N | 0.3 µM | /5Alex647N/CAAA+AAC+ACK+GG | | (SEQ ID NO: 69) |
| | L2_Ent004 (LNA) | Alexa647N | 0.3 µM | /5Alex647N/TGC+AT+CCTTA | | (SEQ ID NO: 70) |
| | Ent003 H1 | No label | 5.6 µM | AGGAATATCAACTGTTTCC | | (SEQ ID NO: 71) |
| | Ent003 H2_1 | No label | 5.6 µM | CTMCTGCGTCCTCCATTGCTCA | | (SEQ ID NO: 72) |
| | Ent003 H3 | No label | 5.6 µM | GTTTRCGGTACGGGCMGYGT | All probes were used in same mixture | (SEQ ID NO: 73) |
| | Ent003 H4 | No label | 5.6 µM | TTCTCACTAGAAGCTTTCT | | (SEQ ID NO: 74) |
| | Ent004 H4_2 | No label | 5.6 µM | CAGGAACTTCGSTACTATTAT | | (SEQ ID NO: 75) |
| | Ent004 H2 Efis | No label | 5.6 µM | GGACATGCCACTTCCAATGCA | | (SEQ ID NO: 76) |

FIG. 22

*K. pneumoniae* 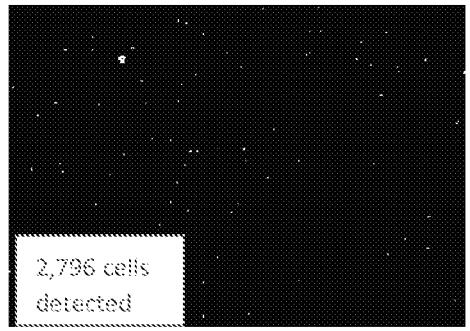 *P. aeruginosa* 
*K. oxytoca* 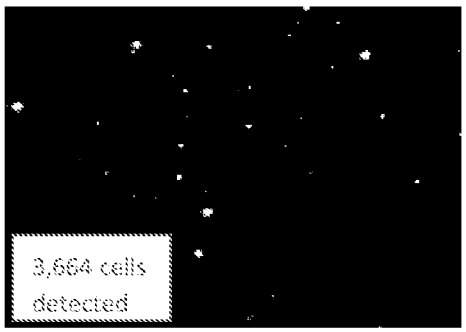 *E. coli* 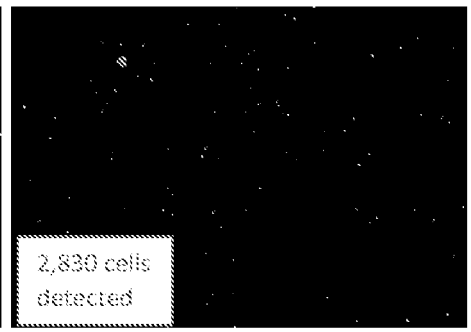
FIG. 25

| Bacterial Target | FISH Probes | Labeled | Color Channel | Final Concentration | Sequence | |
|---|---|---|---|---|---|---|
| E. coli | Eco469 | Alexa647N | Red | 0.3 µM | /5Alex647N/GTCAATGAGCAAAGG | (SEQ ID NO: 77) |
| | Eco469 H1 | No label | N/A | 3 µM | ACTCCCTTCCCCCGCTG | (SEQ ID NO: 78) |
| | Eco469 H2 | No label | N/A | 3 µM | GGTGCTTCTCTGGGGTAA | (SEQ ID NO: 79) |
| P. aeruginosa | Pae002 | Alexa532N | Yellow | 0.2 µM | /5Alex532N/CTTCAAAGATCCTTT/3Alex532N/ | (SEQ ID NO: 80) |
| | Pae002 H1 | No label | N/A | 1.5 µM | CGGCGTACGGGCTATCACCCA | (SEQ ID NO: 81) |
| | Pae002 H2 | No label | N/A | 1.5 µM | GCTCCGTCCTACTGGATTCA | (SEQ ID NO: 82) |
| | Pae004 H1 | No label | N/A | 1.5 µM | GGGCTAATCCCCGGTTCGCTG | (SEQ ID NO: 83) |
| | Pae004 H2 | No label | N/A | 5 µM | ACTTCAGAGCGTTCGGTA | (SEQ ID NO: 84) |
| | Pae005 H2 | No label | N/A | 1.5 µM | CCAGTGAGATTCATCTTGAG | (SEQ ID NO: 85) |
| | Pae005 H3 | No label | N/A | 5 µM | CGTCGTAGTCTTCGAACGCCC | (SEQ ID NO: 86) |
| K. pneumoniae | Kpn003_2 | Alexa488N | Green | 0.2 µM | /5Alex488N/CTTCGACTGGTCTCAGC/3Alex488N/ | (SEQ ID NO: 87) |
| | Kleb001 H1 | No label | N/A | 6 µM | TGCCTTCCCGAAGTTACGG | (SEQ ID NO: 88) |
| | Kleb23S H3 | No label | N/A | 1.5 µM | GCCAACTGGTATCTTGACTG | (SEQ ID NO: 89) |
| | Kpn003 H3 | No label | N/A | 6 µM | ACAGTTGCAGCCAGCTGGTAT | (SEQ ID NO: 90) |
| K. oxytoca | Koxy_1717 | Alexa560N | Orange | 0.6 µM | /5Alex560N/CTTCATGAGCAAGT/3Alex560N/ | (SEQ ID NO: 91) |
| | Koxy_1717 H1 | No label | N/A | 3 µM | ACTTACCATCAGCGTGCCTT | (SEQ ID NO: 92) |
| | Koxy_1717 H2 | No label | N/A | 3 µM | CTGGTATCTTCGACTGATTT | (SEQ ID NO: 93) |

FIG. 26

| Bacterial Target | FISH Probes | Labels | Final Concentration | Sequence | # of Samples used for analysis | |
|---|---|---|---|---|---|---|
| E.coli | Eco469 | Alexa647N | 0.6 µM | /5Alex647N/GTCAATGAGCAAAGG | | (SEQ ID NO: 94) |
| | Eco469 H1 | No label | 3 µM | ACTCCCTTCCTCCCCGCTG | 19 | (SEQ ID NO: 95) |
| | Eco469 H2 | No label | 3 µM | GGTGCTTCTTCTGCGGGTAA | | (SEQ ID NO: 96) |
| | Eco469 | Alexa647N | 0.3 µM | /5Alex647N/GTCAATGAGCAAAGG | | (SEQ ID NO: 97) |
| | Eco469 H1 | No label | 3 µM | ACTCCCTTCCTCCCCGCTG | 17 | (SEQ ID NO: 98) |
| | Eco469 H2 | No label | 3 µM | GGTGCTTCTTCTGCGGGTAA | | (SEQ ID NO: 99) |
| | Eco649 | Alexa647N | 0.3 µM | /5Alex647N/TACGAGACTCAAGCT | | (SEQ ID NO: 100) |
| | Eco649 H1 | No label | 3 µM | AGTATCAGATGCAGTTCCAG | 12 | (SEQ ID NO: 101) |
| | Eco649 H2 | No label | 3 µM | TCGCACCTGAGCGTCAGTC | | (SEQ ID NO: 102) |

FIG. 31

| Target | Antibiotic | Essential Agreement |
|---|---|---|
| E. coli | Ciprofloxacin | 100% |
| | Trimethoprim/sulfamethoxazole | 100% |
| | Meropenem | 100% |
| | Ceftazidime | 100% |
| | Nitrofurantoin | 75% (3/4) |
| P. aeruginosa | Ciprofloxacin | 100% |
| | Meropenem | 100% |
| | Ceftazidime | 100% |
| Klebsiella spp. (K. pneumoniae and K. oxytoca) | Ciprofloxacin | 100% |
| | Trimethoprim/sulfamethoxazole | 89% (8/9) |
| | Meropenem | 100% |
| | Ceftazidime | 100% |
| | Nitrofurantoin | 100% |
| P. mirabilis | Ciprofloxacin | 100% |
| | Trimethoprim/sulfamethoxazole | 100% |
| | Meropenem | 100% |
| | Ceftazidime | 100% |

FIG. 34

| Bacterial Target | FISH Probes | Labeled | Final Concentration | Sequence | |
|---|---|---|---|---|---|
| E. coli | Eco649 | Alexa647N | 0.3 μM | /5Alex647N/GTCAATGAGCAAAGG | (SEQ ID NO: 103) |
| | Eco649 H1 | No label | 3 μM | ACTCCCTTCCTCCCCGCTG | (SEQ ID NO: 104) |
| | Eco649 H2 | No label | 3 μM | GGTGCTTCTTGCGGGTAA | (SEQ ID NO: 105) |
| P. aeruginosa | Pae002 | Alexa647N | 0.2 μM | /5Alex647N/CTTCAAAGATCCTTT/3Alex647N/ | (SEQ ID NO: 106) |
| | Pae002 H1 | No label | 1.5 μM | CGCGTACGGGCTATCACCA | (SEQ ID NO: 107) |
| | Pae002 H2 | No label | 1.5 μM | GCTCCGTCCTACTCGATTCA | (SEQ ID NO: 108) |
| | Pae004 H1 | No label | 1.5 μM | GGGCTAATCCCGGTTCGCTCG | (SEQ ID NO: 109) |
| | Pae004 H2 | No label | 5 μM | ACTTTCCAGAGGGTCCGCTA | (SEQ ID NO: 110) |
| | Pae005 H2 | No label | 1.5 μM | CCAGTGAGATCTATCTTGAG | (SEQ ID NO: 111) |
| | Pae005 H3 | No label | 5 μM | CGTCGTAGTCTTCGACGGCCC | (SEQ ID NO: 112) |
| K. pneumoniae | Kpn003_2 | Alexa647N | 0.2 μM | /5Alex647N/CTTCGACTGGTCCAG/3Alex647N/ | (SEQ ID NO: 113) |
| | Kleb001 H1 | No label | 6 μM | TGCCTTCTCCGAAGTTAGG | (SEQ ID NO: 114) |
| | Kleb23S H2 | No label | 1.5 μM | GCCAGCTGGTATCTTCGACTG | (SEQ ID NO: 115) |
| | Kpn003 H3 | No label | 6 μM | ACAGTTGCAGCCAGTCGGTAT | (SEQ ID NO: 116) |
| K. oxytoca | Kox001_3 | Alexa647N | 0.6 μM | /5Alex647N/TCACYTACCATCCAG/3Alex647N/ | (SEQ ID NO: 117) |
| | Kleb001 H1 | No label | 3 μM | TGCCTTCTCCGAAGTTAGG | (SEQ ID NO: 118) |
| | Kleb23S H3 | No label | 3 μM | GCCAGCTGGTATCTTCGACTG | (SEQ ID NO: 119) |
| P. mirabilis | Prot631-2 dye | Alexa647N | 0.6 μM | /5Alex647N/C+TGACTTAATT+GACC | (SEQ ID NO: 120) |
| | Prot631 H1 | No label | 3 μM | CCTGCGTGCGCTTTACGCC | (SEQ ID NO: 121) |
| | Prot631 H2 | No label | 3 μM | TTAAGCTCGGGGCTTTCACA | (SEQ ID NO: 122) |

FIG. 35

| Antibiotics | Concentration 1 (μg/mL) | Concentration 2 (μg/mL) |
|---|---|---|
| Ciprofloxacin (CIP) | 0.25 | 0.5 |
| Nitrofurantoin (NIT) | 32 | 64 |
| Cefazolin (CFZ) | 8 | 16 |
| Trimethoprim/ Sulfamethoxazole (TMP/SXT) | 1/19 | 2/38 |

| Bacteria Target | FISH Probes | Labeled | Final Concentration | Sequence | |
|---|---|---|---|---|---|
| E. coli | Eco469 N | Alexa647 | 0.3 µM | /5Alex647N/GTCAATGAGCAAAGG | (SEQ ID NO: 123) |
| | Eco469 H1 | No label | 3 µM | ACTCCCTTCCTCCCCGCTG | (SEQ ID NO: 124) |
| | Eco469 H2 | No label | 3 µM | GGTGCTTCTTCTGCGGGTAA | (SEQ ID NO: 125) |

FIG. 38

| Target | Antibiotic | Essential Agreement | Categorical Agreement |
|---|---|---|---|
| E. coli | CIP | 100% | 100% |
| | CFZ | 100% | 100% |
| | NIT | 100% | 100% |
| | TMP/SXT | 100% | 100% |
| P. aeruginosa | CIP | 100% | 100% |
| | NIT | 100% | 100% |
| Klebsiella spp. | CIP | 100% | 100% |
| | CFZ | 100% | 100% |
| | NIT | 100% | 60% |
| | TMP/SXT | 100% | 100% |

FIG. 41

| Inoculum (CFU/mL) | MIC (µg/mL of NIT) |
|---|---|
| 2.E+03 | 8 |
| 2.E+04 | 8 |
| 1.E+05 | 8 |
| 2.E+05 | 16 |
| 3.E+05 | 16 |
| 5.E+05 | 8 |
| 2.E+06 | 16 |
| 6.E+06 | 16 |
| 6.E+07 | 16 |

| Bacterial Target | FISH Probes | Labeled | Final Concentration | Sequence | Comment | |
|---|---|---|---|---|---|---|
| E. coli | P2 Coli Dye-10 | Alexa647N | 0.3 µM | /5Alex647N/GTCAATGAGCAAAGG | Not specific to E. coli | (SEQ ID NO: 126) |
| | P1 Universal Dye | No label | 3 µM | ACTCCCTTCCTCCCCGCTG | Not specific to E. coli | (SEQ ID NO: 127) |
| | P1 coli Helper 1 | No label | 3 µM | CGTGCTTCTTCTGCGGGTAA | Not specific to E. coli | (SEQ ID NO: 128) |
| | Eco001 | Alexa647N | 1.2 µM | /5Alex647N/GTATTAACTTACTTCC/3Alex647N/ | Specific to E. coli | (SEQ ID NO: 129) |
| | Eco001 H1 | No label | 1.5 µM | CGGTAACGTCAATGAGCAAAG | Specific to E. coli | (SEQ ID NO: 130) |
| | Eco001 H2 | No label | 1.5 µM | CTTCCTCCCCGCTGAAAGTAC | Specific to E. coli | (SEQ ID NO: 131) |
| P. aeruginosa | Pae002 | Alexa647N | 600 nM | /5Alex647N/CTTCAAAGATCCTT/3Alex647N/ | Specific to P. aeruginosa | (SEQ ID NO: 132) |
| | Pae004 | Alexa647N | 600 nM | /5Alex647N/AAATCAATGAAGCTTAA/3Alex647N/ | Specific to P. aeruginosa | (SEQ ID NO: 133) |
| | Pae002 H1 | No label | 3 µM | CGGGTACCGGGCTATCACCA | Specific to P. aeruginosa | (SEQ ID NO: 134) |
| | Pae002 H2 | No label | 3 µM | GCTCGGTCCTAATCCGTTCA | Specific to P. aeruginosa | (SEQ ID NO: 135) |
| | Pae004 H1 | No label | 3 µM | CGGCTAATCCCGTTCGCTCG | Specific to P. aeruginosa | (SEQ ID NO: 136) |
| | Pae004 H2 | No label | 3 µM | ACTTTCCAGCGGTTCCGCTA | Specific to P. aeruginosa | (SEQ ID NO: 137) |
| K. pneumoniae | Kpn001 | Alexa647N | 1 µM | /5Alex647N/CACCTACACACCG/3Alex647N/ | Specific to K. pneumoniae | (SEQ ID NO: 138) |
| | Kpn001_2 | Alexa647N | 0.4 µM | /5Alex647N/CTTCGACTGGTCACC/3Alex647N/ | Specific to K. pneumoniae | (SEQ ID NO: 139) |
| | Kleb001 H1 | No label | 6 µM | TGCCTTTCCTCCGGAAGTACCG | Specific to K. pneumoniae | (SEQ ID NO: 140) |
| | Kleb 23S H3 | No label | 6 µM | GCCAGCTGGTATCTTCGACTG | Specific to K. pneumoniae | (SEQ ID NO: 141) |
| | Kpn003 H3 | No label | 6 µM | ACAGTTGACAGCCTGGTAT | Specific to K. pneumoniae | (SEQ ID NO: 142) |

FIG. 44

| Target | Off-target microbe added | Essential Agreement | Categorical Agreement |
|---|---|---|---|
| 1E+05 CFU per assay for E. coli | 1e+05 CFU per assay | 100% | 100% |
| | 1E+06 CFU per assay | 100% | 100% |
| | 1E+07 CFU per assay | 96% | 100% |

| Fold Growth threshold of 4.5 | Bug | ABX | MIC in ug/ml according to: | | Resistance profile | | |
|---|---|---|---|---|---|---|---|
| | | | MultiPath | CLSI Compliant BMD | MP | BMD | Agree/Disagree |
| E.coli with S.aureus | 1e5E.coli with 1e5 S.aureus | LVX | 16 | 16 | R | R | Agree |
| | | CIP | 256 | 256 | R | R | Agree |
| | | NIT | 8 | 8 | S | S | Agree |
| | 1e5E.coli with 1e6 S.aureus | LVX | 16 | 16 | R | R | Agree |
| | | CIP | 256 | 256 | R | R | Agree |
| | | NIT | 8 | 8 | S | S | Agree |
| | 1e5E.coli with 1e7 S.aureus | LVX | 16 | 16 | R | R | Agree |
| | | CIP | 256 | 256 | R | R | Agree |
| | | NIT | 8 | 8 | S | S | Agree |
| E.coli with S.epidermi s | 1e5E.coli with 1e5 S.epiderm | LVX | 16 | 16 | R | R | Agree |
| | | CIP | 256 | 256 | R | R | Agree |
| | | NIT | 8 | 8 | S | S | Agree |
| | 1e5E.coli with 1e6 S.epiderm | LVX | 16 | 16 | R | R | Agree |
| | | CIP | 256 | 256 | R | R | Agree |
| | | NIT | 4 | 8 | S | S | Agree |
| | 1e5E.coli with 1e7 S.epiderm | LVX | 16 | 16 | R | R | Agree |
| | | CIP | 256 | 256 | R | R | Agree |
| | | NIT | 16 | 8 | S | S | Agree |
| E.coli with Citrobacte r | 1e5E.coli with 1e5 Citro | LVX | 16 | 16 | R | R | Agree |
| | | CIP | 256 | 256 | R | R | Agree |
| | | NIT | 8 | 8 | S | S | Agree |
| | 1e5E.coli with 1e6 Citro | LVX | 16 | 16 | R | R | Agree |
| | | CIP | 256 | 256 | R | R | Agree |
| | | NIT | 4 | 8 | S | S | Agree |
| | 1e5E.coli with 1e7 Citro | LVX | 16 | 16 | R | R | Agree |
| | | CIP | 256 | 256 | R | R | Agree |
| | | NIT | <1 | 8 | S | S | Agree |

FIG. 47

| Fold Growth threshold of 4.5 | | | MIC in µg/ml according to: | | Resistance profile | | |
|---|---|---|---|---|---|---|---|
| | Bug | ABX | MultiPath | CLSI Compliant BMD | MP | BMD | Agree/Disagree |
| E. coli with M. luteus | 1e5E.coli with 1e5 M.lut | LVX | 32 | 16 | R | R | Agree |
| | | CIP | 256 | 256 | R | R | Agree |
| | | NIT | 8 | 8 | S | S | Agree |
| | 1e5E.coli with 1e6 M.lut | LVX | 16 | 16 | R | R | Agree |
| | | CIP | 256 | 256 | R | R | Agree |
| | | NIT | 8 | 8 | S | S | Agree |
| | 1e5E.coli with 1e7 M.lut | LVX | 32 | 16 | R | R | Agree |
| | | CIP | 256 | 256 | R | R | Agree |
| | | NIT | 4 | 8 | S | S | Agree |
| E. coli with A. baumannii | 1e5E.coli with 1e5 Abaum | LVX | 16 | 16 | R | R | Agree |
| | | CIP | 256 | 256 | R | R | Agree |
| | | NIT | 8 | 8 | S | S | Agree |
| | 1e5E.coli with 1e6 Abaum | LVX | 16 | 16 | R | R | Agree |
| | | CIP | 256 | 256 | R | R | Agree |
| | | NIT | 4 | 8 | S | S | Agree |
| | 1e5E.coli with 1e7 Abaum | LVX | 16 | 16 | R | R | Agree |
| | | CIP | 256 | 256 | R | R | Agree |
| | | NIT | 4 | 8 | S | S | Agree |
| E. coli with Corynybacteria | 1e5E.coli with 1e5 Corny | LVX | 16 | 16 | R | R | Agree |
| | | CIP | 256 | 256 | R | R | Agree |
| | | NIT | 8 | 8 | S | S | Agree |
| | 1e5E.coli with 1e6 Corny | LVX | 16 | 16 | R | R | Agree |
| | | CIP | 256 | 256 | R | R | Agree |
| | | NIT | 4 | 8 | S | S | Agree |
| | 1e5E.coli with 1e7 Corny | LVX | 16 | 16 | R | R | Agree |
| | | CIP | 256 | 256 | R | R | Agree |
| | | NIT | 4 | 8 | S | S | Agree |

FIG. 48

| Fold Growth threshold of 1.5 | | MIC in ug/ml according to | | Resistance profile | | |
|---|---|---|---|---|---|---|
| | Bug | ABX | MP | CLSI Compliant BMD | MP | BMD | Agree/Disagree |
| Polymicrobial with Klebsiella | E.coli 2469 control (no Klebsiella) | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e3 K. pneumoniae | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e4 K. pneumoniae | NIT | 16 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e5 K. pneumoniae | NIT | 16 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e6 K. pneumoniae | NIT | 4 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 2.5e7 K. pneumoniae | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |

FIG. 49

| Bacterial Target | FISH Probes | Labeled | Final Concentration | Sequence | |
|---|---|---|---|---|---|
| E. coli | Eco001 | Alexa647N | 0.8 μM | /5Alex647N/GTATTAACTTACTCC/3Alex647N/ | (SEQ ID NO: 143) |
| | Eco002 | Alexa647N | 0.4 μM | /5Alex647N/ACACACACTGATTCA/3Alex647N/ | (SEQ ID NO: 144) |
| | Eco001 H1 | No label | 3 μM | GGGTAACGTCAATGAGCAAAG | (SEQ ID NO: 145) |
| | Eco0001 H2 | No label | 3 μM | CTTCCTCCCGGCTGAAAGTAC | (SEQ ID NO: 146) |
| | Eco002 H6 | No label | 3 μM | TTTCAGAGCGTTCCACTAAC | (SEQ ID NO: 147) |
| | Eco002 H7 | No label | 3 μM | GGCTCTGGGCTCCTCCCCGT | (SEQ ID NO: 148) |

FIG. 50

| Bacterial Target | FISH Probes | Labeled | Final Concentration | Sequence | |
|---|---|---|---|---|---|
| E. coli | Eco001 | Alexa647N | 0.7 µM | /5Alex647N/GTATTAACTTTACTCC/3Alexf647N/ | (SEQ ID NO: 149) |
| | Eco002 | Alexa647N | 0.4 µM | /5Alex647N/ACACACACTGATTCA/3Alexf647N/ | (SEQ ID NO: 150) |
| | Eco001 H1 | No label | 3 µM | GGGTAACGTCAATGAGCAAAG | (SEQ ID NO: 151) |
| | Eco001 H2 | No label | 3 µM | CTTCCTCCCGCTGAAAGTAC | (SEQ ID NO: 152) |
| | Eco002 H6 | No label | 3 µM | TTTCCAGAGCGTTCCACTAAC | (SEQ ID NO: 153) |
| | Eco002 H7 | No label | 3 µM | GGCTCTGGGCTCCTCCCGT | (SEQ ID NO: 154) |

FIG. 53

| Urine Sample | Essential Agreement Across 5 Antibiotics* | Categorical Agreement Across 5 Antibiotics* |
|---|---|---|
| Urine A | 100% | 100% |
| Urine B | 100% | 100% |
| Urine C | 100% | 100% |
| Urine D | 100% | 100% |
| Urine E | 100% | 100% |
| Urine F | 100% | 100% |
| Urine G | 100% | 100% |
| Urine H | 100% | 100% |
| Urine I | 100% | 100% |
| Urine J | 100% | 100% |
| Urine K | 100% | 100% |
| Urine L | 100% | 100% |
| Urine M | 100% | 100% |
| Urine N | 100% | 100% |
| Urine O | 100% | 100% |

FIG. 55

| Antibiotics | LVX | CIP | CFZ | TMP/SXT | NIT |
|---|---|---|---|---|---|
| CLSI Compliant | 16 | 128 | >128 | >128 | 8 |
| Urine A | 16 | 128 | >128 | >128 | 8 |
| Urine B | 16 | >128 | >128 | >128 | 8 |
| Urine C | 32 | >128 | >128 | >128 | 4 |
| Urine D | 8 | 128 | >128 | >128 | 4 |
| Urine E | 16 | 128 | >128 | >128 | 8 |
| Urine F | 32 | >128 | >128 | >128 | 8 |
| Urine G | 16 | 128 | >128 | >128 | 8 |
| Urine H | 16 | >128 | >128 | >128 | 8 |
| Urine I | 16 | >128 | >128 | >128 | 8 |
| Urine J | 16 | 128 | >128 | >128 | 8 |
| Urine K | 8 | 128 | >128 | >128 | 8 |
| Urine L | 16 | 128 | >128 | >128 | 8 |
| Urine M | 16 | 128 | >128 | >128 | 8 |
| Urine N | 8 | 128 | >128 | >128 | 8 |
| Urine O | 16 | >128 | >128 | >128 | 8 |

FIG. 56

| Bacterial Target | FISH Probes | Labeled | Final Concentration | Sequence | Comment | |
|---|---|---|---|---|---|---|
| E. coli | P1 Universal Dye 647 | Cy3 | 300 nM | CGGTACTCCCCA/iCy3/GGC | Not specific to E. coli | (SEQ ID NO: 155) |
| | P2 Coli Dye-10 647 | Cy5 | 300 nM | GGT/iCy5/CGACTTA | Not specific to E. coli | (SEQ ID NO: 156) |
| | Helper-1 Coli | No label | 6 µM | 5'ACGGTTAGCTCCGGAAGCCA | Not specific to E. coli | (SEQ ID NO: 157) |

FIG. 57

| Bacteria | Strain ID | Susceptibility to Ciprofloxacin |
|---|---|---|
| E. coli | ATCC 25922 | Sensitive |
| E. coli | BAA 2469 | Resistant |
| K. pneumoniae | CDC 0076 | Sensitive |
| K. pneumoniae | CDC 0043 | Resistant |
| P. aeruginosa | CDC 0233 | Sensitive |
| P. aeruginosa | CDC 0236 | Resistant |
| E. faecalis | ATCC 29212 | Sensitive |
| E. faecium | ATCC 19434 | Resistant |

FIG. 61

| Bacterial Target | FISH Probes | Labeled | Final Concentration | Sequence | |
|---|---|---|---|---|---|
| E. coli | Eco001 | Alexa647N | 1.2 μM | /5Alex647N/GTATTAACTTACTCC | (SEQ ID NO: 158) |
| | Eco002 | Alexa647N | 0.6 μM | /5Alex647N/ACACACTGATTCA/3Alex647N/ | (SEQ ID NO: 159) |
| | Eco002 H6 | No label | 3 μM | TTCCAGAGCGTTCCACTAAC | (SEQ ID NO: 160) |
| | Eco002 H7 | No label | 3 μM | GGCTCTGGGCTCCTCCCCGT | (SEQ ID NO: 161) |
| | Eco001 H2 | No label | 3 μM | CTTCCTCCCGCTGAAAGTAC | (SEQ ID NO: 162) |
| | Eco001 H1 | No label | 3 μM | GGCTAAGGTCAATGAGCAAAG | (SEQ ID NO: 163) |
| P. aeruginosa | Pae002 2 dye | Alexa647N | 0.4 μM | /5Alex647N/CTTCAAAGATCCTTT/3Alex647N/ | (SEQ ID NO: 164) |
| | Pae004 2 dye | Alexa647N | 0.5 μM | /5Alex647N/AAATCAATGAAGCTTAA/3Alex647N/ | (SEQ ID NO: 165) |
| | Pae005 1 2 dye | Alexa647N | 1.1 μM | /5Alex647N/TTCAGGGAATCAAGTTC/3Alex647N/ | (SEQ ID NO: 166) |
| | Pae002 H1 | No label | 1.5 μM | CGGCTACGGGCTATCACCCA | (SEQ ID NO: 167) |
| | Pae002 H2 | No label | 1.5 μM | GCTCCGTCCTACTCGATTCA | (SEQ ID NO: 168) |
| | Pae004 H1 | No label | 1.5 μM | GGGCTAATCCCCGTTCGCTCG | (SEQ ID NO: 169) |
| | Pae004 H2 | No label | 5 μM | ACTTCCAGAGCGTTCCGCTA | (SEQ ID NO: 170) |
| | Pae005 1H2 | No label | 1.5 μM | CCAGTGAGATCTCATTTGAG | (SEQ ID NO: 171) |
| | Pae005 1H3 | No label | 5 μM | CGTCGTAGTCTTCGACGGCCC | (SEQ ID NO: 172) |

FIG. 62

| Organism | Name | Label | Conc. | Sequence | SEQ ID |
|---|---|---|---|---|---|
| K. pneumoniae | Kpn003_2 | Alexa647N | 0.4 µM | /5Alex647N/CTTCGACTGGTTCAGC/3Alex647N/ | (SEQ ID NO: 173) |
| | Kpn001-A | Alexa647N | 1 µM | /5Alex647N/CACCTACACACCAGCG/3Alex647N/ | (SEQ ID NO: 174) |
| | Kleb001 H1 | No label | 6 µM | TGCTTCTCCGAAGTTACGG | (SEQ ID NO: 175) |
| | Kleb23S H3 | No label | 1.5 µM | GCCAGCTGGTATCTTCGACTG | (SEQ ID NO: 176) |
| | Kpn003 H3 | No label | 6 µM | ACAGTTCAGCCAGCTGGTAT | (SEQ ID NO: 177) |
| Enterococcus spp. | Ent001-2 dye | Alexa647N | 0.8 µM | /5Alex647N/TTGTACTTCCCA/3Alex647N/ | (SEQ ID NO: 178) |
| | Ent023-2 dye | Alexa647N | 0.8 µM | /5Alex647N/AACAAAACAACKGGTAC/3Alex647N/ | (SEQ ID NO: 179) |
| | Ent004-2 dye | Alexa647N | 0.8 µM | /5Alex647N/TGCATTCCTTAGC/3Alex647N/ | (SEQ ID NO: 180) |
| | Ent006-2 dye | Alexa647N | 0.8 µM | /5Alex647N/CATCATTCTCAATTC/3Alex647N/ | (SEQ ID NO: 181) |
| | Ent003H1 | No label | 2.85 µM | AGGAAATATCAACTGTRTCC | (SEQ ID NO: 182) |
| | Ent003H3 | No label | 2.85 µM | GTTTCGGTACGGCMGYTGT | (SEQ ID NO: 183) |
| | Ent003H4 | No label | 2.85 µM | TTTCCACTAGAAGCTTTCT | (SEQ ID NO: 184) |
| | Ent004H2_1 | No label | 2.85 µM | CTMCTGCGTCCTCCATTGCTCA | (SEQ ID NO: 185) |
| | Ent004H2his | No label | 2.85 µM | GGACATGCACTTCAATCGCA | (SEQ ID NO: 186) |
| | Ent004H2fum | No label | 2.85 µM | TTGACAGAACATTCCGATCG | (SEQ ID NO: 187) |
| | Ent004H4_2 | No label | 2.85 µM | CAGGAACTTCGSTACTATTAT | (SEQ ID NO: 188) |
| | Ent006H1 | No label | 2.85 µM | GTCAAACAGTGCTCTTACTC | (SEQ ID NO: 189) |
| | Ent006H2 | No label | 2.85 µM | TCGGTAACCCGAGATGGCCCTA | (SEQ ID NO: 190) |
| | Ent006H3 | No label | 2.85 µM | CGAGGCTAGCCCTAAAGCTAT | (SEQ ID NO: 191) |
| | Ent006H1 | No label | 2.85 µM | TTGTAAGACAGTGTGTAGCCC | (SEQ ID NO: 192) |
| | Ent006H4 | No label | 2.85 µM | TGAGAGAAGCTTTAAGAGATT | (SEQ ID NO: 193) |

FIG. 63

| Labeled Target ↓ | Unlabeled Second Target | | | | | | | |
|---|---|---|---|---|---|---|---|---|
| | Sensitive E. coli | Resistant E. coli | Sensitive P. aeruginosa | Resistant P. aeruginosa | Sensitive K. pneumoniae | Resistant K. pneumoniae | Sensitive Enterococcus | Resistant Enterococcus |
| Sensitive E. coli | | | 100% | 100% | 100% | 100% | 100% | 100% |
| Resistant E. coli | | | 100% | 100% | 100% | 100% | 100% | 100% |
| Sensitive P. aeruginosa | 100% | 100% | | | 100% | 100% | 100% | 100% |
| Resistant P. aeruginosa | 100% | 100% | | | 100% | 100% | 100% | 100% |
| Sensitive K. pneumoniae | 100% | 100% | 100% | 100% | | | 100% | 100% |
| Resistant K. pneumoniae | 100% | 100% | 100% | 100% | | | 100% | 100% |
| Sensitive Enterococcus | 100% | 100% | 100% | 100% | 100% | 100% | | |
| Resistant Enterococcus | 100% | 100% | 100% | 100% | 100% | 100% | | |

FIG. 64

| Labeled Target ↓ | Unlabeled Second Target | | | | | | | |
|---|---|---|---|---|---|---|---|---|
| | Sensitive E. coli | Resistant E. coli | Sensitive P. aeruginosa | Resistant P. aeruginosa | Sensitive K. pneumoniae | Resistant K. pneumoniae | Sensitive Enterococcus | Resistant Enterococcus |
| Sensitive E. coli | | | 100% | 100% | 100% | 100% | 100% | 100% |
| Resistant E. coli | | | 100% | 100% | 100% | 100% | 100% | 100% |
| Sensitive P. aeruginosa | 100% | 100% | | | 100% | 100% | 100% | 100% |
| Resistant P. aeruginosa | 100% | 100% | | | 100% | 100% | 100% | 100% |
| Sensitive K. pneumoniae | 100% | 100% | 100% | 100% | | | 100% | 100% |
| Resistant K. pneumoniae | 100% | 100% | 100% | 100% | | | 100% | 100% |
| Sensitive Enterococcus | 100% | 100% | 100% | 100% | 100% | 100% | | |
| Resistant Enterococcus | 100% | 100% | 100% | 100% | 100% | 100% | | |

FIG. 65

| Organisms Spiked into Culture Negative Urine | | Culture Negative Urine | Did probe detect organisms spiked into culture negative urine? | | |
|---|---|---|---|---|---|
| | | | E. coli Probe n=2 | K. pneumoniae Probe n=2 | P. aeruginosa Probe n=2 |
| E. coli | K. pneumoniae | 1 | Y | Y | N |
| | | 2 | Y | Y | N |
| | | 3 | Y | Y | N |
| | | 4 | Y | Y | N |
| | | 5 | Y | Y | N |
| | | 6 | Y | Y | N |
| | | 7 | Y | Y | N |
| | | 8 | Y | Y | N |
| | | 9 | Y | Y | N |
| | | 10 | Y | Y | N |
| E. coli | P. aeruginosa | 1 | Y | N | Y |
| | | 2 | Y | N | Y |
| | | 3 | Y | N | Y |
| | | 4 | Y | N | Y |
| | | 5 | Y | N | Y |
| | | 6 | Y | N | Y |
| | | 7 | Y | N | Y |
| | | 8 | Y | N | Y |
| | | 9 | Y | N | Y |
| | | 10 | Y | N | Y |
| K. pneumoniae | P. aeruginosa | 1 | N | Y | Y |
| | | 2 | N | Y | Y |
| | | 3 | N | Y | Y |
| | | 4 | N | Y | Y |
| | | 5 | N | Y | Y |
| | | 6 | Invalid | | |
| | | 7 | N | Y | Y |
| | | 8 | N | Y | Y |
| | | 9 | N | Y | Y |
| | | 10 | N | Y | Y |

FIG. 69

| Bacterial Target | FISH Probes | Labeled | Final Concentration | Sequence | |
|---|---|---|---|---|---|
| E. coli | Eco469 | Alexa647N | 0.8 μM | /5Alex647N/GTCAATGAGCAAAGG | (SEQ ID NO: 193) |
| | Eco469 H1 | No label | 3 μM | ACTCCCTTCCTCCCCGCtg | (SEQ ID NO: 194) |
| | Eco469 H2 | No label | 3 μM | GGTGCTTCTCTGCGaGTAA | (SEQ ID NO: 195) |
| P. aeruginosa | Pae002 | Alexa647N | 0.2 μM | /5Alex647N/CTTCAAAGATCCTTT/3Alex647N/ | (SEQ ID NO: 196) |
| | Pae002 H1 | No label | 1.5 μM | CGGTACGGGCTAATCACCCA | (SEQ ID NO: 197) |
| | Pae002 H2 | No label | 1.5 μM | GCTCGGTCCTACTCGATTCA | (SEQ ID NO: 198) |
| | Pae004 H1 | No label | 1.5 μM | GGGCTAATCCCCGGTCGCTG | (SEQ ID NO: 199) |
| | Pae004 H2 | No label | 5 μM | ACTTCAGACGGTCGGCTA | (SEQ ID NO: 200) |
| | Pae005 H2 | No label | 1.5 μM | CCAGTGAGATTCATCTTGAG | (SEQ ID NO: 201) |
| | Pae005 H3 | No label | 5 μM | CGTCGTAGTGTTCGACGGCCC | (SEQ ID NO: 202) |
| K. pneumoniae | Kpn003_2 | Alexa647N | 0.2 μM | /5Alex647N/CTTCGACtGGTCtCAGC/3Alex647N/ | (SEQ ID NO: 203) |
| | Kleb001 H1 | No label | 6 μM | TGCCTTCCTCCGAAGTTACGs | (SEQ ID NO: 204) |
| | Kleb23S H3 | No label | 1.5 μM | GCCAGCTGGTATCTTCGACTG | (SEQ ID NO: 205) |
| | Kpn003 H3 | No label | 6 μM | ACAGTTCACCCAGCAGTCGGTAT | (SEQ ID NO: 206) |

FIG. 70

TEST CARTRIDGES

GOVERNMENT SUPPORT

This invention was made with government support under grant numbers R01 AI117058, R44 AI055195, and R44 AI080016 awarded by the National Institutes of Health as well as contract number HHSO100201500022C awarded by the Biomedical Advanced Research and Development Authority. The government has certain rights in the invention.

TECHNICAL FIELD

The disclosure relates to systems, devices, and methods useful for detecting infections, identifying the infectious pathogens, and determining the effective antimicrobial treatments for the infections.

BACKGROUND

The epidemic of life-threatening infections caused by antibiotic-resistant bacteria is fueling a global healthcare crisis. The problem is driven, in part, by the fact that conventional diagnostic methods require days to determine the optimal antimicrobial treatments to treat infection. Delays caused by slow testing lead to suboptimal treatment, poor medical outcomes, and overuse of powerful broad-spectrum antibiotics that cause the spread of antibiotic resistance. The mortality due to infections caused by resistant bacteria is increasing precipitously. A 2014 report by the Review on Antimicrobial Resistance estimates that by the year 2050, antimicrobial resistance will be responsible for more than 10 million fatalities per year.

Unfortunately, conventional methods used to identify the effective targeted antibiotics, called antimicrobial susceptibility testing (AST) methods, require days to deliver results. One reason that conventional antimicrobial susceptibility testing takes so long is that the tests require a large number—on the order of millions—of purified pathogen cells. One or more days are needed, using the more than 130-year-old colony purification method, in order to purify that number of cells by culturing in petri dishes. Once the purified cells are available, one or more days are needed to identify the pathogens and determine which antibiotics will be effective for treating the patient.

In the meantime, patients are treated "empirically" with broad-spectrum antibiotics that kill a broad range of pathogens that might be causing the infection. Although these drugs can treat a broad range of pathogens, they are generally not the optimal therapy for a patient's particular pathogen and can fail to effectively treat the infection. Empiric use of broad-spectrum antibiotics also causes the spread of antibiotic resistance. These broad-acting drugs cause resistance not only in the disease-causing pathogens, but also in the trillions of benign microbes that populate the human body. Further exacerbating the spread of antibiotic resistance is the fact that, in the absence of rapid diagnostics to determine which patients actually have infections, uninfected patients are frequently treated unnecessarily with the resistance-causing antibiotics.

Quickly determining effective antimicrobial treatments not only can improve medical outcomes, but can lower the cost of healthcare. For example, common life-threatening hospital acquired infections, such as surgical site infections and ventilator-acquired pneumonia, are responsible for nearly $10B of healthcare costs in the United States. The length of stay in the hospital is the largest cost attributable to these infections. Treating patients with optimal antimicrobial therapy closer to the onset of symptoms can significantly accelerate patient recovery and reduce lengthy, costly hospitalizations.

SUMMARY

Rapidly and accurately identifying patients with infections and rapidly implementing effective therapy to these patients can save lives and attenuate the spread of antimicrobial resistance. The present invention provides cartridge devices that can accurately identify the patients that have infections in about 30 minutes and determine targeted therapy for a patient's infection in several hours compared to the days required by today's methods. By detecting infections and identifying effective targeted antimicrobial agents much closer to the onset of symptoms, the invention may dramatically improve medical outcomes and minimize empirical treatment with resistance-causing broad-spectrum antibiotics.

Cartridges according to the invention can be used to eliminate the time-consuming steps needed by conventional methods for generating large numbers of purified cells. The cartridges can be pre-loaded with reagents for conducting antimicrobial susceptibility testing (AST).

To detect infections, the invention can detect, quantify, and identify a broad range of pathogens including bacteria, fungi, viruses, and parasites. Also valuable for rapidly and accurately identifying patients with infections is the invention's ability to detect and quantify diagnostically informative toxins, disease-specific biomarkers, human or host cells, and host-response biomarkers. The invention can include any combination of the above capabilities in a single test to most effectively assess a patient specimen for the presence of an infection and to determine the infectious agent.

Diagnostically informative host cells include cells that indicate an inflammatory response to infection (for example, neutrophils), cells infected by pathogens (e.g., virally infected cells), or cells that indicate the quality and anatomical origin of the patient specimen (for example, squamous epithelial cells).

Examples of toxins diagnostic of life-threatening infections include *Clostridiodes difficile* Toxin B, the presence of which indicates *C. difficile* infection and *Bacillus anthracis* Lethal Toxin (or the toxin subunit Lethal Factor) which indicates anthrax infection indicates disease. Host factors that can help identify infected patients include cytokines such as IL-4 and IL-6.

After detecting an infection and identifying and quantifying the infectious pathogen, the cartridge invention and associated inventive methods can determine which patient therapies will be most effective. This type of analysis is called antimicrobial susceptibility testing (AST). The invention differs from current methods for antimicrobial susceptibility testing, in that it can deliver accurate results directly from the patient specimen in a matter of hours rather than current conventional methods which take days. The conventional methods, unlike the inventive method, require time consuming microbiological culture steps to get millions of purified pathogen cells. The invention's novel antimicrobial susceptibility testing methods, in contrast, can rapidly determine effective therapies directly from patient specimens, without time consuming culture steps, because it does require large numbers of cells or cell purification.

The novel and potentially medically impactful capabilities and practicality of the inventive are enabled by the inventive cartridge and associated inventive systems and methods for enabling single molecule counting and single cell counting using non-magnified digital imaging of informative biological targets directly from patient specimens. Using simple and low-cost cameras without complex and expensive microscopes and optics to digitally count microscopic cells and sub-microscopic molecules allows detection of infections by rapid, sensitive, and automated quantification of disease-causing toxins and disease-specific biomarkers. The invention's systems and methods for identifying and digitally counting pathogen cells underlie the ability to rapidly determine susceptibility or resistance to antimicrobial agents. The inventive method determines if a pathogen is susceptible to an antimicrobial agent by determining if the agent stops the normal pathogen growth (that is, increase in cell number by cell division) when incubated in nutrient microbiological medium. This can be done in the inventive cartridge device by counting the pathogen cells before and after incubation in the medium containing the antimicrobial.

The cartridges can be operable by an instrument to automatically and simultaneously run a variety of tests requiring only a specimen input and providing actionable results in a variety of venues ranging from point-of-care to centralized hospital and reference laboratories. Such testing is made possible by a combination of application-specific cartridges pre-loaded with all required reagents, direct specimen input into cartridges and full automation of all processing and analysis to minimize hands-on time for users, and an instrument designed for scalable throughput.

The inventive cartridge can operable by an automated instrument to perform tests using methods for counting single molecules and single cells can include fluorescent labeling of the target molecules or cells, magnetically tagging the targets, using magnetic force to deposit the fluorescently labeled magnetic targets on an imaging surface of a device, imaging the targets without (or with minimal) magnification, and counting the targets using image analysis.

The invention allows for simultaneous processing of the steps outlined above in cartridge devices. A single random-access instrument can simultaneously process multiple test cartridges for different diagnostics applications containing different types of patient specimens. The automated nature of the inventive instruments and cartridges allow for operation by medical professionals without significant specialized training. Additionally, the breadth of the potential test menu of application-specific cartridges designed to work with an instrument for the instrument offers the potential for reducing benchtop space allowing for more cost-saving utilization of facilities and enabling near-patient diagnostic testing to provide potentially life-saving diagnostic information to clinicians near the onset of infections when they can have the greatest impact.

Application-specific cartridges can be pre-loaded with test reagents. Preferably, cartridges can be assembled and packaged with the required test reagents during manufacturing and distributed so that a user need only add a specimen to be tested (e.g., a respiratory specimen from a patient) and insert the cartridge into the instrument. In some instances, a specimen to be tested, such as a blood specimen, may be pre-enriched. For example, blood specimens may undergo pre-enrichment by culture before analysis because many blood infections cannot be tested directly without pre-enrichment due to having too low of a concentration of pathogen cells.

Cartridges can be pre-loaded with fluorescent probes and reagents that for identification and quantifying target cells or molecules. For example for detecting cells using a FISH-based method, the cartridge might contain pre-loaded reagents for permeabilizing target cells, hybridization reagents, fluorescent target-specific oligonucleotide probes, and target-binding magnetic particles. AST cartridges could contain microbiological medium and antimicrobial agents to promote differential growth in addition to reagents for the FISH-based method for quantifying target cells after differential growth.

In a preferred embodiment of the invention, the cartridges are used for antimicrobial susceptibility testing, and a specimen is divided into separate portions containing nutrient growth medium to promote microbiological cell replication or growth. One or more of the portions may be used as a reference or baseline portion which is directly processed and analyzed before incubation at a temperature that promotes growth to determine the number and quality of pathogen cells. One or more of the portions may be incubated at a temperature that promotes growth of the pathogen cells to ascertain if the pathogen cells are viable. Other portions each contain, in addition, one or more antimicrobial agents at particular concentrations, and are incubated to determine the impact of the antimicrobial agents on pathogen cellular replication.

The cartridges can interface with instruments operable to manipulate the specimen within, incubate the cartridge, and perform the required processing and imaging steps such that a user need only load a specimen into the cartridge and receive results. Cartridges can contain growth media and antimicrobial agents specifically selected for a specific microbe such that, when a specific infection is suspected such as *E. coli*, a user can select the appropriate cartridge pre-loaded with *E. coli*-specific reagents (e.g., media, antimicrobials, and FISH probes). Through a combination of the AST-specific cartridges pre-loaded with all required reagents, automatic instruments with separate stations for carrying out assay steps and random access thereto within the instrument, and computerized scheduling and manipulation of multiple cartridges and assays, the systems and methods of the invention can automatically and simultaneously run a variety of assays requiring only a specimen input and providing actionable results in a point-of-care environment. The automated nature of the cartridges and associated instruments allow for operation by medical professionals without significant specialized training.

Cartridges can be set up with the required reagents during manufacturing and distributed to point-of-care facilities so that a user need only add a specimen to be tested (e.g., a blood specimen from a patient) and insert the cartridge into the instrument. The instruments described herein use a variety of different stations for performing different assay steps positioned around a carousel which is used to receive, store, and transfer assay-specific cartridges between the stations according to the assay being performed.

Cartridges may include a specimen chamber for receiving a specimen and a number of division or incubation wells pre-loaded with different antimicrobial agents. The cartridges may also include multiple imaging wells with each imaging well corresponding to a single division well. The imaging wells can contain the necessary reagents for processing and imaging the target microbe after incubation in the presence of the various agents in order to provide differential growth analysis thereof and to determine the most effective treatment for a patient's infection with the specific target microbe.

The specimen chamber, division or incubation, and imaging wells can be coupled to each other through a series of channels and valves such as a sliding bar disposed between the division and imaging wells. The bar may include vertical channels and be horizontally slidable so that the channels can be aligned with an outlet channel of a division well and an inlet channel of a corresponding imaging well to create a fluidic pathway therebetween. When horizontally slid in either direction the channels of the bar may become misaligned with the wells thereby isolating them and preventing fluid communication therein. The valve may be externally manipulated by instruments as described herein depending on the assay steps to be carried out.

The cartridge can include a pneumatic or other interface for coupling to a pneumatic source for applying pressure gradients within the cartridge to move the specimen between the various compartments. When manipulated in conjunction with the valves, the pneumatic source can be used to open channels between the various compartments within the cartridge and then direct the specimen fluids through the open channels.

The inventive cartridges can be operable by instruments described herein that use a variety of different stations for performing different test steps on the inventive cartridge device outlined above. The stations can be positioned around a carousel which is used to receive, store, and transfer application-specific cartridges between the stations according to the test being performed. Stations can include a fluidics station for interfacing with the cartridge and manipulating the specimen and reagents therein, magnetic selection station for magnetically depositing targets on the detection surfaces of a cartridge's imaging wells, imaging stations for detecting the deposited targets in specimens, and waste stations for disposing of used cartridges.

In preferred embodiments, tests use a constant temperature or cyclic temperature throughout all steps or are modified such that the interior of the instrument can be maintained at the required temperature and the carousel can serve as a storage station for incubation steps. The temperature may be physiological temperature or may be below or above physiological temperature.

An instrument that operates the cartridges can use the carousel to access the different stations so that test steps can be performed in the order and with the timing required for various types of tests. Precise computer scheduling and computer-controlled access to the various stations in the instrument are used to automatically carry out all steps of a variety of tests without additional user input. After loading a cartridge into the instrument, a user's next interaction can be receiving or viewing results of the test either at the instrument or remotely. Depending on the test type, the reported results of the platform's automatic analyses may indicate detection of infection; detection, identification, and quantification of pathogens, toxins, biomarkers, or diagnostically informative host cells; or antimicrobial susceptibility results and profiles. Some testing applications perform different kinds of measurements on a single specimen in the same cartridge on the same instrument run. In this case multiple types of results can be reported for the single test.

The cartridge can be labeled with one or more barcodes or other identifiers that can be read by a human or automatically read by an automated instrument for associating patient, test application-specific, or factory information with the cartridge. The instrument can also use that input to record and track information associated with the specimen being tested including patient information for reporting results. The instrument can also use that input to record and track information associated with the specimen being tested including patient information for reporting results.

Instruments for processing the inventive cartridge may include a computer comprising a processor and a non-transitory, tangible memory and operable to schedule and control the test being performed within the instrument and track the cartridges therein. The computer can include a user interface for prompting and receiving information from the user and displaying results and status information. The computer can be connected to a network and operable to process test results and send to connected devices over the network.

Instruments designed to operate the cartridges can include a mechanical conveyor arm for moving the cartridges between the carousel and the various stations for the performance of required test steps. In preferred embodiments, the carousel and the stations comprise slots sized to accept and position the cartridge within the station. Rotation of the carousel can align the carousel slot with a corresponding slot in the relevant station and the mechanical conveyor arm may be operable to contact a side of the cartridge and slide the cartridge along the aligned slots and into the selected station. The mechanical conveyor arm avoids gripping the cartridges and reduces jams associated with gripping mechanisms. The mechanical conveyor arm can comprise two rotatable prongs operable to flank the cartridge and provide motivating force to one side thereof. The sides of the carousel and stations slots can provide the lateral guidance as the cartridge is slid, avoiding the need for a gripping mechanism for moving the cartridges.

Pre-loaded cartridges can allow for control of reagent volumes and distribution on the manufacturing side and the automated instrument controls performance of the test steps and the timing thereof. Accordingly, systems and methods can greatly reduce the potential for user error allowing inexpert staff to conduct a variety of tests without specialized training and to obtain reliable and actionable results without the delay and cost of dedicated off-site testing.

In a preferred embodiment, application-specific cartridges include microbe-specific antimicrobial susceptibility testing cartridges for measuring differential growth of a pathogen in a specimen in the presence of various antimicrobial agents and microbiological growth medium that are selected based on the identity of the pathogen. According to the invention, patient specimens, such as urine, stool, or blood are directly analyzed with minimal or no specimen preparation or culturing. Specimens processed according to the invention are identified and exposed to various antimicrobials or other treatment modalities, allowing the selection of the most-effective treatment. Microbial infections can be identified and the appropriate treatment determined in a matter of hours, greatly reducing the delay in appropriately targeted therapy and avoiding the need for empiric treatment with aggressive broad spectrum antimicrobials. The invention allows health care providers to prescribe effective therapies at the outset to appropriately treat infected patients. Thus, the invention provides an opportunity to improve patient outcomes and reduce the spread of antimicrobial resistance.

Cartridges can be designed to perform infection detection, target identification, and determination of effective treatment directly from patient specimens, such as urine, sputum or other respiratory specimens, blood, stool, wound specimens, or cerebrospinal fluid with little or no specimen preparation steps. For example, a urine specimen is directly pipetted into a cartridge testing device for pathogen identification (ID) and antimicrobial susceptibility testing (AST) which is completed in several hours. This contrasts with current culture-based methods which require one or more days of colony purification to produce a large population of pure microbial culture for testing. The invention provides testing devices and instruments capable of receiving and internally processing a patient specimen to identify microbes or cells and/or to determine therapeutic susceptibility and efficacy all within the cartridge testing device. Multiple target cells or pathogens in a specimen can be identified and susceptibility to multiple antimicrobials or treatments can be tested in a single cartridge device. Testing systems and methods of the invention are robust with respect to specimen matrices, variable inoculum, and the presence of commensal microbes in the specimen. Tests of the invention also deliver accurate results for polymicrobial infections.

The inventive cartridges can allow for direct processing and imaging of specimens to determine the presence and identity of target cells present in the specimen in an inventive cartridge device. As noted above, the processing and imaging steps can occur with the specimen in a cartridge testing device that can require little to no specimen preparation outside of the cartridge. By foregoing time-consuming specimen preparation techniques and using target-specific, distinguishable labels, systems and methods of the invention allow for identification and enumeration of targets in a specimen in as little as thirty minutes or less.

Cartridges can be used for identifying the pathogen that is causing an infection. For example, the inventive cartridges can be use to identify and quantify pathogens directly in a patient specimen without requiring culture-based microbiological pre-enrichment or nucleic acid amplification. A preferred method enumerates the target pathogen(s) in a single reaction mixture by labeling using fluorescent in situ hybridization (FISH)-based method combined with magnetic selection that can be carried out in about 30 minutes in microtiter plates or cartridges in the instrument described herein.

The inventive cartridges can be used for diagnostic antimicrobial susceptibility testing (AST), that is, for determining which antimicrobials can prevent the growth of a microbial pathogen in a patient's specimen. This information provides information to clinicians about which antimicrobials should be used to effectively treat that particular patient's infection.

Antimicrobial susceptibility testing can be thought of as stepwise process. The goal is to determine which members of a panel of antimicrobial agents are effective for the particular pathogen strain that is causing a patient's infection. Typically, when an infection is detected, the species of pathogen is first identified. Identifying the species of the pathogen is useful for choosing the antimicrobials and dosing that can generally be used for treating that species. However, since the particular pathogen strain causing the infection may have become resistant to any of the antimicrobials, antimicrobial susceptibility testing must be done to determine to which of the potential treatments the pathogen is actually susceptible.

After species identification the pathogen cells from the patient's specimen are apportioned, or aliquoted, into a series of liquid solutions containing nutrient growth medium various antimicrobials at various concentrations. Then, the aliquots are allowed to incubate at a temperature conducive to microbial replication (generally 35-37° C.). If the pathogen is susceptible to the antimicrobial it can replicate normally, that is, the number of pathogen cells increase as they do in microbiological growth medium the absence of antimicrobials. If the pathogen is susceptible to the antimicrobial, it fails to replicate, replicates to a much lesser extent, or shows morphological or other abnormalities, indicative of effectiveness of the antimicrobial agent.

Finally, the replication of pathogen cells is assessed in the various aliquots to determine which antimicrobial agents are effective. We refer to the set of a pathogen's antimicrobial susceptibility/resistance results for a for a series of antimicrobials as its antimicrobial susceptibility profile.

Both conventional methods for antimicrobial susceptibility testing and the methods that can be used for more rapid testing in the inventive cartridge follow the steps above, but the method that can be enabled by the invention determines a pathogen's antimicrobial susceptibility profile in several hours while conventional methods require several days. The rapid antimicrobial susceptibility testing results using the inventive method arise from the new method's ability to test patient specimens directly without time-consuming culture-based pre-enrichment growth to achieve high concentrations of pure cells. This enrichment and purification is most commonly done using colony purification on petri dishes.

For conventional methods, the cells recovered after colony purification are first identified using biochemical, microbiological, nucleic acid methods, or Matrix-Assisted Laser Desorption/Ionization-Time Of Flight (MALDI-TOF) mass spectrometry (MS). Once the identity of the pathogen species is known, appropriate antimicrobials and concentrations can be chosen that are appropriate for determining the antimicrobial susceptibility profile for pathogens of that species.

Several novel aspects of the methods enabled by the inventive cartridge allow the rapidly delivery antimicrobial susceptibility results directly from patient specimens.

Firstly, patient specimens generally contain orders of magnitude fewer cells than are required for traditional antimicrobial susceptibility testing. The cartridge, in contrast to current culture-pre-enrichment dependent methods, can be operated to enumerate small numbers of pathogen cells by sensitive single cell counting using non-magnified digital imaging. Furthermore, because the method enumerates small numbers of individual cells, it can very quickly—in only a few bacterial generations—determine whether the cells have increased in number in an aliquot containing an antimicrobial and growth medium.

Secondly, patient specimens contain sample matrix and commensal microbes unrelated to the infectious pathogens. Guidelines for conventional methods (for example, from the Clinical Laboratories Standards Instituter or the European Committee on Antimicrobial Susceptibility Testing) require purified culture cells resulting from clonal growth of colonies on agar-based growth media in petri dishes. These cells contain only a single microbial species and no sample matrix.

As discussed above, the identity of the pathogen species must be known in order to interpret antimicrobial susceptibility testing results correctly for arriving at effective clinical treatment options. This is a key reason underlying why conventional and most emerging antimicrobial susceptibility testing methods require a pure culture of cells.

To determine the antimicrobial susceptibility profile, as described above, the conventional and most emerging methods assess the impact of different antimicrobials at different concentrations on the growth of the target pathogen. The reason why these methods require a pure population of identified cells to interpret the antimicrobial susceptibility testing results is that these methods use non-specific methods, for example light-scattering or microscopy, for assessing growth in the antimicrobial-containing aliquots. Consider the case if there were more than one species present, for example a pathogen and species of normal microbes that are part of the human microbiome—which is the case in most primary patient specimens. If growth were observed in an antimicrobial-containing aliquot, it would be impossible to tell, using a general method for detecting growth, whether the disease-causing pathogen or one or more of the commensal species was resistant and capable of growing.

In contrast, to conventional methods and others that require purified pathogen cells because they use non-specific methods for detecting whether the pathogen grows in the presence of antimicrobials, the methods deployed in the inventive cartridge use pathogen-specific detection to assess growth of the pathogen in antimicrobials. Because only the disease-causing pathogen cells are enumerated after the incubation step (any commensal microbes are not enumerated) the inventive method can be used to determine antimicrobial susceptibility directly in the non-sterile primary specimen containing one or many commensal microbial species.

The cartridge device can be used to identify target cells or microbes and to, separately or within the same cartridge, test for antimicrobial susceptibility of the target in the specimen. In a preferred embodiment of the invention, testing devices internally divide a specimen into separate portions where some of the portions may be incubated in the presence of various antimicrobial agents before imaging to determine differential growth. One or more of the portions may be directly processed and imaged to provide a baseline reference for determining growth, growth inhibition, or morphology changes in the incubated portions. By quantifying the growth of portions incubated in various antimicrobials, the effectiveness of each antimicrobial agent in reducing or preventing growth of the target is determined. By observing changes in target cell count or cell morphology, the effectiveness of treatments can be determined.

Cartridges described herein and the instruments that operate them are capable of identifying and testing efficacy of agents on varying classes of targets (e.g., viruses, human cells, bacterial cells, or fungal cells) and also simultaneously performing such identifications and antimicrobial susceptibility testing for multiple different targets in a single device, thereby allowing development of a single instrument that performs tests typically conducted by multiple testing devices designed for different testing applications (e.g., blood, urinary tract, gastrointestinal, and respiratory infections). Accordingly, robust functionality is provided by the cartridges and the instruments that operate them described herein.

Cartridges of the invention are used to rapidly deliver antimicrobial susceptibility results directly from patient specimens. The patient specimens generally contain orders of magnitude fewer cells than are required for traditional antimicrobial susceptibility testing. Using cartridges of the invention, small numbers of pathogen cells can be enumerated by sensitive single cell counting using non-magnified digital imaging, in contrast to current culture-pre-enrichment dependent methods. Furthermore, because small numbers of individual cells are enumerated, the invention can very quickly—in only a few bacterial generations—determine whether the cells have increased in number in an aliquot containing an antimicrobial and growth medium.

Once a target is identified, the antimicrobial susceptibility testing can include antimicrobial agents or treatments relevant to that target (e.g., those commonly used in treatment or known to inhibit growth of the identified target). As noted earlier, identification of the target cell or microbe can be important for determining the appropriate target-specific therapies. Identification can be performed using the same processing and imaging techniques as used in the antimicrobial susceptibility testing methods described herein and can be performed using the same types of cartridge devices, instruments, and methods used for the differential growth or therapeutic efficacy analyses. In certain embodiments, identification and therapeutic susceptibility testing can be performed on the same specimen (divided into separate portions) in the same device. Target identification can also be performed using other techniques, not falling with the scope of this invention, such as amplification with target-specific primers, immunoassays, mass spectrometry, nucleic acid sequencing, or oligonucleotide probe array analysis. If identification is performed separately, a cartridge of the invention can be used as an antimicrobial susceptibility testing device containing the appropriate reagents and antimicrobials for the identified pathogen may be used according to the present invention.

Detecting differential growth in the presence of various antimicrobial agents may require different amounts of time depending on the target pathogen, but is greatly reduced from the days required for standard antimicrobial susceptibility testing techniques. For example, differential growth of microbes commonly associated urinary tract infections can be observed in urine specimens using techniques of the invention after about 4 hours or less. As noted above, identifying and quantifying microbes in a specimen can be accomplished in thirty minutes or less thereby allowing for antimicrobial susceptibility testing results to be obtained within hours after introduction of the specimen to the testing device.

In certain embodiments, a test suite of cartridge devices could be used for infection detection and pathogen identification (ID) and antimicrobial susceptibility testing (AST) for a syndromic infection (for example, pneumonia or urinary tract infection). Such a test suite, referred to as an ID/AST test suite, could comprises an ID cartridge and an infection-specific family of AST cartridges each of with contain appropriate antimicrobials for testing individual pathogens or related groups of pathogens. For example, a urinary tract infection (UTI) test suite could comprise a UTI ID cartridge and a family of UTI AST cartridges.

The ID cartridge in such an infection-specific test suite could detect infections and identify and quantify the bioburden, or concentration, of the infectious pathogen(s) in the specimen. The same cartridge could also simultaneously test the specimen for diagnostically informative markers including host response biomarkers (e.g., cytokines) and inflammatory cells (eg, neutrophils), or cellular markers of sample quality (e.g., squamous epithelial cells) on the same device. The ability to combine detection and quantification, of pathogens, biomarkers, and diagnostically informative host cells in the same specimen, cartridge, and instrument is a novel and potentially powerful advantage of the inventive System and methods.

If an infection were detected and pathogen identified using the ID cartridge (or an alternative identification method aside from the inventive method) an AST cartridge would be chosen from the family of AST cartridges for AST analysis. The AST cartridge chosen for analysis would contain the appropriate antimicrobials that might be used for treating the particular pathogen and the appropriate FISH reagents to enumerate the particular pathogen.

Antimicrobial susceptibility testing results obtained using inventive cartridges are then used to determine the antimicrobial susceptibility profile for the infectious pathogen and to inform treatment decisions of patients so that the patient may be treated with an effective antimicrobial agent.

Detectable labels incorporated in the inventive cartridges for specifically detecting and quantifying target cells may include target-specific fluorescent oligonucleotide probes (including probes comprising modified nucleotides or nucleotide analogues), fluorescent antibodies, specific and nonspecific ligands, lectins, stains, or dyes that bind targets. In certain embodiments, magnetic tags are used in combination with the detectable labels to bind to target microbes before magnetically selecting and imaging the target microbes. Separation can occur within a testing device as described herein and magnetic fields may be used to deposit the labelled microbes on a detection surface in the testing device to be imaged. In certain embodiments, a dye cushion layer, as described in U.S. Pat. No. 9,643,180, incorporated by reference herein, can be used in the separation and imaging steps to minimize or eliminate specimen preparation steps by the user, eliminate wash steps, and reduce background signal. Digital, non-magnified imaging techniques as described in U.S. Pat. Nos. 9,643,180 and 8,021,848, each of which is incorporated herein by reference, can be used to quantify labelled microbes including, for example, single cells.

Inventive cartridges can be designed to implement methods for determining antimicrobial susceptibility. Such methods preferably include the steps of obtaining a specimen from a patient suspected of having a syndromic infection wherein the specimen type would potentially contain the infectious pathogen(s). The specimen is then introduced into the cartridge device, divided into a plurality of aliquots. One aliquot is analyzed immediately to determine the baseline concentration of pathogen cells before incubation. For this aliquot the pathogen cells are fluorescently labeled, magnetically tagged, drawn through the dye-cushion, and deposited on the imaging surface of an imaging well in the cartridge, imaged, and quantified using image analysis. The other aliquots are incubated at 35° C. in the presence of growth media and various antimicrobial agents, all within the cartridge. After differential growth in the presence of the various antimicrobials the pathogen cells are fluorescently labeled, magnetically tagged, drawn through the dye-cushion, and deposited on the imaging surface of an imaging well in the cartridge, imaged, and quantified using image analysis. The number of pathogen cells enumerated in the aliquots containing antimicrobials are compared to the number of pathogen cells enumerate initially (before incubation) to determine the antimicrobial susceptibility profile and which antimicrobials would be effective for treating the patient.

Methods of the invention may include detecting infections and detecting and identifying the infectious pathogen cell before introducing the specimen into the cartridge and selecting the plurality of different antimicrobial agents based on the identity of the target cell or microbe. Identification of a target pathogen preferably includes exposing a first specimen from the patient to magnetic tags and fluorescent labels that can bind to the first targets such that complexes comprising magnetically tagged and fluorescently labeled targets are specifically formed. Applying a magnetic field to the testing device to attract the complex to a detection surface; and imaging the detection surface to detect and quantify the detectable label where presence and concentration of the detectable label indicates whether there is target pathogen present and how much of that target pathogen is present. The detection step may take less than about 30 minutes.

For the cartridges designed for antimicrobial susceptibility testing applications, the target pathogen cells can be specifically detected after differential growth as described above.

Cartridges of the invention can use a similar strategy for detecting and quantifying subcellular targets (for example, toxins, biomarkers, host-response factors, viral-specific molecules, or virus particles). Target-specific magnetic tags and fluorescent labels are preferably used to bind to such targets to form complexes. The systems and methods of the invention are used to deposit these complexes on the imaging surface of for enumeration by imaging and image analysis. The target-specific magnetic tags and fluorescent labels for detecting subcellular targets are preferably magnetic and fluorescent particles that are conjugated to target-specific binding agents (e.g., antibodies, aptamers, receptors, ligands). Specific formation of the magnetically tagged and fluorescently labeled target complexes occurs in various ways. Either the magnetic tag or the fluorescent label may be designed to specifically bind to the target. Alternatively, both the magnetic tag and fluorescent label may be designed to specifically bind to the target. In either case, magnetic selection combined with imaging of the magnetically selected complexes results in detection and enumeration of the specific targets in a specimen. There are various mechanisms by which that magnetic tags and fluorescent labels can associate with the targets.

There are various ways that magnetic tags or fluorescent labels may bind non-specifically to targets. For example, binding magnetic tags or fluorescent labels that bind to a conserved site across various categories of targets can be achieved by conjugating the magnetic tags or fluorescent labels to moieties that bind to those sites (e.g., antibodies or other protein binding partners, lectins, or ligands). Magnetic tags or fluorescent labels may also bind non-specifically due to general chemical or colloidal attributes. For example, positively-charged magnetic particles or fluorescent labels can bind non-specifically to bacterial cells, which are generally negatively charged. Cells can be labeled non-specifically by various dyes (e.g., calcofluor) or fluorogenic dyes (e.g., propidium iodide, fluorescein diacetate). Dyed fluorescent particles can be used as fluorescent labels that bind non-specifically to target cells by virtue of their chemical or colloidal attributes or by conjugating them to non-specific binding molecules such as those described above.

Magnetic tags or fluorescent labels can also be chosen in various ways so that they bind to targets specifically. For example, magnetic tags (or fluorophores) can be conjugated to antibodies that bind to target-specific antigens. To similar effect, magnetic tags or fluorophores could be conjugated to a molecule (e.g., avidin) that binds specifically to a ligand (e.g., biotin) that is bound to (or can bind to) such a target specific antibody. Cells can be also labeled specifically by reassociation or hybridization with target-specific nucleic acid probes (or nucleic acid analog probes) that are themselves labeled with fluorophores. Dyed fluorescent particles can be used as fluorescent labels that bind specifically to target cells by conjugating them to target specific binding molecules such as those described for certain embodiments, the labelling and imaging steps include exposing the specimen portions to a fluorophore-labelled target-specific binding molecule and a magnetic particle wherein the fluorophore-labeled target-specific binding molecule and the magnetic particle bind to the target forming a complex; applying a magnetic field to the testing device to attract the complex to an detection surface; and imaging the detection surface. The fluorophore-labeled target-specific binding molecule may include an oligonucleotide probe that binds specifically to the target cell. The exposing and imaging steps can include fluorescent in situ hybridization (FISH) methodology and analysis.

The cartridges and associated methods may be operable to determine a recommended antimicrobial agent for treating patient's infection, usually comprising the antimicrobial or other treatment determined to inhibit growth of the target. Determination of the treatment that inhibits growth of the target can occur in several hours (eg, 4 hours) after introducing the specimen into the testing device. The bodily specimen can be a tissue specimen (e.g., a wound or biopsy specimen) or a bodily fluid specimen. Preferred bodily fluids for use with the invention include, but are not limited to, respiratory (for example, sputum endotracheal aspirate, protected specimen brush, broncho-alveolar lavage), blood, urine, stool, swabs (for example, nasal, oral/pharyngeal, surgical site, skin and soft tissue, rectal), and cerebrospinal fluid.

In certain aspects, the inventive cartridge is operable to determine therapeutic susceptibility of a target cell or microbe in a specimen. Such a cartridge can receive a specimen comprising a bodily fluid from a patient and a target cell or microbe as well as an instrument or instrument. The instrument is preferably operable to manipulate the testing device to divide the specimen into a plurality of portions within the testing device; incubate the portions in the presence of a plurality of different therapeutic agents within the testing device; fluorescently label and magnetically tag the target cell within the incubated portions within the testing device; separate the magnetically tagged and fluorescently labeled target complexes from the unbound fluorescent labels; and image the portions within the testing device to quantify the target complexes so as to determine which treatment(s) inhibit replication of the target cells.

Systems may comprise a cartridge testing device that, for microbiological applications, can be used to detect infections and identify pathogens. A patient specimen can be added to the device where it can be split into multiple aliquots, each of which can be contacted with magnetic tags and multiple types of target-specific detectable labels (e.g., binding molecules with distinct fluorophore labels) such that labeled, magnetically tagged target complexes are formed; apply a magnetic field to the testing device to attract the complex to an detection surface; and image the detection surface to detect the labeled complexes, wherein detection of complexes labeled with a particular detectable label in a particular aliquot indicate the presence of a particular target.

The cartridge may be operable by an instrument to contact the specimen aliquots with various antimicrobial agents for antimicrobial susceptibility applications; to contact aliquots or portions containing specimen to magnetic tags and detectable labels chosen so that complexes are specifically formed with a target, the magnetic tags, and the detectable label; apply a magnetic field to the testing device to attract the complex to a detection surface; image the detection surface; and perform image analysis to determine the test results.

In the inventive cartridge detecting the number of identified target cells or microbes in each of the incubated specimens may include contacting the incubated specimens magnetic tags and detectable labels chosen so that complexes are specifically formed with a target, the magnetic tags, and the detectable label; applying a magnetic field to the complex to attract the complex to an detection surface; and imaging the detection surface to determine an effect of each of the therapeutic agents on growth of each of the identified target.

Multiple aliquots may be combined with the same antimicrobial agent present in different concentrations, preferably corresponding to 2-fold serial dilutions of the antimicrobial agent or to concentrations corresponding to CLSI breakpoints for antimicrobial susceptibility testing. The number of such portions and concentrations of antimicrobials can be chosen so as to deliver a Susceptible/Resistant result, a categorical (Susceptible, Intermediate Resistant, Resistant or SIR result), or a Minimum Inhibitory Concentration (MIC) result. The relevant concentrations of antimicrobials for specific microbial pathogen species are documented by the Clinical Laboratory Standards Institute (CLSI).

Cartridges according to the invention can be used to eliminate the time-consuming steps needed by conventional methods for generating large numbers of purified cells. The cartridges are pre-loaded with reagents for conducting antimicrobial susceptibility testing (AST) and FISH testing. The cartridges of the invention are used to detect infections, identify the infectious pathogens, and the effective antimicrobial agents in several hours rather than the days required by conventional methods. By detecting infections and identifying effective targeted antimicrobial agents much closer to the onset of symptoms, the invention may dramatically improve medical outcomes and minimize empirical treatment with resistance-causing broad-spectrum antibiotics.

In particular, cartridges of the invention are used to rapidly deliver antimicrobial susceptibility results directly from patient specimens. The patient specimens generally contain orders of magnitude fewer cells than are required for traditional antimicrobial susceptibility testing. Using cartridges of the invention, small numbers of pathogen cells can be enumerated by sensitive single cell counting using non-magnified digital imaging, in contrast to current culture-pre-enrichment dependent methods. Furthermore, because small numbers of individual cells are enumerated, the invention can very quickly—in only a few bacterial generations—determine whether the cells have increased in number in an aliquot containing an antimicrobial and growth medium.

Moreover, patient specimens contain sample matrix and commensal microbes unrelated to the infectious pathogens. Guidelines for conventional methods such as those from the Clinical Laboratories Standards Institute (CLSI) or the European Committee on Antimicrobial Susceptibility Testing (ECAST) require purified culture cells resulting from clonal growth of colonies on agar-based growth media in petri dishes. These cells contain only a single microbial species and no sample matrix.

As discussed above, the identity of the pathogen species must be known in order to interpret antimicrobial susceptibility testing results correctly for arriving at effective clinical treatment options. This is a key reason underlying why conventional and most emerging antimicrobial susceptibility testing methods require a pure culture of cells. To determine the antimicrobial susceptibility profile, conventional and most emerging methods assess the impact of different antimicrobials at different concentrations on the growth of the target pathogen. The reason why these methods require a pure population of identified cells to interpret the antimicrobial susceptibility testing results is that these methods use non-specific methods, for example light-scattering or microscopy, for assessing growth in the antimicrobial-containing aliquots. Consider the case if there were more than one species present, for example a pathogen and species of normal microbes that are part of the human microbiome—which is the case in most primary patient specimens. If growth were observed in an antimicrobial-containing aliquot, it would be impossible to tell, using a general method for detecting growth, whether the disease-causing pathogen or one or more of the commensal species was resistant and capable of growing.

In contrast to conventional methods and others that require purified pathogen cells because they use non-specific methods for detecting whether the pathogen grows in the presence of antimicrobials, the invention uses pathogen-specific detection to assess growth of the pathogen in the presence of various antimicrobials. Because only the disease-causing pathogen cells are enumerated after the incubation step (any commensal microbes are not enumerated) cartridges of the invention can be used to determine antimicrobial susceptibility directly in the non-sterile primary specimen containing one or many commensal microbial species.

Cartridges according to the invention may be used for pathogen identification to determine whether a specimen contains cells of pathogen species in sufficient numbers to be suspected of causing an infection. Cartridges according to the invention may be used for antimicrobial susceptibility testing to determine which of one or more antimicrobial agents can prevent normal cellular replication of a pathogen that is suspected of causing an infection in a patient specimen. Such antimicrobial agents can potentially be used to effectively treat a patient's infection.

Cartridges include various division or incubation wells that can be pre-loaded with growth media and various antimicrobial agents so that a single specimen can be added to the cartridge and divided among the wells to allow a target microbe present in the specimen to be incubated in the presence of the various agents. After incubation, the specimens can be processed and imaged using, for example, fluorescent in situ hybridization (FISH) to provide a differential growth analysis for determining the susceptibility of the target microbe to the various antimicrobial agents. The AST may use FISH at constant physiological temperature. Using the FISH protocol, the cartridges are useful for microbial identification tests or for antibiotic susceptibility testing. Clinical specimens studied using cartridges of the disclosure are incubated, and tests performed, at temperatures matched to the patient's temperature, so relevant infectious bacteria growing in the patient continue to grow in the cartridge.

Cartridges are pre-loaded with fluorescent probes and reagents that chemically permeabilize microbes, so that pathogenic bacteria can be fluorescently labeled and imaged without heating significantly above body temperature. Because the FISH protocol is performed at physiological temperature, clinical specimens are not exposed to extremes of heat that promote clinically-misleading bacterial growth patterns. Cartridges are designed for microbial identification or susceptibility testing directly from patient specimens, such as stool or urine, without any required specimen preparation. The cartridges and associated reader instrument provide tests results within hours, giving clinicians the ability to rapidly and easily identify the cause of an infection or what antibiotic treatment will be effective.

In a preferred embodiment of the invention, the cartridges are used for antimicrobial susceptibility testing, and a specimen is divided into separate portions containing nutrient growth medium to promote microbiological cell replication or growth. One or more of the portions may be used as a reference or baseline portion which is directly processed and analyzed before incubation at a temperature that promotes growth to determine the number and quality of pathogen cells. One or more of the portions may be incubated at a temperature that promotes growth of the pathogen cells to ascertain if the pathogen cells are viable. Other portions each contain, in addition, one or more antimicrobial agents at particular concentrations, and are incubated to determine the impact of the antimicrobial agents on pathogen cellular replication.

The cartridges can interface with instruments operable to manipulate the specimen within, incubate the cartridge, and perform the required processing and imaging steps such that a user need only load a specimen into the cartridge and receive results. Cartridges can contain growth media and antimicrobial agents specifically selected for a specific microbe such that, when a specific infection is suspected such as $E.\ coli$, a user can select the appropriate cartridge pre-loaded with $E.\ coli$-specific reagents (e.g., media, antimicrobials, and FISH probes). Through a combination of the AST-specific cartridges pre-loaded with all required reagents, automatic instruments with separate stations for carrying out assay steps and random access thereto within the instrument, and computerized scheduling and manipulation of multiple cartridges and assays, the systems and methods of the invention can automatically and simultaneously run a variety of assays requiring only a specimen input and providing actionable results in a point-of-care environment. The automated nature of the cartridges and associated instruments allow for operation by medical professionals without significant specialized training.

Cartridges can be set up with the required reagents during manufacturing and distributed to point-of-care facilities so that a user need only add a specimen to be tested (e.g., a blood specimen from a patient) and insert the cartridge into the instrument. The instruments described herein use a variety of different stations for performing different assay steps positioned around a carousel which is used to receive, store, and transfer assay-specific cartridges between the stations according to the assay being performed.

Cartridges may include a specimen chamber for receiving a specimen and a number of division or incubation wells pre-loaded with different antimicrobial agents. The cartridges may also include multiple imaging wells with each imaging well corresponding to a single division well. The imaging wells can contain the necessary reagents for processing and imaging the target microbe after incubation in the presence of the various agents in order to provide differential growth analysis thereof and to determine the most effective treatment for a patient's infection with the specific target microbe.

The specimen chamber, division wells, and imaging wells can be in selectably coupled to each other through a series of channels and valves such as a sliding bar disposed between the division and imaging wells. The bar may include vertical channels and be horizontally slidable so that the channels can be aligned with an outlet channel of a division well and an inlet channel of a corresponding imaging well to create a fluidic pathway therebetween. When horizontally slid in either direction the channels of the bar may become misaligned with the wells thereby isolating them and preventing fluid communication therein. The valve may be externally manipulated by instruments as described herein depending on the assay steps to be carried out.

The cartridge can include a pneumatic or other interface for coupling to a pneumatic source for applying pressure gradients within the cartridge to move the specimen between the various compartments. When manipulated in conjunction with the valves, the pneumatic source can be used to open channels between the various compartments within the cartridge and then direct the specimen fluids through the open channels.

Instruments for receiving and manipulating cartridges can use the carousel to randomly access the different stations so that multiple tests can be performed. Precise computer scheduling and random, computer-controlled access to the various stations in the instrument are used to automatically carry out all steps of a variety of assays without additional user input. After loading a cartridge into the instrument, a user's next interaction can be receiving or viewing results of the assay either at the instrument or remotely. Results may be as simple as an image obtained of a processed specimen or may include automatic interpretations such as microbe identification and susceptibility scores for various antimicrobial agents.

Stations can include fluidics modules for interfacing with the cartridge and manipulating the specimen and reagents therein; magnetic pulldown stations for magnetic selection of targets; waste stations for disposing of used cartridges; imaging stations for analyzing assayed specimens; incubation stations for maintaining temperatures in on-cartridge specimens and reagents for as required for various assay steps; and waste stations for disposal of used cartridges. In preferred embodiments, assays may use a constant temperature throughout all steps or be modified to do so such that the interior of the instrument can be maintained at the required temperature and the carousel can serve as a storage station for incubation steps.

The instrument can read a code or tag on the cartridge or receive an input from a user to determine the assay to be performed and the required steps for that assay for any given cartridge. The instrument can also use that input to record and track information associated with the specimen being tested including patient information for reporting results.

Instruments may include a computer comprising a processor and a non-transitory, tangible memory and operable to schedule and control the assays being performed within the instrument and track the cartridges therein. The computer can include a user interface for prompting and receiving information from the user and displaying results and status information. The computer can be connected to a network and operable to process assay results and send to connected devices over the network.

Instruments of the invention can include a mechanical conveyor arm for moving cartridges between the carousel and the various stations for the performance of required assay steps. In preferred embodiments, the carousel and the stations comprise slots sized to accept and position the cartridge within the station. Rotation of the carousel can align the carousel slot with a corresponding slot in the relevant station and the mechanical conveyor arm may be operable to contact a side of the cartridge and slide the cartridge along the aligned slots and into the selected station. The mechanical conveyor arm avoids gripping the cartridges and reduces jams associated with gripping mechanisms. The mechanical conveyor arm can comprise two rotatable prongs operable to flank the cartridge and provide motivating force to one side thereof. The sides of the carousel and stations slots can provide the lateral guidance as the cartridge is slid, avoiding the need for a gripping mechanism for moving the cartridges.

The pre-loaded cartridges allow for control of reagent volumes and distribution on the manufacturing side and the automated instrument controls performance of the assay steps and the timing thereof. Accordingly, systems and methods can greatly reduce the potential for user error allowing inexpert staff to conduct a variety of assays without specialized training and to obtain reliable and actionable results without the delay and cost of dedicated off-site testing.

In a preferred embodiment, assay-specific cartridges include microbe-specific AST cartridges for measuring differential growth of a specimen microbe in the presence of various antimicrobial agents selected based on the specimen microbe. The robust nature of the described techniques and systems also allow for analysis on non-microbial targets, such as cancer or other cells. For example, the invention is useful for determining therapeutic efficacy, resistance monitoring (both with respect to antimicrobials and other chemotherapeutics), and therapeutic choice. According to the invention, patient specimens, such as urine, stool, or blood are directly analyzed with minimal or no specimen preparation or culturing. Specimens processed according to the invention are identified and exposed to various antimicrobials or other treatment modalities (e.g., chemotherapies for cancer cells), allowing the selection of the most-effective treatment. Microbial infections can be identified and the appropriate treatment determined in a matter of hours, greatly reducing the delay in appropriately targeted therapy and avoiding the need for empiric treatment with aggressive broad spectrum antimicrobials. The invention allows health care providers to prescribe effective therapies at the outset to appropriately treat infected patients. Thus, the invention provides an opportunity to improve patient outcomes and reduce the spread of antimicrobial resistance. Monitoring of cancer or other cells and therapeutic efficacy of treatments thereof using systems and methods of the invention allow for rapid identification of the most effective treatments and further allow for timely intervention upon development of therapeutic resistance.

Infection detection, target identification, and determination of effective treatment is accomplished directly from patient specimens, such as saliva, urine, blood, stool, swabs, or cerebrospinal fluid with little or no specimen preparation steps. For example, a urine specimen is directly pipetted into a testing device for identification (ID) and antimicrobial susceptibility testing (AST) which is completed in several hours. This is in contrast to current culture-based methods which require one or more days of colony purification to produce a large population of pure microbial culture for testing. The invention provides testing devices and instrument instruments capable of receiving and internally processing a patient specimen to identify microbes or cells and/or to determine therapeutic susceptibility and efficacy all within the testing device. Multiple target cells or pathogens in a specimen can be identified and susceptibility to multiple antimicrobials or treatments can be tested in a single device. Testing systems and methods of the invention are robust with respect to specimen matrices, variable inoculum, and the presence of commensal microbes in the specimen. Tests of the invention also deliver accurate results for poly-microbial infections.

Systems and methods of the invention provide images of labelled microbes target cells that allow for tracking of differential growth, morphology, or other observable changes to determine susceptibility and effectiveness of various therapies. Specimens are directly processed and imaged to determine the presence and identity of target cells, microbes, or pathogens present in the specimen. As noted above, the processing and imaging steps occur with the specimen in a testing device such as a cartridge and require little to no specimen preparation outside of the testing device. By foregoing time-consuming specimen preparation techniques and using target-specific, distinguishable labels, systems and methods of the invention allow for the identification and enumeration of targets in a specimen in thirty minutes or less.

Specimens may also be incubated in the presence of antimicrobial agents or other treatments of various types and at various concentrations before imaging. The incubation can occur in the same testing device in which the processing and imaging steps take place or in different testing devices.

Systems and methods of the invention can be used to identify target cells or microbes and to (separately or within the same device) test for therapeutic efficacy or antimicrobial susceptibility of the target in the specimen. In a preferred embodiment of the invention, testing devices internally divide a specimen into separate portions where some of the portions may be incubated in the presence of various antimicrobial agents before imaging to determine differential growth. One or more of the portions may be directly processed and imaged to provide a baseline reference for determining growth, cytotoxicity, or morphology changes in the incubated portions. By quantifying the growth of portions incubated in various antimicrobial or other therapeutic agents, the effectiveness of each antimicrobial agent in reducing or preventing growth of the target is determined.

Testing devices and instrument instruments as described herein are not only capable of identifying and testing efficacy of agents on varying classes of targets (e.g., viruses, human cells, bacterial cells, or fungal cells) but as will be apparent through the following descriptions, are capable of simultaneously performing such identifications and therapeutic testing through the selection and manipulation of multiple different targets in a single device and multiple testing devices designed for different testing applications (e.g., blood infections and respiratory infections) in a single instrument. Accordingly, robust functionality if provided by the instrument instruments and testing devices described herein.

Once a target is identified, the analysis can be limited to antimicrobial agents or treatments relevant to that target (e.g., those commonly used in treatment or known to inhibit growth of the identified target). As noted earlier, identification of the target cell or microbe allows for selective exposure to target-specific therapies. As such, an initial identification step is preferred before AST or therapeutic efficacy testing is begun. Identification can be performed using the same processing and imaging techniques as used in the AST methods described herein and can be performed using the same types of devices, instrument instruments, and methods used for the differential growth or therapeutic efficacy analyses. In certain embodiments, identification and therapeutic testing can be performed on the same specimen (divided into separate portions) in the same device. Target identification can also be performed using other conventional techniques such as amplification with target-specific primers, immunoassays, mass spectrometry, or oligonucleotide probe array analysis. If identification is performed separately, a dedicated differential growth analysis device may be used. A dedicated identification device compatible with processing techniques and instrument instruments of the invention can forgo the need for an incubation step or reservoir.

Observable differential growth in the presence of various antimicrobial agents will require different amounts of time depending on the test cell or microbe, but is greatly reduced from the days required for standard AST techniques. For example, differential growth of microbes commonly associated urinary tract infections can be observed in urine specimens using techniques of the invention after about 4 hours or less. As noted above, identifying and quantifying microbes in a specimen can be accomplished in thirty minutes or less thereby allowing for AST results to be obtained within hours after introduction of the specimen to the testing device. In certain embodiments, AST or therapeutic efficacy testing devices are provided containing subsets of antimicrobial agents or other therapeutics specific to various target cells or microbes such that a technician can select the appropriate testing device and directly introduce a patient specimen therein to perform the relevant AST or therapeutic efficacy analysis.

AST results obtained using systems and methods of the invention are then used to identify antimicrobial resistance and to inform treatment decisions of patients wherein the patient may be treated with the antimicrobial agent found to best inhibit growth or viability of the target in the AST analysis.

Detectable labels may include fluorescent oligonucleotide or antibody probes, specific and nonspecific ligands, lectins, stains, and dyes that bind targets. In certain embodiments, magnetic tags are used in combination with the detectable labels to bind to target microbes before magnetically selecting and imaging the target microbes. Separation can occur within a testing device as described herein and magnetic fields may be used to deposit the labelled microbes on a detection surface in the testing device to be imaged. In certain embodiments, a dye-cushion layer, as described in U.S. Pat. No. 9,643,180, incorporated by reference herein, can be used in the separation and imaging steps to reduce background signal and provide a more accurate quantification of labelled microbes. Digital, non-magnified imaging techniques as described in U.S. Pat. Nos. 9,643,180 and 8,021,848, incorporated herein by reference, can be used to quantify labelled microbes including, for example, single cells.

Aspects of the invention provide methods for determining antimicrobial susceptibility or other the response to other treatments of a target in a specimen. Such methods preferably include the steps of obtaining a tissue or body fluid specimen suspected to contain one or more types of targets. The specimen is then introduced into a testing device, divided into a plurality of portions, and incubated in the presence of a plurality of different antimicrobial agents, all within the testing device. Also within the testing device, targets within the incubated portions are labelled and imaged to determine which antimicrobial agents inhibit growth of the targets.

Methods of the invention may include identifying the target cell before introducing the specimen into the testing device and selecting the plurality of different antimicrobial agents based on the identity of the target cell or microbe. Identification of a target cell or microbe preferably includes exposing a first specimen from the patient to magnetic tags and fluorescent labels that can bind to the first targets such that complexes comprising magnetically tagged and fluorescently labeled targets are specifically formed. Applying a magnetic field to the testing device to attract the complex to a detection surface; and imaging the detection surface to detect the detectable label where presence of the detectable label indicates presence of the first target. The identification step may take less than about 30 minutes.

Specific formation of the magnetically tagged and fluorescently labeled target complexes occurs in various ways. Either the magnetic tag or the fluorescent label may be designed to specifically bind to the target. Alternatively, both the magnetic tag and fluorescent label may be designed to specifically bind to the target. In either case, magnetic selection combined with imaging of the magnetically selected complexes results in detection and enumeration of the specific targets in a specimen. There are various mechanisms by which that magnetic tags and fluorescent labels can associate with the targets.

There are various ways that magnetic tags or fluorescent labels may bind non-specifically to targets. For example, binding magnetic particles (or a fluorophore) to a conserved site across various categories of targets (e.g., peptidoglycan, LPS, or glucan) can be achieved by conjugating magnetic particles (or fluorophores) to antibodies that bind to the site. Magnetic tags or fluorescent labels may also bind non-specifically due to general chemical attributes. For example, positively-charged magnetic particles or fluorophore labels can bind non-specifically to bacterial cells, which are generally negatively charged. Cells can be labeled non-specifically by various dyes (e.g., calcofluor) or fluorogenic dyes (propidium iodide, fluorescein diacetate).

Magnetic tags or fluorescent labels can also be chosen in various ways so that they bind to targets specifically. For example, magnetic tags (or fluorophores) can be conjugated to antibodies that bind to target-specific antigens. To similar effect, magnetic tags or fluorophores could be conjugated to a molecule (e.g., avidin) that binds specifically to a ligand (e.g., biotin) that is bound to (or can bind to) such a target specific antibody. Cells can be also labeled specifically by re-association or hybridization with target-specific nucleic acid probes (or nucleic acid analog probes) that are themselves labeled with fluorophores.

In certain embodiments, the labelling and imaging steps include exposing the specimen portions to a target-specific binding molecule, a magnetic particle, and a detectable label, wherein the target-specific binding molecule forms a complex comprising the target, the magnetic particle, and the detectable label; applying a magnetic field to the testing device to attract the complex to an detection surface; and imaging the detection surface. The detectable label can include a fluorescent marker and the target-specific binding molecule may include an oligonucleotide probe. The exposing and imaging steps can include fluorescent in situ hybridization (FISH) analysis.

Methods of the invention may include determining a recommended antimicrobial or other therapy for the patient, usually comprising the antimicrobial or other treatment determined to inhibit growth of the target. Determination of the treatment that inhibits growth of the target can occur in less than about 4 hours after introducing the specimen into the testing device. The bodily specimen can be a tissue specimen (e.g., a biopsy from the patient) or a bodily fluid specimen. Preferred bodily fluids for use with the invention include, but are not limited to, respiratory (for example, sputum endotracheal aspirate, protected specimen brush, broncho-alveolar lavage), blood, urine, stool, swabs (for example, nasal, oral/pharyngeal, surgical site, skin and soft tissue, rectal), and cerebrospinal fluid.

In certain aspects, the invention provides systems for determining therapeutic susceptibility of a target cell or microbe in a specimen. Preferred systems include a testing device operable to receive a specimen comprising a bodily fluid from a patient and a target cell or microbe as well as an instrument. The instrument is preferably operable to manipulate the testing device to divide the specimen into a plurality of portions within the testing device; incubate the portions in the presence of a plurality of different therapeutic agents within the testing device; fluorescently label and magnetically tag the target cell within the incubated portions within the testing device; separate the magnetically tagged and fluorescently labeled target complexes from the unbound fluorescent labels; and image the portions within the testing device to quantify the target complexes so as to determine which treatment(s) inhibit replication of the target cells.

Systems may further comprise a first testing device operable to receive a first specimen from the patient and the instrument may be further operable to expose the first specimen from the patient to magnetic tags and detectable labels chosen so that complexes are specifically formed with a first target, the magnetic tags, and the detectable label; apply a magnetic field to the testing device to attract the complex to an detection surface; and image the detection surface to detect the detectable label wherein presence of the detectable label indicates presence of the first target.

The instrument may be operable to expose the incubated specimen portions to magnetic tags and detectable labels chosen so that complexes are specifically formed with a target, the magnetic tags, and the detectable label; apply a magnetic field to the testing device to attract the complex to a detection surface; and image the detection surface.

Aspects of the invention provide methods for determining therapeutic susceptibility of target cells or microbes in a specimen. Methods may include identifying one or more targets in a first specimen from a patient using an identification assay performed by an instrument; selecting one or more therapeutic agents based on the identified target cells or microbes in the first specimen; separately incubating a specimen from the patient within the instrument in the presence of each of the therapeutic agents; detecting, using the instrument, a number of target cells, CFUs, viral load, viable target cells, or other indicator of therapeutic efficacy (or treatment impact) in each of the incubated specimens; and determining a susceptibility (or treatment impact) to each of the therapeutic agents (or treatments) for each of the identified targets based on the detected amount, morphology, or other phenotypic attribute of the targets.

The identification assay can include contacting the first specimen with magnetic tags and detectable labels chosen so that complexes are specifically formed with a target, the magnetic tags, and the detectable label; applying a magnetic field to the complex to attract the complex to an detection surface; and imaging the detection surface to determine the presence of the complex wherein presence of the complex identifies the target as present in the specimen.

Detecting the amount of the identified target cells or microbes in each of the incubated specimens may include contacting the incubated specimens magnetic tags and detectable labels chosen so that complexes are specifically formed with a target, the magnetic tags, and the detectable label; applying a magnetic field to the complex to attract the complex to an detection surface; and imaging the detection surface to determine an effect of each of the therapeutic agents on growth of each of the identified target.

Multiple portions may be combined with the same antibiotic present in different concentrations, preferably corresponding to 2-fold serial dilutions of the antimicrobial. In this way it is possible to determine the level of antibiotic that inhibits growth of the target. The number of such portions and concentrations of antimicrobials can be chosen so as to deliver a Susceptible/Resistant result, a categorical (Susceptible, Intermediate Resistant, Resistant or SIR result), or a Minimum Inhibitory Concentration (MIC) result. The relevant concentrations of antimicrobials for specific microbial pathogen species are documented by the Clinical Laboratory Standards Institute (CLSI).

In certain aspects, the invention provides a cartridge. The cartridge includes an incubation well; a species-specific microbial probe; and a permeabilization agent. When a specimen comprising microbes is delivered into the mixing well, the permeabilization agent promotes entry of the probe into a microbe while the specimen is maintained at temperatures beneath about 40 degrees C. The probe may include a fluorescently labeled oligonucleotide complementary to a segment of ribosomal RNA of a specific bacterial species. The permeabilization agent may include one or more detergents (e.g., CHAPSO, SB3-12, TRITON X100). Preferably, the permeabilization agent and the probe are provided in lyophilized beads that are rehydrated and dissolved by delivery of the specimen into the incubation well.

In some embodiments, the cartridge includes magnetic particles that bind to bacterial cell surfaces and a dye-cushion adjacent a transparent wall. When a magnetic field is applied across the dye-cushion, the magnetic field pulls the magnetic particles through the dye-cushion to the transparent wall. The dye-cushion may include a solution (optionally dried or lyophilized) of density gradient medium (e.g., iodixanol or polyvinylpyrrolidone-coated colloidal silica particles) that further includes a dye that absorbs light from unbound probes. Preferably, the dye-cushion and the transparent wall are provided in an imaging well in fluidic communication with the incubation well. The dye-cushion is provided may be provided in a dried or lyophilized state in the imaging well within the cartridge until wetted by specimen. The magnetic particles may be linked to a chemical group that binds to the bacterial cell surfaces (e.g., diethylamine ethyl-starch; dextran-sulfate; polyaspartic acid; polyacrylic acid; polyglutamic acid; poly-styrenesulfonate; or poly-diallyldimethylamin) and the cartridge may further be pre-loaded with a chemical compound that promotes the binding of the chemical group to the bacterial cell surfaces. The compound that promotes binding of the chemical group to the cell surface may include cetrimide.

The cartridge may include a plurality of paired imaging well/incubation well sets in parallel to one another. The cartridge may further include a receiving reservoir into which a user can pipette the specimen into the cartridge.

In certain embodiments, the cartridge includes a slideable gate with a gasket with channels therethrough. When the gate is positioned at a first position, the receiving reservoir is in fluid communication with at least the first incubation well. When the gate is in a second position, the receiving reservoir, the first incubation well, and a first imaging well are all sealed from one another. When the gate is in a third position, the first incubation well and the first imaging well are in fluid communication with each other. The cartridge may include a fitting for coupling to an external instrument to receive pneumatic pressure therefrom to divide the specimen from the receiving reservoir into the incubation wells and to subsequently pass liquid from the incubation wells into corresponding imaging wells.

In preferred embodiments, the probe comprises a fluorescently labeled oligonucleotide complementary to a segment of ribosomal RNA of a specific bacterial species. Optionally, the cartridge also includes at least one helper probe oligonucleotide that binds to the ribosomal RNA at a location within 1 to 30 bases from the segment. Preferably, the fluorescently-labeled oligonucleotide is between 10 and 18 bases in length and includes at least one conformationally-restricted nucleic acid. In preferred embodiments of the cartridge, the reagent composition, the probe, the helper probe, and the compound are provided as lyophilized beads that are rehydrated and dissolved by delivery of the specimen into the cartridge; the dye-cushion comprises a solution of density gradient medium that further includes a dye that absorbs light from unbound probes; and the cushion is provided in a dried or lyophilized state in the imaging well within the cartridge until wetted by specimen.

BRIEF DESCRIPTION OF THE DRAWINGS

FIG. 17 is a table of Probe sequences used in example.
FIG. 20 is a table giving Probe sequences used in example.
FIG. 21 shows the bacterial species and strains tested.
FIG. 22 is a table showing Probe sequences used in example.
FIG. 25 shows a portion of the full acquired image.
FIG. 26 is a table of Probe sequences used in example 4.
FIG. 31 is a table of Probe sequences used in example 6.
FIG. 34 shows the overall performance across all strains tested.
FIG. 35 is a table of Probe sequences used in example 7.

FIG. 37 is a table showing Antibiotic concentrations tested.

FIG. 38 is a table of Oligonucleotides used in example 8.

FIG. 39 shows BIUR0067 Results.

FIG. 41 compares the results obtained with the novel AST method.

FIG. 41 is a Summary of the overall essential and categorical agreement for all organisms, antibiotics and inoculum levels.

FIG. 42 shows MIC results for various inoculum levels generated using the new methods described here compared to the conventional BMD method.

FIG. 44 is a table of Probe sequences used in example 9.

FIG. 47 shows the data for *E. coli* BAA-2469.

FIG. 48 shows agreement of *E. coli* with varying inoculum levels of off-target microbe (*Micrococcus luteus, Acinetobacter baumannii, Corynebacterium minutissimum*) standard BMD.

FIG. 49 shows agreement of *E. coli* with varying inoculum levels of off-target microbe (*K. pneumoniae*) standard BMD.

FIG. 50 is a table of Probe sequences used in example 10.

FIG. 51 is a comparison of the novel rapid AST and BMD methods for determining Imipenem MIC for *E. coli* in the presence of a resistant carbapenem hydrolyzing B-lactamase strain of *K. pneumoniae*.

FIG. 52 shows the MIC for *E. coli* stays consistent with the method describe above with varying inoculum of a resistant carbapenem hydrolyzing B-lactamase strain of *K. pneumoniae* while standard BMD does now.

FIG. 53 is a table of probe sequences used in example 11.

FIG. 55 summarizes the results obtained for all 5 antibiotics. 100% essential and 100% categorical agreement to standard BMD was observed across 15 culture negative clinical urine samples using the novel AST method.

FIG. 56 shows the MIC determined.

FIG. 57 shows results form a test.

FIG. 61 shows that the sensitive and resistance categorical determinations.

FIG. 61 shows Ciprofloxacin-sensitive and resistant strains used in example

FIG. 62 is a first half of a Table of probe sequences used in example 13.

FIG. 63 is a second half of a Table of probe sequences used in example 13.

FIG. 64 shows essential agreement for a polymicrobial infection with 2 target organisms. As seen below, the AST method described above yields 100% essential agreement to standard BMD FIG. 65 shows categorical agreement for a polymicrobial infection with 2 target organisms. As seen below the AST method described above yields 100% categorical agreement to standard BMD.

FIG. 69 is a table "Table A of Example 14", showing target pathogens were detected while other non-target pathogens were not.

FIG. 70 is a table, "Table B of Example 14", showing probe sequences used in example 14.

DETAILED DESCRIPTION

Figure 1:
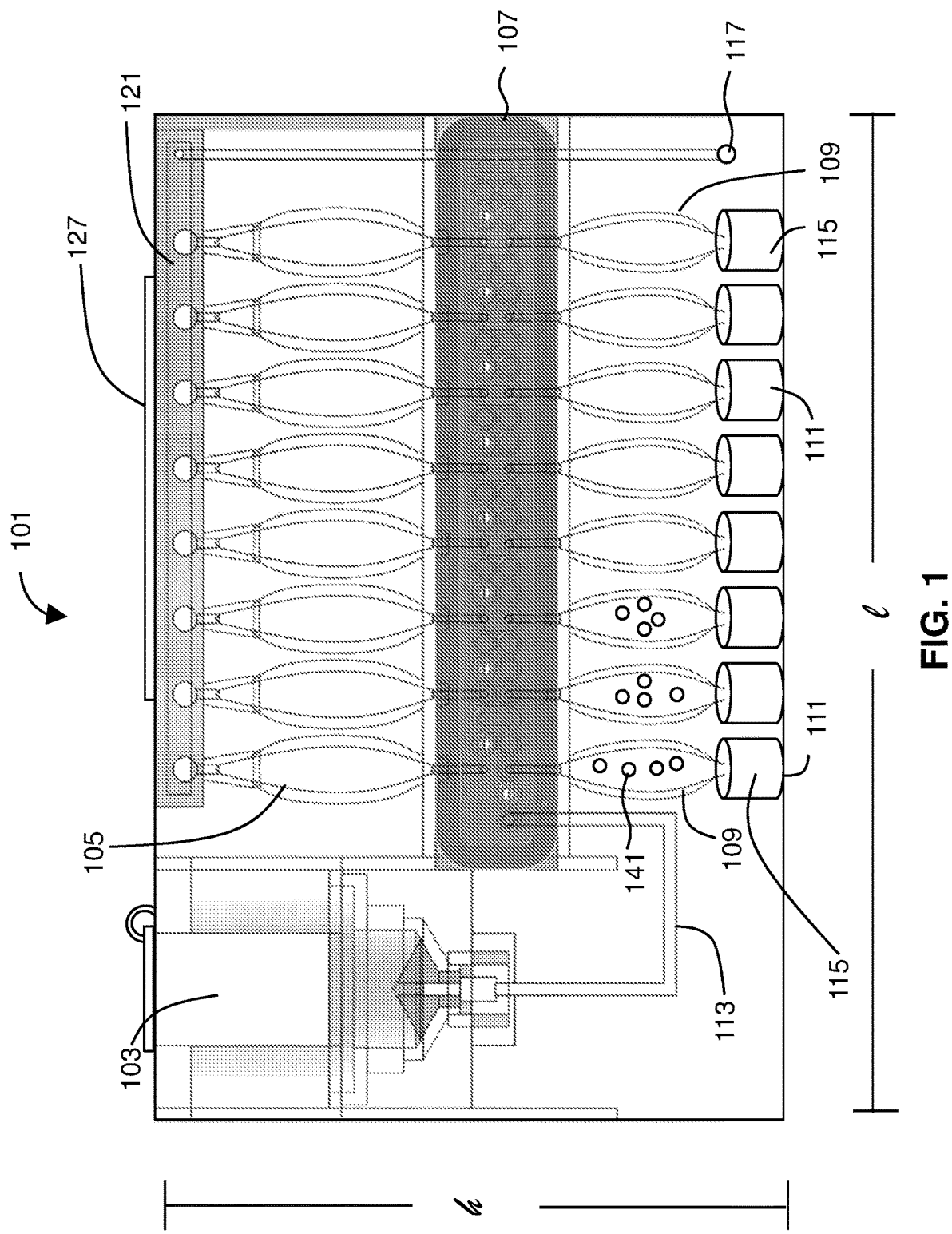
FIG. 1 shows a cartridge of the disclosure.
Figure 1A:
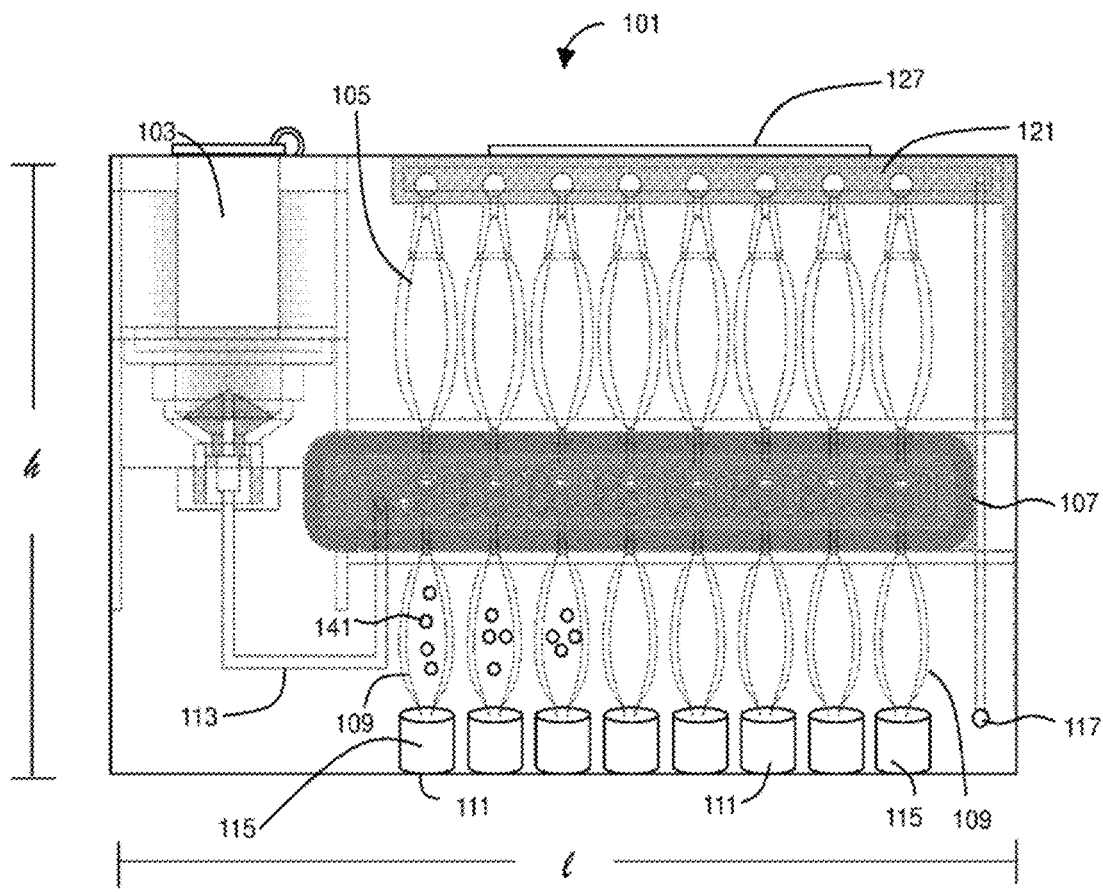
FIG. 1A shows the cartridge of FIG. 1 with the sliding bar in a second position.

The invention provides cartridges for automatically performing antimicrobial susceptibility testing (AST) analysis of target microbes in specimens in conjunction with automated instruments and requiring little or no specimen preparation by the user. Target cells such as cancer cells may also be identified and the therapeutic efficacy of various treatments assessed using systems and methods of the invention. Cells or microbes in specimens can be analyzed for differential growth in the presence of various antimicrobial agents or the effects of therapeutic agents on cell viability, morphology, viral load, cell functionality, or other measures of therapeutic efficacy can be determined using systems and methods described herein. Specimen manipulation, incubation, processing, and analysis steps are performed within a single testing device in under about thirty minutes for target cell identification and under about four and a half hours for AST analysis in the case of urine analysis for common causes of urinary tract infection. Analysis time may vary based on the targets being analyzed (e.g., depending on the growth rate of the target) and the therapeutic agent being tested. Systems and methods detect specific targets using non-magnified digital imaging and image analysis to accurately and quickly quantify targets in a specimen.

Embodiments of the invention allow testing without requiring cell purification steps by the user. By reducing extraneous steps, and using imaging methods and image analysis capable of quantifying single cells or colony forming units (CFU) in certain instances, actionable results directly from patient specimens for target cell or microbe identification and AST analysis are obtained in a matter of hours as compared to multiple days with conventional techniques. Testing devices can be automatically manipulated by an instrument to carry out each of the steps of dividing a specimen, culturing in the presence of different antimicrobial agents or other treatments, and processing and imaging the resulting specimen portions to measure differential growth and determine effectiveness of the tested antimicrobial agents.

In a preferred embodiment of the invention, the cartridges are used for antimicrobial susceptibility testing, and a specimen is divided into separate portions containing nutrient growth medium to promote microbiological cell replication or growth. One or more of the portions may be used as a reference or baseline portion which is directly processed and analyzed before incubation at a temperature that promotes growth to determine the number and quality of pathogen cells. One or more of the portions may be incubated at a temperature that promotes growth of the pathogen cells to ascertain if the pathogen cells are viable. Other portions each contain, in addition, one or more antimicrobial agents at particular concentrations, and are incubated to determine the impact of the antimicrobial agents on pathogen cellular replication.

The invention can then be used to analyze pathogen cell number and quality in the incubated portions and to compare these results to the number and quality of the pathogen cells in the un-incubated reference portion. If the pathogen cells are significantly impaired in their ability to replicate normally in a portion containing a particular antimicrobial agent, the pathogen scored as susceptible to the antimicrobial agent at the concentration in that portion by the analysis software. Alternatively, if normal growth in not impaired significantly in the portion, the pathogen scored as susceptible to the antimicrobial agent at the concentration in that portion by the analysis software.

The invention can include assessment criteria, for instance cellular replication is assessed for determination of a pathogen or microbial target's antimicrobial susceptibility or resistance in a portion containing antimicrobial agent(s). These criteria may be determined for specific combinations of parameters including but not limited to the species of the target microbe, specimen type, antimicrobial agents, growth medium composition, temperature, and incubation time.

The assessment criteria are preferably determined empirically by correlation with an accepted reference method for antimicrobial susceptibility testing. One standard reference method is broth microdilution (BMD) and understood by those familiar with the art. Broth microdilution is a method by which the antimicrobial susceptibility of a microbial strain to an antimicrobial agent is assessed under standard conditions. Purified cells of the target microbe are added at a defined concentration to a series of portions or aliquots of a defined nutrient growth medium containing serial 2-fold dilutions of various antimicrobial agents. The antimicrobial susceptibility of the microbial strain is determined after visually assessing the turbidity of the various portions after a defined period of growth incubation. The lowest concentration of an antimicrobial agent in which turbidity is visually absent or significantly lowered compared to a portion containing no antimicrobial agent is called the minimum inhibitory concentration (MIC). Organizations that determine standards for antimicrobial susceptibility testing (for example, CLSI or EUCAST) have correlated MIC values for combinations of particular microbial species and particular antimicrobial agents with the efficacy of particular therapeutic doses of the antimicrobial agent in clinical practice. The MIC values are generally binned into categorical ranges: Susceptible, Intermediate Resistant, and Resistant. These are called SIR or categorical antimicrobial susceptibility testing results In this way, the MIC for a of a particular strain of a particular species for a particular antimicrobial agent can be reported as an SIR or categorical result. Other standard methods used for determining include the -Bauer or disk-diffusion and agar-dilution. These methods are described in CLSI and EUCAST documents and known to those familiar with the art.

Assessment criteria for determining antimicrobial susceptibility testing results using the invention are determined empirically by using the invention to assess the degree and quality of cellular replication of various strains of a particular species in various concentrations of a particular antimicrobial agent, similar to the broth microdilution method. Criteria for assigning an antimicrobial susceptibility testing result (generally, an MIC or a SIR categorical result) to a strain of a particular species for a particular antimicrobial agent are chosen such that the results for the various strains, using the invention, correlate consistently with the results of the reference broth microdilution method. For example, a criterion that can be used by the inventive systems and methods for determining antimicrobial susceptibility testing results is assessment of the fold-growth (the fold-increase in number of target cells) of target microbes of a certain species over a certain period of incubation in the presence of various concentrations of a certain antimicrobial agent in nutrient growth medium at a certain temperature. In this case the empirical studies to determine effective criteria to use for the inventive systems and methods to assess the antimicrobial susceptibility would assess the fold-growth of various strains of the species in various concentrations of the antimicrobial agent. A threshold value for fold-growth can be chosen such that if the fold-growth measured for a strain using the invention correlates with the results of the broth microdilution for the same strain grown in the presence of the same antimicrobial agent. The threshold is chosen empirically using various strains of the target species such that if the fold-growth of the strain exceeds the threshold, the strain is categorized by the invention as having grown significantly in the presence of the antimicrobial agent at that concentration. If the fold-growth of the strain is less than the fold-growth threshold, the strain is categorized by the invention as not having grown significantly. Thus, the threshold value for fold-growth, in this example, is chosen such that the both the reference broth microdilution method and the inventive method return the same result as to whether or not the various strains are determined to have grown significantly or not in the various antimicrobial agent concentrations.

Other assessment criteria can also be used by the invention to determine antimicrobial susceptibility testing results. For example, the invention can include assessment of morphological characteristics reflecting perturbation of normal cellular replication caused by incubation in an antimicrobial agent. As another example, the degree of growth inhibition, in a portion containing an antimicrobial agent, compared to a portion containing no antibiotic after the incubation step can be assessed. Multiple assessment criteria can also be used in concert to determine whether or not an antimicrobial agent at a particular concentration causes a significant perturbation to normal cellular replication of target cells. Thus, the invention can be used to detect infections, identify the infectious pathogens, and determine which antimicrobials will be effective for treatment directly from patient specimens.

Patient specimens such as urine, stool, respiratory, wound, cerebral spinal fluid, or blood are preferably transferred directly into an analytical cartridge for microbial analysis without any specimen preparation by the user. Thus, there is preferably no requirement for users to carry out colony purification to isolate large numbers of pure pathogen cells, nucleic acid purification, or other time- or labor-intensive specimen preparation protocols. Specimens are preferably loaded directly into test cartridges without any pre-enrichment or cleanup to, for example, remove biological detritus.

The cartridge contains reagents for the microbial quantification and identification and the antimicrobial susceptibility tests of the disclosure. Steps such as species-specific labelling and imaging of microbes in the specimen all occur on the cartridge into which the specimen has been directly loaded. The cartridges include target cell-specific labels such as fluorescent probes that are used to identify microbes in the specimen by the systems and methods of the invention. To identify microbes, the instruments preferably include an imaging subsystem to image labelled microbes in the cartridge.

Rapidly detecting infections, identifying pathogens, and determining antimicrobial susceptibility using the systems and methods of the invention offers the potential for delivering actionable results to guide effective treatment of patient infections much more quickly than conventional methods, which require lengthy culture steps. Systems and methods of the invention can provide clinicians with the ability to detect infections and identify the infectious pathogens in about 30 minutes, and determine antimicrobial susceptibility testing results in several hours by simply transferring a patient specimen directly into an analytical cartridge and loading the cartridge into an instrument.

In some embodiments, the invention includes microbe detection and identification of effective treatment directly from patient specimens. In certain aspects, the invention provides for identifying a microorganism. Microbial identification is accomplished directly from patient specimens, such as whole blood, plasma, serum, urine, sputum, saliva, stool, cerebrospinal fluid, amniotic fluid, peritoneal fluid, pus, lymph, vaginal secretions, nasal secretions, vomit, sweat, and tissue with no specimen preparation steps. For example, the method may involve transferring a urine specimen directly into an analytical cartridge device for microbe identification. In some embodiments, the method includes transferring a patient specimen directly into a sample well of an analytical cartridge and operating the cartridge to label a microbe in species-specific manner, image the labelled microbe and identify the labelled microbe.

In various embodiments of the invention microbes in the specimen are tagged with magnetic particles and labeled with species-specific detectable labels. In some embodiments the detectable labels may comprise species-specific fluorescent nucleic acid probes. Other detectable labels include target-specific fluorescent antibodies or aptamers, a member of receptor-ligand pairs, lectins, or stains. Target-specific nucleic acid probes may be chosen such that is complimentary only to nucleic acid sequences of the target microbe. Magnetic particles used in various embodiments can bind specifically or non-specifically to the target microbes. In some embodiments, multiple species may be detected.

In some embodiments, operating the cartridge may include loading the cartridge into an instrument to detect infections; identify and quantify pathogens in the specimen; and to determine antimicrobial susceptibility within an inventive cartridge device. The invention provides analytical cartridges and instruments capable of directly receiving and processing a patient specimen to identify microbes and/or to determine therapeutic susceptibility and efficacy all within the cartridge.

In some preferred embodiments, separate cartridges are deployed for different successive diagnostic functions. For example, in a preferred embodiment a cartridge detects infections, identifies pathogens, and quantifies pathogens in a specimen. If an infection is detected and pathogen identified, then another portion of the patient specimen is tested on a cartridge containing antimicrobial agents that are candidates for treating the identified pathogen. Using the systems and methods of the invention for antimicrobial susceptibility testing the cartridge can be used to determine which of the antimicrobial agents can be effective for treating the particular strain of the pathogen causing the patient's infection.

Cartridges of the invention can also be used for sensitive detection biologically important molecules such as toxins and biomarkers.

Systems and methods of the invention include instruments or analyzers that can be used to interact with analytical cartridges to carry out methods of the invention. The instrument may include a plurality of subsystems to perform methods of the invention. The analytical cartridge may be loaded into the instrument having a plurality of subsystems to process the specimen within the cartridge. In a preferred embodiment, one of the plurality of subsystems may be an imaging subsystem to image a labelled microbe within the cartridge. Subsystems of the instrument may also include a pneumatic subsystem, a magnetic subsystem, and a waste subsystem. The instrument may also include a carousel, a pusher mechanism and a task scheduler to move and manipulate the cartridge within the instrument. The instrument is capable of performing all of the processing steps at a constant temperature.

Systems and methods of the invention, including instruments and devices, can perform a broad range of diagnostic functions including detecting infections; detecting, identifying, and quantifying pathogen cells of all types; determining antimicrobial susceptibility; detecting and quantifying toxins, viruses, and biomarkers including host-response factors; and detecting and quantifying diagnostically informative human or host cells. The systems and methods of the invention are capable of simultaneously performing such diagnostic functions alone or in combination on a single specimen in a in a single device (e.g., an analytical cartridge). The systems and methods of the invention include the capability of random access processing, such that multiple such devices performing different types diagnostic tests (e.g., for urinary tract infections, blood infections, and respiratory infections) can be simultaneously processed on a single instrument. As such, the instruments and cartridges described herein provide such functionality and can be manipulated to process the specimens within a device accordingly.

The AST cartridges can include a series of interconnected compartments preloaded with the reagents required for the assay. A user need only add a specimen from the patient directly to the cartridge based on the desired assay and the type of specimen and then load the cartridge into an instrument for automatic processing. The instrument can identify the type of assay to be run through user input or through reading the cartridge itself (e.g., scanning a code thereon). Instruments as described herein can include a variety of stations for performing various steps that may be required for the different assays and may include a carousel or other mechanism for storing multiple in-process cartridges and transferring them between the stations as required for performance of the assay steps.

The cartridge can include various valves and channels for connecting different compartments therein as needed to perform the steps of the desired assay. For example, a cartridge for an AST assay may include a series of growth reservoirs pre-loaded with growth media and different antimicrobials to be analyzed. Cartridges may also include compartments for processing the post-growth specimens and labeling targets therein as well as imaging wells providing a window for imaging the labelled targets. Instruments may include a fluidics module to interface with the cartridge to allow for external manipulation of the valves and pressures in the cartridge to connect different compartments and move the specimen volumes therebetween as required for the various assays.

FIG. 1 shows a cartridge 101 used in various systems and methods of the invention. The testing cartridge 101 includes a specimen well 103 for receiving a specimen, division wells 105, reagent wells 109, imaging wells 111, and channels 113 for moving the specimen between the wells, as well as a sliding valve 107 for controlling that movement. The cartridge 101 may include reagents for specific assays. For example, in the reagent wells 109, the cartridge may include a target-specific probe, permeabilization reagents, or other materials, and those may be provided included in beads 141 (e.g., lyophilized beads).

As shown, the cartridge may include a plurality of paired imaging well/incubation well sets in parallel to one another. Here, the cartridge 101 is shown as including 8 parallel "channels" in which each channel includes a division well 105, a reagent well 109, and an imaging well 111. Embodiments of the cartridge may include 2 gangs of 8 channels (the additional 8 channels would be behind the eight visible channels) for 16 channels through one cartridge. The cartridge may be described according to its dimensions such as height h, length l, and width w (where w is measured orthogonal to h & l). Height h may be between about 3 and 10 cm. Length l may be between about 5 and 12 cm. Width w may be between about 0.5 and 3 cm. For example, in one embodiment, h is about 6 cm, l is about 8 cm, and w is about 2 cm.

The cartridge 101 preferably includes a specimen well 103 into which a user can pipette the specimen into the cartridge. In certain embodiments, the cartridge 101 includes a sliding valve 107 comprising a gasket with channels therethrough. When the sliding valve 107 is positioned at a first position, the specimen well 103 is in fluid communication with at least the first division well 105. When the sliding valve 107 is in a second position, the specimen well 103, the first division well 105, and a first reagent well 109 are all sealed from one another. When the sliding valve 107 is in a third position, the first division well 105 and the first reagent well 109 are in fluid communication with each other.

The cartridge 101 may include a fitting for coupling to an external instrument to receive pneumatic pressure therefrom to divide (hence, "division") the specimen from the specimen well 103 into the division wells 105 and to subsequently pass liquid from the division wells 105 into corresponding reagent wells 109. The imaging wells 111 preferably include a dye-cushion 115 and a transparent window (e.g., on the bottom of the cartridge 101).

The dye-cushion 115 is a material in the bottom of the imaging wells 111. Once a portion of a specimen is transferred into the imaging well 111, it will form a liquid specimen layer, and the dye-cushion 115 underlies the liquid specimen layer. The dye-cushion is preferably a material that resists migration of particles (e.g., a density medium, a gel, or the like) and inhibits passage of light (e.g., through the inclusion of a pigment or dye). Due to the dye-cushion 115, probes are only pulled to a detection zone when bound to a target that is also bound to a magnetic bead. The dye-cushion 115 excludes unbound material from the window that provides a detection zone (because it sits as a cushion layer underlying the liquid specimen layer) and it inhibits light from unbound signaling moieties from reaching the detection zone (because the dye-cushion layer includes dye and is not transparent).

The cartridge 101 can interface with a fluidics module of an instrument via a pneumatic port 117. The sliding valve 107 can control the movement of fluid between the division wells 105 and the reagent wells 109 by opening and closing connections. The sliding valve 107 may allow one or more portions of a specimen to bypass the division wells 105 and proceed directly to a reagent well 109 and an imaging well 111, e.g., to provide a zero growth reference for AST analysis or in applications focused on identifying the presence of a target cell or microbe and not related to AST analysis. The sliding valve 107 may be manipulated by the fluidics module of an instrument 201. In preferred embodiments, the cartridge 101 includes a diluent reservoir 121 and a button 127. Pressing the button (e.g., manually by an operator or mechanically within an instrument of the disclosure) distributes diluent (e.g., saline) that is pre-loaded in the diluent reservoir 121 into the division wells 105. In other embodiments of the invention, the valves 107 may also be configured to allow one or more portions to bypass the distribution wells 105 and proceed directly to one or more reagent wells 109 and imaging wells 111 to provide a zero growth reference or baseline for AST analysis. The distribution wells 105 can be pre-filled with growth media and/or one or more antimicrobial agents. The valves 107 can hold the specimen portions in the distribution wells 105 to be incubated in the presence of the various antimicrobial agents for any period of time.

Figure 2:
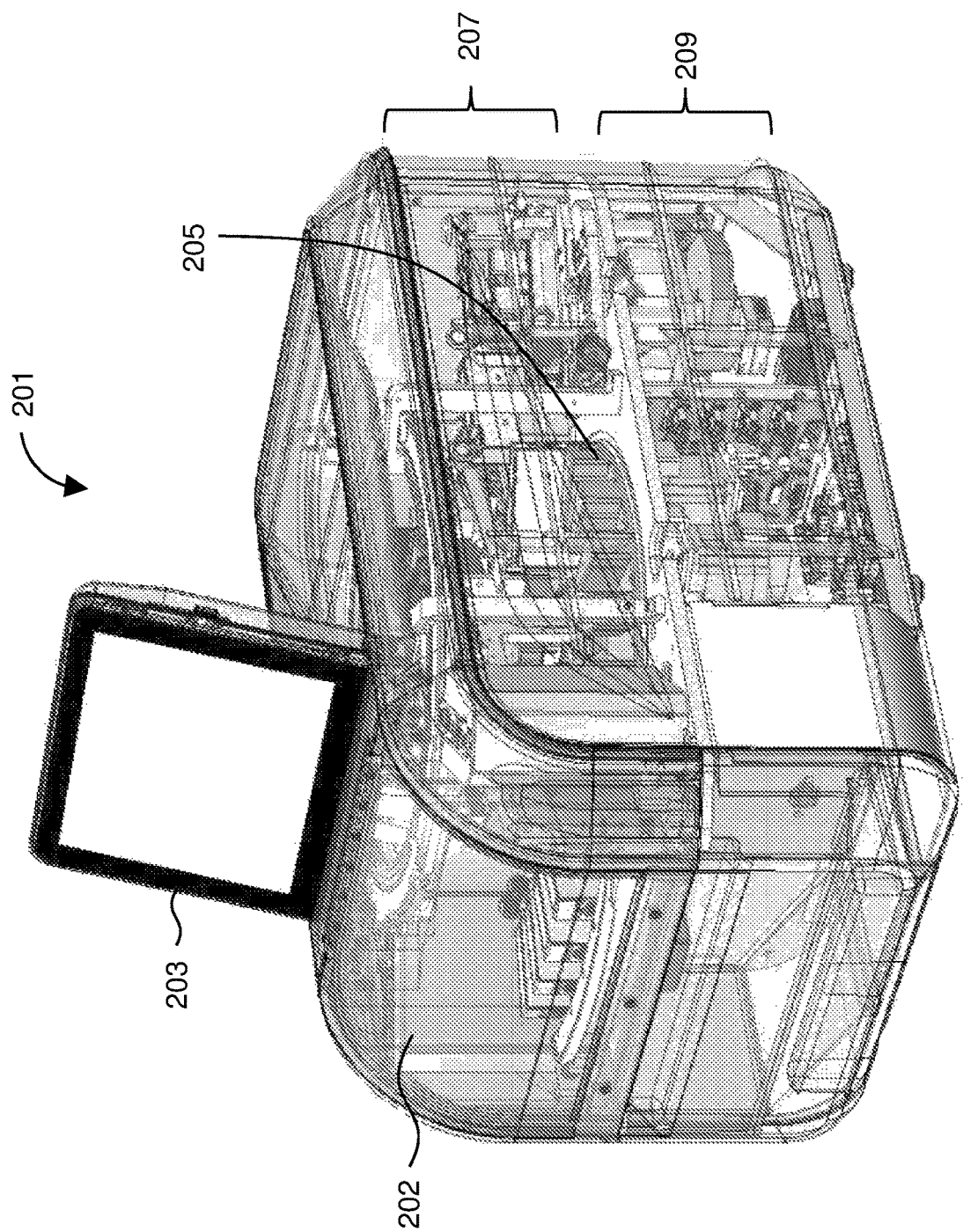
FIG. 2 shows an instrument for use with the cartridge.

FIG. 2 shows an instrument 201 (e.g., analyzer) for performing microbe identification and antibiotic susceptibility testing (AST) using a cartridge 101. The instrument 201 may be used to interact with cartridges 101 to carry out target cell identification and AST analysis of specimens. A lift-to-open loading door 202 may be included to provide access to a loading tray.

The instrument 201 includes at least one user interface 203 (e.g., a touch screen) to display prompts, results, reports and to receive commands. The instrument 601 can comprise different functional areas and subsystems. The compartments may include a carousel 205 for transporting and incubating analytical cartridges, an upper compartment 207 housing processing and incubation equipment, and a lower compartment 209 housing electronics, imaging and pneumatic equipment. The instrument 201 and methods of the disclosure may be used to identify and quantify a variety of target cells or microbes including viruses, bacteria, fungi, parasites, human cells, animal cells, plant cells. By tailoring the growth media and the antimicrobial agents to the target cell or microbe, AST analysis can be performed on a variety of target cells.

Figure 3:
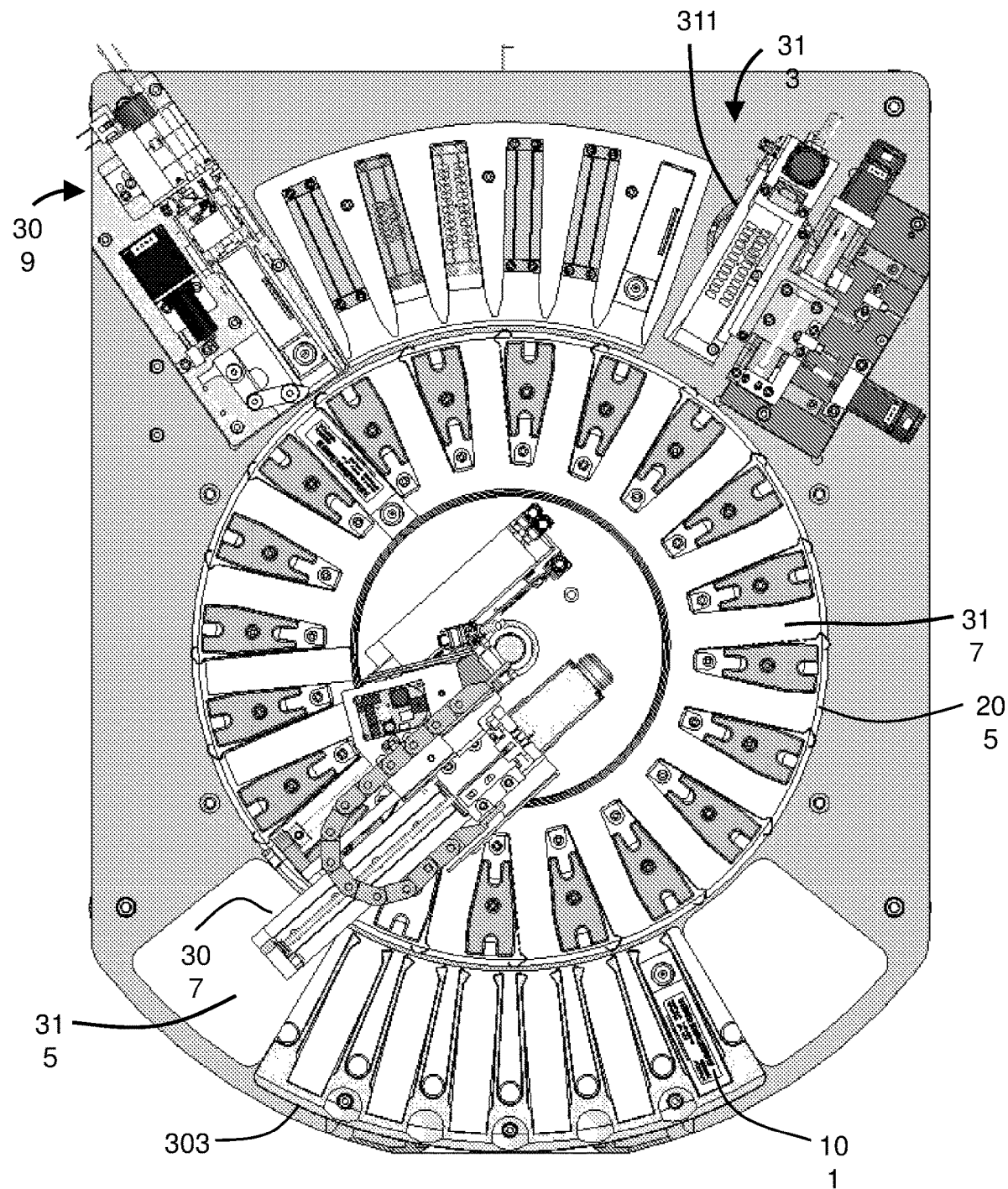
FIG. 3 shows hardware within the instrument.

FIG. 3 is an exemplary top view of the instrument 201. The instrument 201 may include an input mechanism 303, such as a loading tray, for accepting and cataloging a plurality of analytical cartridges 101.

The instrument 201 may include a carousel 205 and a mechanical conveyor arm 307 to accept, move and manipulate cartridges 101 within the instrument 201. The instrument 201 may also include a task scheduler. The instrument 201 is preferably controlled by a computer to automate manipulation of analytical cartridges, performance of microbe identification and AST analyses, and generation of results. The instrument 201 may include a plurality of subsystems to perform methods of the invention.

Subsystems of the instrument 201 may include a pneumatic subsystem 309, a magnetic subsystem 311, an imaging subsystem 313 and a waste subsystem 315. The magnetic subsystem 311 may include, for example, a permanent magnet or an electro-magnet to provide a magnetic field to deposit complexes of magnetic particles and targets on the detection surface of the analytical cartridge for imaging. The imaging subsystem 313 may be such as those described in U.S. Pat. Nos. 9,643,180 and 8,021,848, as discussed above and a stage to manipulate the detection surface of the analytical cartridge 101 relative to the imaging module of the instrument 201. The imaging subsystem 313 can be operably associated with the computer to provide image processing, analysis, and display capabilities. The pneumatic subsystem 309 may be operable to drive movement of the specimen and reagents within the analytical cartridge 101 through, for example, manipulation of sliding valve 107 (e.g., plungers and actuators) using functionality provided by pneumatic pressure or vacuum. In some embodiments, hydraulic or mechanical means may also be incorporated into the pneumatic subsystem 309 to effectuate movement of the specimen. The waste subsystem 315 may include a receptacle (e.g., a removable bin) for disposal of cartridges 101 after use.

The instrument 201 may also include one or more incubation areas for holding (or storing) analytical cartridges during incubation for growth and/or assay incubation. The incubation area may include a heating and/or cooling element and a thermostat to control that element to maintain the incubation area at a desired temperature for growth of the target cells or microbes (e.g., 35° C.) or for carrying out assay incubation.

In some embodiments the mechanical conveyor arm 307 may be operable to manipulate the analytical cartridge 101 amongst the various subsystems within the instrument 201. In some embodiments of the invention, the mechanical conveyor arm 307 transfers each of the analytical cartridges 101 between the carousel 205 and the various subsystems of the instrument. The mechanical conveyor arm 307 applies a pushing force to transfer analytical cartridges 101 onto and off of the carousel 205. The carousel 205 rotates to position an analytical cartridge 101 adjacent another one of the subsystems and the mechanical conveyor arm 307 may then apply force to slide the analytical cartridge 101 onto the subsystem. Analytical cartridges 101 are preferably never grabbed, e.g., by a squeezing or compressive force, within the instrument 201. Sliding, or pushing the analytical cartridge 101 within the instrument 201 reduces exposure to debris. The various stations or subsystems within the instrument as well as the carousel 205 may comprise slots 317 sized to accept and guide the cartridge 101 as it is slid between the carousel 205 and the various stations. Rotation of the carousel 205 functions to align the slots 317 thereon with a corresponding slot on a station such that a guide or track is formed along which the cartridge 101 can be slid by the mechanical conveyor arm 307.

In some embodiments, the instrument 201 includes a task scheduler for managing the analytical cartridges 101. The task scheduler is operable to control the movement, such as the transport and transfer of each of the analytical cartridges 101 amongst the plurality of subsystems. In some embodiments, the time each analytical cartridge 101 spends in a subsystem may also be managed by the task scheduler. The task scheduler may reserve time on various subsystems as needed for analysis of each of the analytical cartridges 101. In some embodiments of the invention, the task scheduler may manage the movement of an analytical cartridge 101 (i.e., the steps/parameters of the analysis to be performed) by identifying the contents of the cartridge. The scheduler can comprise software stored on a tangible, non-transitory memory and operated by a processor. The processor can be within, and/or in communication with, the instrument 201 and the various motors and subsystems or stations thereon to, for example, operate the carousel and mechanical conveyor arm mechanism and to control the imaging devices and record images in the memory as received from the imaging subsystem or station. The processor and memory can make up a computer which can also include input/output devices 203 such as a monitor, keyboard, mouse, or touchscreen.

In some embodiments, the instrument 201 may also include a reader operable to analyze identifiers (e.g., barcodes) located on an analytical cartridge 101. The contents of an analytical cartridge 101 and the required processing may be associated with an identifier on the analytical cartridge 101. Each of the analytical cartridges 101 may include an identifier readable by the instrument 201. The instrument 201 may read the identifier via a reader and associate the identifier with a particular set of instructions for the task scheduler to execute.

Upon reading of the identifier, the computer processor can access an assay associated with that identifier (e.g., an AST analysis for *E. coli*). The processor can then determine a schedule for perform the required steps of the assay and determine, upon commencement, when each station or subsystem will be needed and for how long to complete the assay. The processor can access the schedules of other cartridges currently running in the instrument from its memory and compare the availability of the various stations at the required time. Certain steps may be flexible (e.g., incubation) and the schedule may offer a range of lengths that can be altered in order to accommodate other scheduled operations on other cartridges. If beginning a test at a certain time would result in irreconcilable conflicts for any of the subsystems or stations, the instrument may reject the cartridge and notify the user of an acceptable later time at which to start and run the assay conflict-free. In certain embodiments, instruments may comprise two or more of any of the subsystems or stations to avoid such conflicts. For example, high-traffic stations such as the fluidics module, may warrant the inclusion of two or more depending on the desired capacity of the instrument.

The instrument 201 includes a user interface 203 for receiving user inputs and displaying results, status, and other information. The instrument 201 is enclosed in order to maintain a desired incubation or reaction temperature within the instrument 201. The instrument has an access door which is open to allow access to a loading tray 303 into which a user can load cartridges for analysis. The instrument 201 can read identifiers on the cartridge within the loading tray 303 before opening an internal door and bringing the cartridge into the carousel to begin processing. That way, if there are any errors or scheduling conflicts, they can be addressed before onboarding the cartridge. The loading tray 303 positions the cartridges in set locations relative to the instrument allowing the instrument to scan a known location for the identifier and for the mechanical conveyor arm mechanism to engage the cartridge and bring it into the carousel. The cartridges and the loading tray may comprise an asymmetric footprint such that the cartridges can only be inserted into the tray in one orientation to avoid jamming or errors such as the identifier pointing away from the instrument's scanner.

The instrument 201 and the carousel 205 operate to perform tests using the cartridges 101. Using the instrument 201, the cartridge 101 is useful to perform rapid antibiotic susceptibility testing (AST) from a polymicrobial specimen based on differential growth and species-specific detection. Differential growth useful for determining AST can be observed after incubation for a matter of hours for many target cells and microbes in the division wells 105. In various embodiments, specimen portions may be incubated in the division wells 105 for less than about 1 hour, 2 hours, 3, hours, 4 hours, 5 hours, 6 hours, 12 hours, or 24 hours before processing and imaging in the imaging wells. The growth media and/or antimicrobial agents may be selected and included in the cartridge 101 based on the target cell or microbe to be analyzed in the specimen. For example, growth media known to support growth of an identified target cell or microbe and therapeutic or antimicrobial agents commonly used to treat the identified target may be selected. In various embodiments, a cartridge 101 may be pre-loaded with growth media and therapeutic agents for a certain target such that a user, having identified a target in a specimen (e.g., determined the source of a patient's infection or a specific cancer type) can select the appropriate pre-packaged testing device for AST analysis of the target microbe or therapeutic efficacy analysis of the target cell.

After an appropriate incubation period, the sliding valve 107 can be manipulated to transfer the incubated specimen portions from the division wells 105 to the reagent wells 109. The reagent wells 109 may be pre-filled with processing reagents for labelling the target cell or microbe for imaging. The processing reagents may be lyophilized for storage and activated upon contact with the fluid specimen portion and growth media. The reagent wells 109, for example, may contain species-specific detectable probes and microbe-binding magnetic particles. As specimen portion passes through the reagent well 109, the microbe-binding magnetic particles bind to all microbes present while the species-specific detectable probes bind to organisms of interest for detection (e.g., by microscopy).

For some applications, magnetic particles or other detectable labels may be non-specific such as avidin coated mag particles and SYBR-green dye. For example, a biotin-labeled target-specific antibody (i.e., a target-specific binding molecule) could be used to target a specific cell or microbe which would then be tagged by the avidin magnetic particle for specific magnetic selection. All cells would be labeled by SYBR-green, but only the magnetically separated (i.e., biotin tagged) targets would be deposited on the detection surface for imaging.

The instrument 201 may use a magnetic field to pull the complexes to the detection surface on the bottom of the imaging well 111. The imaging wells 111 may contain a dye-cushion that forms a dense opaque aqueous layer lying below the upper assay layer in the imaging well as described herein. The complexed magnetic particles are forced through the lower dye-cushion layer and deposited on the detection surface of the imaging well 111. The detection surface may be clear to allow for optical detection of labelled target cells or microbes. After processing and pull-down with the magnetic field, the cartridge 101 can be placed on an imaging stage for imaging. Target-specific, fluorescent oligonucleotide probes may be used to fluorescently label the target cell such that imaging of the fluorescent labels provides a quantification of target cell (e.g., a cell count for a target bacterium in the specimen).

The cartridges 101 may have any number of growth or division wells and corresponding processing and imaging wells but preferably have at least three wells for a zero-growth reference specimen, and differential growth analysis of at least two separate therapeutic agents. In some embodiments, testing devices comprise at least eight or even sixteen wells.

By counting a number of species-specifically labeled cells present in each specimen portion after differential growth in the presence of various antimicrobial agents, the effect of each therapeutic agent on the specific species may be determined. By determining which antimicrobial agents best inhibited growth, an effective therapy can be determined to treat the patient's infection.

Antimicrobial selection may be random in cases where the bacteria or target cell in the specimen is unknown and a large number of wells and large amount of specimen are available to permit expansive random testing. Preferably, the bacteria or other target cell has already been identified and the various antimicrobials have been selected accordingly as, for example, antimicrobials commonly used to treat the identified bacteria. Each division well may contain a single antimicrobial agent or a unique combination of antimicrobial agents to assess combined effects on target cell growth. Different antimicrobial agents at different concentrations may be combined with the specimen portions or aliquots in different division wells and some division wells may be used for replicating treatment with the identical antimicrobial agents to strengthen results. Specimen portions or aliquots in some division wells may not be combined with antimicrobial agents to quantify uninhibited growth and/or to detect growth inhibition due to either non-antimicrobial inferences or reagent instability.

Figure 4:
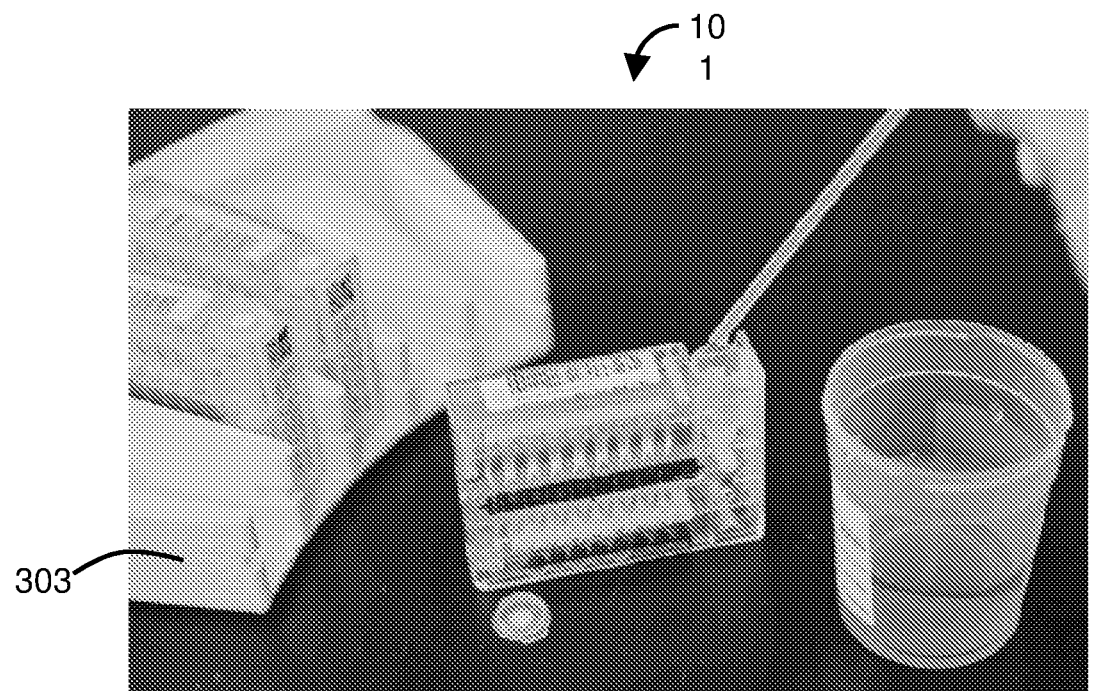
FIG. 4 shows transferring a specimen into the cartridge.

FIG. 4 shows transferring a portion of a specimen into a cartridge 101. Initially, the loading tray 303 may be carried away from the instrument 201 and set on a bench top. To use the cartridge 101, a specimen is placed in the specimen well 103 of the cartridge 101. This may be done by pipette from a specimen collection device, such as a specimen collection container, a swab, etc. The cartridge 101 may then be placed into the loading tray 303.

Figure 5:
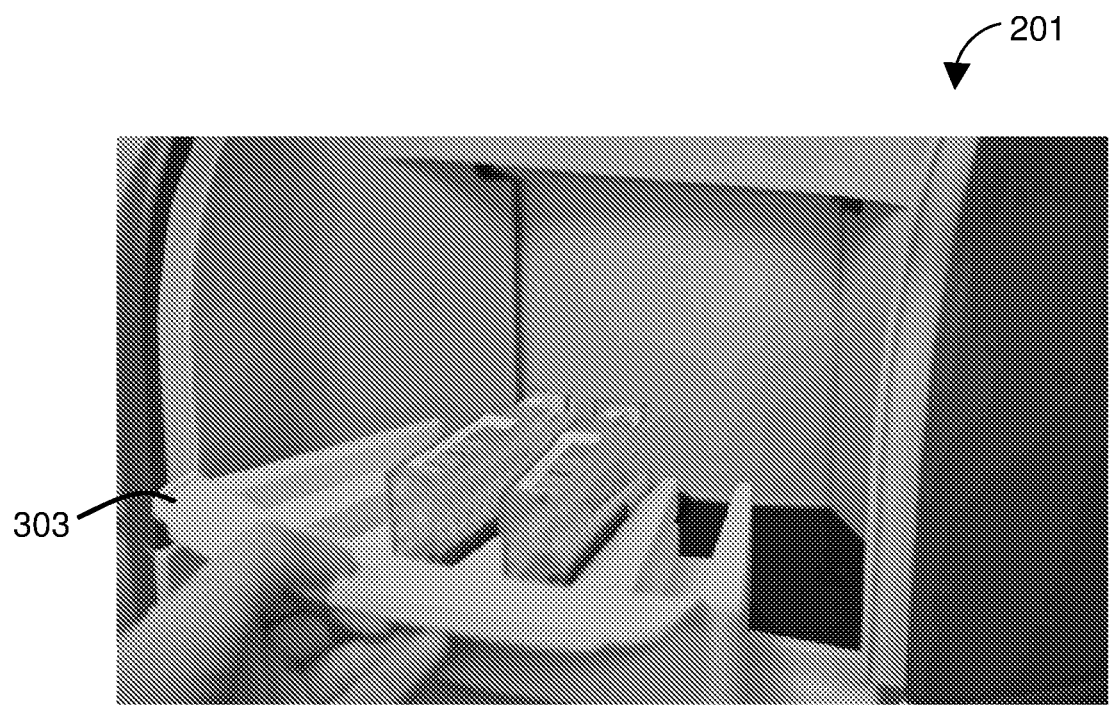
FIG. 5 shows a loading tray of the instrument.

FIG. 5 shows a user loading the loading tray 303 into the instrument 201 for use of the cartridge 101. Preferably, the cartridge 101 is loaded into the instrument 201 for analyzing the specimen. After the cartridge 101 is placed in the instrument, a pneumatic or similar force may be used to divide the specimen from the specimen well 103 into the division wells 105 through the channels 213.

The specimen may be mixed with an amount of growth media within the cartridge 101 at any point between introduction and incubation of a specimen. The incubation 115 step may last less than about 30 minutes, 1 hour, 2 hours, 3, hours, 4 hours, 5 hours, 6 hours, 12 hours, or 24 hours or more but is preferably about 4 hours to allow for measurable differential growth of the target cells or microbes in the specimen 105.

After incubation 115, the incubated portions 117 can be exposed to, for example, magnetic tags and detectable labels that can form complexes with 119 the specific target cell in the specimen portions for imaging 123. The labelled target 121 complex can then be imaged 123 in the portions and the images 125 can be analyzed (manually or by computing device) to quantify the amount of labelled target 121 present in each portion.

By comparing the quantity of target cells or microbes in portions that had been incubated in the presence of various antimicrobial agents, one can determine which of those agents inhibited growth. Comparison preferably includes a target cell quantity from a "time zero" growth reference portion that has been divided off of the original specimen, processed, and imaged without incubation.

Target microbes and cells contemplated for testing using systems and methods of the invention include viruses, bacteria or fungal cells or human cells such as cancer cells or β cells. In the case of bacterial targets, for example, specimens can be incubated in the presence of various antibacterial agents and the effects of those agents on target bacterial growth in the specimen can be analyzed to determine effectiveness. The systems and methods described herein can equally be applied to measuring cytotoxic effects of chemotherapeutic agents on cancer cells or to measure the effectiveness of various antiviral agents on viral load in a specimen. The only changes that may be required across various target cells and microbes are the target specific binding molecules (e.g., bacterial cell surface-specific antibodies, viral-specific oligonucleotide probes, or cell specific dyes), the treatments being tested (e.g., antivirals, antibacterial agents, or cancer therapies), incubation times, and, in some cases, the characteristic being analyzed in image analysis (e.g., CFU quantification, viral load, or cell number, morphology, or function).

A specimen may be directly inserted into the receiving well 103. The pneumatic port 117 may be opened to apply pressure or vacuum to distribute the specimen to the wells within the cartridge 101. The specimen may first be distributed from the specimen well 103 to the division wells 105 and held there by sliding valve 107 during incubation and released to the reagent wells 109 for labelling and then to the imaging wells 111 for imaging. The fluidics module of the instrument may interface with the cartridge to control the valve movement in coordination with specimen and reagent distribution according to the requirements of a particular assay.

Figure 6:
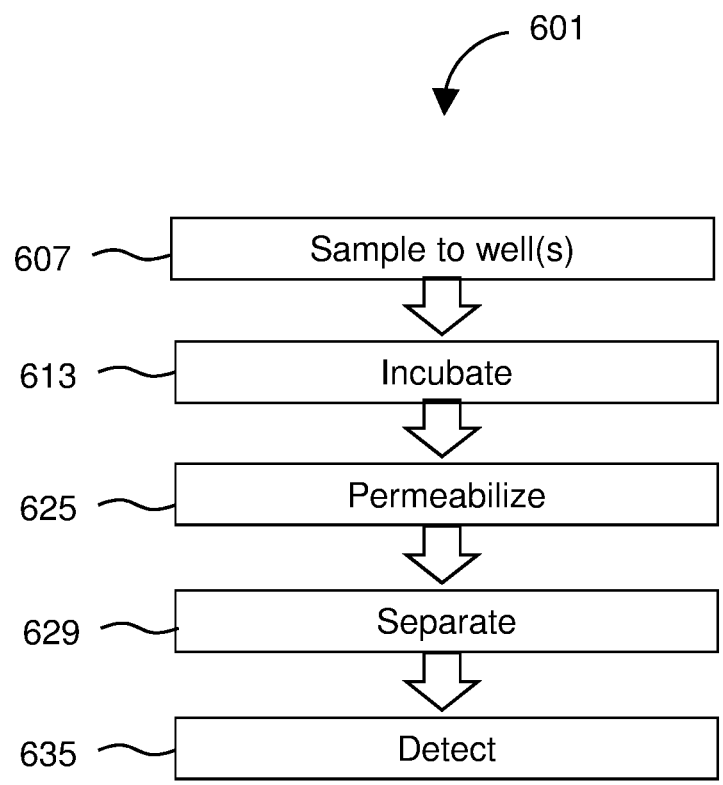
FIG. 6 diagrams a method for identifying a microorganism.

FIG. 6 diagrams an exemplary method 601 of the invention. The method 601 preferably includes obtaining a specimen from a patient. The specimen can include a bodily specimen from a patient such as blood or a portion thereof (e.g., plasma or serum), urine, sputum, cerebrospinal fluid, stool, wound, or any other specimen obtained from the human body. In certain embodiments, non-medical specimens may be tested including, but not limited to veterinary, environmental, agricultural, and food specimens. The specimen may be delivered 607 or introduced directly into a collection tube, well or reservoir of a cartridge without requiring prior target cell purification. For example, a urine specimen, direct from a patient may be pipetted into an analytical cartridge without the need for colony purification or specimen preparation including, up-front mixing with reagents, target purification, treatment to remove components of the specimen, centrifugation, biochemical enrichment, or other treatments. Once obtained, the specimen is introduced 607 into an analytical cartridge (e.g., device). The specimen can contain biological detritus and other material. The method 601 includes incubating 613 the specimen with labels that bind only to one species of microorganism, i.e., a label that is specific for the target species. Optionally, a permeabilization agent may be introduced to permeabilize 625 cells in the specimen. The method 601 further includes separating 629 cells in the specimen from unbound labels and detecting 635 bound labels among the cells to show the presence of the species in the specimen. Note that in certain embodiments, the label is species specific and cells at large are separated from unbound probe.

The disclosure provides cartridges that are pre-loaded with reagents for performing fluorescent in situ hybridization (FISH) that can be performed at constant physiological temperature. Cartridges of the disclosure may be used for probing and detecting genetic content of cells and organisms within specimens without the requirement of subjecting the specimen to extremes of heat that may otherwise lyse cells of interest, denature proteins, unduly influence the relative, differential growth rates of different cells or organisms, or otherwise have adverse effects on chemical constituents and process steps of the specimen analysis protocol. One important feature of being able to perform FISH at constant physiological temperature is that specimens can be fluorescently probed and imaged within one cartridge while loaded on an instruments with other cartridges that are also, simultaneously being used to perform other biological assays that are optimal at physiological temperature. Cartridges of the disclosure include all the hardware, tooling, and reagents to perform microbial identification or antibiotic susceptibility testing using FISH at physiological temperature. Where some of the test steps include incubation to promote growth of organisms of interest, the ability to perform fluorescent probe hybridization simultaneously within other wells of the same cartridge without heating significantly above physiological temperatures allows the multiple steps to all proceed at their own times and paces including chronologically overlapping or even simultaneously. Moreover, where fluorescent probe hybridization is performed within a well within a cartridge that is loaded and operated within an analytical instrument, the instrument can multiplex cartridges, routing and scheduling multiple different cartridges to different test steps while maintaining a constant temperature within the instrument.

Preferred embodiments of the disclosure provide reagent-loaded cartridges for performing a fluorescent probe hybridization protocol that operate at physiological temperature. Generally, physiological temperature refers to bodily temperature of an organism such as an animal. The process steps, molecular species, and chemical reagents disclosed herein are useful for hybridizing fluorescent probes to nucleic acids within cells, and imaging those probes, at physiological temperature without lysing the cells. There is flexibility as to what temperatures the specimen is exposed to and the steps are performed at. Methods of the disclosure may be usefully performed at temperatures that fluctuate but do not exceed 45 degrees C. and even work at temperatures that do not exceed 40 degrees C. Methods and compositions of the disclosure are useful and functional when used at temperatures within a range of 36 to 39 degrees C., for example. In fact, methods of the disclosure may be implemented on instruments that maintain temperatures essentially at, or at about, human body temperature, i.e., about 37 degrees C. for a healthy human, 38 degrees C. for a human with a fever, or 36 degrees C. for some nocturnal human temperature fluctuation patterns. To say "about" is to mean within a decimal point or so. That is, 36.3 is about 36.5 and 37.7 counts as being about 37.5. What is important is to understand that the FISH protocol disclosed herein can be performed entirely at about physiological temperature of a body, such as of a mammal, and preferably of a human.

One benefit of the temperature range permitted by the methods is that microorganisms in clinical specimens can be studied under temperature conditions that approximate the in vivo conditions, thus avoiding an effect by which heat promotes the differential growth of one organism that wouldn't otherwise be clinically significant while suppressing the appearance of another. For example, if a person is suffering from a urinary tract infection in which the primary underlying irritant is *Proteus mirabilis*, and a clinical test is performed that involves heating a urine specimen, if the heat promotes growth of an otherwise insignificant few cells of

*Streptococcus agalactiae*, then that clinical test will not direct the clinician to the appropriate treatment. That test would miss-identify the microorganism that needs to be treated. To avoid such an outcome, the disclosure provides compositions, devices, and methods that allow for performing FISH at constant physiological temperature, which compositions, devices, and methods have particular utility in identifying a microorganism.

Figure 7:
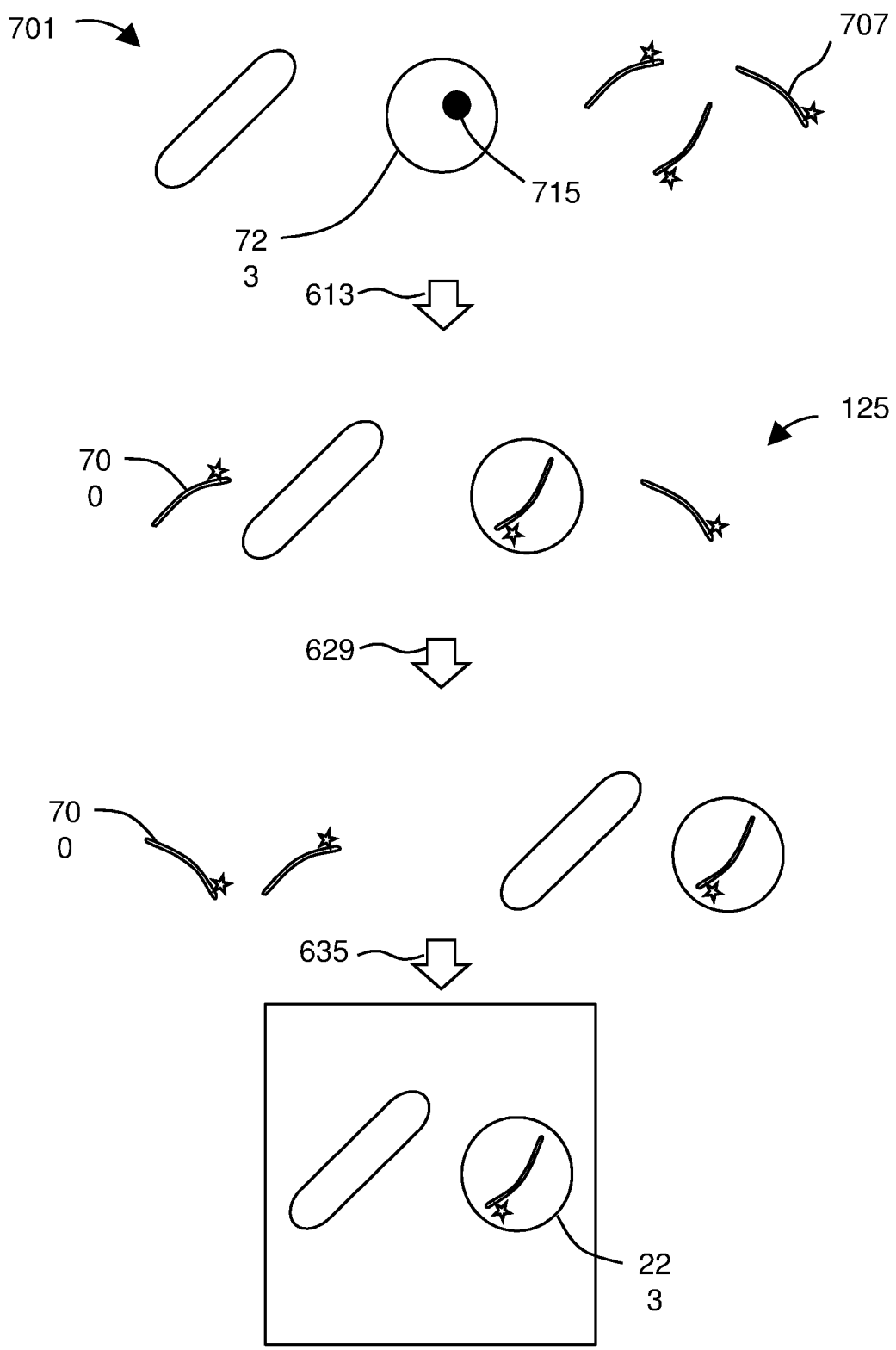
FIG. 7 shows steps of a microbial identification method.

FIG. 7 shows how steps of the method 601 proceed. A specimen may include a mixture of cells 701 with one or more target cells 723 there among the cells 701. The cells are incubated with the probes 707. Preferably, a permeabilization agent is used to permeabilize 625 the cells 701 including the target cell 723, allowing the labels to diffuse therein. In preferred embodiments, the labels 707 specifically bind to a nucleic acid 715 target within the target cell 723. The cells are separated 629 from the labels, and the portion that includes the cells is examined to detect 635 label. As discussed herein, the labels are preferably probes such as fluorescently labelled oligonucleotides (e.g., about 10 to 18 bases in length). The cells may be separated 629 from unbound probes 707 by using magnetic particles that bind to the cells 701 and pulling the cells, using a magnetic field B, through a density medium that causes the unbound probes to get left behind. The detection 625 may be performed by imaging (e.g., with a microscope) the separated cells. The cells may be imaged within or under the density medium and the density medium, also referred to as a dye-cushion, may further include a dye or pigment to prevent light from unbound probes from reaching the imaging device such that any light spots in the image show the presence of target cells 723 having fluorescently-labelled oligonucleotide probes hybridized to target nucleic acid 715 there.

Figure 8:
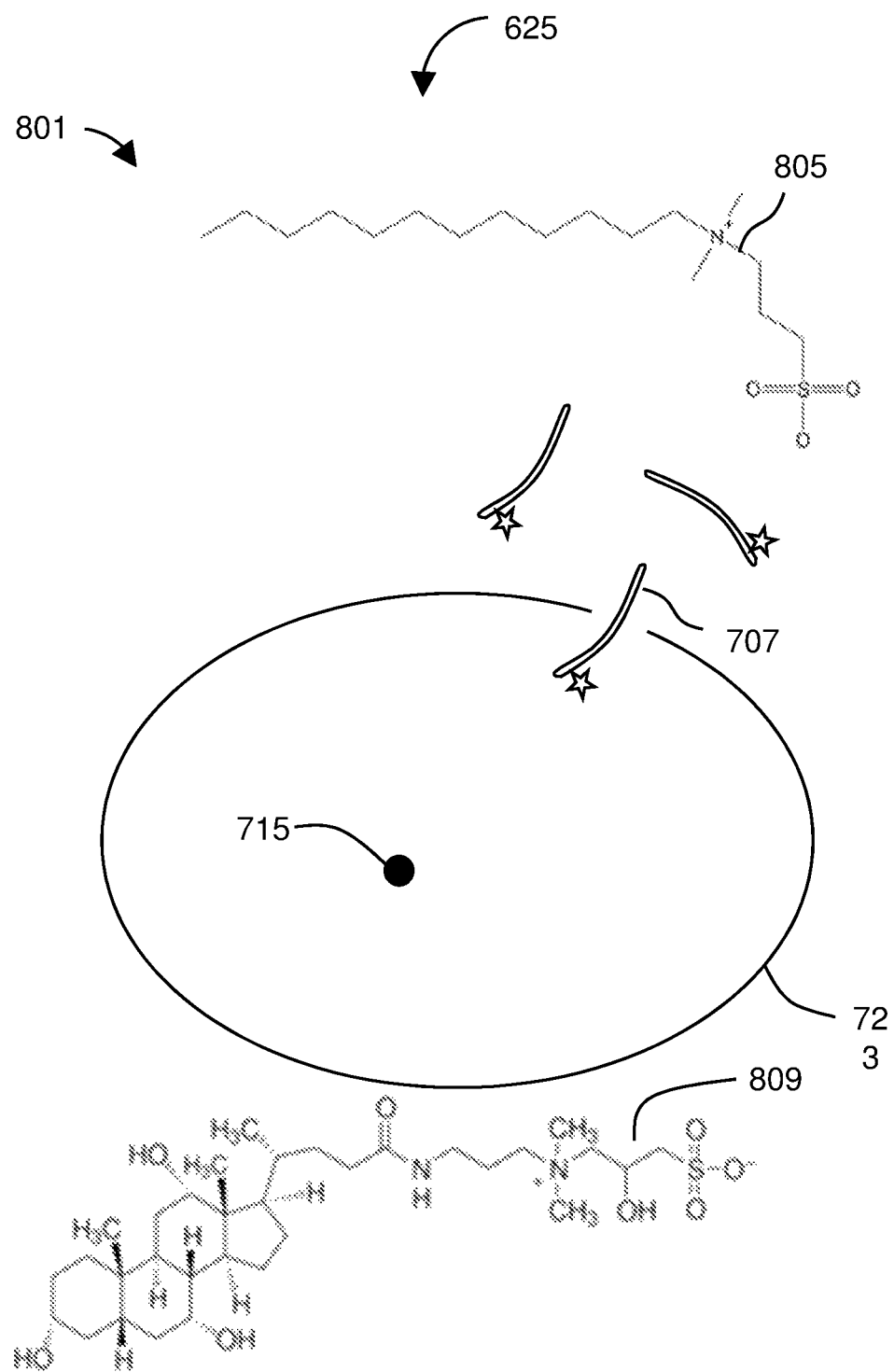
FIG. 8 illustrates a permeabilization agent.

FIG. 8 illustrates a permeabilization agent 801 in use to permeabilize 625 cells 701 according to methods herein. In the depicted embodiment, the agent 801 includes a mixture of 3-([3-cholamidopropyl]dimethylammonio)-2-hydroxy-1-propanesulfonate (sold under the name CHAPSO by Millipore Sigma, St. Louis, MO) and sulfobetaine 3-12 (available as SB3-12 from B-Biosciences, St. Louis, MO). These detergents permeabilize 625 the cells 701, allowing the probes 707 to enter to bind to microbial target nucleic acid 715. Any suitable probe may be used with methods herein. The incubating step may include exposing the cells to reagents that permeabilize the cells, thus allowing the labels to enter the cells and bind to targets therein.

When a specimen comprising cells 701 is delivered into the reagent well 109, the permeabilization agent 801 promotes entry of the probe 707 into a microbe (e.g., target cell 723) while the specimen is maintained at temperatures beneath about 40 degrees C. The probe 707 may comprise a fluorescently labeled oligonucleotide 901 complementary to a segment of ribosomal RNA of a specific bacterial species. Preferably the permeabilization agent 801 comprises one or more detergents (e.g., CHAPSO, SB3-12, TRITON X100).

As shown, the probe 707 and the permeabilization agent 801 are provided in lyophilized beads 141 that are rehydrated and dissolved by delivery of the specimen into the incubation well.

Thus the method includes introducing a species-specific label (such as a fluorescently labeled oligonucleotide complementary to a RNA in the target cell) into a specimen, optionally permeabilizing the cells using an agent (such as a detergent such as 3-([3-Cholamidopropyl]dimethylammonio)-2-hydroxy-1-propanesulfonate (aka CHAPSO); sulfobetaine 3-12 (aka sb3-12); Polyethylene glycol p-(1,1,3,3-tetramethylbutyl)-phenyl ether (aka TRITON X100); nonyl phenoxypolyethoxylethanol (aka NP-40); others; or some combination thereof); separating unbound label from cells in the specimen; and imaging the cells to detect the label. The method is useful for testing specimens that include microbes such as a clinical specimens (e.g., to test for or detect the causative agent of UTI). When performed according to the disclosure, the method provides for FISH that can be at any desired temperature, such as a variable or constant physiological temperature.

Fluorescence in situ hybridization has been proposed for applications such as gene mapping and diagnosis of chromosomal aberrations. See Nature Methods 2(3):237 (2005). Those protocols have involved the hybridization of biotin- or digoxigenin-labeled probes to denatured chromosomal DNA and detection of the probes using fluorochrome-conjugated reagents. Generally, those protocols require denaturing steps in which the probes themselves and the target DNA are separately denatured at 70 to 80 degrees C. before probe hybridization, incubation, and visualization. Methods of the disclosure do not require that heating step and do not require any portion of the specimen or reagents to be heated about 70 degrees C. or even above 40 degrees C. One important feature providing for the temperature ranges allowable for methods of the disclosure involves the use of a permeabilization agent (rather than heat) to deliver the probes 707 into the cells 701.

Probes suitable for use with methods herein may include nucleic acid probes that include DNA, RNA, peptide nucleic acids, modified bases, conformationally restricted nucleic acids, or combinations thereof. Suitable probes may include antibodies or antigens, binding molecules such as mannose-binding lectin or other collectins. Molecular or chemical structures and compositions such as polyethylene glycol, dyes, stains, intercalating dyes, crystal violet, safranin/carbol fuchsin, or any other composition or structure that may bind specifically to targets. In a preferred embodiment, the probes 707 include oligonucleotides.

Figure 9:
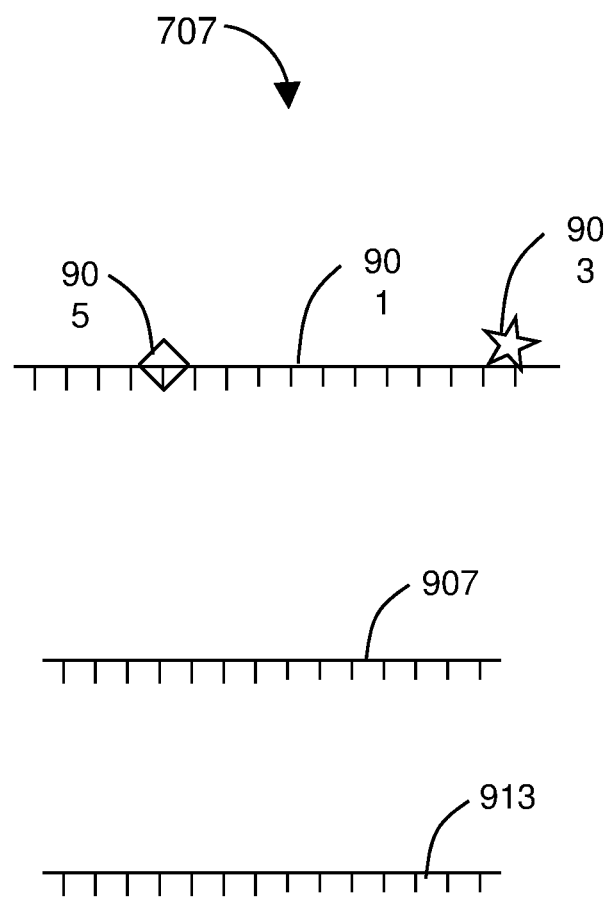
FIG. 9 shows a species-specific probe.

FIG. 9 shows a probe 707 according to preferred embodiments. In the preferred embodiment, the probe 707 includes an oligonucleotide 901 with a length between about 8 and 22 bases long, preferably between about 10 and 22 bases long. The probes preferably include DNA bases to avoid autocatalysis catalyzed by nucleophilic attack by free electrons of a 2' hydroxyl group (although RNA bases may optionally be used or included). The probes preferably have a melting temperature of about 45 degrees C., e.g., between 40 and 50. Each oligonucleotide 901 is preferably labeled with at least one fluorophore 403. In a preferred embodiment, each oligonucleotide 901 also includes one to a few conformationally restricted nucleotides 905 (sometimes variously referred to as locked nucleic acids or bridged nucleic acids). Thus, the probes 707 include fluorescently-labelled DNA oligos 901 with optional conformationally-restricted nucleic acids 905 and more preferably also include at least one helper probe 907, optionally with a second helper probe 913, as well.

In certain embodiments, the labels or probes 707 comprise probe oligonucleotides 901 that are complementary to microbial RNAs. For probes oligos 901 that are complementary to microbial ribosomal RNA, the oligos 901 preferably have length generally between 10 and 18 nt. Tm is approximately 45 degrees C. They are designed by looking at the structure of rRNA. The helper probes disrupt the ribosomal structure. One reason to target rRNA is that copy number is very high. There are thousands of copies per cell, so one gets a de facto signal amplification. Thus, preferred embodiments of the method 101 use reagents that include one or more detergents (e.g., one or more of CHAPSO and SB3-12) and use probe oligonucleotides to target microbial ribosomal RNAs. Specifically, the probes are fluorescently-labeled probe oligonucleotides complementary to a segment of ribosomal RNA exclusive to a target species of interest. Preferably, the fluorescently-labeled probe oligonucleotide is between 10 and 18 bases in length and includes at least one conformationally-restricted nucleic acid. Also preferably, the probes oligos 901 are provided along with at least one helper probe 907 and optionally a second helper probe 913.

Figure 10:
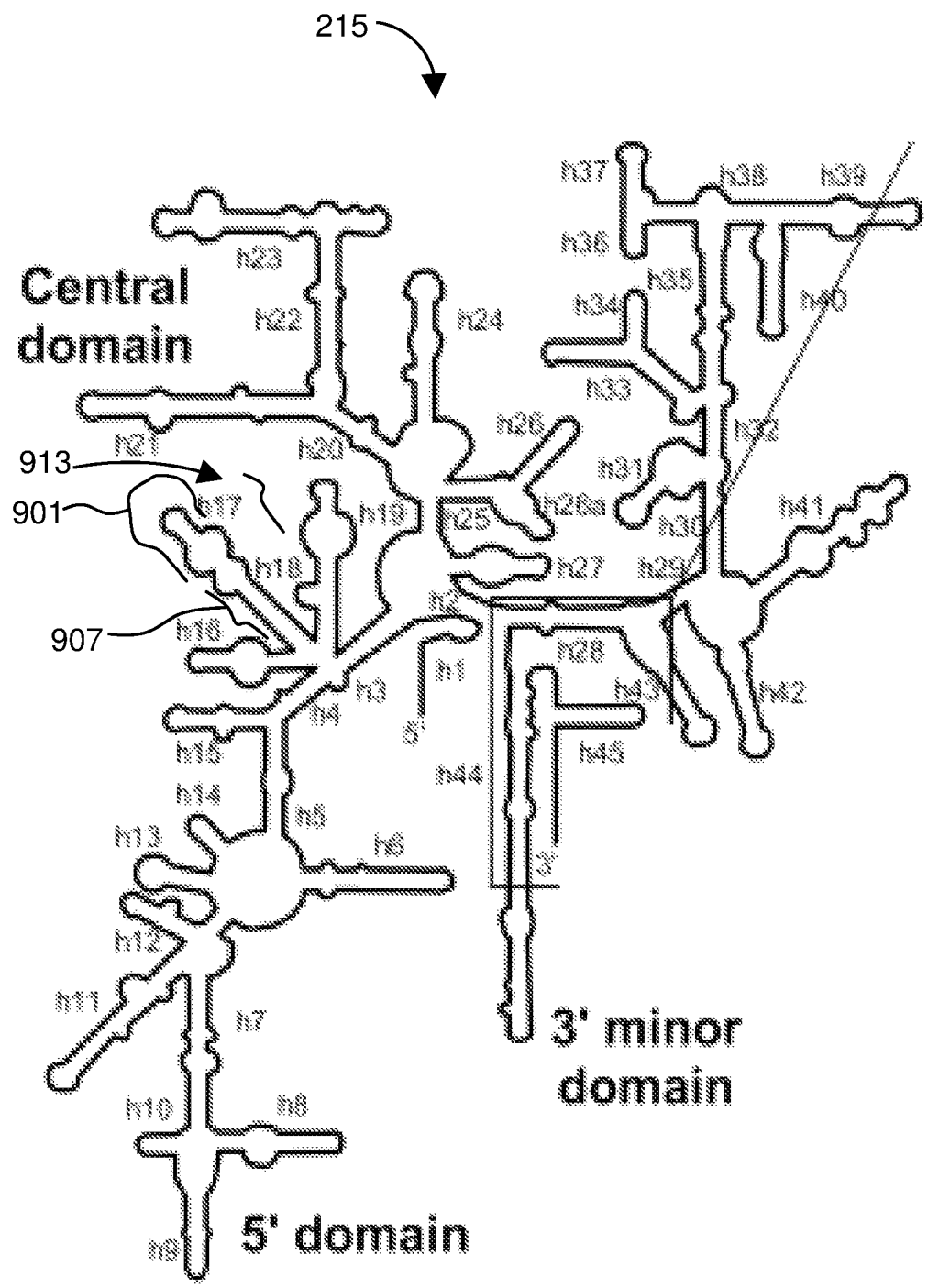
FIG. 10 shows a secondary structure of an rRNA.

FIG. 10 shows a secondary structure of a small-subunit ribosomal ribonucleic acid (ssrRNA) 215, specifically, *E. coli* 16s rRNA. While other bacteria will not have exactly the same 16S rRNA as *E. coli*, the secondary structure of ribosomes is highly conserved (see Woese & Fox, 1977) so most of the depicted helices will have easily identifiable homologues in other bacteria. Preferred targets within 16S rRNA include: h44; h27; h16; h17; h18; h25; h27; h9; h10; h13; h23; h19; and h43. See Fuchs, 2000, Unlabeled helper oligonucleotides increase the in situ accessibility to 16S rRNA of fluorescently labeled oligonucleotide probes, Appl Environ Microbiol 66(8):3603-7, incorporated by reference. Having settled on a provisional probe design, one may test the specificity and inclusivity using an online tool such as SILVA, "high quality ribosomal RNA databases", available as a website supported by the German network for bioinformatics infrastructure. See Pruesse, 2007, SILVA: a comprehensive online resource for quality checked and aligned ribosomal RNA sequence data compatible with ARB, Nucl Acids Res 35:7188-7196 and Quast, 2013, The SILVA ribosomal RNA gene database project: improved data processing and web-based tools, Nucl Acids Res 41 (D1):D590-D596, both incorporated by reference. The probe oligo 901 preferably includes at least one bridged or locked nucleic acid. For the helper probes 907, 913 it is permissible for them to have lower specificity (see SILVA tools) than the oligo 901. The helper probes 907, 913 may preferably be about 20 nt in length.

The secondary structure of ribosomal RNA is helpful to illustrate the principles of probe design and the design and role of the helper probes. Preferably, where the oligo 901 hybridizes to a segment of microbial ribosomal RNA, the helper probe 907 and any optional second helper probe 913 are oligonucleotides that bind to the ribosomal RNA at a location within 1 to 30 bases from the segment where the fluorescently-labeled probe oligonucleotide binds. For example, the helper probes may hybridize to the microbial ribosomal RNA immediately upstream and downstream of the hybridized probe oligo 901. Without helper probes 907, 913 target site inaccessibility may present issues for hybridization of 16S rRNA with oligonucleotide probes. Here, unlabeled oligonucleotides (helpers 907, 913) that bind adjacent to the probe target site are used to increase weak probe hybridization signals. Helper probes may be used to enhance the fluorescence signal. See Fuchs, 2000, Unlabeled helper oligonucleotides increase the in situ accessibility to 16S rRNA of fluorescently labeled oligonucleotide probes, Appl Environ Microbiol 66(8):3603-7, incorporated by reference.

Considerations in picking probe target sequences include determining theoretical specificity and inclusivity of FISH probes, optimizing location of LNA bases, and designing helper probes for specific probes. Many pathogen targets already have FISH probes that have been shown to be specific that may be used (as published, or shortened to accommodate temperatures of this disclosure). One find many of them in probeBase, an online resource for rRNA-targeted oligonucleotide probes. See Loy, 2007, probeBase—an online resource for rRNA-targeted oligonucleotide probes: new features 2007, Nucleic Acids Res 35: D800-D804 and Loy, 2003, probeBase—an online resource for rRNA-targeted oligonucleotide probes, Nucleic Acids Res 31:514-516, both incorporated by reference. Note that FISH is usually done at much higher temperatures, so probes from those sources may need to be shortened or modified for the method 101. One may also use the on-line tool "DECIPHER" to input a genus, and have the DECIPHER tool suggest regions on the 16S that will be specific for the genus. See Wright, 2014, Automated Design of Probes for rRNA-Targeted Fluorescence In Situ Hybridization Reveals the Advantages of Using Dual Probes for Accurate Identification, Applied Env Microbiology, incorporated by reference.

Whether starting with an online tool, or designing a probe by hand, it may be valuable to examine alignments (e.g., probe to 16S rRNA pairwise sequence alignment as made by ClustalW) and select regions where the target sequences (preferably have multiple) match, but other pathogens do not. It may be valuable to examine Inclusivity (coverage) and specificity. Tm should be over 40 degrees C. (since methods of the disclosure operate at 35 degrees C.). Higher melting temperatures may be preferable, but how high you can go depends on how many mismatches there are to off-target sequences. Probe oligos according to the disclosure have melting temperature between 40 and 60 degrees C. (e.g., when 10 to 18 nt-length, DNA probes, complementary to helix h17 in 16S rRNA with 2 or 3 LNA bases). Mismatches at the center are more discriminating than mismatches at the end. Order of strength of mismatches: (least bad to most bad): G/T, G/G, A/G, A/A, T/T, A/C, T/C, C/C. Preferably, pick a region of the rRNA that is more accessible.

The probes 707 are used to label specific target microbes. Another part of the method 601 involves separating 629 cells 701 from unbound probes. Any suitable method or technique may be used to separate 629 the cells 701 from unbound probes. Suitable techniques for separating cells 701 from unbound probes includes centrifugation, flow cytometry, fluorescent activated cell sorting, a column separation, digestion of unbound probe via one or more nucleases, others, or combinations thereof. In a preferred embodiment, the cells 701 are separated 629 from unbound probe 707 by the use of magnetic particles. For example, the incubation 613 step may include exposing the cells to magnetic particles that bind to surfaces of the cells.

Any suitable magnetic particle that binds to surfaces of the cells may be used including for example magnetic particles bound to an antibody, a collagen-containing C-type lection (aka collectin such as mannose-binding lectin), or a chemical group that binds bacterial cells. In certain preferred embodiments, the magnetic particles preferably include PAA.

Figure 11:
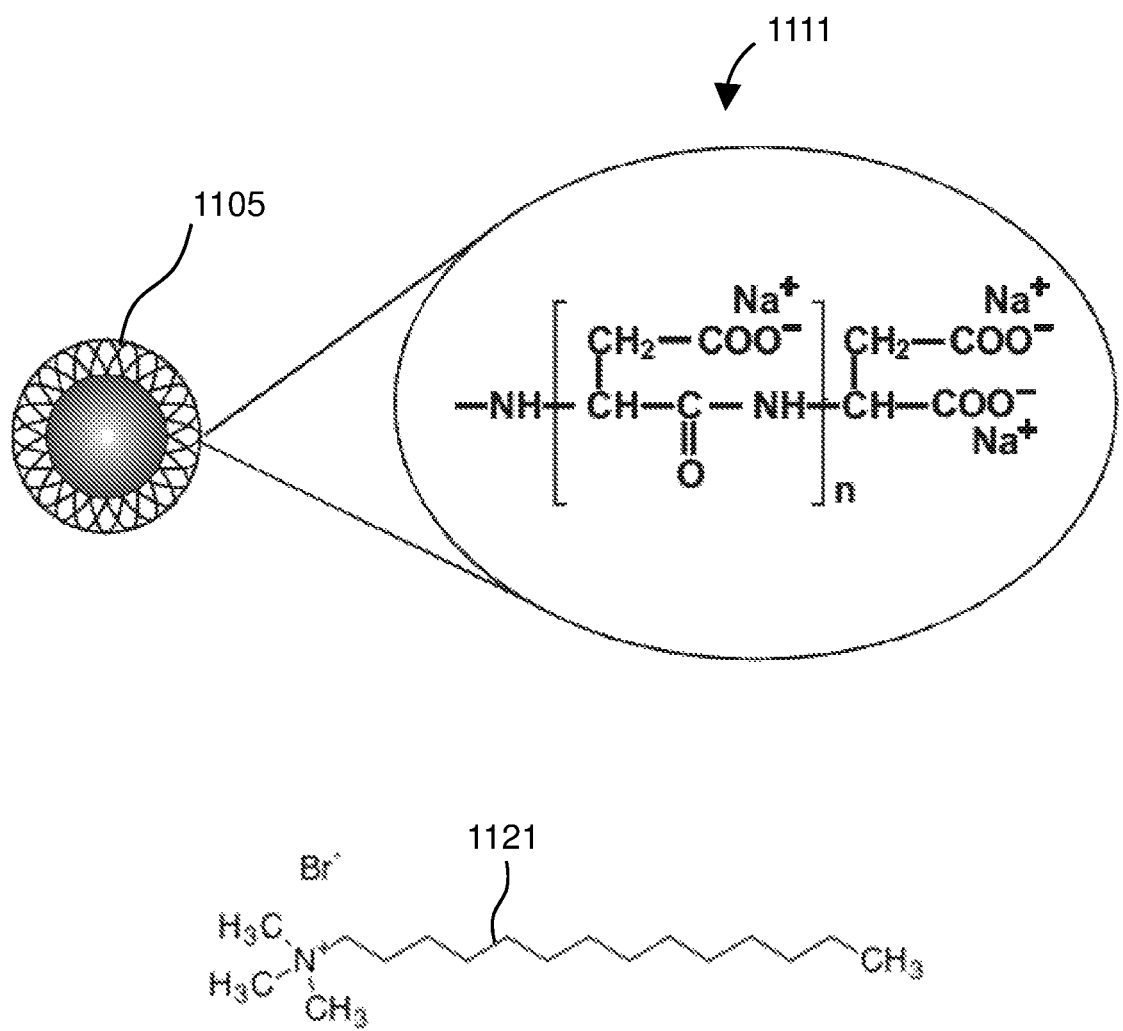
FIG. 11 shows a microbe-binding magnetic particle.

FIG. 11 shows a magnetic particle 1105 that include a chemical group 1111 that binds to bacterial cell surfaces. The chemical group 1111 may include, for example, diethylamine ethyl-starch; dextran-sulfate; polyaspartic acid; polyacrylic acid; polystyrenesulfonate; poly-diallyldimethylamin; or a combination thereof. As shown, magnetic particle 1105 includes a polyaspartic acid chemical group 1111. This particle is sold as fluidMAG-PAA by chemicell GmbH (Berlin, Germany). The fluidMAG-PAA particle is a polyaspartic acid that binds to the surface of bacteria. The cells may be exposed to the magnetic particles 1105 in the presence of a compound 1121 that promotes the binding of the chemical group 1111 to the bacterial cell surfaces.

To effectively bind the particles 1105 to the cells 701 it may be helpful to include an agent 1121 that promotes the binding of PAA to cell surfaces. Any suitable agent 1121 may be included to promote binding. For example, in some embodiments, the agent includes a mixture of different quaternary ammonium salts including cetrimonium bromide (CTAB), also known as cetrimide. Cetrimide promotes binding of PAA to cell surfaces for magnetic capture, and solves particular trouble with Gram+organisms. It may be found that Gram−organisms bind to the fluidMAG-PAA without trouble. Where the target microorganism of interest is Gram+, it may be preferable to include the agent 1121 (e.g., cetrimide). Thus, in preferred embodiments of the method 601, the labels include fluorescently-labeled probe oligonucleotides 901 complementary to ribosomal RNA 215 exclusive to the species; the incubating 613 step also includes exposing the cells to magnetic particles 1105 that bind to surfaces of bacterial cells 701; and the separating 629 step includes applying a magnetic field B to the cells 701.

Figure 12:
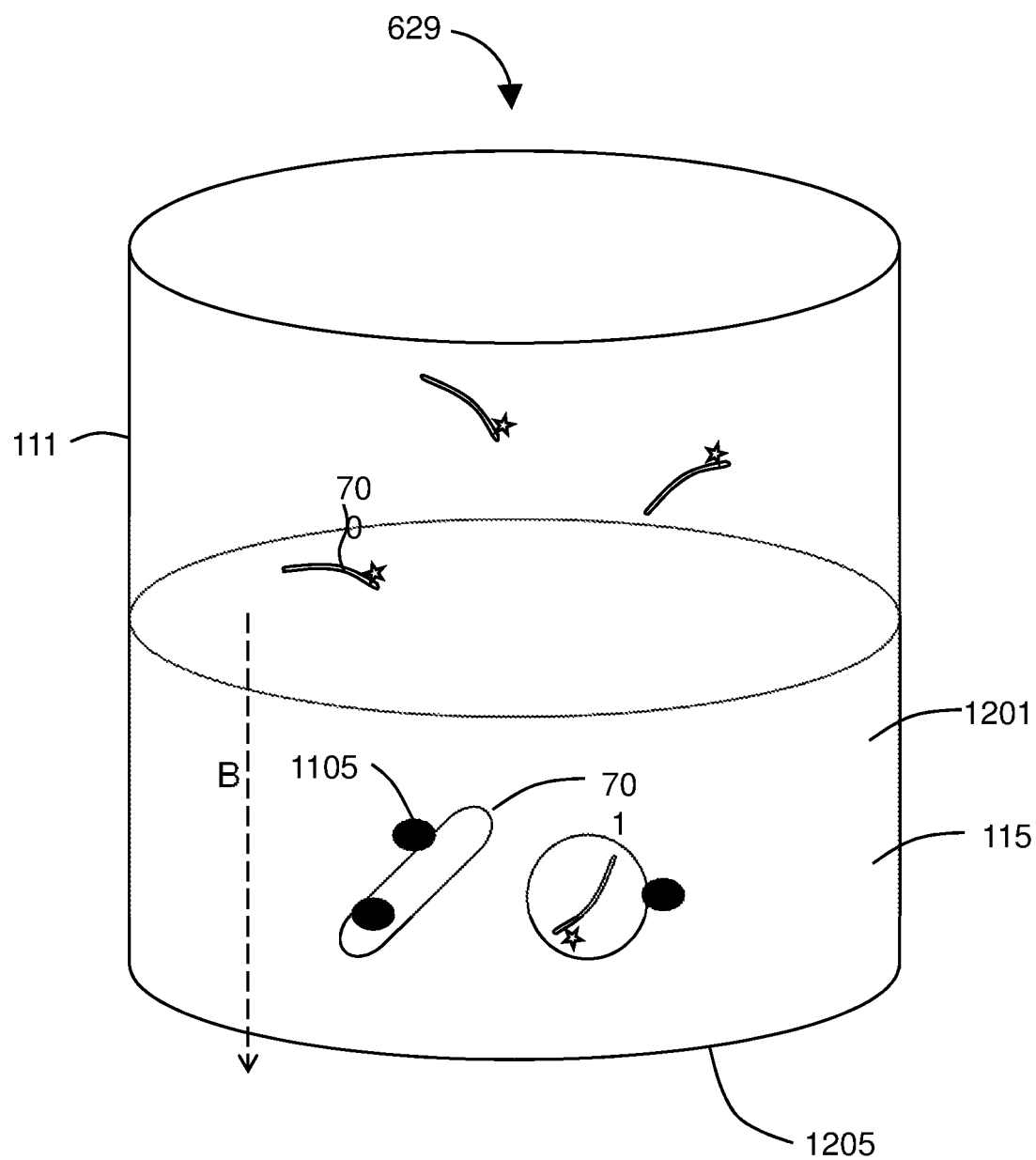
FIG. 12 shows magnetic particle bound cells being separated from unbound probe.

FIG. 12 shows magnetic particle 1105-bound cells 701 being separated 629 from unbound probes 700 by pulling the cells 701 through a density gradient medium 1201 using an applied magnetic field B. The density medium 1201 may be supplied within a tube or imaging well 111 (and may include a dye to provide a "dye-cushion 115") as pictured, such that the separating 629 may include distributing magnetic particle 1105-bound cells 701 over the dye-cushion 115 and using a magnetic field B to pull bound cells 701 through the dye-cushion 115 and onto an imaging surface 1205, leaving the unbound probes 700 on the surface of the dye-cushion 115. The detecting step 635 may then include imaging the imaging surface 1205 with a fluorescence microscope and all of the steps may be performed at temperatures below 40 degrees C. Preferably the steps are performed at temperatures between about 36 and 39 degrees C. Thus, as shown the incubating 613 step includes exposing the cells to magnetic particles 1105 that bind to surfaces of bacterial cells and the separating step 629 includes using a magnetic field B to pull bound cells away from the unbound labels. Preferably, the separating step 629 includes distributing magnetic particle bound cells over a surface of a dye-cushion 115, and using the magnetic field to pull bound cells through dye-cushion 115 and onto an imaging surface 1205, leaving the unbound labels on the surface of the dye-cushion.

As discussed, embodiments of the separation 629 make use of a density gradient medium 1201 that may include a dye to provide a dye-cushion. Thus, a dye-cushion 115 is a material that includes a density gradient medium that further includes a dye.

The dye-cushion 115 may be, for example, a density gradient medium (such as a solution of iodixanol or polyvinylpyrrolidone-coated colloidal silica particles, optionally dried or lyophilized prior to exposure to the specimen) that further includes a dye that absorbs light from unbound probes 700. The cushion may include a high density material for excluding unselected components of the reaction from the detection zone. The cushion is a layer (liquid or dried or lyophilized) generally of higher density than the reaction components. The cushion can include various density agents singly or in combination (and at various concentrations) including for example, sucrose, diatrizoate, iodixanol (aka OptiPrep), NaCl, CsCl, Percoll, or albumin. Embodiments can also incorporate other density agents, such as other commonly used density agents such as iodixanol, sodium diatrizoate, sodium, sucrose, and other sugars, oligosaccharides, synthetic polymers (e.g., Ficoll), and salts such as cesium chloride, potassium bromide, and others. Embodiments may use dyes to match different signaling character and moieties in use. For example the dye Toluidine Blue O could be used with the fluorescent label Texas Red (sulforhodamine). One embodiment uses a 65 µL aliquot of dye-cushion reagent, which is 2 mg/mL Chromotrope R2 and 10% v/v OptiPrep (a 60% w/v solution of iodixanol) plus 5% w/v trehalose pipetted into assay wells. The dye-cushion may be 15% OptiPrep and 5 mg/mL Chromotrope R2 pre-aliquoted into the imaging wells 111 of a cartridge 101.

With reference to the imaging well 111, the dye-cushion 115 can be formed by preparing a solution of iodixanol or polyvinylpyrrolidone, including any optional dye, and drying or lyophilizing the solution there in the imaging well 111 to form the dye-cushion 915. The dye-cushion 915 will then be essentially a solid (e.g., dried, e.g., the imaging well 111 can be stored in any orientation including upside-down until use). When a liquid specimen is delivered into the imaging well 111, the liquid rehydrates the dye-cushion 115. In fact, the reagents disclosed and discussed throughout herein for use in the method 601 may be provided in dried or lyophilized form for later use in a protocol for FISH, such as at constant physiological T. This allows the reagents to be prepared and loaded dry onto a cartridge that may then be shipped or stored and later used in methods of the disclosure.

In preferred embodiments, the cartridge 101 also includes magnetic particles 1105 that bind to bacterial cell surfaces; and a dye-cushion 115 adjacent a transparent wall that provides an imaging surface 1205. When a magnetic field is applied across the dye-cushion 115, the magnetic field pulls the magnetic particles 1105 through the dye-cushion to the transparent wall. Preferably, the magnetic particles 1105 (and any compound to promote binding 621) are also included in lyophilized beads 141. The dye-cushion 115 comprises a solution of density gradient medium 1201 that further includes a dye that absorbs light from unbound probes 700. In the depicted embodiment, the dye-cushion 115 and the transparent wall 1205 are provided in an imaging well 111 in fluidic communication with the reagent well 109. The dye-cushion 115 may be provided as a gel or in a dried or lyophilized state in the imaging well within the cartridge until wetted by specimen.

Preferably, the magnetic particles 1105 in the lyophilized beads 141 include a chemical group that binds to the bacterial cell surfaces and the cartridge further comprises a compound that promotes the binding of the chemical group to the bacterial cell surfaces. The compound that promotes binding of the chemical group to the cell surface may be cetrimide, and the chemical group may be, for example, diethylamine ethyl-starch; dextran-sulfate; polyaspartic acid; polyacrylic acid; polyglutamic acid; poly-styrenesulfonate; or poly-diallyldimethylamin.

The probe 707 may be provided, in the lyophilized beads 141, as a fluorescently labeled oligonucleotide 901 complementary to a segment of ribosomal RNA 215 of a specific bacterial species, and the beads 141 preferably also include at least one helper probe oligonucleotide that binds to the ribosomal RNA at a location within 1 to 30 bases from the segment. The fluorescently-labeled oligonucleotide 901 may be between 10 and 18 bases in length and include at least one conformationally-restricted nucleic acid for use in FISH, such as in some embodiments, which are at a constant physiological temperature.

The reagent composition, the probe, the helper probe, and the compound are provided as lyophilized beads 141 that are rehydrated and dissolved by delivery of the specimen into the cartridge 101. The dye-cushion 115 comprises a density gradient medium 1201 that further includes a dye that absorbs light from unbound probes. The dye-cushion 115 may be provided in a dried or lyophilized state in the imaging well within the cartridge until wetted by specimen. The method 601 and the cartridge 101 may be used to perform an antibiotic susceptibility test.

Figure 13:
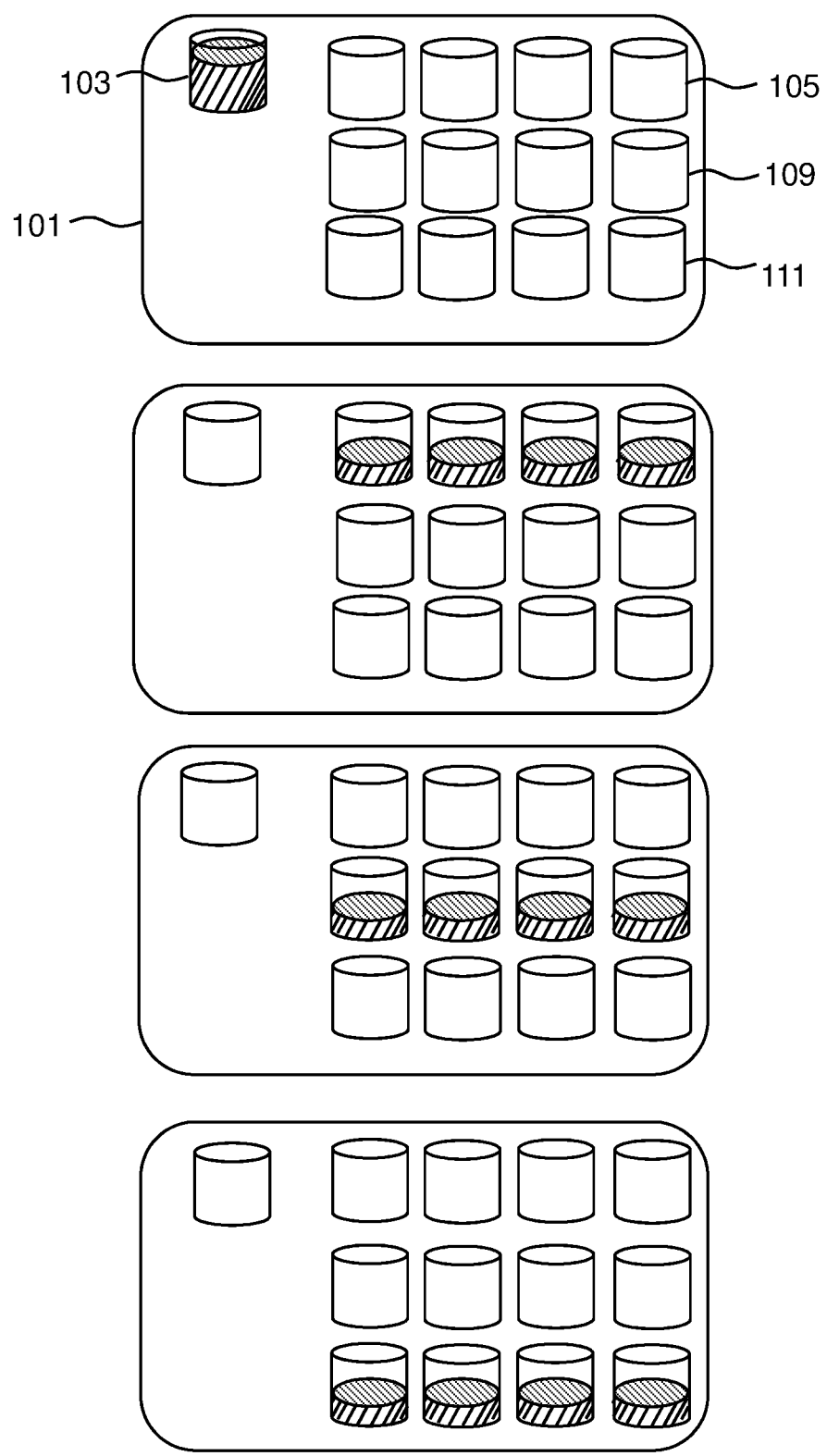
FIG. 13 diagrams a workflow for FISH at physiological temperature.

FIG. 13 diagrams a workflow in which FISH at physiological temperature is used to perform antibiotic susceptibility testing (AST). A specimen is loaded into a specimen well 103 of a cartridge 101. The division wells 105 include antibiotics, either different antibiotics or different concentrations of an antibiotic. One "channel" may include no antibiotic as a control, or to establish a baseline of growth. The cartridge is connected to a source of pneumatic pressure, a gate switch, and a fluorescent microscope or similar imaging instrument. The gate switch slides the sliding valve into a first position, the specimen well 103 is in fluid communication with the division wells 105. Pneumatic pressure is applied through a fitting and the specimen is divided among the division wells. Here, the specimen may be incubated with a plurality of antibiotics distributed across the division wells 105.

The sliding valve 107 is slid to the third position in which the division wells 105 are in fluid communication with the reagent wells 109. Pneumatic pressure is applied and the aliquots of specimen are delivered from the division wells 105 to the respective reagent wells 109. In each reagent well 109, a specimen aliquot is incubated, without exceeding 45 degrees C., with probes specific for target nucleic acid of a species of microorganism as well as with magnetic particles. The sliding valve 107 is slid to second position in which reagent wells are sealed. The specimen is delivered to the imaging wells 111 and a magnetic field is applied to separate intact cells in the specimen from unbound probes. This may be performed by sliding the cartridge onto a magnet. The field B draws the cells onto the imaging surface. Bound probes within the intact cells are detected to quantify growth of the species within each aliquot the specimen. Growth or lack thereof may be correlated back to which antibiotic was present in which division well 105. For an imaging well 111 in which no pathogen growth is detected (e.g., fluorescent microscopy shows no fluorescence), the specimen is shown to be susceptible to the antibiotic that was present in the corresponding division well 105.

A benefit of the cartridges 101 is that they are amenable to use with an instrument that interacts with the cartridge 101 to automate the steps.

Detectable labels may include fluorescent molecules, radioactive isotopes, mass tags for mass spectrometry, or chemiluminescent molecules. The detectable label may comprise a target-specific portion to preferentially bind to a target cell or microbe. The target-specific binding molecule may include for example, an antibody to a target-specific molecule or antigen or an oligonucleotide or polynucleotide probe complementary to a target-specific nucleic acid sequence. In preferred embodiments detectable labelling of microbes comprises fluorescent in situ hybridization (FISH). FISH analysis uses fluorescent probes comprising nucleic acid (or nucleic acid analog) probe moieties and fluorophore probe moieties to bind via re-association with target-specific nucleic acid sequences so that the targets can then be detected optically. For example, probes targeting target-specific 16S rRNA can be used to selectively tag and detect microorganisms. See, Volkhard, et al., 2000, Fluorescent In Situ Hybridization Allows Rapid Identification of Microorganisms in Blood Cultures, J Clin Microbiol., 38(2):830-838, incorporated herein by reference. For identification assays, a number of distinct target-specific fluorescent probes may be used to independently identify multiple distinct categories of targets in a single specimen. The distinct fluorescent probes can comprise distinct nucleic acid probe moieties designed such that under assay re-association conditions, the nucleic acid probe moieties of the fluorescent probes preferentially re-associate with target-specific cellular nucleic acid sequences for distinct categories of target cells or microbes. Detailed discussion of probe re-association can be found in United States Patent Publication 20030228599, incorporated herein by reference.

The fluorophores on the distinct fluorescent probes can have distinct photonic signals so that the fluorescent signal for the different categories of target cells or microbes in the assay can be differentiated by their distinct photonic signals. Imaging methods to distinguish multiple distinct photonic signals are known to those familiar with the art. For example, multiple images can be acquired using distinct pairs of excitation and emission optical filters that correspond to the action spectrum of the distinct fluorophores. Accordingly, a single specimen portion can be tested for the presence of multiple specific target cells or microbes in a single processing and imaging well.

In certain embodiments, FISH analysis for identification and/or quantification of target cells or microbes in a specimen can be performed isothermally, without reagent changes, and without cell fixation allowing for automatic, on-device processing in about 30 minutes or less between initiating of the reaction and obtaining imaging results.

FISH analysis, as described herein, can be performed at constant physiological temperature such that a number of cartridges can be maintained at the same temperature for incubation and FISH analysis thereby only requiring a single temperature for the interior of an instrument and avoiding the need for separate incubation chambers held at different temperatures.

Generally, physiological temperature refers to bodily temperature of an organism such as an animal. The process steps, molecular species, and chemical reagents disclosed herein are useful for hybridizing fluorescent probes to nucleic acids within cells, and imaging those probes, at physiological temperature without lysing the cells. There is flexibility as to what temperatures the specimen is exposed to and the steps are performed at. Methods of the disclosure may be usefully performed at temperatures that fluctuate but do not exceed 45 degrees C. and even work at temperatures that do not exceed 40 degrees C. Methods and compositions of the disclosure are useful and functional when used at temperatures within a range of 36 to 39 degrees C., for example. In fact, methods of the disclosure may be implemented on instruments that maintain temperatures essentially at, or at about, human body temperature, i.e., about 37 degrees C. for a healthy human, 38 degrees C. for a human with a fever, or 36 degrees C. for some nocturnal human temperature fluctuation patterns. To say "about" is to mean within a decimal point or so. That is, 36.3 is about 36.5 and 37.7 counts as being about 37.5. What is important is to understand that the FISH protocol disclosed herein can be performed entirely at about physiological temperature of a body, such as of a mammal, and preferably of a human.

One benefit of the temperature range permitted by the methods is that microorganisms in clinical specimens can be studied under temperature conditions that approximate the in vivo conditions, thus avoiding an effect by which heat promotes the differential growth of one organism that wouldn't otherwise be clinically significant while suppressing the appearance of another. For example, if a person is suffering from a urinary tract infection in which the primary underlying irritant is *Proteus mirabilis*, and a clinical test is performed that involves heating a urine specimen, if the heat promotes growth of an otherwise insignificant few cells of *Streptococcus agalactiae*, then that clinical test will not direct the clinician to the appropriate treatment. That test would miss-identify the microorganism that needs to be treated. To avoid such an outcome, the disclosure provides compositions, devices, and methods for performing FISH, which may be performed at a constant physiological temperature, and which compositions, devices, and methods have particular utility in identifying a microorganism.

Species-specific labels (such as a fluorescently labeled oligonucleotide complementary to a RNA in the target cell) can be introduced into a specimen, and the cells can optionally be permeabilized using an agent (such as a detergent such as 3-([3-Cholamidopropyl]dimethylammonio)-2-hydroxy-1-propanesulfonate (aka CHAPSO); sulfobetaine 3-12 (aka sb3-12); Polyethylene glycol p-(1,1,3,3-tetramethylbutyl)-phenyl ether (aka TRITON X100); nonyl phenoxypolyethoxylethanol (aka NP-40); others; or some combination thereof). The labeled species can be separated from unbound label in the specimen; the cells can be imaged to detect the label. Such methods are useful for testing specimens that include microbes such as a clinical specimens (e.g., to test for or detect the causative agent of UTI). When performed according to the disclosure, the method allows for performing FISH, which can be performed at any variable temperature, such as at constant physiological temperature.

Fluorescence in situ hybridization has been proposed for applications such as gene mapping and diagnosis of chromosomal aberrations. See Nature Methods 2(3):237 (2005). Those protocols have involved the hybridization of biotin- or digoxigenin-labeled probes to denatured chromosomal DNA and detection of the probes using fluorochrome-conjugated reagents. Generally, those protocols require denaturing steps in which the probes themselves and the target DNA are separately denatured at 70 to 80 degrees C. before probe hybridization, incubation, and visualization. Methods of the disclosure do not require that heating step and do not require any portion of the specimen or reagents to be heated about 70 degrees C. or even above 40 degrees C. One important feature providing for the temperature ranges allowable for methods of the disclosure involves the use of a permeabilization agent (rather than heat) to deliver the probes into the cells.

Permeabilization agents can include a mixture of 3-([3-cholamidopropyl] dimethyl-ammonio)-2-hydroxy-1-propanesulfonate (sold under the name CHAPSO by Millipore Sigma, St. Louis, MO) and sulfobetaine 3-12 (available as SB3-12 from B-Biosciences, St. Louis, MO). Those detergents permeabilize cells, allowing the probes to enter to bind to microbial target nucleic acid. Any suitable probe may be used with methods herein.

Probes suitable for use with methods herein may include nucleic acid probes that include DNA, RNA, peptide nucleic acids, modified bases, conformationally restricted nucleic acids, or combinations thereof. Suitable probes may include antibodies or antigens, binding molecules such as mannose-binding lectin or other collectins. Molecular or chemical structures or compositions such as polyethylene glycol, dyes, stains, intercalating dyes, crystal violet, safranin/carbol fuchsin, or any other composition or structure that may bind specifically to targets. In a preferred embodiment, the probes 707 include oligonucleotides.

Probes may include an oligonucleotide with a length between about 8 and 22 bases long, preferably between about 10 and 22 bases long. The probes preferably include DNA bases to avoid autocatalysis catalyzed by nucleophilic attack by free electrons of a 2' hydroxyl group (although RNA bases may optionally be used or included). The probes preferably have a melting temperature of about 45 degrees C., e.g., between 40 and 50. Each oligonucleotide is preferably labeled with at least one fluorophore. In a preferred embodiment, each oligonucleotide also includes one to a few conformationally restricted nucleotides (sometimes variously referred to as locked nucleic acids or bridged nucleic acids). Thus, the probes include fluorescently-labelled DNA oligos with optional conformationally-restricted nucleic acids and more preferably also include at least one help probe, optionally with a second helper probe, as well.

In certain embodiments, the labels or probes comprise probe oligonucleotides that are complementary to microbial RNAs. For probes oligos that are complementary to microbial ribosomal RNA, the oligos preferably have length generally between 10 and 18 nt. Tm is approximately 45 degrees C. Helper probes may be used to disrupt the ribosomal structure. One reason to target rRNA is that copy number is very high relative to messenger and transfer RNA within bacterial cells. There are thousands of copies per cell, so linking signaling molecules such as fluorophores to rRNA-targeting probes results in a de facto signal amplification with thousands of targets in a single cell. Picking out single cells in subsequent fluorescent imaging is therefore easier given the signal-to-noise ratios afforded by such high concentrations of labels in the target bacterial cells. Thus, preferred embodiments of the method use reagents that include one or more detergents (e.g., one or more of CHAPSO and SB3-12) and use probe oligonucleotides to target microbial ribosomal RNAs. Specifically, the probes can be fluorescently-labeled probe oligonucleotides complementary to a segment of ribosomal RNA exclusive to a target species of interest. Preferably, the fluorescently-labeled probe oligonucleotide is between 10 and 18 bases in length and includes at least one conformationally-restricted nucleic acid. Also preferably, the probes oligos are provided along with at least one helper probe and optionally a second helper probe.

Preferably, where the oligo hybridizes to a segment of microbial ribosomal RNA, the helper probe and any optional second helper probe are oligonucleotides that bind to the ribosomal RNA at a location within 1 to 30 bases from the segment where the fluorescently-labeled probe oligonucleotide binds. For example, the helper probes may hybridize to the microbial ribosomal RNA immediately upstream and downstream of the hybridized probe oligo. Without helper probes target site inaccessibility may present issues for hybridization of 16S rRNA with oligonucleotide probes. In certain embodiments, unlabeled oligonucleotides that bind adjacent to the probe target site are used to increase weak probe hybridization signals. Helper probes may be used to enhance the fluorescence signal. See Fuchs, 2000, Unlabeled helper oligonucleotides increase the in situ accessibility to 16S rRNA of fluorescently labeled oligonucleotide probes, Appl Environ Microbiol 66(8):3603-7, incorporated by reference. Considerations in picking probe target sequences include determining theoretical specificity and inclusivity of FISH probes, optimizing location of LNA bases, and designing helper probes for specific probes. Many pathogen targets already have FISH probes that have been shown to be specific that may be used (as published, or shortened to accommodate temperatures of this disclosure). One may find many of them in probeBase, an online resource for rRNA-targeted oligonucleotide probes. See Loy, 2007, probeBase—an online resource for rRNA-targeted oligonucleotide probes: new features 2007, Nucleic Acids Res 35: D800-D804 and Loy, 2003, probeBase—an online resource for rRNA-targeted oligonucleotide probes, Nucleic Acids Res 31:514-516, both incorporated by reference. Of note, traditional FISH reactions are usually carried out at much higher temperatures than used in the preferred constant physiological temperature methods. Accordingly, probes from traditional sources may need to be shortened or modified for use in the presently-described methods. One may also use the on-line tool "DECIPHER" to input a genus, and have the DECIPHER tool suggest regions on the 16S that will be specific for the genus. See Wright, 2014, Automated Design of Probes for rRNA-Targeted Fluorescence In Situ Hybridization Reveals the Advantages of Using Dual Probes for Accurate Identification, Applied Env Microbiology, incorporated by reference. Whether starting with an online tool, or designing a probe by hand, it may be valuable to examine alignments (e.g., probe to 16S rRNA pairwise sequence alignment as made by ClustalW) and select regions where the target sequences (preferably have multiple) match, but other pathogens do not. It may be valuable to examine Inclusivity (coverage) and specificity. Tm should be over 40 degrees C. (since methods of the disclosure operate at 35 degrees C.). Higher melting temperatures may be preferable, but how high you can go depends on how many mismatches there are to off-target sequences. Probe oligos according to the disclosure have melting temperature between 40 and 60 degrees C. (e.g., when 10 to 18 nt-length, DNA probes, complementary to helix h17 in 16S rRNA with 2 or 3 LNA bases). Mismatches at the center are more discriminating than mismatches at the end. Order of strength of mismatches: (least bad to most bad): G/T, G/G, A/G, A/A, T/T, A/C, T/C, C/C. Preferably, pick a region of the rRNA that is more accessible.

Having settled on a provisional probe design, one may test the specificity and inclusivity using an online tool such as SILVA, "high quality ribosomal RNA databases", available as a website supported by the German network for bioinformatics infrastructure. See Pruesse, 2007, SILVA: a comprehensive online resource for quality checked and aligned ribosomal RNA sequence data compatible with ARB, Nucl Acids Res 35:7188-7196 and Quast, 2013, The SILVA ribosomal RNA gene database project: improved data processing and web-based tools, Nucl Acids Res 41 (D1):D590-D596, both incorporated by reference. The probe oligo preferably includes at least one bridged or locked nucleic acid. For the helper probes it is permissible for them to have lower specificity (see SILVA tools) than the oligo. The helper probes may preferably be about 20 nt in length.

After target cells have been labelled, cartridges and instruments described herein are operable to separate the labelled cells from unbound labels for imaging in order to reduce background signal. Any suitable method or technique may be used to separate the cells from unbound probes. Suitable techniques for separating cells from unbound probes includes centrifugation, flow cytometry, fluorescent activated cell sorting, a column separation, digestion of unbound probe via one or more nucleases, others, or combinations thereof. Because the methods are carried out within a closed cartridge, conventional wash steps to remove unbound labels are impractical. In a preferred embodiment, the cells are separated from unbound probe by the use of magnetic particles. For example, the incubation step may include exposing the cells to magnetic particles that bind to surfaces of the cells.

Magnetic particles can include a chemical group that binds to bacterial cell surfaces. The chemical group may include, for example, diethylamine ethyl-starch; dextransulfate; polyaspartic acid; polyacrylic acid; polystyrenesulfonate; poly-diallyldimethylamin; or a combination thereof. Such particles are sold, for example, as fluidMAG-PAA by chemicell GmbH (Berlin, Germany). The fluidMAG-PAA particle is a polyaspartic acid that binds to the surface of bacteria. The cells may be exposed to the magnetic particles in the presence of a compound that promotes the binding of the chemical group to the bacterial cell surfaces.

To effectively bind the particles to the cells it may be helpful to include an agent that promotes the binding of PAA to cell surfaces. Any suitable agent may be included to promote binding. For example, in some embodiments, the agent includes a mixture of different quaternary ammonium salts including cetrimonium bromide (CTAB), also known as cetrimide. Cetrimide promotes binding of PAA to cell surfaces for magnetic capture, and solves particular trouble with Gram+organisms. It may be found that Gram−organisms bind to the fluidMAG-PAA without trouble. Where the target microorganism of interest is Gram+, it may be preferable to include the agent (e.g., cetrimide). Thus, in preferred embodiments of the method, the labels include fluorescently-labeled probe oligonucleotides complementary to ribosomal RNA exclusive to the species; the incubating step also includes exposing the cells to magnetic particles that bind to surfaces of bacterial cells; and the separating step includes applying a magnetic field B to the cells.

Magnetic particle-bound cells can be separated from unbound probes by pulling the cells through a density gradient medium using an applied magnetic field such as provided by a magnetic subsystem or station within the instrument. The density medium may be supplied within a tube or well (and may include a dye to provide a "dye-cushion"), such that the separating may include distributing magnetic particle-bound cells over the dye-cushion and using a magnetic field to pull bound cells through the dye-cushion and onto an imaging or detection surface, leaving the unbound probes on the surface of the dye-cushion. The detecting step may then include imaging the imaging surface with a fluorescence microscope and all of the steps may be performed at temperatures below 40 degrees C. Preferably the steps are performed at temperatures between about 36 and 39 degrees C.

As discussed, embodiments of the separation make use of a density gradient medium that may include a dye to provide a dye-cushion. Thus, a dye-cushion is a material that includes a density gradient medium that further includes a dye.

The dye-cushion may be, for example, a density gradient medium (such as a solution of iodixanol or polyvinylpyrrolidone-coated colloidal silica particles, optionally dried or lyophilized prior to exposure to the specimen) that further includes a dye that absorbs light from unbound probes. The cushion may include a high density material for excluding unselected components of the reaction from the detection zone. The cushion is a layer (liquid or dried or lyophilized) which is generally of higher density than the reaction components. The cushion can include various density agents singly or in combination (and at various concentrations) including for example, sucrose, diatrizoate, iodixanol (aka OptiPrep), NaCl, CsCl, Percoll, or albumin. Embodiments can also incorporate other density agents, including other commonly used density agents such as iodixanol, sodium diatrizoate, sodium, sucrose, and other sugars, oligosaccharides, synthetic polymers (e.g., Ficoll), and various salts such as cesium chloride, potassium bromide, and others. Embodiments may use dyes to match different signaling character and moieties in use. For example the dye Toluidine Blue O could be used with the fluorescent label Texas Red (sulforhodamine).

Dye-cushions can be formed by preparing a solution of iodixanol or polyvinylpyrrolidone, including any optional dye, and drying or lyophilizing the solution in the imaging well of the cartridge. The dye-cushion will then be essentially a solid (e.g., dried, e.g., the well can be stored in any orientation including upside-down until use). When a liquid specimen is delivered into the well, the liquid rehydrates the dye-cushion. In fact, the reagents disclosed and discussed throughout herein for use in the method may be provided in dried or lyophilized form for later use in a protocol for FISH at constant physiological temperature or cyclic temperature, which may be below or exceed physiological temperature. This allows the reagents to be prepared and loaded dry onto a cartridge that may then be shipped or stored and later used in methods of the disclosure.

The magnetic particles, detectable labels, and target-specific binding molecules preferably form complexes with any target present in the specimen. Magnetic particles and applied magnetic fields can be used to physically separate bound detectable labels from unbound detectable labels, in solution, without a wash step. Dye-cushion layers, as described in U.S. Pat. No. 9,643,180 can be used in conjunction with the magnetic particles and a magnetic field to pull labelled target cells or microbes through a dense dye layer and deposit them on a detection surface in a well of a testing device for imaging analysis. The dye in the dye-cushion layer is preferably chosen to absorb the excitation and emitted light used by the instrument for imaging. Thus, the signal from unbound labeling moieties in the assay layer does not significantly interfere with detecting the signal from the labeled target-cell or microbe complexes that are magnetically deposited on the detection surface. Similarly, the use of the dye-cushion prevents any auto-fluorescence from the specimen matrix, also contained in the assay layer, from significantly interfering with detection of the signal from the deposited labeled target-cell complexes. These attributes of the dye-cushion can make it possible to detect the target-cells or microbes without specimen preparation by the user and without wash steps to remove the unbound label from the test device.

Digital imaging of labelled target cells or microbes can be accomplished using digital imagers. In the preferred case of fluorescent labelling, various lenses, illumination sources, excitation light sources, and filters may be used. Imaging modules may include any device capable of producing a digital image of the detectably labeled target cells or microbes in a solution or pulled to an detection surface in a well or testing device. Imaging modules may include, for example, CCD cameras, CMOS cameras, line scan cameras, CMOS avalanche photodiodes (APD's), photodiode arrays, photomultiplier tube arrays, or other types of digital imaging detectors.

Imaging can be carried out under a single set of conditions or light sources, filters, and/or lenses may be changed between images to detect different optically distinguishable labels (e.g., different fluorescent probes corresponding to different target cells or microbes). The imaging techniques and instruments described in U.S. Pat. Nos. 9,643,180 and 8,021,848 may allow for observation and enumeration of individual bacterium or other target cells.

Systems and methods of the invention may include a computer operable to control the instrument and testing device and/or to process imaging results. Computers can comprise a processor coupled to a non-transitory memory device. The memory preferably stores instructions executable by the processor to cause the system to manipulate the testing device within the instrument and to obtain and process images of labelled target cells.

Processor refers to any device or system of devices that performs processing operations. A processor will generally include a chip, such as a single core or multi-core chip, to provide a central processing unit (CPU). A process may be provided by a chip from Intel or AMD. A processor may be any suitable processor such as the microprocessor sold under the trademark XEON E7 by Intel (Santa Clara, CA) or the microprocessor sold under the trademark OPTERON 6200 by AMD (Sunnyvale, CA).

Memory refers a device or system of devices that store data or instructions in a machine-readable format. Memory may include one or more sets of instructions (e.g., software) which, when executed by one or more of the processors of the disclosed computers can accomplish some or all of the methods or functions described herein. Preferably, the computer includes a non-transitory memory such as a solid state drive, flash drive, disk drive, hard drive, subscriber identity module (SIM) card, secure digital card (SD card), micro SD card, or solid-state drive (SSD), optical and magnetic media, others, or a combination thereof.

An input/output device is a mechanism or system for transferring data into or out of a computer. Exemplary input/output devices include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. Input/output devices may be used to allow a user to control the instrument and receive data obtained from the testing devices by the instrument.

The analytical cartridge 101 has an identifier such as a barcode sticker that when analyzed or read by an instrument or a reader in the instrument, associates the cartridge with a set of instructions for processing within the instrument and can include information regarding the specimen source for associated assay results with a certain patient.

EXAMPLES

Example 1. Limit of Detection (LoD) for Gram-Negative Bacteria Using a Novel, Rapid Fluorescence In Situ Hybridization Assay Overview: The following example demonstrates that very low concentrations of cells can be detected using the novel isothermal fluorescence in situ hybridization method. The limit of detection for three common human urinary tract infection (UTI) pathogens are shown.
Experimental Methods:
Bacterial cell preparation: Bacterial cultures for *E. coli* ATCC 19138, *K. pneumoniae* ATCC 700603 and *P. aeruginosa* ATCC 9721 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. After the cells had reached an optical density reading at 600 nm of 0.15-0.30, cells were placed on ice for at least 15 minutes before dilution. After cooling, the cells were diluted in 1X cation-adjusted Mueller-Hinton broth (MHBII, Teknova cat. M5860) to the concentrations to be assayed (approximately 19200, 9600, 4800, 2400, 1200, 600, 300, and 150 colony-forming units (CFU)/reaction). For more accurate cellular concentrations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours. Using the average plate counts, the actual CFU present in each concentration tested was computed.

Preparation of Magnetic Particles: Polyaspartic acid-conjugated magnetic particles (Fluidmag-PAA, Chemicell, cat. 4108) and carboxyl-coated magnetic particles with high iron (Carboxyl Magnetic Particles, Spherotech, cat. CM-025-10H) were used to non-specifically capture bacterial cells. Each particle was diluted 1:40 into 50 mM Epps buffer, pH 8.2, with final concentrations of approximately $1.38 \times 10^9$ particles per reaction for the polyaspartic acid particles and $3.46 \times 10^9$ particles per reaction for the carboxyl particles. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation.

Preparation of FISH probes: Two species-specific DNA oligomer sets for *E. coli* and *K. pneumoniae* and one for *P. aeruginosa* was heated in a water bath between 80-85° C. for 10 minutes and then placed on ice to reduce aggregation. A DNA oligomer set contained a species-specific DNA oligonucleotide labeled with a fluorescent dye (Alexa647N, Thermo Fischer) on either the 5' end, or on both the 5' and 3' ends of the oligonucleotide, and 2-6 helper oligonucleotides that bind adjacent or near the specific probe and are designed to disrupt the local secondary structure of the ribosomal subunit, and allow the labeled, specific probe greater hybridization efficiency to the target rRNA. Probe sequences used in this example are shown in Table A in FIG. 17.

Preparation of the dried hybridization buffer plates: A mixture of 10×SSC (1.5M NaCl, 0.15M Sodium citrate, Sigma, cat. S6639), 2.6% w/v CHAPSO (Sigma cat. C3649), 2.4% w/v SB3-12 (Sigma cat. D0431), 0.43M Guanidine thiocyanate (Sigma cat. G9277) and 0.6% w/v Cetrimide (Sigma cat. M7365) was prepared. 30 uL of this mixture was added to each well of a 96 well plate. The plates were placed into a convection oven at 50° C. and allowed to dry overnight. When 100 uL of liquid is added to these wells, the correct hybridization buffer concentrations of 3×SSC (0.45M NaCl, 0.045M Sodium citrate), 0.77% w/v CHAPSO (Sigma cat. C3649), 0.72% w/v SB3-12 (Sigma cat. D0431), 0.13M Guanidine thiocyanate (Sigma cat. G9277) and 0.18% w/v Cetrimide (Sigma cat. M7365) are achieved.

Limit of Detection (LoD) Assay procedure: A mixture of DNA oligonucleotide sets appropriate for the bacteria of interest was combined with urine and a concentrated cation-adjusted Mueller Hinton Stock (MHBII) to make a final solution containing 1×MHBII and 30% pooled human urine (Innovative Research, cat. IRHUURE500ML). Probe concentrations varied between different bacterial species but ranged from 0.2-0.6 μM for the labeled oligonucleotide and 1.5-6 μM for the corresponding helper probes. 90 uL of this mixture was placed into the appropriate dried hybridization buffer plate. 10 uL of the magnetic particle mixture was added, followed by 10 uL of the appropriate cell dilution. Twelve replicates of each cell concentration and 24 replicates of the blank (media containing no bacteria) were assessed for each target bacteria tested. 100 μL of the final reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes to allow for the simultaneous rehydration of the "dye-cushion", labeling of bacterial cells, and binding of magnetic particles to bacterial cell surfaces. After incubation, microtiter plates were placed onto a magnetic field (Dexter magnetic technologies, cat. 54170260) for 4 minutes to bring magnetic particles, a fraction containing labelled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: At each cell concentration, the number of fluorescent objects detected was determined. The data from all eight cell concentrations was fit to a linear regression line, and the slope, intercept and standard deviation of the lowest 3 cell inputs was used to determine the limit of the blank (LoB) and limit of detection (LoD) for each bacterium tested.

Figure 14:
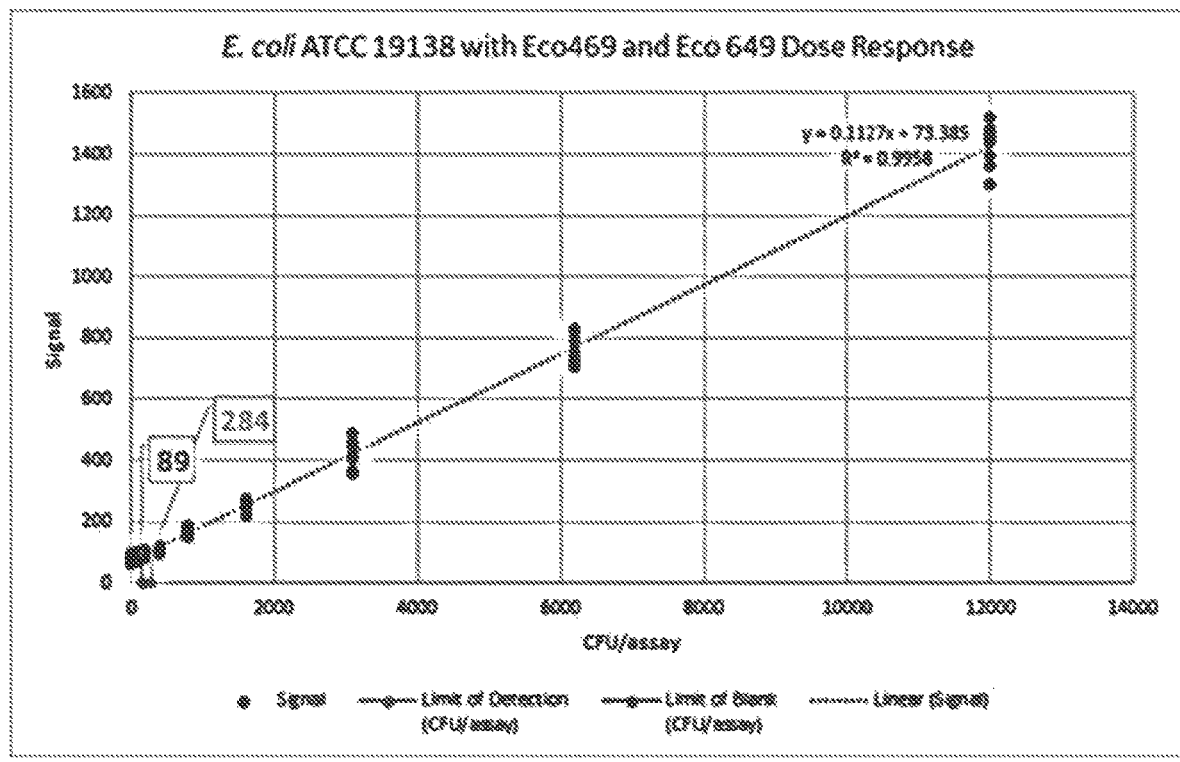
FIG. 14 shows Limit of detection (LoD) of E. coli ATCC 19138 is shown. Limit of blank (LoB) was 89 CFU/assay and the LoD was 284 CFU/assay. corresponds to an LoD of 9,467 CFU/ml of urine.
Figure 15:
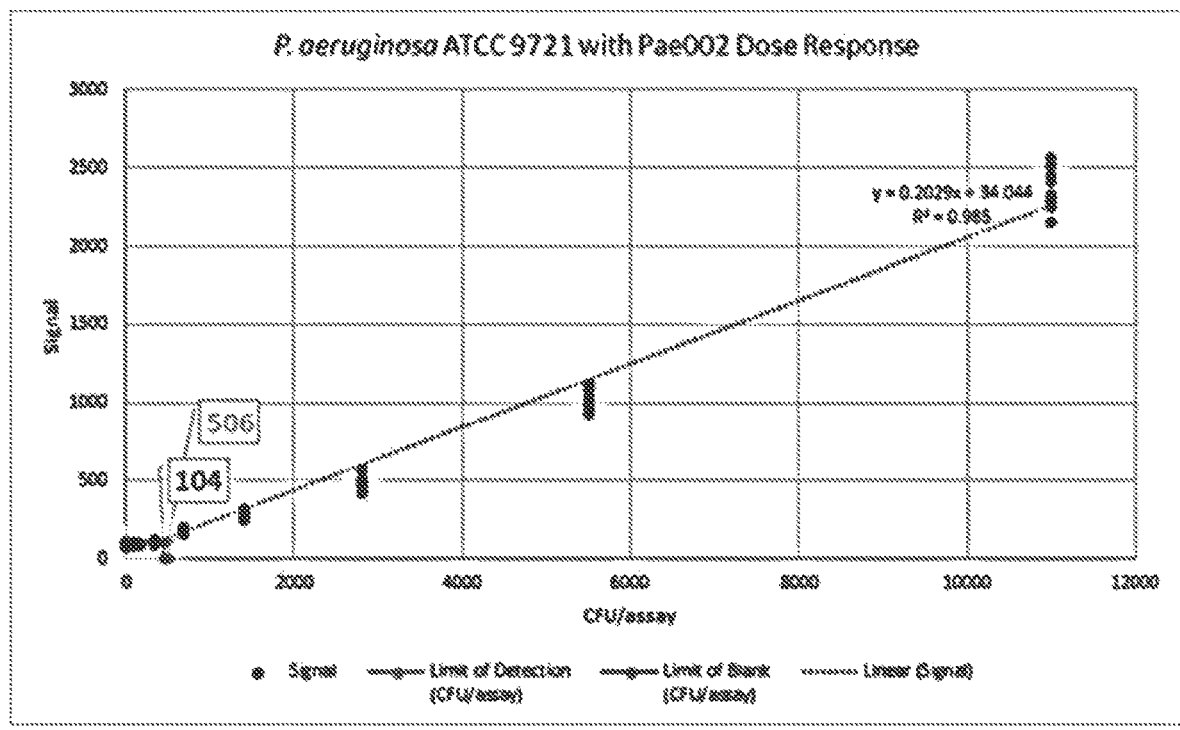
FIG. 15 shows Limit of detection (LoD) of P. aeruginosa ATCC 9721 is shown. Limit of blank (LoB) was 104 CFU/assay and the LoD was 506 CFU/assay. corresponds to an LoD of 16,867 CFU/ml of urine.
Figure 16:
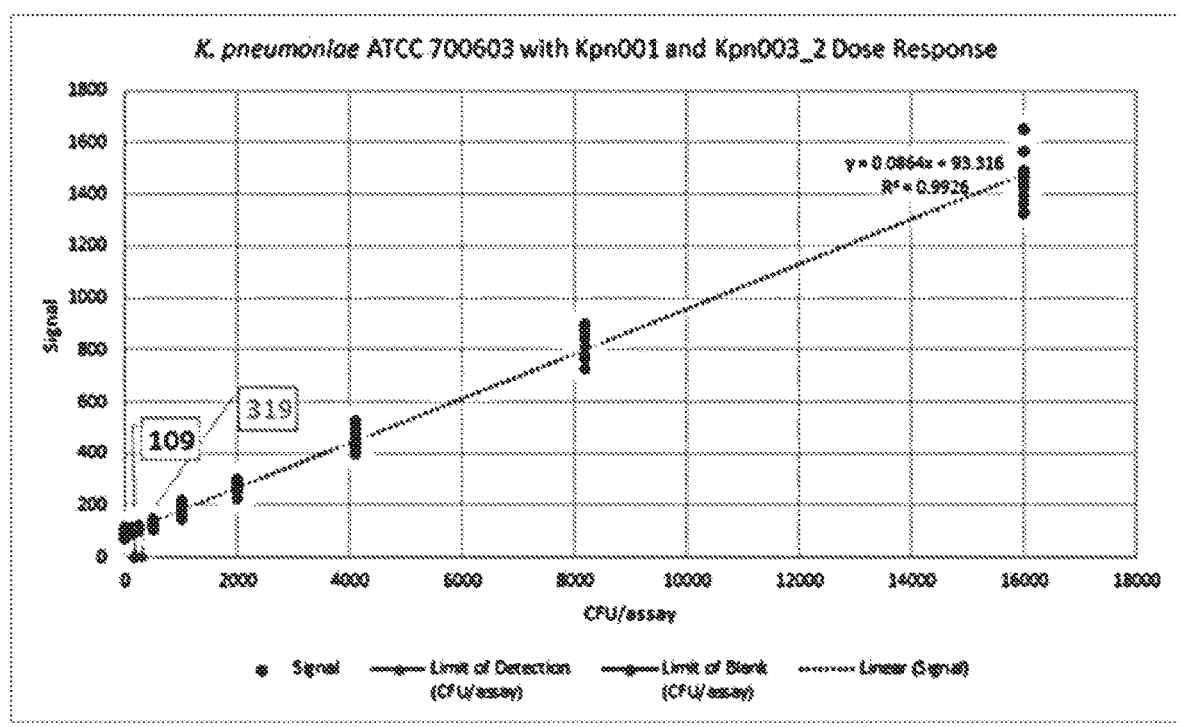
FIG. 16 shows Limit of detection (LoD) of K. pneumoniae ATCC 700603 is shown. Limit of blank (LoB) was 109 CFU/assay and the LoD was 319 CFU/assay. corresponds to an LoD of 10,633 CFU/ml of urine.

Results:

All three bacteria tested showed low limits of detection. FIG. 14, FIG. 15, and FIG. 16 show the data generated for *E. coli*, *K. pneumoniae*, and *P. aeruginosa* with the linear fit used to calculate the LoB and LoD. The LoB and LoD are indicated in CFUs detectable in a single reaction well.

Conclusions. The novel and rapid FISH method described in this example is shown to be a sensitive method with limits of detection of about 500 CFU or less per reaction, using minimally processed urine matrix.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

FIG. 14 shows Limit of detection (LoD) of *E. coli* ATCC 19138 is shown. Limit of blank (LoB) was 89 CFU/assay and the LoD was 284 CFU/assay. This corresponds to an LoD of 9,467 CFU/ml of urine.

FIG. 15 shows Limit of detection (LoD) of *P. aeruginosa* ATCC 9721 is shown. Limit of blank (LoB) was 104 CFU/assay and the LoD was 506 CFU/assay. This corresponds to an LoD of 16,867 CFU/ml of urine.

FIG. 16 shows Limit of detection (LoD) of *K. pneumoniae* ATCC 700603 is shown. Limit of blank (LoB) was 109 CFU/assay and the LoD was 319 CFU/assay. This corresponds to an LoD of 10,633 CFU/ml of urine.

FIG. 17 is a table of Probe sequences used in this example.

Example 2. Inclusivity: Detecting and Identifying Different Strains of a Bacterial Species Using the Inventive Rapid FISH Method Overview. This example demonstrates the use of the invention to detect different strains for a targeted bacterial species. Raw data for 11 different *E. coli* strains are presented and data for *K. pneumoniae, P. aeruginosa, P. mirabilis* and *Enterococcus* spp. are summarized. Bacterial cell targets were labeled in 30 minutes using isothermal fluorescence in situ hybridization (FISH) and detected on the MultiPath™ CCD-camera-based detection system.

Experimental Methods.

Bacterial cell preparation: Bacterial cultures for different strains were obtained by inoculating Trypticase Soy Broth (TSB, Hardy Diagnostics Cat. U65) with 3 to 5 colonies from fresh tryptic soy agar plates (TSA, BD cat. 221185) and growing for 1.5 to 3 hours at 35° C. to achieve log-phase growth. Using optical density at 600 nm to estimate cell concentration, cells were diluted to approximately 600 CFU and 3000 CFU per reaction in 1× cation-adjusted Mueller-Hinton broth (MHBII, Teknova cat. M5860). For more accurate percent cellular detection calculations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75 \times 10^{12}$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Labeling of Bacterial Cells: 100 μL labeling reactions were prepared by combining diluted cells, isothermal hybridization buffer (0.9×MHBII, 3×SSC (1.5M NaCl, 0.15M Sodium citrate, Sigma, cat. S6639), 0.77% w/v CHAPSO (Sigma cat. C3649), 0.72% w/v SB-3-12 (Sigma cat. D0431), 0.13M Guanidine thiocyanate (Sigma cat. G9277), 0.18% w/v Cetrimide (Sigma cat. M7365)), species-specific Alexa647N-labelled DNA or LNA-containing DNA probes (Integrated DNA Technologies, IDT) targeted to the 16S or 23S bacterial rRNA, helper probes to facilitate effective hybridization (IDT) and 30 μL of pooled human urine (Innovative Research, cat. IRHUURE500ML). Probe sequences are shown in the Table in FIG. 20.

The urine was first processed through a Zeba 7K MWCO spin column (Thermo Fisher, Cat. 89893 or 89892 depending on urine volume) according to the manufacturer's instructions. 10 μL of the magnetic particle preparation was then added to this mixture. The final reaction mixture was transferred to a microtiter plate containing 50 μL (previously dried) "dye cushion" (50 mM TRIS pH 7.5 (Teknova cat. T1075), 7.5% v/v Optiprep (Sigma cat. D1556), 50 mg/mL Direct Black 19 (Orient cat. 191L) incubated at 35° C. for 30 minutes to allow for the simultaneous rehydration of the "dye cushion", labeling of bacterial cells, and binding of magnetic particles to bacterial cell surfaces. After incubation, microtiter plates were placed onto a magnetic field (Dexter magnetic technologies, cat. 54170260) for 4 minutes to bring magnetic particles, a fraction containing labelled cells, through the "dye cushion" and into proximity to the imaging surface at the bottom of the wells.

Imaging of labeled cells: Labeled bacterial cells on the MultiPath laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: For each bacterium, the number of fluorescent objects was determined (assay signal). A bacterial strain was considered detected if signal was detected above three standard deviations of the signal in the no cell condition.

Figure 18A:
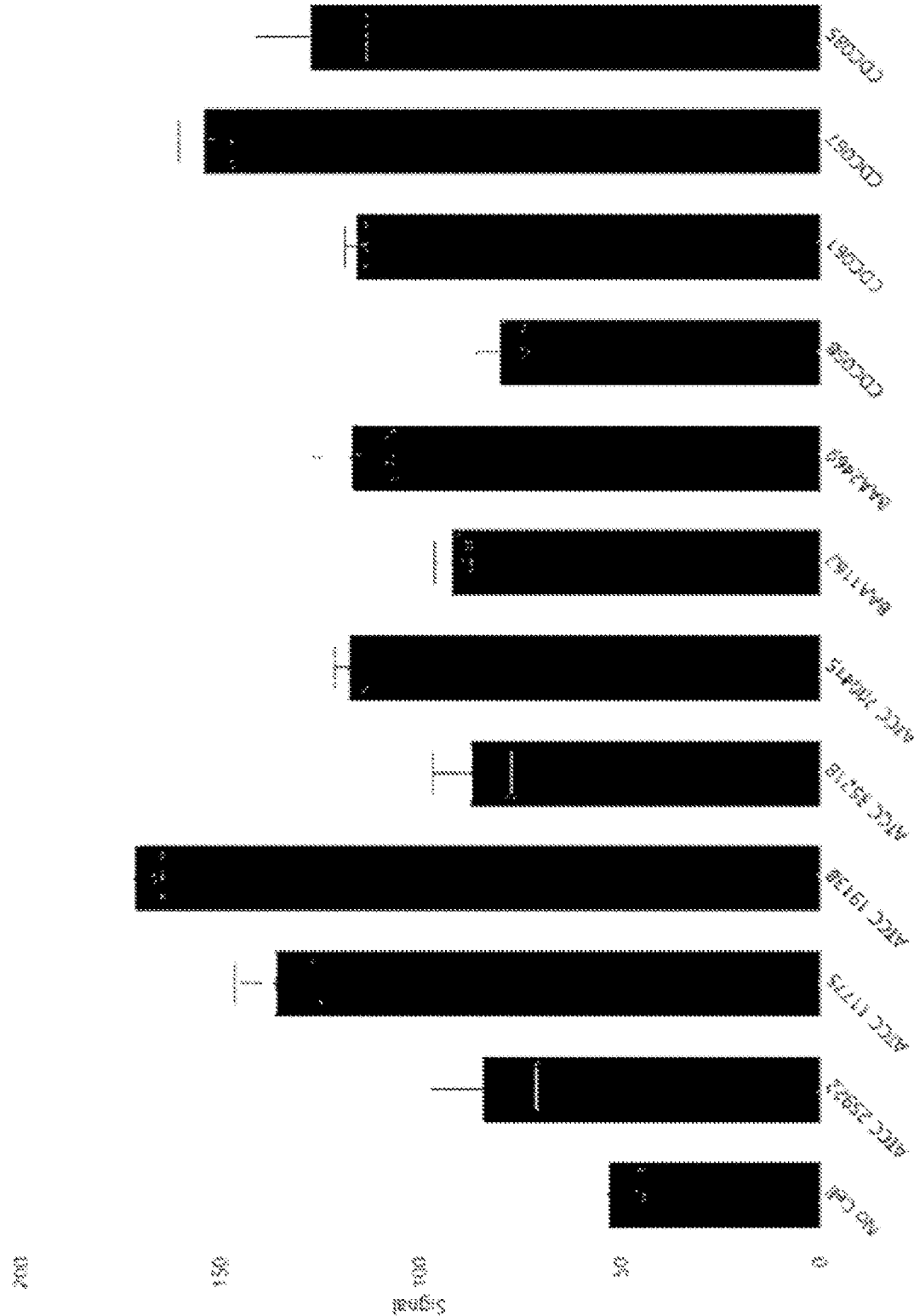
FIG. 18A shows the respective signals associated with input cells.

Results. FIG. 105 shows assay signal for 11 *E. coli* strains. All 11 strains were detected above the background "no cell" condition for at a cell input of approximately 600 CFU per assay. FIG. 18 shows the data represented as percentage of cells detected (total assay signal in cell input well−background assay signal/total cell input*100). Although the detection efficiency is somewhat variable from strain to strain, this did not inhibit the assay's ability to detect each of the 11 different *E. coli* strains.

Figures 18B, 19:
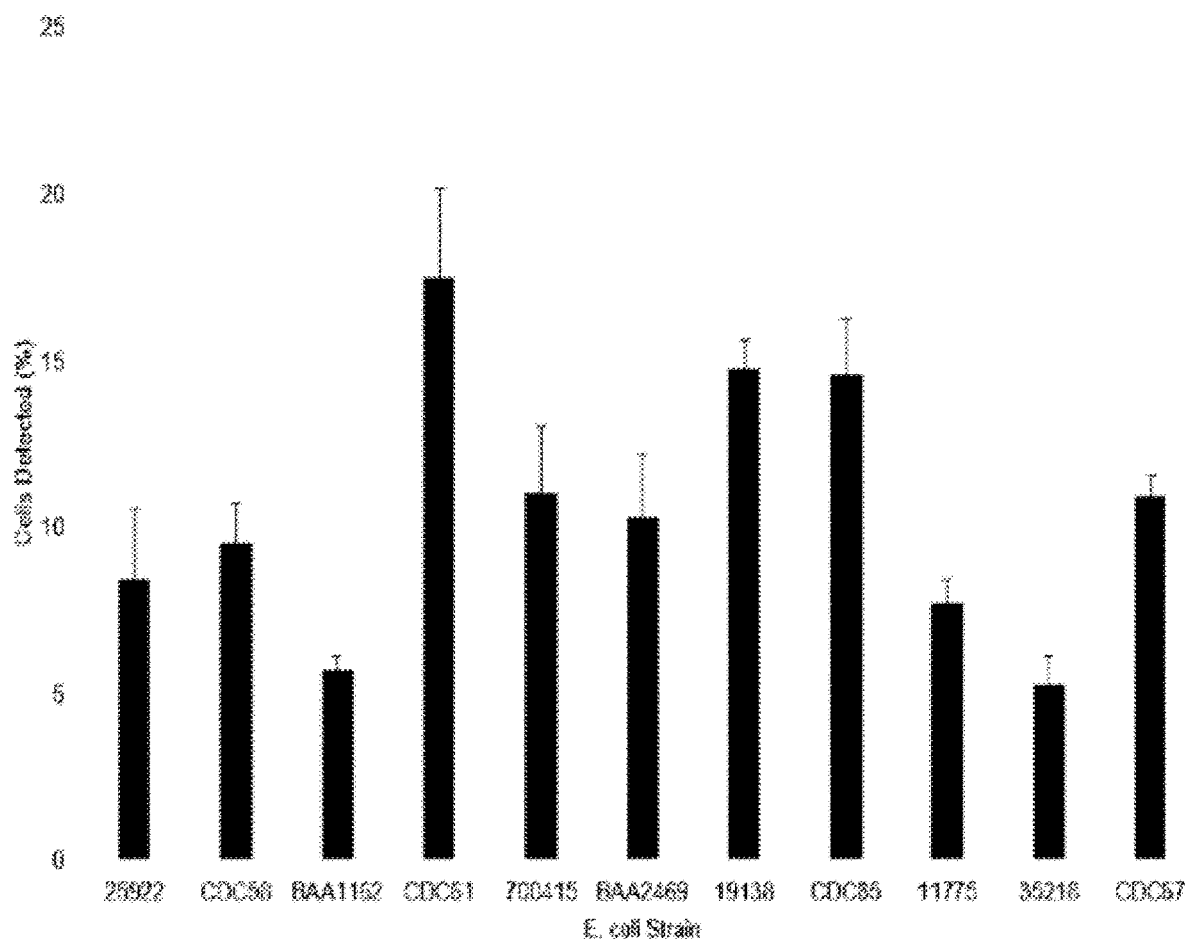
FIG. 18B shows the percentage of input cells that were detected.
FIG. 19 is a table giving Inclusivity results for 4 additional bacteria.

The table in FIG. 19 summarizes inclusivity results for *E. coli, K. pneumoniae, P. aeruginosa, P. mirabilis* and *Enterococcus* spp. which were analyzed in the same manner as *E. coli*. Strains tested for *K. pneumoniae* were ATCC 13833, CDC80, CDC44, CDC87, CDC47, CDC43, BAA2470, CDC34, CDC39, ATCC 700603 and BAA-2472. Strains tested for *P. aeruginosa* were CDC263, CDC242, 9721, CDC236, 27853, BAA-2110, CDC233, 15692, CDC234, CDC246 and CDC261. Strains tested for *P. mirabilis* were CDC155, CDC29, CDC159, CDC59, ATCC 7002 and CDC156. Strains tested for *Enterococcus* included ATCC 19433, ATCC 29212, ATCC 33186, ATCC 51575, ATCC 51299 and BAA-2128.

Conclusions. The novel FISH method described in this example detected all strains tested for 5 different bacterial species that are among the major pathogens leading to clinical symptoms in patients with UTI.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

FIG. 105 shows Mean signal (n=3) is plotted for 11 *E. coli* strains for input cell concentrations of approximately 600 CFU/assay (light gray bars) and 3000 CFU/assay (dark gray bars). Signal derived from the no cell control (blank) is shown on left-hand side of the figure. Error bars represent 1 standard deviation.

FIG. 18 shows The percentage of input cells (as determined by plate counts) that were detected are shown for each of the 11 *E. coli* strains. Each bar represents the mean of 6 determinations, 3 from each of the two different input cell levels. Percentage cell detection was calculated as [(assay signal−background signal)/input cells]*100.

FIG. 19 is a table giving Inclusivity results for 4 additional bacteria.

FIG. 20 is a table giving Probe sequences used in this example.

Example 3. Specific Detection of Target Bacteria Using Rapid Isothermal FISH

Overview. This example demonstrates that the novel isothermal FISH method specifically detects a target bacterium while not detecting related non-target bacteria, even at very high concentrations. This example presents assay conditions that specifically detect *E. coli* yet do not detect 16 other bacteria that also cause urinary tract infections (UTI), have similar rRNA sequences or are commensal organisms. Experimental Methods.

Bacterial cell preparation: Bacterial cultures for 16 off-target bacteria (listed in Table 1) and *E. coli* strain ATCC 25922 were grown from a single colony selected from a fresh tryptic soy agar plates (TSA, BD cat. 221185), inoculated into Trypticase Soy Broth (TSB, Hardy Diagnostics cat. U65) and grown with shaking overnight at 35° C. 50-80 µL of the overnight culture was added into fresh TSB and grown for 1.5-2 hours, until the optical density at 600 nm reached 0.15-0.3. Each bacterium was then diluted to approximately $1 \times 10^8$ cells per mL in cation-adjusted Mueller Hinton (MHBII, Teknova cat. M5860).

Selection of bacterial targets to evaluate: Bacterial pathogens to test for specificity were selected for their rRNA sequence similarity to the target bacteria's rRNA sequence or because they are pathogens that are commonly found in urinary tract infections (the disease target) and therefore, cross-reactivity to these organisms would be most problematic. The table in FIG. 21 shows the bacterial species and strains tested.

Preparation of FISH probes: A DNA probe set for *E. coli* was heated in a water bath between 80-85° C. for 10 minutes and then placed on ice to reduce aggregation. This DNA probe set is shown in Table in FIG. 22. The set contains a species-specific DNA oligonucleotide labeled with a fluorescent dye (Alexa647N, Thermo Fischer) and helper oligonucleotides that bind adjacent or near the specific probe and are designed to disrupt the local secondary structure of the ribosomal subunit, and allow the labeled, specific probe greater hybridization efficiency to the target rRNA.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75 \times 10^{12}$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation.

Labeling of Bacterial Cells: 100 µL labeling reactions were prepared by combining diluted cells, isothermal hybridization buffer (0.9×MHBII (Teknova cat. M5860), 3×SSC (0.45M NaCl, 0.045M Sodium citrate, Sigma, cat. cat. S6639), 0.77% w/v CHAPSO (Sigma cat. C3649), 0.72% w/v SB3-12 (Sigma cat. D0431), 0.13M Guanidine thiocyanate (Sigma cat. G9277), 0.18% w/v Cetrimide (Sigma cat. M7365)), species-specific Alexa647N-labelled probes (Integrated DNA Technologies, IDT) targeted to the 16S or 23S bacterial rRNA, helper probes to facilitate effective hybridization (IDT) and 30 µL of pooled human urine (Innovative Research, cat. IRHUURE500ML). The specific probe sets tested are shown in Table in FIG. 22. The urine was first processed through a Zeba 7K MWCO spin column (Thermo Fisher, Cat. 89893 or 89892 depending on urine volume) according to the manufacturer's instructions. 10 µL of the magnetic particle preparation was then added to this mixture. The final reaction mixture was transferred to a microtiter plate containing 50 µL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L)) and incubated at 35° C. for 30 minutes to allow for the simultaneous rehydration of the "dye-cushion", labeling of bacterial cells, and binding of magnetic particles to bacterial cell surfaces. Each bacterium was tested at a final concentration of $1 \times 10^6$ cells per reaction. This concentration is around 3000-fold higher than the determined limit of detection for *E. coli*. After incubation, microtiter plates were placed onto a magnetic field (Dexter magnetic technologies, cat. 54170260) for 4 minutes to bring magnetic particles, a fraction containing labelled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: For each bacterium, the number of fluorescent objects was determined (assay signal). A bacterium was considered cross-reactive if signal was detected within three standard deviations of the signal in the blank (no bacteria added).

Results.

Figure 23:
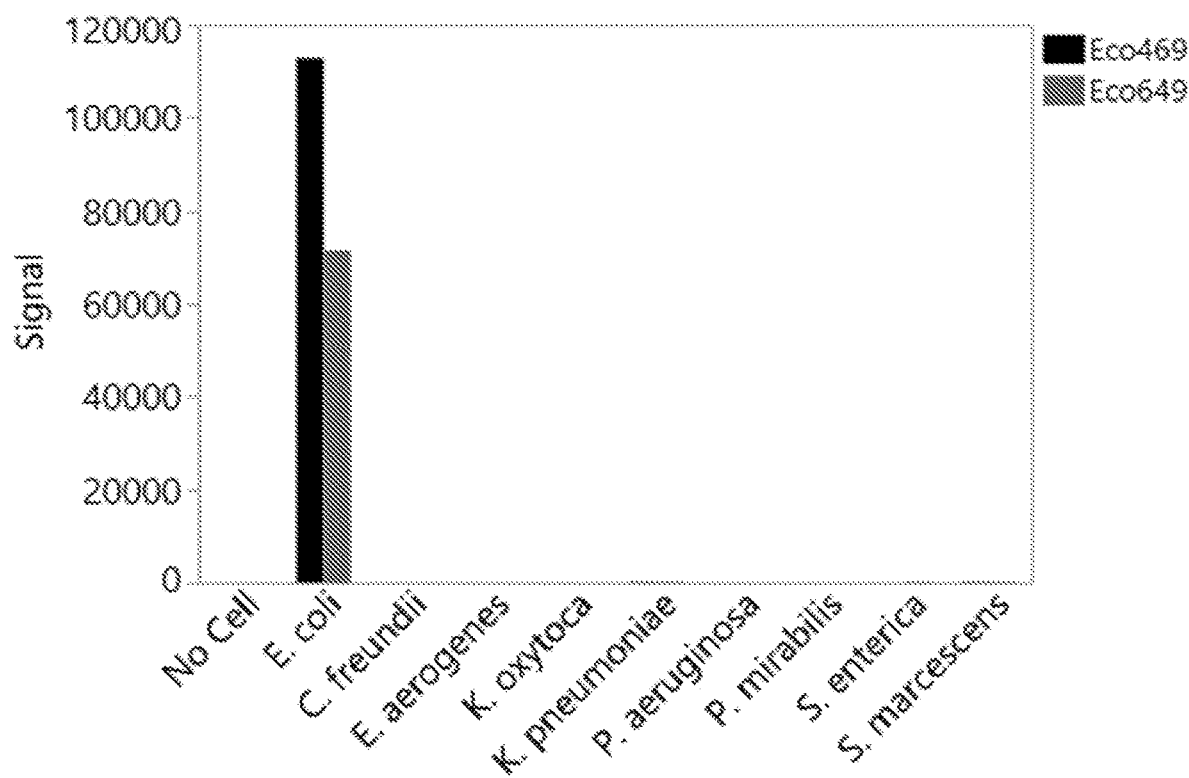
FIG. 23 shows Specific detection of E. coli and no detection of 8 challenge bacteria
Figure 24:
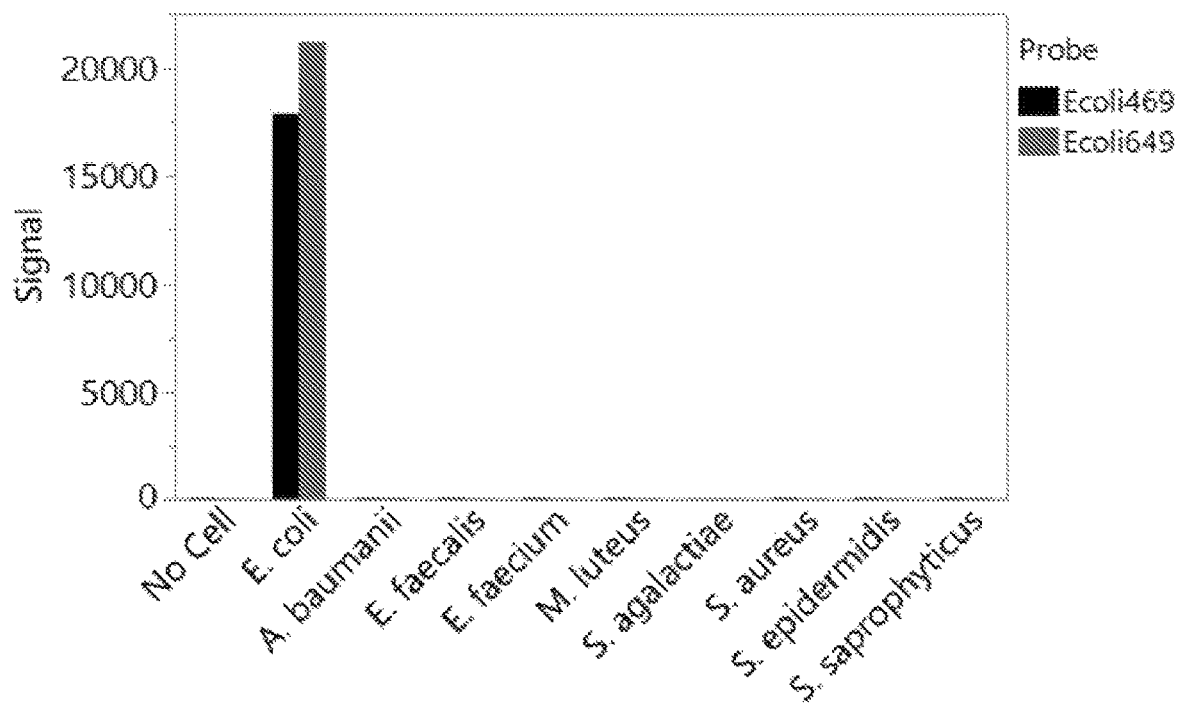
FIG. 24 shows Specific detection of E. coli and no detection of 8 additional challenge bacteria.

FIG. 23 and FIG. 24 show the rapid novel FISH method only detects *E. coli* and not the other 16 different challenge bacteria. FIGS. 1 and 2 each show that very high concentrations ($1\times10^6$ cells per reaction) of 8 clinically relevant challenge bacteria are not detected under the same assay conditions that generate high assay signal for the *E. coli* targeted bacteria. The two bars represent two different probe sets designed to be specific for *E. coli* (see Table in FIG. 22). The assay signal for each of the 16 challenge bacteria was less than the no-cell control plus three standard deviations (125).

Conclusions. The novel rapid FISH method described in this example specifically, by design, detects *E. coli* but does not detect 16 clinically relevant potential cross-reactive bacteria. This demonstrates the method has high specificity for the identification of a target UTI pathogen which is of critical importance for the clinical treatment of the infection.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens. Assays have also been designed that demonstrate high specificity for *K. pneumoniae*, *K. oxytoca*, *P. aeruginosa*, *P. mirabilis* and *E. faecalis*.

FIG. 21 is a table showing challenge bacteria to test the specificity of detecting *E. coli*

FIG. 22 is a table showing Probe sequences used in this example.

FIG. 23 shows Specific detection of *E. coli* and no detection of 8 challenge bacteria FIG. 24 shows Specific detection of *E. coli* and no detection of 8 additional challenge bacteria

Example 4. A Multiplexed FISH Method that Simultaneously Identifies 4 Distinct Microbes Overview. This example demonstrates the use of the invention to simultaneously detect, in a single reaction, *E. coli*, *K. pneumoniae*, *P. aeruginosa*, and *K. oxytoca* using fluorescently labeled probes specific for each bacteria's rRNA. Each pathogen was specifically detected in the mixture through the use of 4 distinct fluorophores—one for each bacterial species—that have different excitation/emission spectral properties.

Experimental Method. Bacterial cell growth: Bacterial cultures for *Escherichia coli* ATCC 25922, *Klebsiella pneumoniae* ATCC 13883, *Pseudomonas aeruginosa* ATCC 27853, and *Klebsiella oxytoca* ATCC 8724 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 37° C. to achieve log-phase growth. Each culture was then diluted in cation-adjusted Mueller-Hinton Broth (MHBII, Teknova, cat. M5860) to an optical density at 600 nm of 0.15, which is approximately $1.0\times10^8$ colony-forming units (CFUs) per mL.

Preparation of Magnetic Particles: Polyaspartic acid-conjugated magnetic particles (Fluidmag-PAA, Chemicell, cat. 4108) and carboxyl-coated magnetic particles (Carboxyl Magnetic Particles, Spherotech, cat. CM-025-10H) were used to non-specifically capture bacterial cells. Each particle was diluted 1:40 into 50 mM Epps buffer, pH 8.2, with final concentrations of approximately $1.38\times10^9$ particles per reaction for the polyaspartic acid particles and $3.46\times10^9$ for the carboxyl particles.

Labeling of Bacterial Cells: 100 µL labeling reactions were prepared by combining diluted cells of all four bacteria, isothermal hybridization buffer (0.9×MHBII, 3×SSC (1.5M NaCl, 0.15M Sodium citrate, Sigma, cat. S6639), 0.77% w/v CHAPSO (Sigma cat. C3649), 0.72% w/v SB3-12 (Sigma cat. D0431), 0.13M Guanidine thiocyanate (Sigma cat. G9277), 0.18% w/v Cetrimide (Sigma cat. M7365)), species-specific DNA probes (Integrated DNA Technologies, IDT) targeted to the 16S or 23S bacterial rRNA, helper probes to facilitate effective hybridization (IDT) and 30 µL of pooled human urine (Innovative Research, cat. IRHUURE500ML). 10 µL of the magnetic particle preparation was then added to this mixture. Probe sequences and the location of their dye modifications are shown in Table in FIG. 26.

The cells/hybridization mixture (1 mL) was transferred into the cartridge. The cartridge was placed onto the analyzer (as described below) which automated the remaining assay steps and image acquisition and analysis. Briefly, the fluidic system of the analyzer moved the reaction mixture into the optical window containing 46 µL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L). The cartridge was incubated within the analyzer at 35° C. for 30 minutes. Following this incubation, the cartridge was moved for 4 minutes onto the magnet station (Dexter magnetic technologies, cat. 54170260) to bring magnetic particles, a fraction containing labeled cells, through the rehydrated "dye-cushion" and into proximity to the imaging surface at the bottom of the wells. After the magnet station, the cartridge was moved to the imaging station within the analyzer and a series of images taken in each of the four color channels (red (excitation 635/25 nm, emission 680/40 nm), yellow (excitation 530/20 nm, emission 572/23 nm), green (excitation 470/40 nm, emission 520/40 nm), orange (excitation 569/25 nm, emission 609/34 nm)).

Imaging of labeled cells: The MultiPath Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. For the red channel, 16 frames were captured at a 100 msec exposure using 635/25 nm excitation and 680/40 nm emission filters. For the orange channel, 24 frames were captured at a 100 msec exposure using 569/25 nm excitation and 609/34 nm emission filters. For the Yellow channel, 48 frames were captured at a 100 msec exposure using 530/20 nm excitation and 572/23 nm emission filters. For the Green channel, 32 frames were captured at a 100 msec exposure using 470/40 nm excitation and 520/40 nm emission filters. The focusing plane for imaging the labeled cells was determined experimentally in this example.

Results.

FIG. 25 shows a portion of the full acquired image in which the fluorescence was detected in each of the 4 color channels, each specific for one of the 4 input bacteria. Each spot corresponds to a single cell or group of cells. An algorithm is used to identify meaningful objects distinct from artifacts (e.g. debris) and counts those objects as cells. As seen in the inserts for each bacterium, a similar number of cells were detected as expected since the input cell concentrations were approximately the same. When overlaid, these spots do not correspond, indicating that different objects were observed in each channel, as expected with 4 different bacterial targets.

Conclusions. This method allows for a single rapid FISH method to simultaneous detect and quantify four different bacteria in a single well of a cartridge.

Variations:

This example is illustrative of the multiplex capability of this novel FISH method and is not limited to the specific details included in the description. One skilled in the art will readily understand that many variations are therefore possible, including using different probe sequences and nucleic acid structures (PNA, LNA, etc.) and alternative assay chemistries (different detergents, chaotropes, fluorophores, buffers, pH, temperatures, reaction times, component concentrations). This methodology can also clearly be extended to other biological specimens and to other bacterial and non-bacterial pathogens for which specific probes can be designed.

FIG. 25 is Images showing the same field of view taken in 4 different color channels using the CCD imaging method and 4 different fluorophores, one for each bacterium. All four bacteria could be detected in a single well.

FIG. 26 is a table of Probe sequences used in this example 4.

Example 6. Automated Rapid AST of *E. coli* in Clinical Urine Specimens in a Cartridge on an Instrument Overview: This example demonstrates the use of the systems, devices, and methods of invention to determine the antimicrobial susceptibility of a targeted bacterial pathogen (*E. coli* in this example) in urine in 4 hours without requiring cell purification. The example using a concerted FISH method for labeling and magnetic selection and quantifies specific target cells after differential growth using non-magnified digital imaging. This new method has comparable performance to the gold standard CLSI broth microdilution (BMD) method.

Experimental Methods:

Urine Specimens: 48 remnant de-identified urine specimens collected from patients with a urinary tract infection (UTI) and known to contain *E. coli* were received from Dr. Kirby's lab at Beth Israel Hospital (Boston, MA). Samples were received 1-5 days post collection and contained a urine preservative to limit loss of cell viability. For each sample, color of urine, pH, and presence of particulates were noted. Upon receipt, conventional urine culture was performed to determine the approximate CFU/mL of bacteria present, and to confirm single or mixed bacterial morphology as reported by Dr. Kirby's lab. Briefly, a calibrated 1 µL loop was placed into a well-mixed urine sample and the 1 µL was evenly spread over a Tryptic soy agar (TSA, BD cat. 221185) plate and incubated in a 35° C. incubator for 18-24 hours. The remainder of the urine samples were processed and assayed as described below.

Urine Processing: Prior to testing, urine preservative and other potentially interfering compounds were removed using size exclusion chromatography. 2.5 mL of each clinically positive urine sample was applied to a pre-washed Zeba™ 7K MWCO spin column (ThermoFisher, cat. #89893) and centrifuged according to the manufacturer's instructions. Urine culture was repeated on this processed sample as described above, to examine bacterial loss following processing.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75 \times 10^{12}$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST Time Zero: Assay signal at time zero (TO) prior to the initiation of bacterial growth in the presence or absence of antibiotics was determined for each clinical urine specimen. 30 µL of each processed urine was added to 70 µL of 1× cation-adjusted Mueller-Hinton Broth (MHBII) containing species-specific Alexa647N-labeled DNA oligonucleotide FISH probes and unlabeled DNA helper probes. Probe sequences used are shown in Table A. The 100 µL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431) 0.13M guanidine thiocyanate (Sigma, cat. #G9277)). 10 µL of the prepared magnetic particle mixture was then added to the well. 100 µL of this reaction mixture was transferred to a microtiter plate containing 50 µL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Preparation of Antibiotic Plates: Microtiter plates containing six concentrations of each antibiotic in a 2-fold serial dilution series were prepared, starting at a 10-fold higher concentration than the expected minimum inhibitory concentration (MIC). Antibiotics used were Cefazolin, Ciprofloxacin, Nitrofurantoin, and Trimethoprim-Sulfamethoxazole. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for *E. coli*. In addition to the wells containing the antimicrobial dilution series, eight wells containing water or diluent were included in the plates to allow for a no antibiotic positive and negative growth control.

Four Hour Growth: While the time zero cell quantification was occurring, 32.4 µL of processed clinical urine and 75.6 µL of 1.43×MHB II (Teknova, cat. #M5860) was added to each well of the antibiotic plate (already containing 12 µL of antibiotics). The samples were allowed to grow in a standard incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 µL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero).

Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results.

FIG. 27 through FIG. 30 shows three examples from our larger data set that demonstrate how this method can be used to generate MICs on three individual urines that match the gold-standard broth microdilution method.

Figure 27:
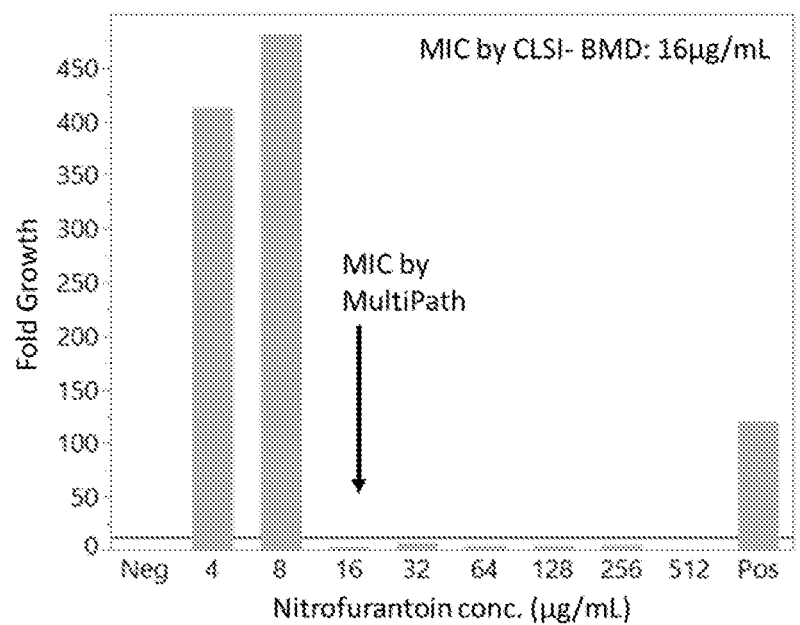
FIG. 27 shows BIUR0017 with Nitrofurantoin

FIG. 27 shows the fold growth numbers at different antibiotic concentrations results for a single clinical urine sample (BIUR0017) against a single drug (Nitrofurantoin). The MIC for the broth microdilution matches exactly with the MIC determined by the fold-growth threshold.

Figure 28:
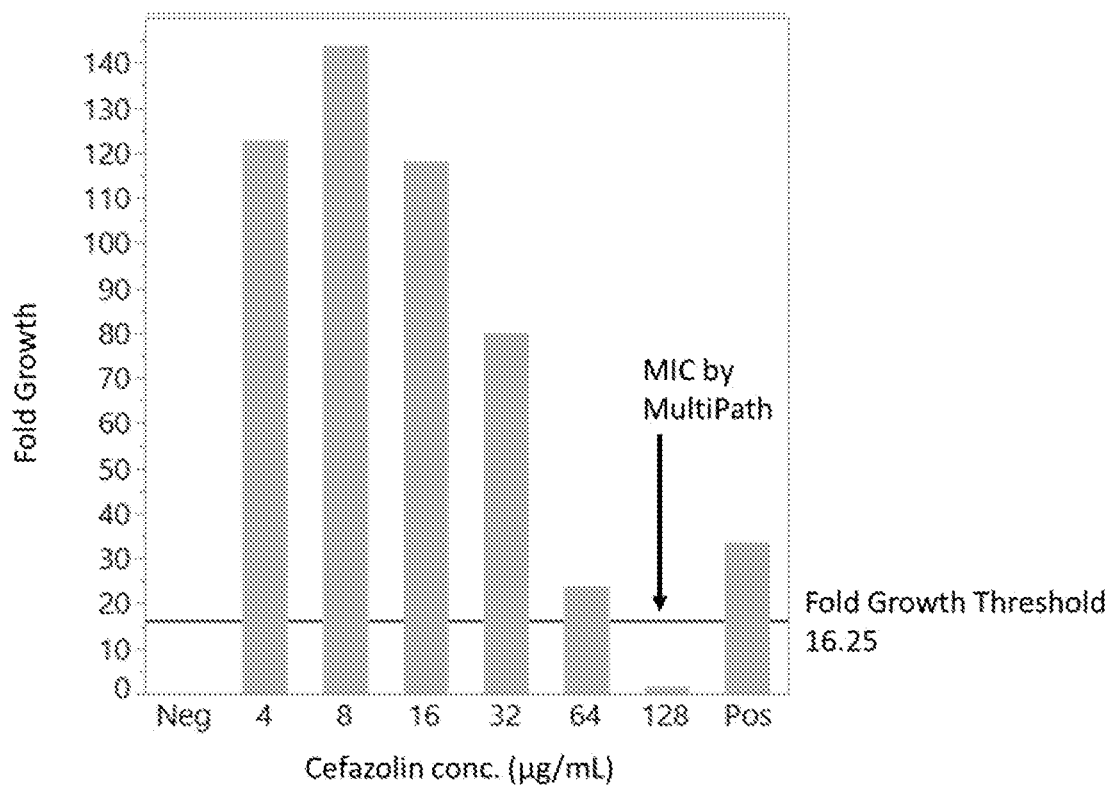
FIG. 28 shows BIUR047 with Cefazolin

FIG. 28 shows the fold growth numbers at different antibiotic concentrations results for a single clinical urine sample (BIUR0047) against a single drug (Cefazolin). The MIC for the broth microdilution matches exactly with the MIC determined by the fold-growth threshold.

Figure 29:
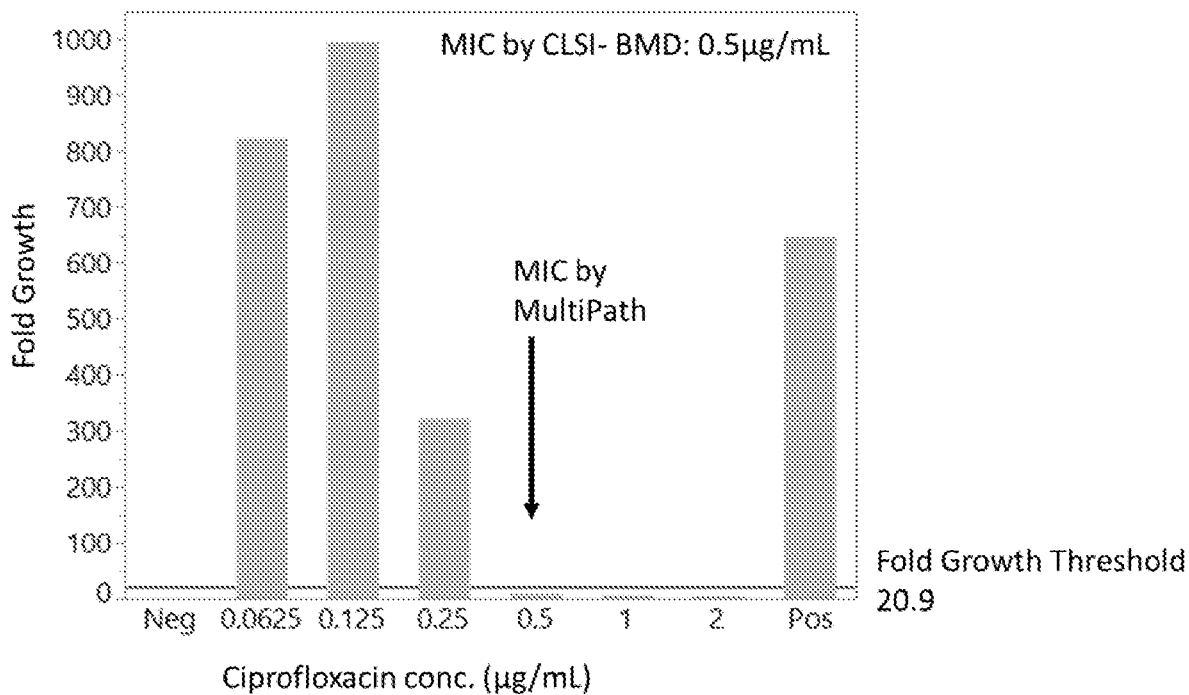
FIG. 29 shows BIUR057 with Ciprofloxacin

FIG. 29 shows the fold growth numbers at different antibiotic concentrations results for a single clinical urine sample (BIUR0057) against a single drug (Ciprofloxacin). The MIC for the broth microdilution matches exactly with the MIC determined by the fold-growth threshold.

Figure 30:
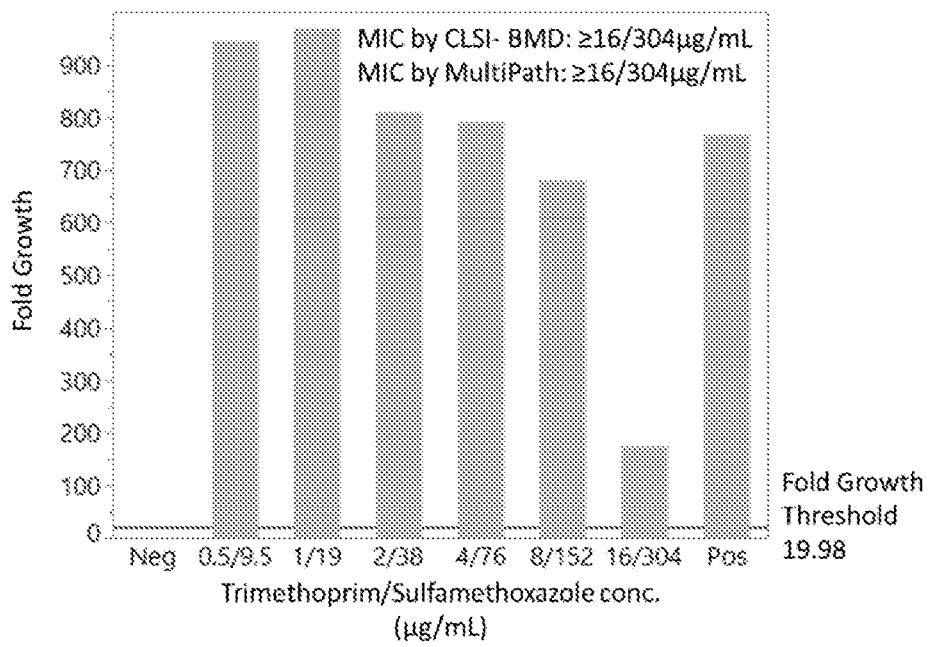
FIG. 30 shows BIUR052 with Trimethoprim/Sulfamethoxazole

FIG. 30 shows the fold growth numbers at different antibiotic concentrations results for a single clinical urine sample (BIUR0052) against a single drug (Trimethoprim/Sulfmethoxazole). The MIC for the broth microdilution matches exactly with the MIC determined by the fold-growth threshold.

Conclusions. This novel method shows that accurate AST results (MIC determinations) may be made with only 4 hours of differential growth of minimally processed urine clinical specimens, notably without lengthy colony purification steps. The AST results, whether reported as MIC categorical antibiotic susceptibility results, compare favorably to the gold standard, broth microdilution method.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also clearly be extended to other antibiotics, biological specimens and to other bacterial and non-bacterial pathogens.

FIG. 27 shows BIUR0017 with Nitrofurantoin
FIG. 28 shows BIUR047 with Cefazolin
FIG. 29 shows BIUR057 with Ciprofloxacin
FIG. 30 shows BIUR052 with Trimethoprim/Sulfamethoxazole
FIG. 31 is a table of Probe sequences used in this example 6.

Example 7. Rapid and Accurate Antimicrobial Susceptibility Testing for Bacteria in Urine Samples Overview. This example demonstrates the use of the invention to accurately determine the antimicrobial susceptibility of pathogens with known antibiotic susceptibility profiles added into bacteria-free urine. Differential growth in microbiological media containing antimicrobial agents followed by assessment of growth using the inventive concerted FISH method for target specific cell quantification required just 4.5 hours. This new method has comparable performance to the gold standard CLSI broth microdilution (BMD) method.

Experimental Methods.

Bacterial cell preparation: 50 bacterial strains with known resistance profiles were collected from either the ATCC or from the CDC antibiotic resistance bank (AR bank) and are shown in Table A. Bacterial cultures for each of these were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. Using optical density at 600 nm to estimate cell concentration, each culture was diluted to approximately $5 \times 10^6$ colony-forming units (CFU)/mL in cation-adjusted Mueller Hinton II (MHBII, Teknova cat. M5860).

Urine Processing: Prior to testing, pooled human urine (Innovative Research, cat. IRHUURE500ML) was applied to a pre-washed Zeba™ 7K MWCO spin column in a ratio of 4 mL urine to one pre-washed 10 mL spin column (ThermoFisher, cat. #89893) and centrifuged according to the manufacturer's instructions.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75 \times 10^{12}$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST Time Zero: Assay signal at time zero (T0) prior to the initiation of bacterial growth in the presence or absence of antibiotics was determined for each bacterium. A reaction mixture was prepared consisting of 30 µL processed urine, 10 µL of the $5 \times 10^6$ CFU/mL bacterial dilution, 60 µL MHBII (1× final concentration in 100 µL) and the appropriate species-specific Alexa647N-labeled DNA oligonucleotide FISH probe and its associated unlabeled DNA helper probes for the target bacterial species. Probe sequences used are shown in Table in FIG. 35. The 100 µL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431), 0.13M guanidine thiocyanate (Sigma, cat. #G9277)). 10 µL of the prepared magnetic particle mixture was then added to the well. 100 µL of this reaction mixture was transferred to a microtiter plate containing 50 µL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Preparation of Antibiotic Plates: Microtiter plates containing six concentrations of each antibiotic in a 2-fold serial dilution series were prepared. The 2-fold dilution series was prepared at a 10-fold higher concentration than the desired concentration in the final broth microdilution, such that addition cells/urine/media mixture would yield the correct antibiotic range. 12 uL of each antibiotic dilution was then aliquoted into the appropriate wells of a 96 well plate. Different antibiotics were tested for different bacteria. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for the appropriate bacterial species such that categorical determinations (sensitive/intermediate/resistant) could be made from this data. In addition to the wells containing the antimicrobial dilution series, several wells containing water or other diluent were included for a no antibiotic positive growth and negative growth (no cell) control. Antibiotic plates were frozen at −80° C. and thawed completely before use.

Four Hour Growth: While the time zero cell quantification was occurring, 12 µL of prepared bacterial culture, 36 uL pooled human urine processed as done for the assay time zero, 60 uL of 2×MHB II (Teknova, cat. #M5860) and 2 uL water was added to each well of the prepared antibiotic plate. The samples were allowed to grow in a standard incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 µL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all concentrations of each antibiotic. For each bacteria sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. Results were then compared to the MIC values and categorical calls reported by ATCC or the CDC. Four-hour growth in the absence of antibiotic is a control condition to ensure viable bacterium were added to each sample or for use when calculating fold inhibition.

Figure 32:
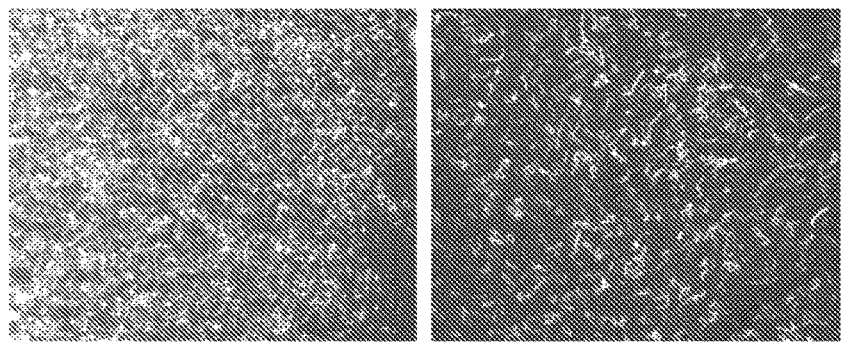
FIG. 32 shows that, in addition, for the bacteria tested against Ceftazidime (CAZ), the presence of exclusively filamentous bacteria (as can be easily distinguished by eye, compare left (normal bacteria) to right (filamentous bacteria)) was taken as an indication of impending cell death.

FIG. 32 shows that, in addition, for the bacteria tested against Ceftazidime (CAZ), the presence of exclusively filamentous bacteria (as can be easily distinguished by eye, compare left (normal bacteria) to right (filamentous bacteria)) was taken as an indication of impending cell death in that antibiotic concentration and the MIC concentration was adjusted accordingly where appropriate. In the case of bacteria tested for Trimethoprim/Sulfamethoxazole (TMP/SXT), thresholds were generated based on fold inhibition (assay signal in the well containing bacteria but no antibiotic divided by the well containing both antibiotic and bacteria). Results.

Figure 33:
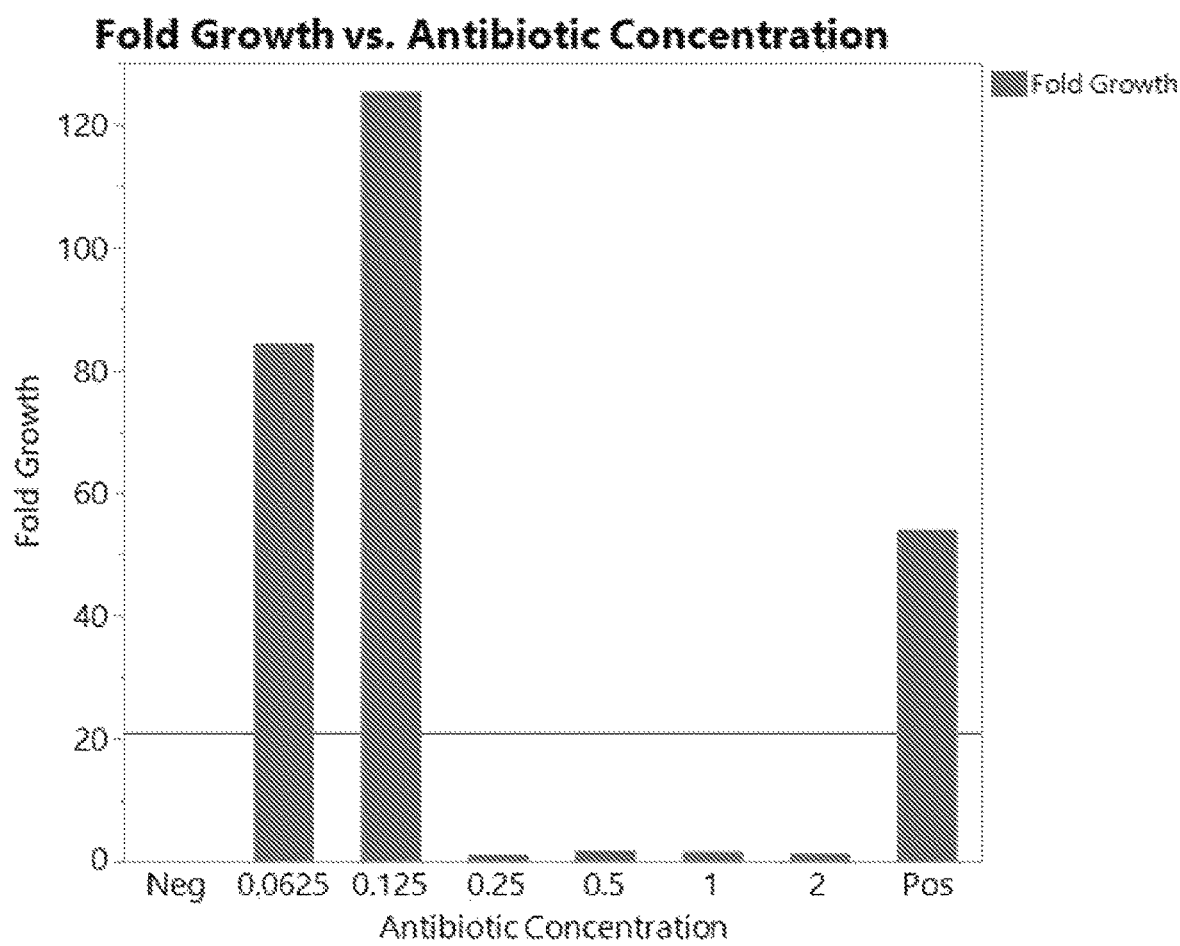
FIG. 33 shows how method can be used to generate MICs.

FIG. 33 shows how this method can be used to generate MICs on individual bacteria in the presence of urine matrix that match the CDC or CLSI-published MIC. The example shows the fold growth numbers at different antibiotic concentrations for a single bacterium, (*K. pneumoniae* CDC0126) against a single drug (Ciprofloxacin). The published MIC (≥0.25 μg/mL) matches exactly with the MIC determined by the novel rapid AST method described in this invention. The threshold for fold-growth (20 in this example) is shown by the horizontal grey line.

The table in FIG. 34 shows the overall performance across all strains tested. A tested MIC is within essential agreement if the MIC determined by the novel AST method matches exactly or is within one 2-fold dilution of the published value. Except for two cases, all bacteria/antibiotic combinations had 100% essential agreement.

Conclusions. This novel method shows that MIC determinations that match the published values for highly characterized strains of bacteria with multiple drug resistance mechanism may be made with only 4 hours of growth in the context of sample matrix.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also clearly be extended to other antibiotics, biological specimens and to other bacteria for which specific probes can be designed.

FIG. 32 is a Visual comparison of normal bacteria (left panel) to filamentous bacteria (right panel).

FIG. 33 shows MIC generated by novel rapid AST method described in this invention is called at 0.25 μg/mL

TABLE A

Bacteria used in this example and their previously determined antibiotic resistance (shown with "X")

| Organism | Number | Ceftazidime | Ciprofloxacin | Meropenem | Trimethoprim/ Sulfamethoxazole | Nitrofurantoin |
|---|---|---|---|---|---|---|
| *E. coli* | CDC0001 | | | X | | |
| *E. coli* | CDC0006 | | | X | | |
| *K. pneumoniae* | CDC0010 | X | | X | X | |
| *K. pneumoniae* | CDC0016 | X | X | X | X | |
| *E. coli* | CDC0017 | | X | | X | |
| *E. coli* | CDC0019 | | X | | X | |
| *E. coli* | CDC0020 | X | | X | | |
| *K. oxytoca* | CDC0028 | X | X | X | X | |
| *P. mirabilis* | CDC0029 | X | X | X | X | Intrinsically resistant |
| *K. pneumoniae* | CDC0034 | | X | X | | |
| *K. pneumoniae* | CDC0041 | X | | | | |
| *K. pneumoniae* | CDC0043 | | | X | | |
| *P. mirabilis* | CDC0059 | X | X | X | X | Intrinsically resistant |
| *E. coli* | CDC0067 | X | | | | |
| *K. oxytoca* | CDC0071 | X | X | X | X | |
| *K. pneumoniae* | CDC0076 | | X | X | | |
| *K. pneumoniae* | CDC0080 | | | X | | |
| *E. coli* | CDC0084 | X | | | X | |
| *E. coli* | CDC0085 | | | X | | |
| *E. coli* | CDC0086 | X | | | | |
| *P. aeruginosa* | CDC0105 | X | | X | Intrinsically resistant | Intrinsically resistant |
| *K. pneumoniae* | CDC0107 | X | | | X | |

TABLE A-continued

Bacteria used in this example and their previously determined antibiotic resistance (shown with "X")

| Organism | Number | Ceftazidime | Ciprofloxacin | Meropenem | Trimethoprim/Sulfamethoxazole | Nitrofurantoin |
|---|---|---|---|---|---|---|
| P. aeruginosa | CDC0111 | X | | X | Intrinsically resistant | Intrinsically resistant |
| E. coli | CDC0114 | | | X | | |
| K. pneumoniae | CDC0117 | | X | | X | |
| K. pneumoniae | CDC0126 | X | X | | X | |
| K. oxytoca | CDC0147 | X | X | X | X | |
| P. mirabilis | CDC0155 | X | X | X | X | Intrinsically resistant |
| P. mirabilis | CDC0156 | X | X | X | X | Intrinsically resistant |
| P. mirabilis | CDC0159 | X | X | X | X | Intrinsically resistant |
| K. pneumoniae | CDC0160 | X | | | | |
| P. aeruginosa | CDC0232 | | | X | Intrinsically resistant | Intrinsically resistant |
| P. aeruginosa | CDC0242 | X | | X | Intrinsically resistant | Intrinsically resistant |
| P. aeruginosa | CDC0247 | | | X | Intrinsically resistant | Intrinsically resistant |
| P. aeruginosa | CDC0251 | X | X | | Intrinsically resistant | Intrinsically resistant |
| P. aeruginosa | CDC0253 | X | X | | Intrinsically resistant | Intrinsically resistant |
| P. aeruginosa | CDC0259 | | X | | Intrinsically resistant | Intrinsically resistant |
| P. aeruginosa | CDC0261 | | X | | Intrinsically resistant | Intrinsically resistant |
| P. aeruginosa | CDC0262 | | X | | Intrinsically resistant | Intrinsically resistant |
| E. coli | CDC0350 | X | | | | |
| P. mirabilis | ATCC 7002 | X | X | X | X | Intrinsically resistant |
| K. pneumoniae | ATCC 13883 | X | X | X | X | |
| E. coli | ATCC 25922 | X | X | X | X | X |
| P. aeruginosa | ATCC 27853 | X | X | | Intrinsically resistant | X |
| K. pneumoniae | BAA-1904 | | | | | X |
| E. coli | BAA-2340 | | | | | X |
| E. coli | BAA-2452 | | X | | | X |
| E. coli | BAA-2469 | | X | | X | X |
| E. coli | BAA-2471 | | X | | X | X |
| K. pneumoniae | BAA-2472 | | | | | X |

FIG. 34 is a table of AST results for all bacteria and antibiotics tested in this example.

FIG. 35 is a table of Probe sequences used in this example 7.

Example 8. Rapid and Accurate Automatic AST Results for Clinical Urine Specimens without Using Cell Purification Overview. This example demonstrates the use of the systems and methods of the invention to automatically determine AST results for a pathogen in a clinical urine sample in 4 hours without requiring lengthy cell purification steps. The automated instrument performs the steps required in the reagent-containing cartridge to determine antimicrobial susceptibility at a constant physiological temperature. The temperature is compatible with both microbial growth and the inventive method for detecting and quantifying target cells. The latter method is performed on the inventive system using FISH-based labeling, magnetic selection, and non-magnified digital imaging.

The instrument's pneumatics subsystem is used to automatically distribute the specimen in the cartridge into portions or aliquots containing various antimicrobial agents in various concentrations plus microbiological medium. One of the portions is used to quantify the pathogen cells before growth incubation. The system incubates the cartridge for 4 hours and then quantifies the number of target cells in the wells containing antimicrobial agents. Comparison of the number of cells in the incubated portions containing antimicrobial agents to the number of cells measured before incubation is used to determine the antimicrobial susceptibility of the pathogen in the various antibiotics.

The example shows the results using the inventive automated systems, devices, and methods for rapid and automated antimicrobial susceptibility testing directly in clinical specimens from hospital patients that had E. coli in their urine. The invention delivered in just 4 hours accurate performance compared to the gold standard CLSI broth microdilution (BMD) method.

Experimental Methods.

Urine Specimens: Remnant de-identified urine specimens collected from patients with a urinary tract infection (UTI) and known to contain *E. coli* were received from Dr. Kirby's lab at Beth Israel Hospital (Boston, MA). Samples were received 1-5 days post collection and contained a urine preservative to limit loss of cell viability. For each sample, color of urine, pH, and presence of particulates were noted. Upon receipt, conventional urine culture was performed to determine the approximate CFU/mL of bacteria present, and to confirm single or mixed bacterial morphology as reported by Dr. Kirby's lab. Briefly, a calibrated 1 μL loop was placed into a well-mixed urine sample and the 1 μL was evenly spread over a Tryptic soy agar (TSA) plate and incubated in a 35° C. incubator for 18-24 hours. The remainder of the urine samples were processed and assayed as described below.

Preparation of the AST Cartridge—Media and Antimicrobials

Days prior the cartridge was prepared by distributing 25 uL of 4×MHB II (Teknova, Cat. #101320-356) into each of the 8 individual growth wells (see FIG. 1 for a diagram of the cartridge) Growth wells 1 and 2 are for the time zero measurement (see description below), so only growth media is contained in the growth wells. Growth wells 3 and 4 also only contained media. These wells serve as a positive control to make sure growth is observed over four hours. Into growth wells 5 and 6, and 7 and 8, 2 concentrations antibiotic was added. To do this 4.5 μL of a 22.2-fold more concentrated antibiotic than the target concentration in micrograms per mL was deposited into appropriate growth wells. Cartridges either contained 2 concentrations of both Ciprofloxacin (CIP) and Nitrofurantoin (NIT) or Cefazolin (CFZ) and Trimethoprim/Sulfamethoxazole (TMP/SXT). For final concentrations of each antibiotic in the cartridge, see Table 1. The media and antibiotics were then dried for 16-20 hours in a 40° C. convection oven.

Preparation of the AST Cartridge—Hybridization Reagents.

Hybridization buffer containing 3×SSC (0.45 M NaCl, 0.045 M sodium citrate, pH 7.5) (Sigma, cat. #S6639), 0.18% w/v cetrimide, 0.77% CHAPSO (Sigma cat. #C3649), 0.72% SB3-12 (Sigma cat. #D0431), and 0.13M guanidine thiocyanate (Sigma, cat. #G9277) was prepared. Trehalose (Sigma, cat. #T9449) was dissolved in this mixture to a final concentration of 10% w/v. This hybridization buffer-trehalose mixture was lyophilized in 8.3 μL volume beads. Two 8.3 uL beads were placed into each of 8 reagent wells (see FIG. 1, for location on cartridges)

Preparation of the AST Cartridge—Magnetic Particles

Poly-aspartic acid-conjugated magnetic particles (Fluidmag-PAA, Chemicell, cat. 4108) were diluted 1:20 into 50 mM Epps buffer, pH 8.2 to a concentration of $2.75 \times 10^{14}$ particles/mL with a final concentration of 10% w/v Trehalose (Sigma, cat. #T9449). To this dilution, fluorescent magnetic microspheres containing a green dye (Dragon Green Fluorescent Microspheres, BANGS Laboratories, cat. MEDG001) were added were added to the suspension at a final concentration of $3 \times 10^6$ particles/mL. The magnetic particle mixture was sonicated for 1 minute prior to immediately use to minimize aggregation. The mixture was then lyophilized in 10 μL volume beads ($2.64 \times 10^{12}$ particles per reaction). One magnetic particle lyophilized bead was placed in each of the 8 reagent wells along with the 2 hybridization mix beads.

Procedure for Placing Samples into the Cartridge—Urine Processing

Prior to testing, urine preservative and other potentially interfering compounds were removed using size exclusion chromatography. 2.5 mL of each clinically positive urine sample was applied to a pre-washed Zeba™ 7K MWCO spin column (ThermoFisher, cat. #89893) and centrifuged according to the manufacturer's instructions. Urine culture was repeated on this processed sample as described above, to examine bacterial loss following processing.

Procedure for Placing Samples into the Cartridge—Putting Samples on Cartridges

750 μL of each processed urine sample was combine with 1705 μL of water and 45 μL of species-specific DNA oligonucleotide fluorescence in situ hybridization (FISH) probes and unlabeled DNA helper probes to make solution containing 30% urine v/v final concentration. Oligonucleotides used for each bacterium, their concentrations and dye labels can be found in Table 2. 1 mL of the mixture was added to the sample pot of the cartridge and the cartridge placed onto the analyzer.

Running the AST Cartridges on an Automated Analyzer

After the cartridge was then placed on the instrument, all subsequent actions other than data analysis were automatically performed. The Urine/water/FISH probe mixture (sample) was first directed under vacuum into the 8 growth wells at the top of the cartridge. Sample in the first two growth wells was then immediately relocated to reaction wells, rehydrating the hybridization buffer/FISH probe mix and lyophilized magnetic particles. Sample then continued to the imaging windows containing 46 μL of dehydrated "dye-cushion" (50 mM TRIS pH 7.5 (Teknova, cat. T5075), 7.5% v/v Optiprep (Sigma, cat. D1556), 5 mg/mL Direct Black-19 (Orient, cat. #3222), dried for 60° C. for 3 hours in a convection oven) and incubated at 35° C. for 30 minutes on the analyzer. After this incubation, the cartridges were then relocated to the magnet station, and placed atop a strong permanent magnet (Dexter magnetic technologies, cat. 54170260) for 4 minutes to bring the labeled and magnetic-particle-interacting bacterial cells into close proximity to the imaging surface. Finally, the cartridge was moved to the imaging station and imaging taken using non-magnified CCD imager described below.

Sample in the remaining six growth wells were held in that location, and the bacteria allowed to grow for 4 hours at 35° C. in the rehydrated media, either in the presence or absence of antibiotics. Following growth, the cell suspensions were relocated to the reagent wells as was done for the time zero assay, and the exact same hybridization reaction, magnetic pull-down, and imaging was performed as described above.

The Analyzer Imaging System and Imaging Process

The MultiPath Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Data analysis: Using the image captured by the CCD camera, detected cells were estimated by an algorithm that looked at both number of objects in the field of view and the intensity of the objects. Number of cells based on this detection algorithm were generated at time zero, and at time four hours without antibiotic and with both concentrations of each antibiotic. For each urine sample/drug concentration, fold growth was calculated as the signal in the well containing antibiotic after growth (time four) to the signal in the urine sample prior to growth (time zero). Comparison of fold growth and the observation of growth in the corresponding well in the CLSI-compliant broth microdilution, thresholds were selected for the fold growth cutoff to maximize agreement with the broth microdilution results. In conditions where cells are growing in the presence of the antibiotic (and thus, resistant at that concentration), the fold growth will be high and in conditions where cells are in the process of dying (and thus, sensitive at that concentration), the fold growth number will be low. In these cartridges, if both concentrations of antibiotic show no growth based on their fold growth numbers, the bacteria in that urine sample is called sensitive. If there is growth in the lower concentration but not the higher concentration, the bacteria in the urine sample is intermediate in the case of Ciprofloxacin, Nitrofurantoin and Trimethoprim/Sulfamethoxazole and resistant in the case of Cefazolin. If both concentrations of antibiotic show growth based on their fold growth thresholds, the bacteria in that urine sample is called resistant. All sensitive/resistant calls data compared to the sensitive/resistance call made by the MIC determination in a CLSI-compliant standard BMD. Four-hour growth in the absence of antibiotic is a control condition to ensure viable bacterial are present in the processed urine sample.

Results.

Figures 36, 37:
FIG. 37 shows the average fold growth of four replicates.
FIG. 36 shows the Multipath™ UTI-AST cartridge

FIG. 37 shows the average fold growth of four replicates in two cartridges containing clinical urine sample BIUR0067, which contained an *E. coli* strain. The graph shows the mean fold growth in each of the 2 concentrations each of Ciprofloxacin and Nitrofurantoin across 4 replicates in 2 different cartridges. Using a fold-growth value of 2 for both antibiotics, the MulitPath assay calls both Ciprofloxacin (CIP) concentrations as growth and both the Nitrofurantoin (NIT) concentrations as no growth. Therefore, by MulitPath, BIUR0067 is resistant to ciprofloxacin and sensitive to Nitrofurantoin. The *E. coli* strain isolated from this urine and tested in a CLSI-standard broth microdilution matched these sensitive/resistant calls.

Figure 39:
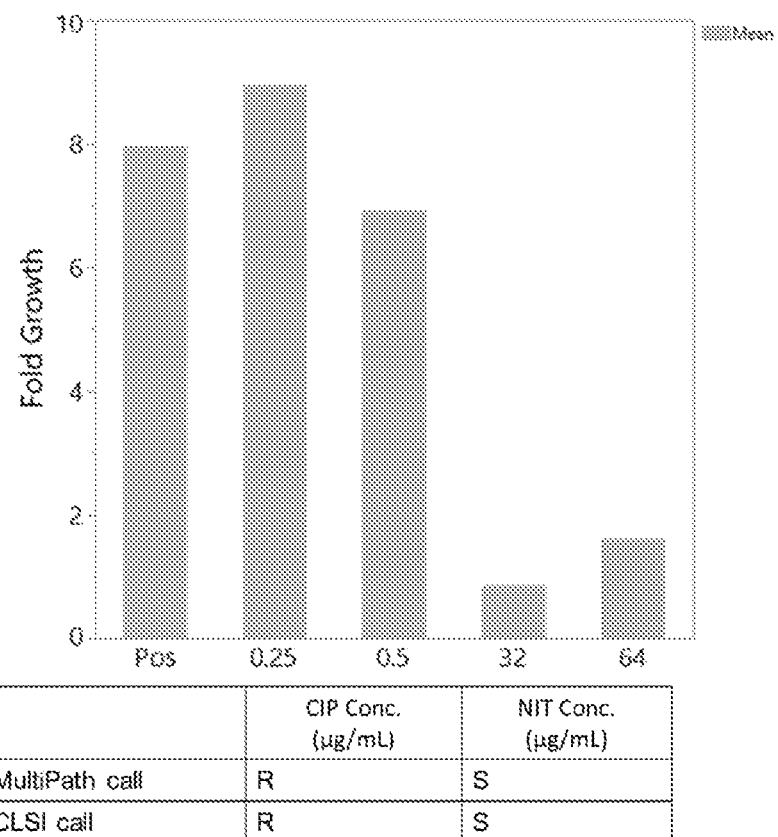
FIG. 39 shows the average fold growth of four replicates.

FIG. 39 shows the average fold growth of four replicates in two cartridges containing clinical urine sample BIUR0084, which contained a *K. pneumoniae* strain. The graph shows the mean fold growth in each of the 2 concentrations each of Cefazolin and Trimethoprim/Sulfamethoxazole across 4 replicates in 2 different cartridges. Using a fold growth value of 2 for both antibiotics, the MulitPath assay calls all the antibiotic concentrations of both Cefazolin and Trimethoprim/Sulfamethoxazole as growth. Therefore, this strain of *K. pneumoniae* is resistant to both antibiotics. This matches both the CLSI-standard broth microdilution done in house.

Conclusions. The example shows the results using the inventive automated systems, devices, and methods for rapid and automated antimicrobial susceptibility testing directly in clinical specimens from hospital patients that had *E. coli* in their urine. The invention delivered in just 4 hours accurate performance compared to the gold standard CLSI broth microdilution (BMD) method.

Variations. This example is illustrative of the performance of this novel AST method on a cartridge and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures and alterations to reactant and antimicrobial stabilization, different bacterial targets, different antimicrobial agents etc. This methodology can also clearly be extended to other biological specimens and to other bacterial and non-bacterial pathogens.

FIG. 36 shows the Multipath™ UTI-AST cartridge

FIG. 37 is a table showing

Antibiotic concentrations tested.

FIG. 38 is a table of Oligonucleotides used in this example 8.

FIG. 39 shows BIUR0067 Results.

Figure 40:
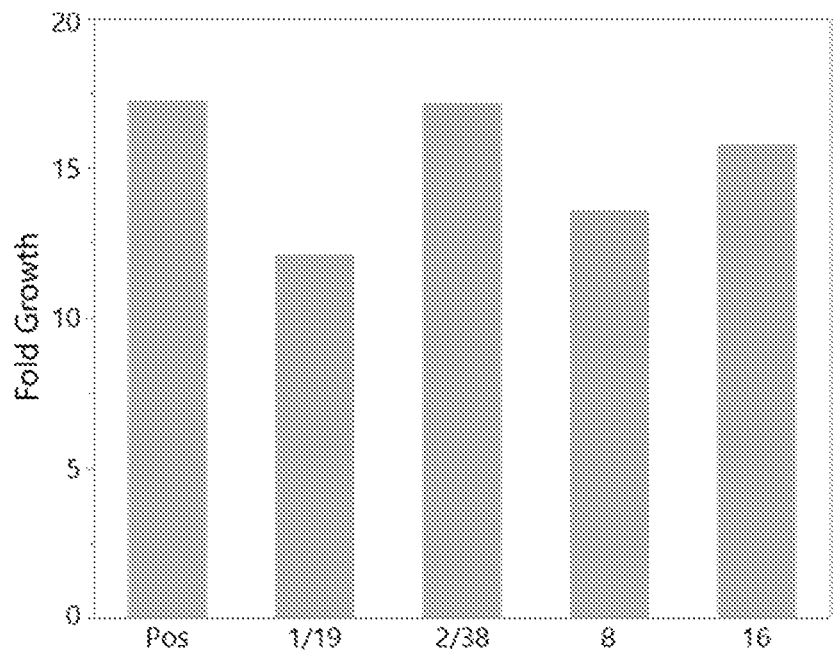
FIG. 40 shows BIUR0084 Results.

FIG. 40 shows BIUR0084 Results

Example 9. Rapid AST Method Directly in Urine Specimens is Robust to Variation Pathogen Concentration Overview. Robustness to variable inoculum concentrations is important for the rapid AST method because when testing specimens directly from specimens the target cell concentration is unknown. This example demonstrates the use of the invention to provide accurate and consistent results directly from a urine specimen when for contrived specimens covering a wide range of target cell concentrations. This example demonstrates that variable cell inputs of *E. coli* BAA-2469, *P. aeruginosa* ATCC 27853, *K. pneumoniae* ATCC 700603 and *K. pneumoniae* CDC-0043 in the presence of 10% urine deliver accurate AST results compared to the Broth Microdilution (BMD) gold standard for AST.

Experimental Procedure.

Preparation of Antibiotic Plates: Antibiotic plates containing either concentrations of three to five antibiotics in a 2-fold serial dilution series were prepared by distributing 10 µL of 10-fold higher concentration than the desired final concentration into the wells of a 96 well plate. The concentrations selected for testing of each antibiotic straddled the CLSI-reported MICs for the bacterial strains tested. Plates were prepared with all or a subset of the following antibiotics: Cefazolin, Ciprofloxacin, Levofloxacin, Nitrofurantoin, and Trimethoprim-Sulfamethoxazole. In addition to the wells containing the antimicrobial dilution series, four wells contained water to allow for positive (bacteria growth in the absence of antibiotic) and negative (no bacterial cells) controls.

Preparation of Cultures: Bacterial cultures for *E. coli* BAA-2469, *P. aeruginosa* ATCC 27853, *K. pneumoniae* ATCC 700603, and *K. pneumoniae* CDC-0043 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. The cells were diluted in 1× cation-adjusted Mueller-Hinton broth (MHBII, Teknova cat. M5860) to various inoculum ($2\times10^3$ CFU/mL–1×10$^7$ CFU/mL). For more accurate cellular concentrations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours. Using the average plate counts, the actual CFU present in each concentration tested was computed.

Preparation of Magnetic Particles: 2 hydroxypropyl trimethylammonium chloride coated silica magnetic particles (SiMag-Q, Chemicell, cat. 1206-5) were diluted 1:20 into 50 mM EPPS buffer, pH 8.2 to 2.75×10$^{12}$ particles/mL. Fluorescent magnetic microspheres containing a green dye (Dragon Green Fluorescent Microspheres, BANGS Laboratories, cat. MEDG001) were added to the suspension at a final concentration of 3×10$^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each organism and inoculum. 10 μL of each sample was added to 80 μL of hybridization buffer to final concentrations of 3×SSC (0.45 M NaCl, 0.045 M Na citrate, Sigma, cat. #S6639), 1% CHAPS (Sigma, cat. #C3023), 1% NOG (Sigma cat. #08001), 1× cation-adjusted Mueller-Hinton Broth (MHBII), species-specific DNA oligonucleotide FISH probes and unlabeled DNA helper probe. The oligonucleotide probes used are shown in Table B. A final concentration of 10% urine was obtained by adding 10 μL of pooled urine (in-house collected and filtered) directly to the mixture. 10 μL of the magnetic particle mixture prepared as described above was then added. 100 μL of this reaction mixture was transferred to a microtiter plate containing 50 μL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222) (dry-cushion plate) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: While the time zero cell quantification was occurring, 10 μL of each organism inoculum, 10 μL of pooled urine, and 70 μL of 1×MHBII was added to the appropriate wells of the antibiotic plate (already containing 10 μL of antibiotic). The samples were allowed to grow in a standard air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 10 μL of the incubated sample-antibiotic plate (10%) was transferred to a microtiter plate and combine with 100 μL hybridization buffer, FISH probes, helper probes, magnetic particles, and focus particles in the same manner as described above for assay time zero.

Comparison Method: Results using the novel AST method described here were compared to broth microdilutions (BMD) performed according to CLSI M07-Ed13E 2018.

Data Analysis and Threshold Generation: Using the image captured by the CCD camera, detected cells were estimated by an algorithm that looked at both number of objects in the field of view and the intensity of the objects. The number of cells based on this detection algorithm were generated at time zero, and at time four hours without antibiotic and with all concentrations of each antibiotic. For each sample inoculum/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results.

The figures below show how this method is robust to varying inoculum levels while matching the gold-standard broth microdilution method.

FIG. 41 compares the results obtained with the novel AST method to results of a standard BMD performed at a single concentration for all drugs tested. Column 3 compared the MICs obtained via the novel AST method and the gold-standard BMD. All MIC calls were within one 2-fold dilution (Essential Agreement) of the CLSI-compliant BMD. Column 4 compared categorical antibiotic susceptibility results (S=susceptible, I=intermediate, R=resistant) based on the MIC (Categorical agreement). Although a subset of *Klebsiella* concentrations gave different categorical calls from the MIC in broth microdilution, all of these were only classified as minor errors by standard AST methodology.

Figures 42, 43:
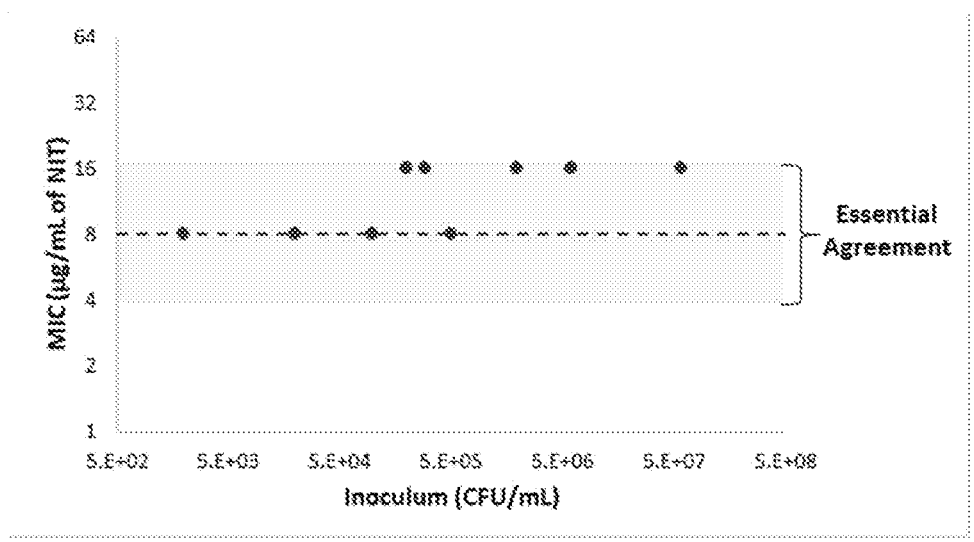
FIG. 42 shows MICs generated with the novel 4-hour method described above for all inoculum levels for *E. coli* BAA-2469 (solid circles) compared to the standard broth
FIG. 43 is a Summary of MIC results for the various inoculum levels generated.

FIG. 42 shows MICs generated with the novel 4-hour method described above for all inoculum levels for *E. coli* BAA-2469 (solid circles) compared to the standard broth microdilution method (24 hr BMD, dashed line). All MICs determined with this novel method are within essential agreement (shaded area). FIG. 43 shows the raw data for FIG. 42.

Conclusion. The rapid 4-hour AST method presented here is robust to initial cell concentration over a wide range of target cell concentrations. Robustness to variable inoculum concentrations is important for the rapid AST method because when testing specimens directly from specimens the target cell concentration is unknown.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens for which specific probes can be designed, and for other antimicrobial or chemical agents.

FIG. 41 is a Summary of the overall essential and categorical agreement for all organisms, antibiotics and inoculum levels.

FIG. 42 shows MIC results for various inoculum levels generated using the new methods described here compared to the conventional BMD method.

FIG. 43 is a Summary of MIC results for the various inoculum levels generated.

FIG. 44 is a table of Probe sequences used in this example 9.

Example 10. Rapid Antimicrobial Susceptibility Testing for Target Pathogens in Urine Clinical Specimen Containing Multiple Bacterial Species without Cell Purification Overview. Current methods for antimicrobial susceptibility testing require lengthy culture-based colony purification to ensure a pure population of the target pathogen cells free of other microbes. The usual method, colony purification requires, 2-5 days to deliver results. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

Current methods require the lengthy cell purification process because these methods use non-specific detection methods, such as increase in turbidity, to determine which antimicrobial agents inhibit the growth of the target pathogen in microbiological medium. When using non-specific measurement of cellular replication one can only know that the growth seen is due to the target pathogen if the contains only cells of the target pathogen. Cell purification must be undertaken for current antimicrobial susceptibility testing methods because most medical specimens are non-sterile. Specimens generally contain microbes that make up the human microbiome, the benign normal bacterial population that populate our bodies.

In contrast, the inventive method can deliver accurate antimicrobial susceptibility testing results directly from specimens without the colony purification step. The method differs from current methods in that it assesses growth specifically for the target pathogen in microbiological medium containing antimicrobial agents.

This example demonstrates that the rapid antimicrobial susceptibility testing method accurately determines the minimum inhibitory concentration (MIC) for an *E. coli* strain in contrived samples comprising urine matrix (10%) for 15 different culture-negative urine samples. Here we show that using the new method antimicrobial susceptibility testing results are accurate and not significantly impacted by off-target bacteria in urine samples containing high concentrations of other microbial species.

Experimental Procedure.

Preparation of Antibiotic Plates: Prior to initiating experimental procedure, a plate containing five concentrations in a 2-fold serial dilution series were prepared by distributing 10 μL of 10-fold higher concentration than the desired concentration. The concentrations selected for testing of each antibiotic straddled the CLSI-reported breakpoints for the antibiotic for *E. coli*. In addition to the wells containing the antimicrobial dilution series, four wells containing water were included in the plates to allow for a positive and negative control.

Preparation of Cultures: Three to five colonies of *E. coli* BAA-2469 as well as eight other off-target species (*S. aureus* ATCC 25923, *C. freundii* ATCC 43864, *A. baumannii* ATCC 19606, *S. epidermidis* ATCC 12228, *M. luteus* (environmental isolate), *C. minutissimum* ATCC 23348-BAA 949, *K. pneumoniae* CDC 0043, and *K. pneumoniae* CDC 0141) were each inoculated separately into 5 mL of Tryptic Soy Broth (TSB, Hardy Diagnostics cat. U65) and incubated while shaking for 1-2 hours at 35° C. The optical density was measured by a spectrophotometer and the organisms were diluted in 1× cation-adjusted Mueller-Hinton Broth (MHBII, Teknova cat. M5860). *E. coli* was diluted to approximately $5\times10^6$ CFU/mL (final assay concentration is $5\times10^5$ CFU/m) while the other off-target species were diluted to various inoculum (ranging from $1\times10^5$ to $5\times10^8$ CFU/mL).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each species of *E. coli*. 10 μL of each sample was added to 80 μL of hybridization buffer (3×SSC (0.45 M NaCl, 0.045 M sodium citrate) (Sigma, cat. #S6639), 1% CHAPS (Sigma, cat. #C3023), 1% SB3-12 (Sigma cat. #08001), 1× Cation-adjusted Mueller-Hinton Broth (MHBII), *E. coli*-specific DNA oligonucleotide FISH probes and unlabeled DNA helper probe)). Probe sequences are shown in Table in FIG. 50. A final concentration of 9.1% urine was obtained by adding 10 μL of pooled urine (in-house collected and filtered) directly to the mixture. 10 μL of the magnetic particle mixture prepared as described above was added directly to this mixture. 100 μL of the sample, now containing the hybridization mixture, urine, and magnetic particles, was transferred to a microtiter plate containing 50 μL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: The $E$. $coli$ BAA 2469, in the presence of $Staphylococcus$ $epidermidis$, $Micrococcus$ $luteus$, $Corynebacterium$ $minutissimum$, $Staphylococcus$ $aureus$, $Acinetobacter$ $baumannii$, $Citrobacter$ $freundii$) were tested for their susceptibility against 3 antimicrobial agents: Ciprofloxacin (CIP), Levofloxacin (LVX), and Nitrofurantoin (NIT). $E$. $coli$ BAA 2469, in the presence of $Klebsiella$ $pneumoniae$ was tested against 5 antimicrobial agents: Cefazolin (CFZ), Ciprofloxacin (CIP), Levofloxacin (LVX), Nitrofurantoin (NIT), and Trimethoprim-Sulfamethoxazole (TMP/SXT). Antibiotic plates containing these antimicrobial agents were prepared according to the method described above. While the time zero cell quantification was occurring, 10 µL of either $E$. $coli$ species ($5 \times 10^6$ CFU/mL), 10 µL of an off-target species ($1 \times 10^5$ to $5 \times 10^8$ CFU/mL), 10 µL of pooled urine, and 60 µL of MHB II (Teknova, cat. #M5860) was added to each well of the antibiotic plate already containing 10 µL of antibiotics. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 10 µL of the incubated sample-antibiotic plate (10%) was transferred to a microtiter plate containing dried "dye cushion" and combined with the 100 µL mixture of hybridization buffer, FISH probes, helper probes, magnetic particles, and focus particles as described above for assay time zero.

Comparison Method: Results for the novel assay method described here were compared to broth microdilutions (BMD) performed according the M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all concentrations of each antibiotic. For each bacteria sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic.

Results.

The data shown demonstrate the 4-hour AST method described above is robust to non-sterile samples while a CLSI BMD method where extra bacteria is present is not.

FIG. 47 shows the data for $E$. $coli$ BAA-2469 in the presence of Nitrofurantoin and with increasing concentrations of $S$. $aureus$ ATCC 25923 up to an excess of 100-fold. The $E$. $coli$ MIC in the CLSI-like broth microdilution method is affected by the addition of the $S$. $aureus$ strain (marked as X in the figure) where the MIC increases from 8 in the absence of $S$. $aureus$ to 32 with a 100-fold excess of $S$. $aureus$. In contrast, the novel 4-hour AST assay described in this invention (MultiPath, circles) had the same MIC (8) (dashed line) regardless of the amount of $S$. $aureus$ cells.

Figures 45, 46:
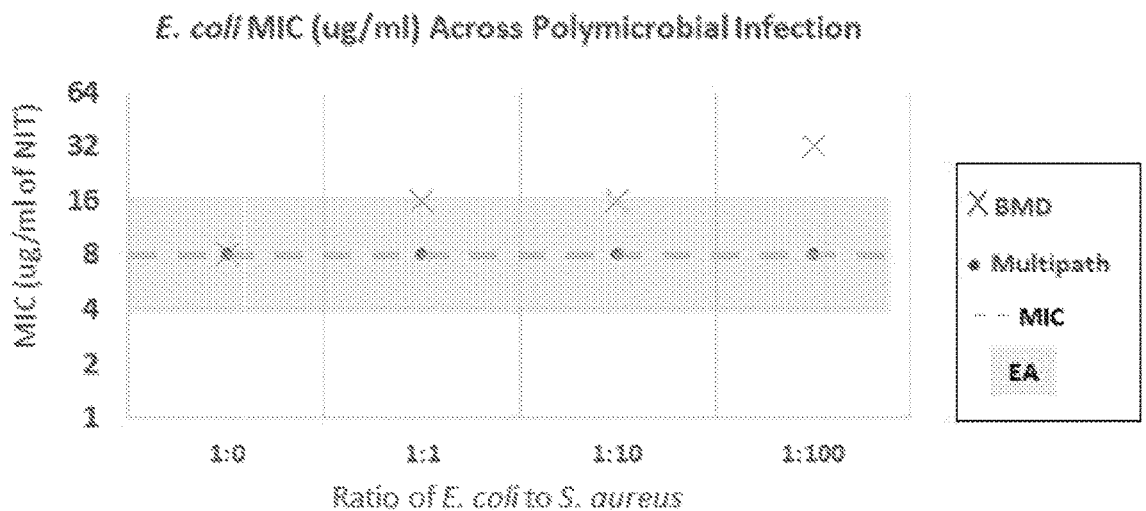

FIG. 47 through FIG. 49 show the raw MIC values determined using this novel method (MultiPath) compared to a CLSI broth microdilution where only the $E$. $coli$ BAA-2469 is present. Table in FIG. 46 shows the overall essential agreement of $E$. $coli$ in the presence of increasing off-target bacteria. Only a single condition—1e7 $Citrobacter$ $freundii$ with Nitrofurantoin—resulted in a lack of essential agreement but this did not change the categorical sensitive/intermediate/resistant determination which had 100% agreement across all antibiotics and all off-target bacteria.

Conclusions. The example demonstrates that using the invention for antimicrobial susceptibility testing, cell purification is not required for achieving accurate antimicrobial susceptibility testing results for a target pathogen in samples containing even large numbers of other microbes of other species.

Variations: This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

FIG. 45 shows the MIC for $E$. $coli$ stays consistent with the method describe above with varying inoculum of $S$. $aureus$ while the MIC for BMD increases with increasing $S$. $aureus$.

FIG. 46 shows a summary of agreement for $E$. $coli$ with varying inoculum levels of off-target microbe to standard BMD.

FIG. 47 shows agreement of $E$. $coli$ with varying inoculum levels of off-target microbe ($S$. $aureus$, $Staphylococcus$ $epidermidis$, and, $Citrobacter$ $freundii$) standard BMD.

FIG. 48 shows agreement of *E. coli* with varying inoculum levels of off-target microbe (*Micrococcus luteus, Acinetobacter baumannii, Corynebacterium minutissimum*) standard BMD.

FIG. 49 shows agreement of *E. coli* with varying inoculum levels of off-target microbe (*K. pneumoniae*) standard BMD.

FIG. 50 is a table of Probe sequences used in this example 10.

Example 11. Rapid Antimicrobial Susceptibility Testing is Accurate for Lactam Antibiotics in the Presence of Bacteria Expressing Beta-Lactamase Overview. Current methods for antimicrobial susceptibility testing require lengthy culture-based colony purification to ensure a pure population of the target pathogen cells free of other microbes. The usual method, colony purification requires, 2-5 days to deliver results. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

One reason that current methods require the lengthy cell purification process because these methods use non-specific detection methods, such as increase in turbidity, to determine which antimicrobial agents inhibit the growth of the target pathogen in microbiological medium. When using non-specific measurement of cellular replication one can only know that the growth seen is due to the target pathogen if the contains only cells of the target pathogen.

In contrast, the inventive method can deliver accurate antimicrobial susceptibility testing results directly from specimens without the colony purification step. The method differs from current methods in that it assesses growth specifically for the target pathogen in microbiological medium containing antimicrobial agents. We demonstrate in another example, that the inventive method is accurate in the presence of large numbers of cells from off-target species.

In this example, we address another challenge that could arise by performing antimicrobial susceptibility testing for a target pathogen in the presence of off-target species. Here we demonstrate that the inventive method delivers accurate antimicrobial susceptibility testing results for a target pathogen in contrived urine specimens containing large numbers of an off-target species that makes an enzyme known to break down the antimicrobial agent being tested. Theoretically this could potentially change the concentration of the antimicrobial agent significantly enough to alter the antimicrobial susceptibility testing result.

In this example, we demonstrate that the rapid antimicrobial susceptibility testing achieves accurate antimicrobial susceptibility testing results for two carbapenem antibiotics (Meropenem and Imipenem) in the presence of large numbers of an off-target pathogen that produces a enzyme that breaks down this type of antimicrobial agent.

Experimental procedure. Preparation of Antibiotic Plates: Antibiotic plates prepared as described in Impact of Non-Sterile Sample on Target MIC example.

Preparation of Cultures: Three to five colonies of *E. coli* ATCC 25922, a strain of bacteria sensitive to most antibiotics and *K. pneumoniae* CDC 0141, a strain that, among many other resistance genes, expresses the beta-lactase OXA-181, were each inoculated separately into 5 mL of Tryptic Soy Broth (TSB, Hardy Diagnostics cat. U65) and incubated while shaking for 1-2 hours at 35° C. The Optical Density was measured by a spectrometer and the organisms were diluted in 1× cation-adjusted Mueller-Hinton Broth (MHBII, Teknova cat. M5860). *E. coli* was diluted to $5 \times 10^5$ CFU/mL (CLSI standard concentration) while *K. pneumoniae* was diluted to various inoculum (ranging from $1 \times 10^6$ and $5 \times 10^8$ CFU/mL).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $3.75 \times 10^6$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal at time zero (T0) prior to the initiation of bacterial growth in the presence or absence of antibiotics was determined for each clinical urine specimen. 30 μL of each processed urine was added to 70 μL of 1× cation-adjusted Mueller-Hinton Broth (MHBII) containing species-specific Alexa647N-labeled DNA oligonucleotide FISH probes and unlabeled DNA helper probes. Probe sequences used are shown in Table A. The 100 μL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431) 0.13M guanidine thiocyanate (Sigma, cat. #G9277)). 10 μL of the prepared magnetic particle mixture was then added to the well. 100 μL of this reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: The *E. coli* was tested in the presence of varying inoculum of *K. pneumoniae*-OXA for susceptibility against 2 antimicrobial agents: Imipenem and Meropenem. While the time zero cell quantification was occurring, 10 μL of the *E. coli* species ($5 \times 10^6$ CFU/mL), 10 μL of the *K. pneumoniae* ($1 \times 10^6$ to $1 \times 10^8$ CFU/mL) or 10 uL media (control), 10 μL of pooled urine, and 60 μL of MHB II (Teknova, cat. #M5860) was added to each well of the antibiotic plate already containing 10 μL of antibiotics. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 μL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results.

Figure 51:
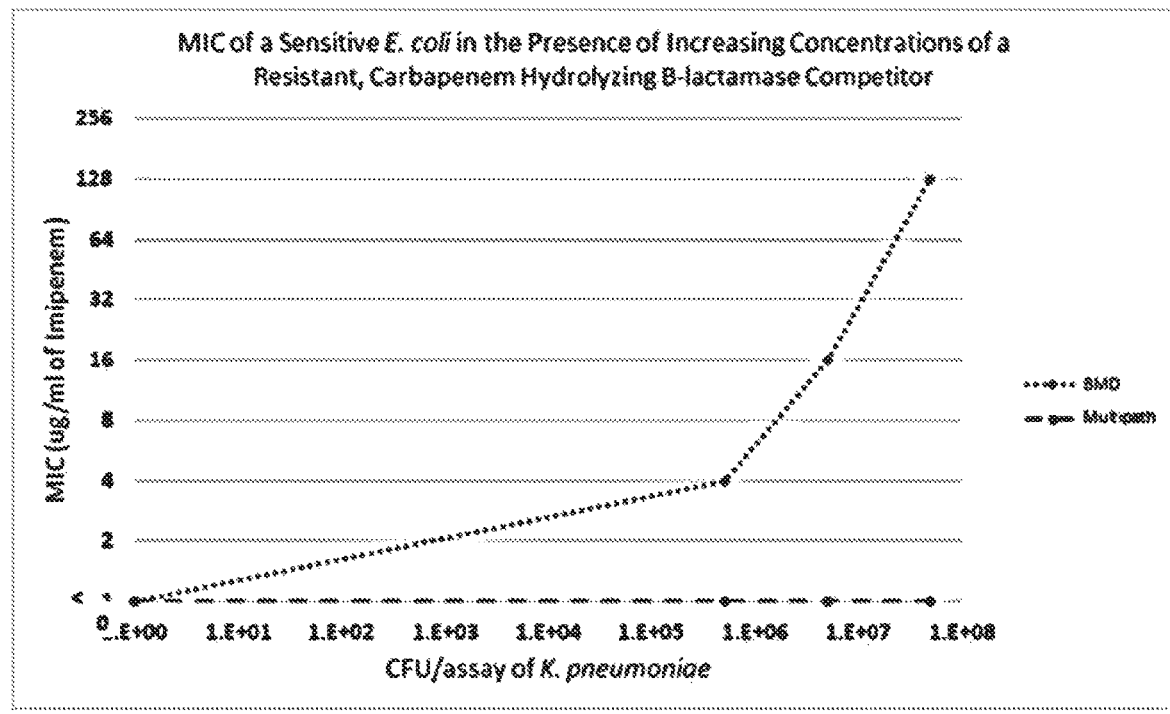
FIG. 51 shows the MIC of a sensitive *E. coli* strain./

FIG. 51 shows the MIC of a sensitive *E. coli* strain to Imipenem in the presence of increasing amounts of a *K. pneumoniae* strain that is resistant to the Imipenem antibiotic by producing a beta-lactamase that degrades it. The novel rapid AST method of this invention is compared to the BMD method. The novel 4.5-hour AST method is unaffected by the presence of even high concentrations of the beta-lactamase producing *K. pneumoniae* with MICs consistently less than 1 μg/mL Imipenem. In contrast, the BMD method after 16-24 hours of growth shows increasing MIC for the sensitive *E. coli* strain with increasing levels of *K. pneumoniae*, which would be falsely determined to be resistant to this antibiotic.

Figure 52:
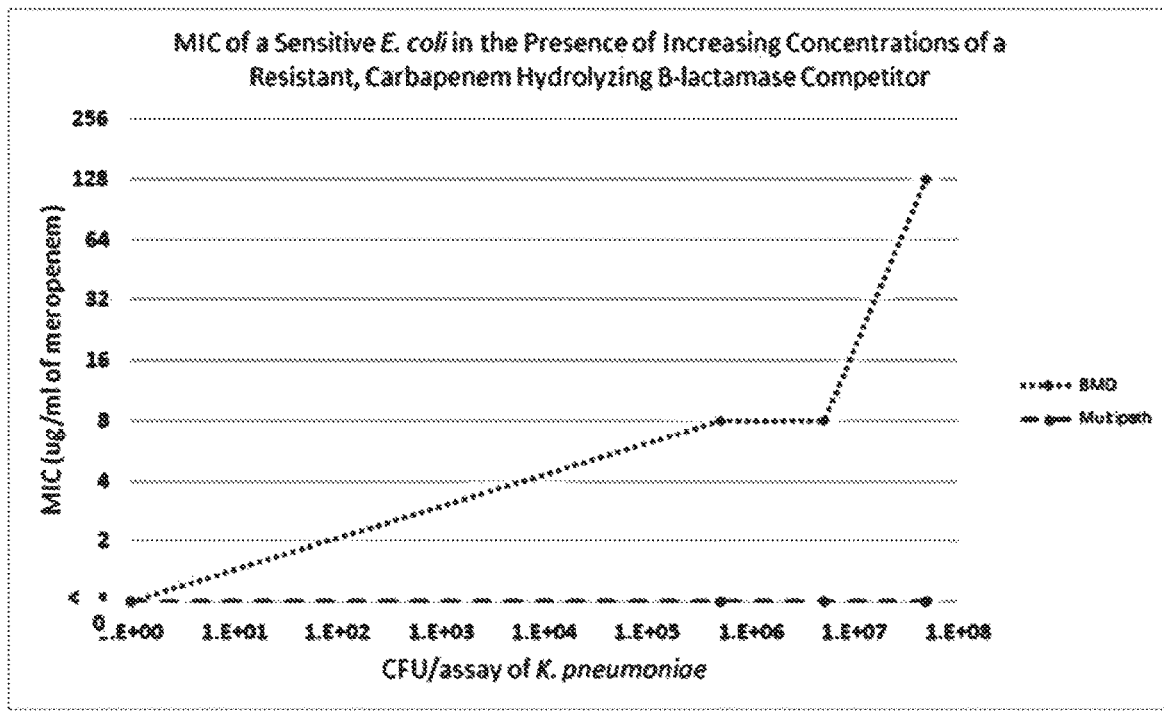
FIG. 52 shows similar results for the lactam antibiotic Meropenem.

FIG. 52 shows similar results for the lactam antibiotic Meropenem.

Conclusions. The novel 4.5-hour AST method of this invention shows accurate MIC determination of bacteria sensitive to carbapenem antimicrobial agents even in the presence of high concentrations of a resistant bacteria expressing a carbapemase enzyme which degrades the antibiotic.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also be extended to additional pairings of lactam sensitive and beta-lactamase expressing bacteria.

FIG. 51 is a comparison of the novel rapid AST and BMD methods for determining Imipenem MIC for *E. coli* in the presence of a resistant carbapenem hydrolyzing B-lactamase strain of *K. pneumoniae*.

FIG. 52 shows the MIC for *E. coli* stays consistent with the method describe above with varying inoculum of a resistant carbapenem hydrolyzing B-lactamase strain of *K. pneumoniae* while standard BMD does now.

FIG. 53 is a table of probe sequences used in this example 11.

Example 12. Accurate Rapid Antimicrobial Susceptibility Testing of Bacteria in Urine without Culture-Based Cell Purification Overview: Current methods for antimicrobial susceptibility testing require lengthy culture-based colony purification to ensure a pure population of just pathogen cells free of the specimen itself. Consequently, antimicrobial susceptibility testing results that indicate which antibiotics are optimal for killing the pathogen causing the infection are not available for 2-5 days. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

In contrast, the inventive method can deliver accurate antimicrobial susceptibility testing results directly from specimens without the lengthy colony purification step. Here we show that the new antimicrobial susceptibility testing results are not significantly impacted when bacteria in urine samples are tested without colony purification. This example demonstrates that the rapid antimicrobial susceptibility testing method accurately determines the minimum inhibitory concentration (MIC) for an *E. coli* strain in contrived samples comprising urine matrix (10%) for 15 different culture-negative urine samples.

Experimental procedure. Urine specimens: Fifteen culture negative clinical urine samples (remnants) were purchased from Discovery Life Sciences. Samples were received >7 days post collection and stored at −80° C. until use. For each sample, color of urine, pH, and presence of particulates were noted. Upon receipt, conventional urine culture was performed on the urines to determine samples were culture negative. Briefly, a calibrated 1 uL loop was placed into a well-mixed urine sample and evenly spread over a Tryptic soy agar (TSA) plate and incubated in a 35° C. air incubator for 18-24 hours. The remainder of the urine samples were assayed as described below.

Preparation of Antibiotic Plates: Microtiter plates containing six concentrations of each antibiotic in a 2-fold serial dilution series were prepared, starting at a 10-fold higher concentration than the expected minimum inhibitory concentration (MIC). Antibiotics used were Cefazolin, Ciprofloxacin, Nitrofurantoin, and Trimethoprim-Sulfamethoxazole. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for *E. coli*. In addition to the wells containing the antimicrobial dilution series, eight wells containing water or diluent were included in the plates to allow for a no antibiotic positive and negative growth control.

Preparation of Cultures: A log culture for *E. coli* (BAA-2469) was grown using three to five colonies inoculated into 5 mL of Tryptic Soy Broth (TSB, Hardy Diagnostics cat. U65) and incubated while shaking for 1-2 hours at 35° C. The Optical Density was measured by a spectrophotometer and the organisms were diluted to $5\times10^6$ CFU/mL (for a final concentration of $5\times10^5$ CFU/mL in each 100 µL reaction) in 1× Cation-adjusted Mueller-Hinton Broth (MHBII, Teknova cat. M5860).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each urine sample. 10 µL of diluted *E. coli* was added to 70 µL of hybridization buffer: final concentration: 3×SSC (0.45 M NaCl, 0.045 M Na citrate) buffer (Sigma, cat. #S6639), 1% CHAPS (Sigma, cat. #C3023), 1% NOG (Sigma cat. #08001), 1× Cation-adjusted Mueller-Hinton Broth (MHBII) (from a 2× stock) (Teknova, cat. M5866), and non-specific DNA oligonucleotide FISH probes and unlabeled DNA helper probe (see Table A for probe labels, sequences, and concentrations). A final concentration of 10% urine was obtained by adding 10 µL of each individual urine directly to the mixture. 10 µL of the magnetic particle mixture prepared as described above was added directly to this mixture. 100 µL of the sample, now containing the hybridization mixture, urine, and magnetic particles, was transferred to a microtiter plate containing 50 µL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222), dried at 60° C. in a convection oven for 3 hours) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: Spiked culture negative clinical UTI urine samples were tested for their susceptibility against 5 antimicrobial agents: Cefazolin, Ciprofloxacin, Levofloxacin, Nitrofurantoin, and Trimethoprim-Sulfamethoxazole. Antibiotic plates containing these antimicrobial agents were prepared according to the method described above. At the same time as the time zero cell quantification was occurring, 10 µL of *E. coli*, 10 µL of urine, and 70 µL of 1×MHB II (Teknova, cat. M5860) were added to each well of the antibiotic plate. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 µL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results. The figures below show there is little to no matrix effect on AST results.

Figure 54:
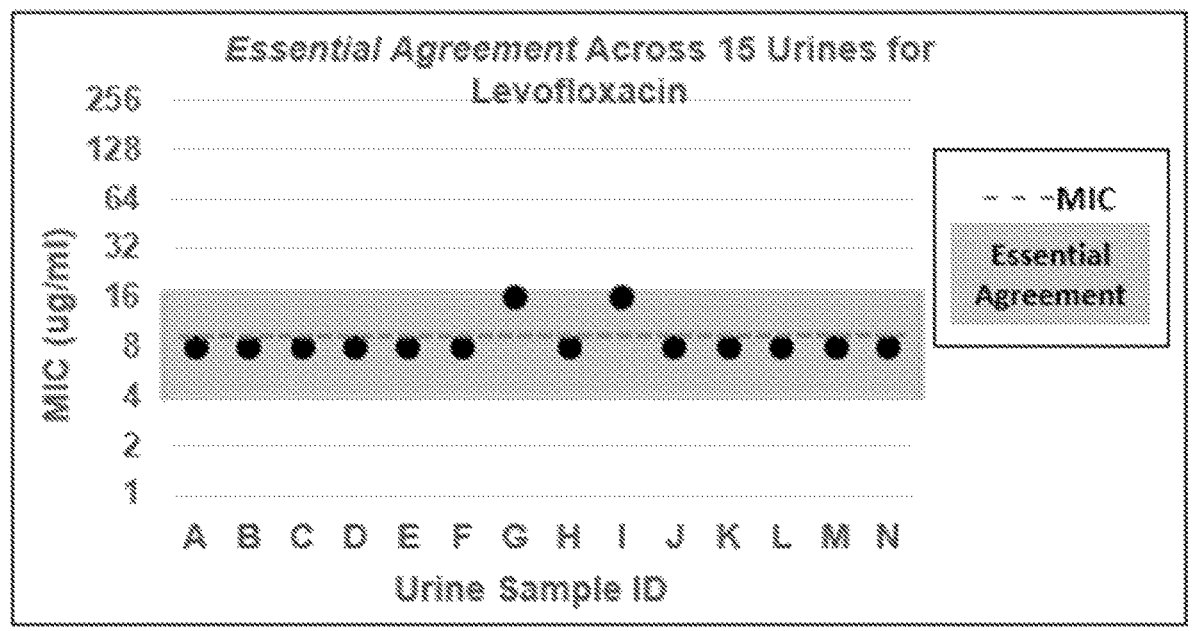
FIG. 54 shows the MIC.

FIG. 54 shows the MIC of *E. coli* BAA-2469 determined via the novel AST method (black circles) as compared to the MIC determined by the gold-standard CLSI BMD method without urine present (dashed line) for Levofloxacin. The shaded area is the essential agreement area, which is generally considered to be within acceptable error for the CLSI-compliant BMD process. Most of the MICs for Levofloxacin determined for *E. coli* BAA-2469 using the novel AST method matched the CLSI method exactly and the remaining two fall within the 2-fold essential agreement zone.

FIG. 55 summarizes the results obtained for all 5 antibiotics. 100% essential and 100% categorical agreement to standard BMD was observed across 15 culture negative clinical urine samples using the novel AST method.

FIG. 56 shows the MIC determined for the 15 culture negative clinical urine samples spiked with *E. coli* using the novel AST method in comparison to the MIC observed in the CLSI-compliant BMD process across the 5 antibiotics tested. The figures shows 100% Essential agreement for Levofloxacin with each of the 15 spiked culture negative clinical UTI urine samples to standard BMD.

Conclusion. The inventive method accurately determined the MIC (within the essential agreement zone relative to the gold standard BMD method) for a UTI pathogen (*E. coli*) for all 5 antibiotics tested in all 15 distinct urine matrices. Thus, this novel 4-hour antimicrobial susceptibility test has the capability to provide accurate results directly from urine specimens without the requirement of lengthily growth-based colony purification, saving substantial time. Rapid AST results can improve patient care by allowing the correct, effective antibiotic treatment to be initiated quickly and avoid adding to the spread of antibiotic resistance.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations) and concentration of urine. This methodology can also clearly be applied to other bacterial and non-bacterial pathogens and to minimally processed clinical matrices other than urine.

FIG. 54 shows essential agreement across 15 urines.

FIG. 55 shows 100% essential agreement and 100% categorical agreement for each of the 15 spiked culture negative clinical UTI urine samples to standard BMD.

Cefazolin, Ciprofloxacin, Levofloxacin, Nitrofurantoin, and Trimethoprim-Sulfamethoxazole.

FIG. 56 shows the MIC for 15 urine samples spiked with *E. coli* as determined by the novel AST method compared to the standard BMD method ("CLSI Compliant"). Concentrations in μg/ml.

Figure 58:
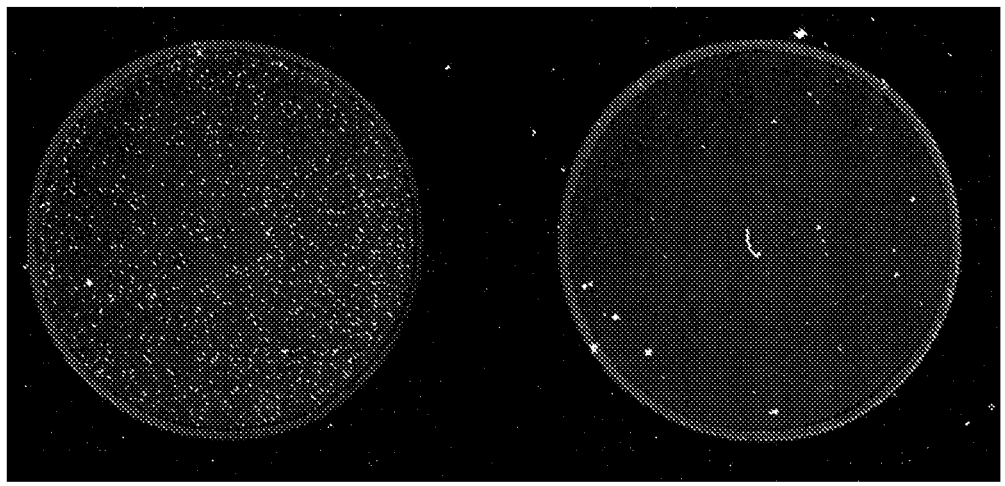
FIG. 58 is a table of probe sequences used in example 12.

FIG. 58 is a table of probe sequences used in this example 12.

Example 13. Rapid and Accurate AST for Multiple Targets in Polymicrobial

Overview. Polymicrobial infections are common in many types of infections including wounds. For such infections, which can be life-threatening it is critical to determine which antimicrobial agents can be effective for each infectious pathogen. Current antimicrobial susceptibility testing methods require 2-5 days to purify large numbers of each infectious pathogen in a polymicrobial infection before they can be analyzed.

This example demonstrates the potential for the inventive systems and methods to generate rapid AST in results in just 4.5 hours directly from a patient specimen without the need for lengthy colony purification. The method achieves accurate AST results (MIC values) for each target species in contrived 2-target polymicrobial mixtures compared to the broth microdilution reference standard result.

Experimental Procedure.

Preparation of Antibiotic Plates: Microtiter plates containing 6 Ciprofloxacin concentrations 2-fold serial dilution series were prepared. The 2-fold dilution series was prepared at a 10-fold higher concentration the desired concentration in the final broth microdilution, such that addition cells/urine/media mixture would yield the correct antibiotic range. 10 uL of each antibiotic dilution was then aliquoted into the appropriate wells of a 96 well plate. Antibiotic dilutions were verified to be within the appropriate tolerance by confirming that the MIC for at least two CLSI QC strains fell within the QC range reported in CLSI document M100Ed29E-2019. In addition to the wells containing the antimicrobial dilution series, enough wells containing water or other diluent were included for a no antibiotic positive growth control. Antibiotic plates were frozen at −80° C. and thawed completely before use.

Preparation of Cultures: Both a susceptible and resistant strain were chosen for four different organisms (*E. coli* ATCC 25922, *E. coli* BAA-2469, *K. pneumoniae* CDC 0076, *K. pneumoniae* CDC 0043, *P. aeruginosa* CDC 0233, *P. aeruginosa* CDC 0236, *E. faecalis* ATCC 29212, and *E. faecium* ATCC 19434). The strains and their resistances to each antibiotic tested are shown in Table A. Each strain was grown separately with three to five colonies inoculated into 5 mL of Tryptic Soy Broth (TSB) and incubated while shaking for 1-2 hours at 35° C. The Optical Density was measured by a spectrometer and the organisms were diluted to $1 \times 10^7$ CFU/mL in 1× Cation-adjusted Mueller-Hinton Broth (MHB II) (Teknova, cat. #M5860).

Preparation of Magnetic Particles: A solution of Polyaspartic acid-conjugated magnetic particles (Fluidmag-PAA, Chemicell, cat. 4108) were diluted 1:20 into 50 mM EPPS buffer, pH 8.2 to $2.75 \times 10^{12}$ particles/mL. Fluorescent magnetic microspheres containing a green dye (Dragon Green Fluorescent Microspheres, BANGS Laboratories, cat. MEDG001) were added to the suspension at a final concentration of $3 \times 10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below). An identical procedure was done with the 2 hydroxypropyl trimethylammonium chloride-coated silica magnetic particles (SiMag-Q, Chemicell, cat. 1206-5).

Bacterial Cell Labeling at AST time zero: Assay signal prior to the initiation of bacterial growth in the presence or absence of antibiotics (time zero or T0) was determined for each species and strain. 5 μl of target A was combined with either 5 μl target B or 5 μl of MHB II for a final concentration of $5 \times 10^6$ CFU/mL per organism was added to 80 μL of hybridization buffer (final concentration: 3×SSC (0.45 M NaCl, 0.045 M sodium citrate pH 7) (Sigma, cat. #S6639), 0.25M Guanidine Thiocyanate (Sigma, cat. #503-84-0), 5% PEG MW 3350 (Sigma, cat. #P-3640), 7.5% Igepal CA-630 (Sigma, cat. #13021), 0.2% cetrimide (Sigma, cat. #H9151), 1× Cation-adjusted Mueller-Hinton Broth (MHBII), species-specific DNA oligonucleotide FISH probes and unlabeled DNA helper probe (sequences and concentrations found in Table B)). A final concentration of 10% urine was obtained by adding 10 µL of pooled urine (Innovative Research, cat. IR100007P-24203) directly to the mixture for a 100 µL total reaction. 10 µL of the either the SiMag-Q magnetic particle mixture (for conditions where *E. coli, K. pneumoniae* and *P. aeruginosa* strains were being labeled) or the Fluidmag-PAA magnetic particle mixture (for conditions where *Enterococcus* spp. were labeled), prepared as described above, was added directly to this mixture. 100 µL of the sample, now containing the hybridization mixture, urine, and magnetic particles, was transferred to a microtiter plate containing 50 µL of dye-cushion (50 mM TRIS pH 7.5 (Teknova, cat. T5075), 7.5% v/v Optiprep (Sigma, cat. D1556), 5 mg/mL Direct Black-19 (Orient, cat. #3222), dried down at 60° C.) (dry-cushion plate) and incubated at 35° C. for 30 minutes. After this incubation, the microtiter plates were placed onto a strong permanent magnet (Dexter magnetic technologies, cat. 54170260) for 4 minutes to bring the labeled and magnetic-particle-interacting bacterial cells into close proximity to the imaging surface.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: A polymicrobial sample, containing two species, was tested for susceptibility against 1 antimicrobial agent: Ciprofloxacin. Antibiotic plates containing these antimicrobial agents were prepared according to the method described above. At the same time as the time zero cell quantification was occurring, 5 µl of either the species to be labeled and detected and 5 µl of either a bacterial species the might be present in a polymicrobial UTI infection (but will not label) or MHB II as control, 10 µL of pooled urine, and 70 µL of MHB II were added to each well of the antibiotic plate. The samples were allowed to grow in a standing air incubator at 35° C. for 4 hours. Each strain in this example served in once instance as the labeled target species, and in another instance as the unlabeled member of the polymicrobial pair.

Bacterial Cell Labeling at AST time four-hour growth: After samples had incubated in the presence and absence of antibiotics for four hours (T4), cells were labeled and quantified to determine how much growth, if any, occurred. 10 µL of the incubated sample-antibiotic plate (10%) was transferred to a microtiter plate and combine with 100 µL hybridization buffer, FISH probes, helper probes, magnetic particles, and focus particles in the same manner as described above for assay time zero.

Comparison Method: Results using the novel AST method described here were compared to broth microdilutions (BMD) performed according to CLSI M07-Ed13E 2018.

Data Analysis and Threshold Generation: Using the image captured by the CCD camera, detected cells were estimated by an algorithm that looked at both number of objects in the field of view and the intensity of the objects. The number of cells based on this detection algorithm were generated at time zero, and at time four hours without antibiotic and with all 6 concentrations of Ciprofloxacin. For each sample inoculum/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. MIC results were correspondingly assigned to categories of susceptible, intermediate, or resistant based on the CLSI M100Ed28 2018 guidelines. All data was then compared to CLSI standard BMD.

Results.

Figure 60:
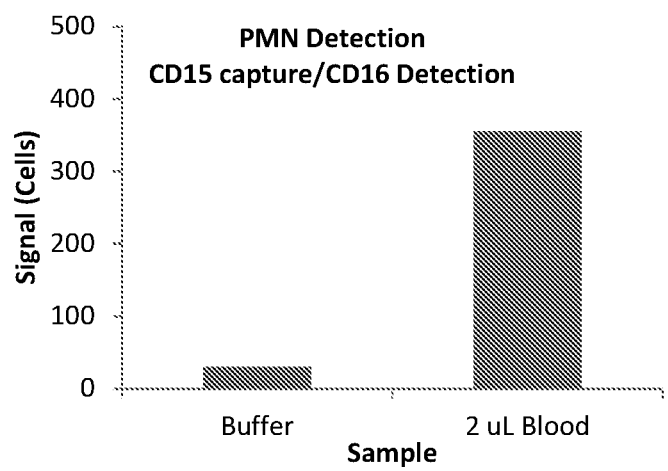
FIG. 60 shows all MICs determined for the target bacteria by the novel 4.5 hour AST method—regardless of the presence of a second susceptible or resistant bacteria—were within the 2-fold tolerance range accepted for the gold-standard BMD method (termed essential agreement) for each target bacteria (determined in the absence of a second bacteria).

FIG. 60 shows all MICs determined for the target bacteria by the novel 4.5 hour AST method—regardless of the presence of a second susceptible or resistant bacteria—were within the 2-fold tolerance range accepted for the gold-standard BMD method (termed essential agreement) for each target bacteria (determined in the absence of a second bacteria).

FIG. 61 shows that the sensitive and resistance categorical determinations for each target bacteria by the new AST method were also not impacted by these pair-wise combinations and were 100% consistent with the BMD determinations.

Conclusions. The inventive AST method can accurately determine antibiotic susceptibility for each species in a polymicrobial sample in 4.5 hours without requiring the time consuming colony purification needed by current methods. The results show the potential for the invention to determine the antimicrobial agents that can effectively treat life-threatening polymicrobial infections in just hours rather than the days required by today's methods.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.) and alternative assay chemistries (different detergents, chaotropes, fluorophores, buffers, pH, temperatures, reaction times, component concentrations). This methodology can also clearly be extended to other biological specimens, to other bacteria and to other antibiotics.

FIG. 61 shows Ciprofloxacin-sensitive and resistant strains used in this example FIG. 62 is a first half of a Table of probe sequences used in this example 13.

FIG. 63 is a second half of a Table of probe sequences used in this example 13.

FIG. 64 shows essential agreement for a polymicrobial infection with 2 target organisms. As seen below, the AST method described above yields 100% essential agreement to standard BMD FIG. 65 shows categorical agreement for a polymicrobial infection with 2 target organisms. As seen below the AST method described above yields 100% categorical agreement to standard BMD.

Example 14. Rapid and Accurate Detection of Multiple Target Pathogens in a Single Specimen in a Cartridge on an Automated Instrument Overview. Polymicrobial infections, that is infections caused by more than one bacterial species, are common. Current, culture-based and MALDI-TOF based methods for identifying pathogens, require lengthy colony purification steps for separately purifying large number of cells each target species. This example demonstrates the use of the inventive FISH method to detect and identify multiple species of target pathogens present in contrived urine samples in 30 minutes on an automated analyzer inside a single-use consumable cartridge containing all assay reagents. The example shows the potential of the systems and methods of the invention to rapidly and specifically identify multiple target pathogens in polymicrobial infections.

Experimental Procedure.

Urine specimens: Ten culture negative clinical urine samples (remnant) were purchased from Discovery Life Sciences. Samples were received >7 days post collection and stored at −80° C. until use. For each sample, color of urine, pH, and presence of particulates were noted. Upon receipt, conventional urine culture was performed on the urines to determine samples were culture negative. Briefly, a calibrated 1 uL loop was placed into a well-mixed urine sample and evenly spread over a Tryptic soy agar (TSA, BD cat. 221185) plate and incubated in a 35° C. air incubator for 18-24 hours. The remainder of the urine samples were processed and assayed as described below.

Urine processing: Prior to performing identification (ID), urine preservative and other potentially interfering compounds were removed using size exclusion chromatography. 2.5 mL of each clinically negative urine sample was applied to a pre-washed Zeba™ Spin Desalting column, 7K MWCO (ThermoFisher, cat. #89893). The sample was passed through the column via centrifugation as described by the manufacturer.

Preparation of Dehydrated Reagents in Cartridge: Prior to performing identification (ID), 45 µL of 2.2× concentrated hybridization buffer (6.7×SSC (1 M NaCl, 0.1 M sodium citrate, (Sigma, cat. #S6639), 0.4% w/v cetrimide (Sigma, cat. #H9151), 1.71% w/v CHAPSO (Sigma cat. #C3649), 1.6% SB3-12 w/v (Sigma cat. #D0431), and 0.29M guanidine thiocyanate (Sigma, cat. #G9277)) was distributed into 6 of the reagent wells of the cartridge. Once rehydrated in the final 100 uL volume after processing by the analyzer, the normal 1× hybridization buffer (3×SSC (0.45 M NaCl, 0.045 M Na citrate), 0.18% cetrimide, 0.77% CHAPSO, 0.72% SB3-12, and 0.13M guanidine thiocyanate) will be achieved. 1.8 µL of each target species-specific DNA oligonucleotide FISH probe and unlabeled DNA helper probe mixture was added to 2 out of 8 of the reagent wells (N=2 for each target in 1 cartridge). *E. coli* FISH oligonucleotide probe sets were added to reagents wells corresponding to cartridge location A1 and A2, *K. pneumoniae* probe sets were added to reagents wells corresponding to cartridge location A3 and A4 and *P. aeruginosa* probe sets were added to reagents wells corresponding to cartridge location A5 and A6. These cartridge wells containing hybridization buffer and specific probes were then incubated in a 50° C. convection oven for 16-20 hours to dehydrate the materials.

Preparation of Magnetic Particles: Poly-aspartic acid-conjugated magnetic particles (Fluidmag-PAA, Chemicell, cat. 4108) were diluted 1:20 into 50 mM Epps buffer, pH 8.2 to a concentration of $2.75 \times 10^{12}$ particles/mL with a final concentration of 10% w/v Trehalose (Sigma, cat. #T9449). To this dilution, fluorescent magnetic microspheres containing a green dye (Dragon Green Fluorescent Microspheres, BANGS Laboratories, cat. MEDG001) were added to the suspension at a final concentration of $3 \times 10^6$ particles/mL. The magnetic particle mixture was sonicated for 1 minute prior to immediately use to minimize aggregation. The mixture was then lyophilized in 10 µL volume beads ($2.64 \times 10^{12}$ PAA particles per reaction) and 1 bead was placed in each of the 6 reagent wells.

Preparation of Cultures: Log cultures of three different target pathogens (*E. coli* ATCC 25922, *K. pneumoniae* ATCC 13883, and *P. aeruginosa* ATCC 27853) were grown separately with three to five colonies inoculated into 5 mL of Tryptic Soy Broth (TSB, Hardy Diagnostics cat. U65) and incubated while shaking for 1-2 hours at 35° C. The Optical Density was measured by a spectrometer and the organisms were diluted to about $5 \times 10^6$ CFU/mL in 1X Cation-adjusted Mueller-Hinton Broth (MHBII, Teknova cat. M5860).

Bacterial Cell Labeling and imaging for Identification: Assay signal was determined for each target pathogen in contrived polymicrobial mixture containing two bacteria of interest (3 total 2-bacteria combinations) in a final concentration of 30% processed urine. Each polymicrobial bacterial combination was tested in 10 unique different culture negative clinical samples (30 urines tested in total). 103.5 µL of bacterial target A ($\sim 5 \times 10^5$ CFU/mL per reaction) 103.5 µL of bacterial target B ($\sim 5 \times 10^5$ CFU/mL per reaction), 360 µL urine, and 633 µL were combined for a total volume of 1.2 mL; 1 mL of that mixture was transferred to the cartridge sample addition port. The cartridge was then placed on the instrument and all subsequent actions were automatically performed. The sample was first directed under vacuum into the 6 growth wells at the top of the cartridge. Sample was then immediately moved to reaction wells, rehydrating the hybridization buffer/FISH probe mix and lyophilized magnetic particles. Sample then continued to the optical windows containing 45 µL of dehydrated "dye cushion" (50 mM TRIS pH 7.5 (Teknova, cat. T5075), 7.5% v/v Optiprep (Sigma, cat. D1556), 5 mg/mL Direct Black-19 (Orient, cat. #3222), dried for 60° C. for 3 hours in a convection oven) and incubated at 35° C. for 30 minutes on the analyzer. After this incubation, the cartridges were relocated to the magnet station, and placed atop a strong permanent magnet (Dexter magnetic technologies, cat. 54170260) for 4 minutes to bring the labeled and magnetic-particle-interacting bacterial cells into proximity to the imaging surface at the bottom of the wells. Finally, the cartridge was moved to the imaging station and imaging taken using non-magnified CCD imager as described below. In brief, focusing on each individual well was performed by taking successive images of the fluorescent magnetic microspheres in the green channel, the plane of focus determined, and a corresponding image at that location taken in the red color channel to image labeled bacterial cells.

Imaging of labeled cells: The MultiPath™ Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Data Analysis: Using the image captured by the CCD camera, detected cells was estimated by an algorithm that looked at both number of objects in the field of view and the intensity of the objects. Signal in a channel was considered detected if assay signal was above 130.

Results. The data demonstrate successful identification of 2 target pathogens in a single sample with no detection of the pathogen that is absent (i.e. no cross reactivity of the FISH probes to the non-target bacteria).

Figure 66:
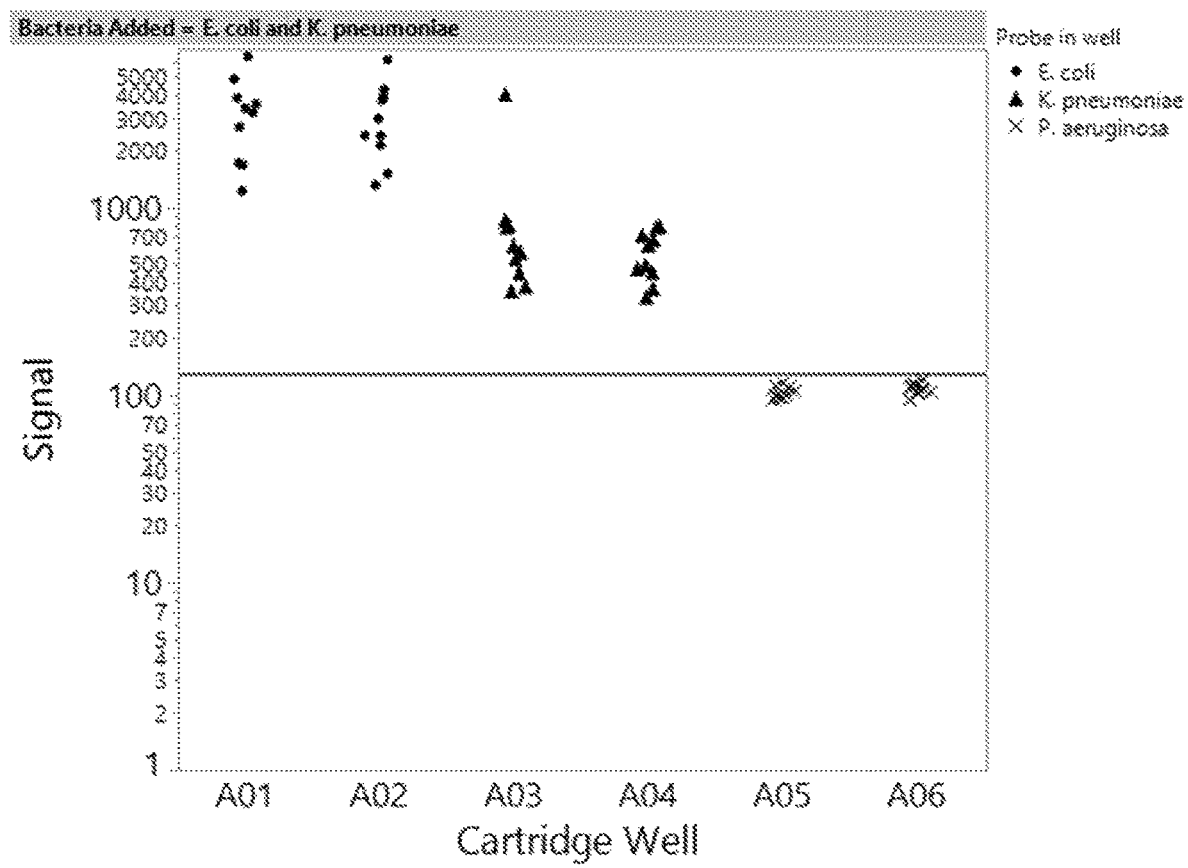
FIG. 66 shows target pathogens are detected only in the wells containing their species-specific DNA oligonucleotide FISH probes.

FIG. 66 shows the cartridges run where the *E. coli/K. pneumoniae*-mixed samples were tested (N=10).

FIG. 66 shows the cartridges run where the *E. coli/P. aeruginosa*-mixed samples were tested (N=10).

Figure 68:
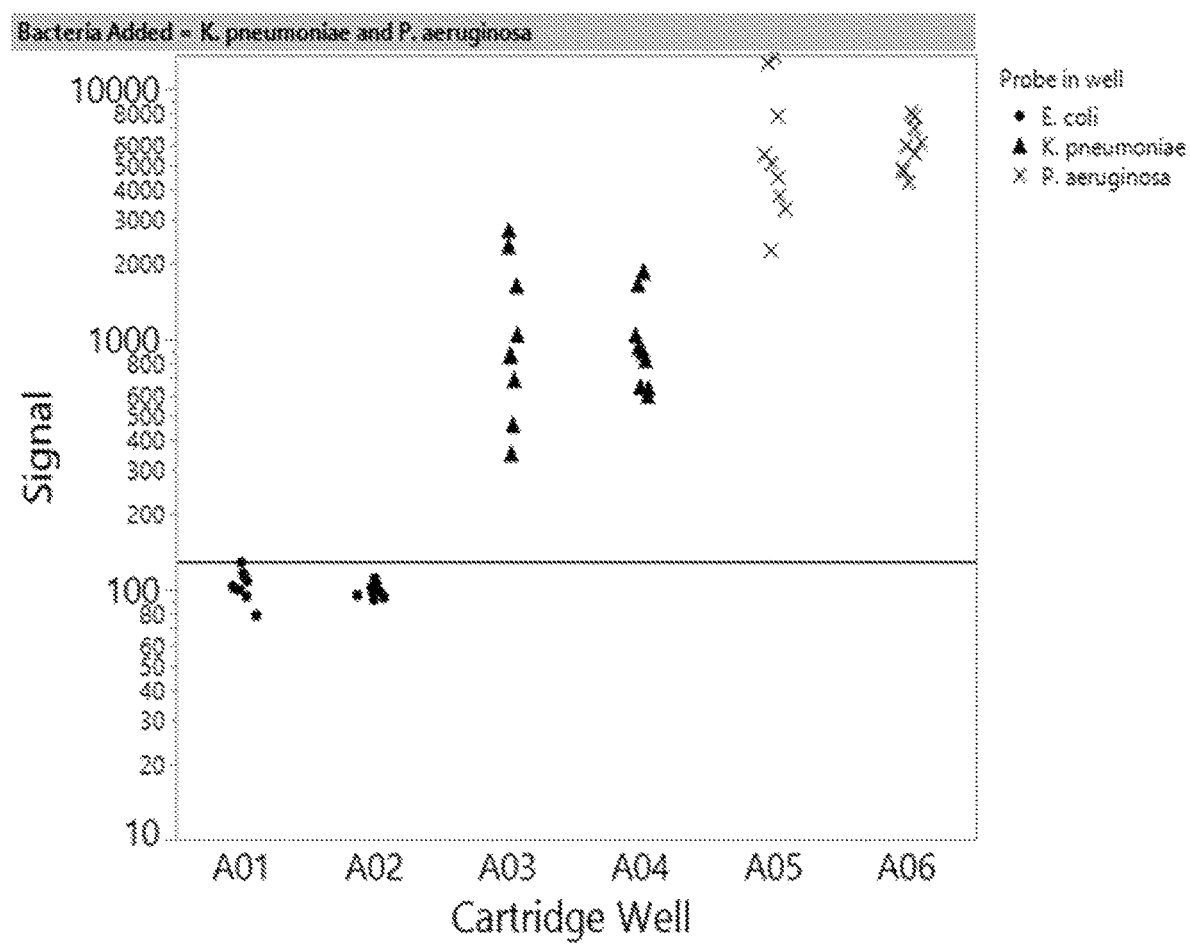
FIG. 68 shows target pathogens are detected only in the wells containing their species-specific DNA oligonucleotide FISH probes.

FIG. 68 shows the cartridges where the *K. pneumoniae/P. aeruginosa*-mixed samples were tested (N=10). *K. pneumoniae/P. aeruginosa* cartridge #6 was removed from the analysis due to failure of that cartridge to produce a valid result. In addition, an artifact was observed in A3 of *E. coli/P. aeruginosa* cartridge #9, which caused the signal in the well to appear abnormally high, so this single replicate was eliminated. The replicate of this excluded point (well A4) did not have this artifact, so *K. pneumoniae* was still categorized as not detected. Although assay signal varied across the different cartridges, in all cases other than those already described, the two bacteria added to the culture negative urine was detected while very low signal is observed in the wells containing the probe for the bacteria that was not added.

Conclusions. This example demonstrates the inventive isothermal FISH method performed on an automated analyzer with stabilized reagents inside a consumable cartridge can specifically identify multiple target bacterial species in a contrived urine sample. This shows the potential of the method to identify multiple pathogens in polymicrobial infections. The example also demonstrates the specificity of the method, as no cross-species detection was observed.

Variations. This example is illustrative of the performance of this novel FISH method on a cartridge and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures and alterations to reactant stabilization (lyophilization of components). This methodology can also clearly be extended to other biological specimens and to other bacterial and non-bacterial pathogens.

FIG. 66 shows target pathogens are detected only in the wells containing their species-specific DNA oligonucleotide FISH probes.

Figure 67:
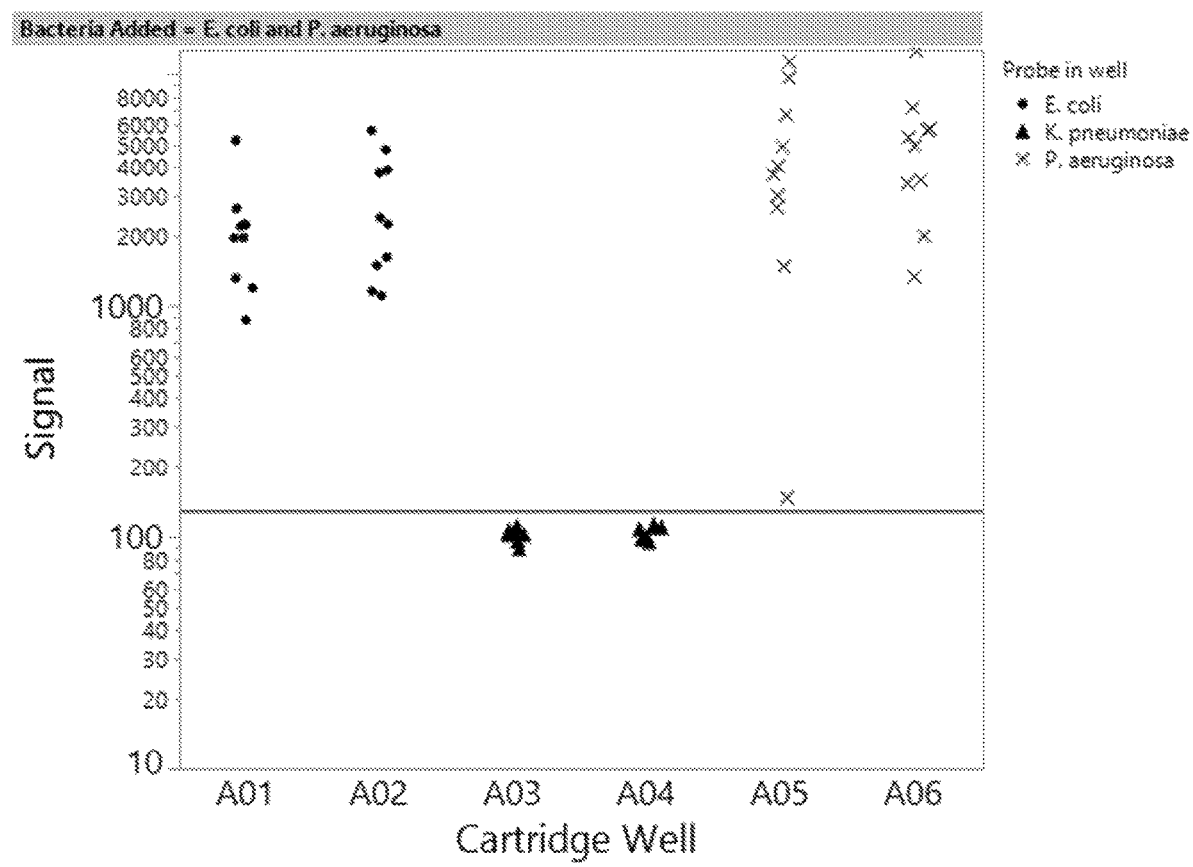
FIG. 67 shows target pathogens are detected only in the wells containing their species-specific DNA oligonucleotide FISH probes.

FIG. 67 shows target pathogens are detected only in the wells containing their species-specific DNA oligonucleotide FISH probes.

FIG. 68 shows target pathogens are detected only in the wells containing their species-specific DNA oligonucleotide FISH probes.

FIG. 69 is a table "Table A of Example 14", showing target pathogens were detected while other non-target pathogens were not.

FIG. 70 is a table, "Table B of Example 14", showing probe sequences used in this example 14.

Example 16: Non-Specific Detection of Live Bacteria Using Carboxy-Fluorescein Diacetate Overview. In this example, large area imaging was used to detect individual *S. aureus* bacterial cell targets that were stained with fluorogenic esterase substrates. The substrates can diffuse through cell membranes of intact living cells where they become both fluorescent and charged when acted upon by esterase enzymes found in metabolically active cells. These charged fluorescent products can no longer passively diffuse through cell membranes and become trapped in intact cells. This technique can thus distinguish live cells from dead cells, as only cells with active esterases and intact cell membranes will stain properly. In this example, *S. aureus* cells are labeled with the fluorogenic substrate carboxy-fluorescein diacetate (cFDA) and imaged using non-magnified digital imaging.

Experimental Methods.

Bacterial Cell Preparation:

*S. aureus* ATCC 29213 was grown overnight in Tryptic Soy Broth (TSB, BD cat. #211822). The log culture of *S. aureus* was made by inoculating 100 uL of overnight culture into 5 ml of fresh TSB media and further incubating for 2.5 hours at 35° C. in a shaking incubator.

Preparation of Magnetic Particles:

Antibody conjugated magnetic particles were made by coupling magnetic particles (Ademtec, 292 nm) to chicken anti-protein A antibodies (Meridian Biosciences) using standard EDAC (1-Ethyl-3-(3-dimethylaminopropyl) carbodiimide) coupling chemistry.

Labeling and Capture of Bacterial Cells:

The assays were carried out in a 96-well microtiter plate and each well included 40 uL of *S. aureus* (10,000 cells in TSB) or only TSB (no cell control), 5 uL of 10 mM cFDA (Life Technologies) and 5 ul of antibody-conjugated magnetic particles (2e10/mL). The reactions were incubated at room temperature for 15 min. After the incubation, 40 uL of reaction mixture was carefully overlaid on 75 ul of "dye cushion" (15% Optiprep with 5 mg/mL Chromotrope 2R) which was pre-aliquoted in black, clear bottom half area microtiter plate (Greiner 675096, VWR part #82050-056). The microtiter plate was placed onto a magnetic field for 4 minutes to bring magnetic particles, a fraction containing labelled cells, through the "dye cushion" and into proximity to the imaging surface at the bottom of the wells.

Imaging of Bacterial Cells:

Following magnetic capture of labeled cell:magnetic particle complexes, the microtiter plate was placed on a stage above a CCD digital camera (IDS, model UI-22505E-M) and illuminated with light from LEDs passing through an optical filter (469 nm, 35 nm FWHM). Fluorescent signal passing through an emission filter (520-35 nm) was detected by the camera to create an image of the fluorescent complexes. The images were analyzed using FLimage software (First Light Biosciences) that enumerates the individual cells.

Results.

FIG. 146 shows that *S. aureus* cells (left panel) are detected as bright fluorescent spots, while media without cells (right panel) contains only objects categorized as debris. The number of spots in the field with labeled *S. aureus* cells is about 5000 and correlates well with the expected number of input bacteria.

Figure 59:
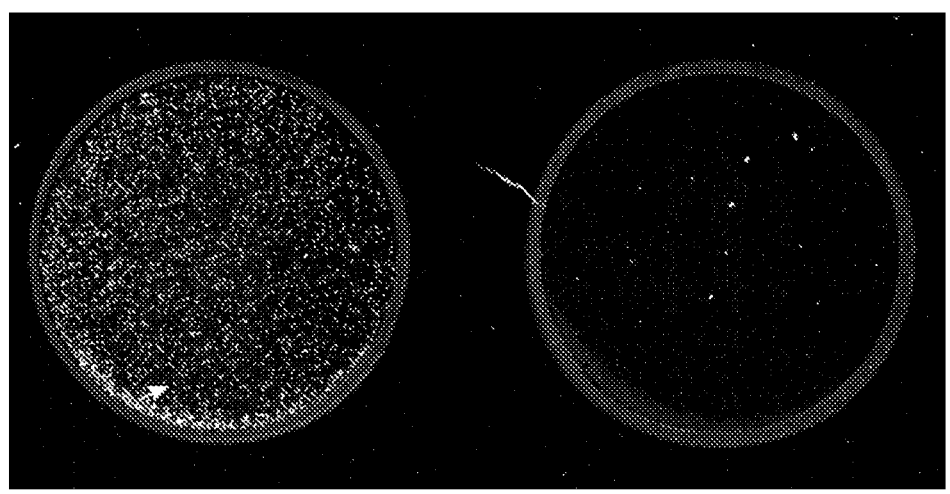
FIG. 59 shows *S. aureus* cells (left panel) and TSB media only (right panel)

FIG. 59 shows *S. aureus* cells (left panel) and TSB media only (right panel)

Conclusions. This example demonstrates a method for enumerating bacteria non-specifically. This approach can be used to count the total number of cells from a mixed population covering a broad range of bacterial species in a specimen. Specifically, the example demonstrated the capability of the inventive non-magnified imaging method to enumerate small numbers bacterial cells labeled with carboxy-fluorescein diacetate, a fluorescence substrate that non-specifically labels viable cells containing the ubiquitous esterase enzymes.

Variations. There are other stains for non-specific cell labeling including nucleic acid stains such as STYO and SYBR family of stains, propidium iodide, and DAPI. Other stains distinguish live or dead cells can be used. For example, other fluorogenic substrates, or DNA stains that can or cannot cross intact cell membranes can be used instead of or in conjunction with cFDA or FDA. Multiple stains and dyes can be distinguished by using multiple excitation and emission wavelengths for fluorescence detection. The spectrum of fluorescence associated with an object can be used to determine whether a cell is counted as live or dead. In addition, fluorogenic substrates that are specific for the biochemical activity of a particular type of bacteria can be used to determine its presence. For example, a fluorogenic □-galactosidase substrate can be cleaved to its fluorescent product by □-galactosidase, which is specific to coliforms. This methodology can also be applied to most bacteria and to specimens that contain multiple bacterial species. The method is suitable to detect bacteria in many different clinical specimen types with minimal processing (e.g. urine, sputum, swabs, spinal fluid, etc.).

Example 15: Non-Specific Detection of Bacteria Using DNA Staining Dyes

Overview. In this example, large area imaging was used to detect individual live *S. aureus* bacterial cell targets that were stained with DNA binding stains. The DNA binding dyes can diffuse through the cell membrane of intact living cells where they become highly fluorescent after binding to DNA of the bacteria. Once bound to DNA, these dyes can no longer easily and passively diffuse through intact cell membranes and become trapped in intact cells. This technique can be useful when it is important to distinguish live cells from dead cells, as live cells with intact cell membranes will stain differently with different dyes compared to dead cells or cells with compromised membranes. In this example, *S. aureus* is labeled with DNA binding fluorescent dye, SyBR Green and imaged using non-magnified large area CCD imaging.

Experimental Methods.

Bacterial Cell Preparation:

*S. aureus* ATCC 29213 was grown overnight in Tryptic Soy Broth (TSB, BD cat. #211822). The log culture of *S. aureus* was made by inoculating 100 uL of overnight culture into 5 ml of fresh TSB media and further incubating for 2.5 hours at 35° C. in a shaking incubator.

Preparation of Magnetic Particles:

Antibody conjugated magnetic particles were made by coupling magnetic particles (Ademtec, 292 nm) to chicken anti-protein A antibodies (Meridian Biosciences) using standard EDAC (1-Ethyl-3-(3-dimethylaminopropyl) carbodiimide) coupling chemistry.

Labeling and Capture of Bacterial Cells:

The assays were carried out in a 96-well microtiter plate and each well included 40 uL of *S. aureus* (10,000 cells in TSB) or only TSB (no cell control), 5 uL of 500-fold diluted SyBR Green dye (Cat #S7563, Life Technologies) and 5 ul of antibody-conjugated magnetic particles (2e10/mL). The reactions were incubated at room temperature for 15 min. After the incubation, 40 uL of reaction mixture was carefully overlaid on 75 ul of "dye cushion" (15% Optiprep with 5 mg/mL Chromotrope 2R) which was pre-aliquoted in black, clear bottom half area microtiter plate (Greiner 675096, VWR part #82050-056). The microtiter plate was placed onto a magnetic field for 4 minutes to bring magnetic particles, a fraction containing labelled cells, through the "dye cushion" and into proximity to the imaging surface at the bottom of the wells.

Imaging of Bacterial Cells:

Following magnetic capture of labeled cell:magnetic particle complexes, the microtiter plate was placed on a stage above a CCD digital camera (IDS, model UI-22505E-M) and illuminated with light from LEDs passing through an optical filter (469 nm, 35 nm FWHM). Fluorescent signal passing through an emission filter (520-35 nm) was detected by the camera to create an image of the fluorescent complexes. The images were analyzed using FLimage software (First Light Biosciences) that enumerates the individual cells.

Results.

FIG. 146 shows that *S. aureus* cells (left panel) are detected as bright fluorescent spots, while media without cells (right panel) contains only objects categorized as debris. The number of spots in the field with labeled *S. aureus* cells is about 5000 and correlates well with the expected number of input bacteria.

FIG. 59 shows *S. aureus* cells (left panel) and TSB media only (right panel)

Conclusions. This large area, non-magnified imaging system is capable of detecting and enumerating bacterial cells that are labeled with SyBR Green, a DNA binding dye that non-specifically labels living cells.

Variations. Other dyes that distinguish live or dead cells can be used. For example, other fluorogenic DNA stains that can or cannot cross intact cell membranes can be used instead of or in conjunction with SyBR Green. Multiple stains and dyes can be distinguished by using multiple excitation and emission wavelengths for fluorescence detection. The spectrum of fluorescence associated with an object can be used to determine whether a cell is counted as live or dead. In addition, fluorogenic substrates that are specific for the biochemical activity of a particular type of bacteria can be used to determine its presence. For example, a fluorogenic □-galactosidase substrate can be cleaved to its fluorescent product by □-galactosidase, which is specific to coliforms. This methodology can also be applied to most bacteria and to specimens that contain multiple bacterial species. The method is suitable to detect bacteria in many different clinical specimen types with minimal processing (e.g. urine, sputum, swabs, spinal fluid, etc.). Other nucleic acid stains can label bacterial cells non-specifically, including the members of the SYTO/SYBR family of stains, propidium iodide, and DAPI.

Example 5: Specific Detection of Polymorphonuclear Neutrophils (PMNs) Using Antibody-Coated Magnetic Particles and Fluorescently Labeled Antibodies Overview. The presence and number of polymorphonuclear neutrophils (PMNs) can be diagnostically informative for detecting infections. For example, a low number of neutrophils in urine samples helps rule out urinary tract infections. In this example, non-magnified digital imaging was used to enumerate polymorphonuclear neutrophil (PMN) targets that were stained with fluorescent labeled antibodies. In this example, we have used anti-CD15 and anti-CD16 antibodies which is specific molecules present on the surface of polymorphonuclear neutrophils (PMNs) for capture and detection. In one embodiment, anti-CD15 antibodies were conjugated to magnetic particles which were used for PMN capture and fluorescently labeled anti-CD16 antibody for detection using non-magnified digital imaging.
Experimental Methods.
Blood Samples Fresh blood sample from healthy donor were obtained from Research Blood Components (Boston, MA) and used as the source of PMN.
Preparation of Magnetic Particles:

Antibody conjugated magnetic particles were made by coupling magnetic particles (Ademtec, 292 nm) to mouse anti-CD15 antibodies (Biolegend) using standard EDAC (1-Ethyl-3-(3-dimethylaminopropyl) carbodiimide) coupling chemistry.
Detection Antibody Alexa Fluor® 488 anti-human CD16 Antibody (Biolegend) was used as detection antibody.
Labeling and Capture of PMNs:

The assays were carried out in a 96-well microtiter plate. Each well included 38 ul of Phosphate-buffered saline (PBS), 2 uL of fresh blood sample or 2 uL of PBS (no PMN control), 5 uL of Alexa-488 labeled anti CD-16 antibody (1 ug) and 5 ul of antibody-conjugated magnetic particles (2e10/mL). The reactions were incubated at room temperature for 15 min. After the incubation, 40 uL of reaction mixture was carefully overlaid on 75 ul of "dye cushion" (15% Optiprep with 5 mg/mL Chromotrope 2R) which was pre-aliquoted in black, clear bottom half area microtiter plate (Greiner 675096, VWR part #82050-056). The microtiter plate was placed onto a magnetic field for 4 minutes to bring magnetic particles, a fraction containing labelled cells, through the "dye cushion" and into proximity to the imaging surface at the bottom of the wells.
Imaging of PMNs:

Following magnetic capture of labeled PMNs:magnetic particle complexes, the microtiter plate was placed on a stage above a CCD digital camera (IDS, model UI-22505E-M) and illuminated with light from LEDs passing through an optical filter (469 nm, 35 nm FWHM). Fluorescent signal passing through an emission filter (520-35 nm) was detected by the camera to create an image of the fluorescent complexes. The images were analyzed using FLimage software (First Light Biosciences) that enumerates the individual cells.
Results.

FIG. 60 shows the result of MultiPath assay indicating that it specifically detects the PMNs present in blood sample while buffer without blood sample have very low detectable fluorescent signal.

Conclusions. This large area, non-magnified imaging system is capable of detecting and enumerating PMNs from blood sample that are labeled with fluorescently labeled antibodies against the cell-surface marker. The results show the potential of the inventive systems and methods for enumerating diagnostically informative human or host cells.

Variations. Using other cell-specific antibodies, different cells can be detection in various biological samples. For example, other cell-surface marker antibodies can recognize different diagnostically informative cells. For example, quantifying squamous epithelial cells is important for assessing respiratory sample quality in pneumonia diagnostics. Multiple antibodies/cell surface markers can be used and labeled cells can be distinguished by using multiple excitation and emission wavelengths for fluorescence detection. The spectrum of fluorescence associated with an object can be used to determine whether a signal of specific type of cell or not.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A cartridge configured to carry out one of a variety of tests on specimens including detection and quantification of individual cellular and molecular targets and antimicrobial susceptibility testing, the cartridge comprising:
a specimen chamber;
a plurality of division wells that are selectably either in fluid communication or not in fluid communication with the specimen chamber;
a plurality of reagent wells in selectable fluid communication with the division wells, each reagent well containing at least one reagent;
a plurality of imaging wells, each imaging well in fluid communication with a corresponding one of the plurality of reagent wells;
a slideable valve that can be moved into a plurality of positions, operable from outside the cartridge to open and close channels of fluid communication between the specimen chamber and the plurality of division wells, and between the plurality of division wells and the plurality of reagent wells, wherein the slideable valve comprises channels that, when the slideable valve is in a first position of the plurality of positions, provide direct fluid communication between the specimen chamber and at least one division well of the plurality of division wells and, when in a second position of the plurality of positions, provide connection from at least one division well to a corresponding reagent well; and a pneumatic port that is configured to interface with a fluidics module to manipulate pressures in the cartridge to move a specimen within the cartridge, wherein a pressure or vacuum applied to the pneumatic port, in combination with a position of the slidable valve, is configured to control distribution of the specimen and the at least one reagent.

2. The cartridge of claim 1, wherein each imaging well comprises a detection surface and a dye-cushion, the dye-cushion comprising a density gradient medium and a dye adjacent to the detection surface.

3. The cartridge of claim 2, wherein the at least one reagent comprises magnetic particles, and wherein the magnetic particles and dye-cushion are configured so that upon application of a magnetic field across the dye-cushion, the magnetic particles and targets bound thereto are pulled through the dye-cushion to the detection surface.

4. The cartridge of claim 1, wherein the at least one reagent comprises magnetic particles and target-specific or non-specific labels.

5. The cartridge of claim 4, wherein the magnetic particles and the target-specific or non-specific labels are provided as lyophilized beads that are rehydrated and dissolved by delivery of the specimen into the reagent wells.

6. The cartridge of claim 4, wherein the magnetic particles are not target-specific.

7. The cartridge of claim 6, wherein the magnetic particles can bind non-specifically to bacterial cell surfaces.

8. The cartridge of claim 4, wherein each of the target-specific or non-specific labels comprises a fluorescently labeled oligonucleotide complementary to a segment of ribosomal RNA of a specific bacterial target.

9. The cartridge of claim 4, wherein the labels are target-specific.

10. The cartridge of claim 4, wherein the magnetic particles can bind non-specifically to microbial cells.

11. The cartridge of claim 4, wherein the magnetic particles are configured to bind to specific features or molecules on bacterial cell surfaces.

12. The cartridge of claim 1, further comprising:
a diluent reservoir having a diluent therein; and
a button that, when pressed, is configured to distribute the diluent from the diluent reservoir to mix with the specimen.

13. The cartridge of claim 1, wherein the sliding valve is configured to be positioned to:
hold the specimen in the division wells during incubation; and
deliver the specimen from the division wells to the reagent wells for labeling and magnetic tagging.

14. The cartridge of claim 1, wherein when the slidable valve is in the second position, each division well is in communication with a corresponding reagent well.

15. The cartridge of claim 1, further comprising identifiers including patient, test application-specific and factory information with the cartridge.

16. The cartridge of claim 1, further comprising focus particles therein that enable an optical system of an analyzer to focus on a focal plane proximal to the detection surface in which labeled and magnetically tagged target cells or molecules have been deposited by magnetic force.

17. The cartridge of claim 1, wherein the cartridge has an asymmetric footprint in order to permit insertion of the cartridge into a tray of an analyzer in only one orientation to avoid jamming.

18. The cartridge of claim 1, wherein at least one of the division wells contains one or more antimicrobial agents.

* * * * *